(12) United States Patent
Hillenkamp

(10) Patent No.: US 6,558,902 B1
(45) Date of Patent: *May 6, 2003

(54) INFRARED MATRIX-ASSISTED LASER DESORPTION/IONIZATION MASS SPECTROMETRIC ANALYSIS OF MACROMOLECULES

(75) Inventor: Franz Hillenkamp, Munster (DE)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/307,006

(22) Filed: May 7, 1999

Related U.S. Application Data

(63) Continuation-in-part of application No. 09/074,936, filed on May 7, 1998.

(51) Int. Cl.$^7$ ............................................. C12Q 1/68
(52) U.S. Cl. ........................................... 435/6; 436/94
(58) Field of Search ................... 435/6, 91.2; 250/281; 436/94

(56) References Cited

U.S. PATENT DOCUMENTS

| | | | |
|---|---|---|---|
| 3,568,735 A | 3/1971 | Lancsaster | 141/238 |
| 3,776,700 A | 12/1973 | Gallant | 422/65 |
| 3,807,235 A | 4/1974 | Lefkovitz | 73/863.32 |
| 3,843,443 A | 10/1974 | Fishman | 195/63 |
| 3,999,689 A | 12/1976 | Ciantro et al. | 222/108 |
| 4,139,346 A | 2/1979 | Rabbani | 422/56 |
| 4,179,402 A | 12/1979 | Kim et al. | 252/431 |
| 4,214,159 A | 7/1980 | Hillenkamp et al. | 250/288 |
| 4,282,287 A | 8/1981 | Giese | 428/407 |
| 4,356,270 A | 10/1982 | Itakura | 435/317 |
| 4,442,354 A | 4/1984 | Hurst et al. | 250/281 |
| 4,461,328 A | 7/1984 | Kenney | 422/100 |
| 4,542,102 A | 9/1985 | Dattagupta et al. | 435/6 |
| 4,548,245 A | 10/1985 | Crandell et al. | 141/237 |
| 4,554,839 A | 11/1985 | Hewett et al. | 73/864.16 |
| 4,562,157 A | 12/1985 | Lowe et al. | 435/291 |
| 4,582,789 A | 4/1986 | Sheldon, III et al. | 435/6 |
| 4,681,870 A | 7/1987 | Balint, Jr. et al. | 502/403 |
| 4,683,194 A | 7/1987 | Saiki et al. | 435/6 |
| 4,683,195 A | 7/1987 | Mullis et al. | 435/6 |
| 4,725,677 A | 2/1988 | Köster et al. | 536/27 |
| 4,729,947 A | 3/1988 | Middendorf et al. | 435/6 |
| 4,731,335 A | 3/1988 | Brigati | 436/180 |
| 4,757,141 A | 7/1988 | Fung et al. | 536/27 |
| 4,762,881 A | 8/1988 | Kauer | 525/54.11 |
| 4,778,993 A | 10/1988 | Waugh | 250/287 |
| 4,779,467 A | 10/1988 | Rainin et al. | 73/864.17 |
| 4,797,355 A | 1/1989 | Stabinsky | 435/6 |
| 4,798,706 A | 1/1989 | Brigati | 422/102 |
| 4,806,546 A | 2/1989 | Carrico et al. | 536/27 |
| 4,844,298 A | 7/1989 | Ohoka et al. | 222/58 |
| 4,855,225 A | 8/1989 | Fung et al. | 435/6 |
| 4,877,745 A | 10/1989 | Hayes et al. | 436/166 |
| 4,882,127 A | 11/1989 | Rosenthal et al. | 422/50 |
| 4,885,250 A | 12/1989 | Eveleigh et al. | 435/181 |
| 4,902,481 A | 2/1990 | Clark et al. | 422/101 |
| 4,920,264 A | 4/1990 | Becker | 250/282 |
| 4,925,629 A | 5/1990 | Schramm | 422/82.05 |
| 4,931,400 A | 6/1990 | Jitsukawa | 435/287 |
| 4,948,442 A | 8/1990 | Manns | 156/73.1 |
| 4,948,882 A | 8/1990 | Ruth | 536/27 |
| 4,952,518 A | 8/1990 | Johnson et al. | 436/518 |
| 4,954,444 A | 9/1990 | Eveleigh et al. | 435/181 |
| 4,983,521 A | 1/1991 | Lingappa et al. | 435/172.3 |
| 4,994,373 A | 2/1991 | Stavrianopoulos et al. | 435/6 |
| 5,000,921 A | 3/1991 | Hanaway et al. | 422/100 |
| 5,003,059 A | 3/1991 | Brennan | 536/27 |
| 5,023,187 A | 6/1991 | Koebler et al. | 436/180 |
| 5,045,694 A | 9/1991 | Beavis et al. | 250/287 |
| 5,047,215 A | 9/1991 | Manns | 422/101 |
| 5,062,935 A | 11/1991 | Schlag et al. | 204/157.41 |
| 5,064,754 A | 11/1991 | Mills | 435/6 |
| 5,077,210 A | 12/1991 | Eigler et al. | 435/176 |

(List continued on next page.)

FOREIGN PATENT DOCUMENTS

| | | |
|---|---|---|
| DE | 3221681 | 12/1983 |
| DE | 3930312 | 4/1990 |
| DE | 4011991 | 10/1990 |
| EP | 0268237 | 5/1988 |
| EP | 0269520 | 6/1988 |
| EP | 0339781 | 11/1989 |
| EP | 0360677 | 3/1990 |

(List continued on next page.)

OTHER PUBLICATIONS

Hahner et al. Matrix–Assisted Laser Desorption/Ionization Mass Spectrometry (MALDI) of Endonuclease Digests of RNA, *Nucleic Acid Research*, v. 25, 10:1957–1964 (1997).
Nordoff E., Matrix–Assisted Laser Desorption/Ionization Mass Spectrometry as a new method for the characterization of nucleic acids, *Trac, Trends in Analytical Chemistry, GB, Analytical Chemistry*, v. 15, 6:240–250 (1996).
Overberg et al., Matrix–Assisted Laser Desorption Mass Spectrometry: A Sensitive Technique for the Analysis of Macromolecules, *Laser und Optoelectronik Fuer Makromolekuele*, v. 24, 1:50–58 (1992).
Crain et al., Current Opinion in Biotechnology, 9:25–34, 1998.

(List continued on next page.)

*Primary Examiner*—Kenneth R. Horlick
(74) *Attorney, Agent, or Firm*—Stephanie L. Seidman; Heller Ehrman White & McAuliffe, LLP

(57) ABSTRACT

Mixtures containing a biological macromolecule, such as a nucleic acid molecule or a polypeptide, and a liquid matrix, which absorbs infrared (IR) radiation, are provided. These mixtures are useful for analysis of the biological macromolecule by IR matrix assisted laser desorption/ionization (IR-MALDI) mass spectrometry. Also provided are processes for analyzing a biological macromolecule using IR-MALDI mass spectrometry. For example, processes for detecting the presence or identity of a biological macromolecule in a sample, or for sequencing a biological macromolecule are provided.

226 Claims, 3 Drawing Sheets

U.S. PATENT DOCUMENTS

| | | | |
|---|---|---|---|
| 5,082,935 A | 1/1992 | Cruickshank | 536/27 |
| 5,108,703 A | 4/1992 | Pfost et al. | 422/65 |
| 5,118,605 A | 6/1992 | Urdea | 435/6 |
| 5,118,937 A | 6/1992 | Hillenkamp et al. | 250/282 |
| 5,135,870 A | 8/1992 | Williams et al. | 436/86 |
| 5,149,625 A | 9/1992 | Church et al. | 435/6 |
| 5,160,840 A | 11/1992 | Vestal | 250/287 |
| 5,171,989 A | 12/1992 | Williams et al. | 250/288 |
| 5,195,657 A | 3/1993 | Wells | 222/330 |
| 5,198,531 A | 3/1993 | Webber et al. | 525/332.2 |
| 5,202,561 A | 4/1993 | Giessmann et al. | 250/281 |
| 5,210,412 A | 5/1993 | Levis et al. | 250/288 |
| 5,221,518 A | 6/1993 | Mills | 422/62 |
| 5,234,824 A | 8/1993 | Mullis | 435/91 |
| 5,237,016 A | 8/1993 | Ghosh et al. | 525/329.4 |
| 5,242,974 A | 9/1993 | Holmes | 525/54.11 |
| 5,262,128 A | 11/1993 | Leighton et al. | 422/100 |
| 5,283,342 A | 2/1994 | Gustavson et al. | 548/304.1 |
| 5,288,644 A | 2/1994 | Beavis et al. | |
| 5,312,233 A | 5/1994 | Tanny et al. | 417/316 |
| 5,324,637 A | 6/1994 | Thompson et al. | 435/68.1 |
| 5,338,688 A | 8/1994 | Deeg et al. | 436/180 |
| 5,373,156 A | 12/1994 | Franzen | 250/288 |
| 5,376,788 A | 12/1994 | Standing et al. | 250/287 |
| 5,380,833 A | 1/1995 | Urdea | 536/22.1 |
| 5,381,008 A | 1/1995 | Tanner et al. | 250/288 |
| 5,382,793 A | 1/1995 | Weinberger et al. | 250/288 |
| 5,410,068 A | 4/1995 | Coull et al. | 548/545 |
| 5,416,193 A | 5/1995 | Desai | 530/334 |
| 5,430,136 A | 7/1995 | Urdea et al. | 536/243 |
| 5,436,327 A | 7/1995 | Southern et al. | 536/25.34 |
| 5,439,649 A | 8/1995 | Tseung et al. | 422/99 |
| 5,443,816 A | 8/1995 | Zamora et al. | 424/1.69 |
| 5,451,683 A | 9/1995 | Barrett et al. | 548/302.7 |
| 5,457,041 A | 10/1995 | Ginaven et al. | 435/172.1 |
| 5,474,895 A | 12/1995 | Ishii et al. | 435/6 |
| 5,478,893 A | 12/1995 | Ghosh et al. | 525/329.4 |
| 5,484,701 A | 1/1996 | Cocuzza et al. | 435/6 |
| 5,492,817 A | 2/1996 | Thompson et al. | 435/68.1 |
| 5,498,545 A | 3/1996 | Vestal et al. | |
| 5,503,980 A | 4/1996 | Cantor | 435/6 |
| 5,506,348 A | 4/1996 | Pieles | 536/23.1 |
| 5,510,613 A | 4/1996 | Reilly et al. | 250/287 |
| 5,512,295 A | 4/1996 | Kornberg et al. | 424/450 |
| 5,512,439 A | 4/1996 | Hornes et al. | 435/6 |
| 5,514,548 A | 5/1996 | Krebber et al. | 436/6 |
| 5,527,675 A | 6/1996 | Coull et al. | 435/6 |
| 5,541,313 A | 7/1996 | Ruth | 536/24.3 |
| 5,545,539 A | 8/1996 | Miller | 435/91.2 |
| 5,547,835 A | 8/1996 | Köster et al. | 435/6 |
| 5,580,733 A | 12/1996 | Levis et al. | 435/6 |
| 5,589,136 A | 12/1996 | Northrup et al. | 422/102 |
| 5,599,500 A | 2/1997 | Jones | 422/62 |
| 5,601,982 A | 2/1997 | Sargent et al. | 435/6 |
| 5,604,099 A | 2/1997 | Erlich et al. | 435/6 |
| 5,605,662 A | 2/1997 | Heller | 422/68.1 |
| 5,605,798 A | 2/1997 | Köster et al. | 435/6 |
| 5,612,474 A | 3/1997 | Patel | 536/27.14 |
| 5,622,824 A | 4/1997 | Köster et al. | 435/6 |
| 5,622,829 A | 4/1997 | King et al. | 435/6 |
| 5,624,711 A | 4/1997 | Sundberg et al. | 427/261 |
| 5,625,184 A | 4/1997 | Vestal et al. | |
| 5,627,369 A | 5/1997 | Vestal et al. | |
| 5,631,134 A | 5/1997 | Cantor | 435/6 |
| 5,641,959 A | 6/1997 | Holle et al. | 250/287 |
| 5,643,722 A | 7/1997 | Rothschild et al. | 435/6 |
| 5,643,798 A | 7/1997 | Beavis et al. | 436/94 |
| 5,654,545 A | 8/1997 | Holle et al. | 250/287 |
| 5,663,242 A | 9/1997 | Shanker et al. | 525/329.4 |
| 5,670,322 A | 9/1997 | Eggers et al. | 435/6 |
| 5,670,381 A | 9/1997 | Jou et al. | 436/518 |
| 5,677,195 A | 10/1997 | Winkler et al. | 436/518 |
| 5,691,141 A | 11/1997 | Köster et al. | 435/6 |
| 5,700,642 A | 12/1997 | Monforte et al. | 435/6 |
| 5,705,813 A | 1/1998 | Apffel et al. | |
| 5,716,825 A | 2/1998 | Hancock et al. | |
| 5,742,049 A | 4/1998 | Holle et al. | 250/282 |
| 5,743,960 A | 4/1998 | Tisone | 118/683 |
| 5,746,373 A | 5/1998 | Sanada | 239/102.2 |
| 5,756,050 A | 5/1998 | Ershow et al. | 422/100 |
| 5,757,392 A | 5/1998 | Zhang | 347/14 |
| 5,760,393 A | 6/1998 | Vestal et al. | 250/282 |
| 5,777,324 A | 7/1998 | Hillenkamp | 250/288 |
| 5,777,325 A | 7/1998 | Weinberger et al. | 250/287 |
| 5,792,664 A | 8/1998 | Chait et al. | 436/89 |
| 5,795,714 A | 8/1998 | Cantor et al. | 435/6 |
| 5,807,522 A | 9/1998 | Brown et al. | 422/50 |
| 5,821,063 A | 10/1998 | Patterson et al. | 435/6 |
| 5,826,214 A | 10/1998 | Lieb et al. | 702/24 |
| 5,830,655 A | 11/1998 | Monforte et al. | 435/6 |
| 5,864,137 A | 1/1999 | Becker et al. | 250/287 |
| 5,869,240 A | 2/1999 | Patterson | 435/6 |
| 5,869,242 A | 2/1999 | Kamb | 435/6 |
| 5,872,003 A | 2/1999 | Köster | 435/283.1 |
| 5,885,775 A | 3/1999 | Haff et al. | 435/6 |

FOREIGN PATENT DOCUMENTS

| | | |
|---|---|---|
| EP | 0396116 | 11/1990 |
| EP | 0412883 | 2/1991 |
| EP | 0455905 | 11/1991 |
| EP | 0456304 | 11/1991 |
| EP | 0500506 | 8/1992 |
| EP | 0655501 | 5/1995 |
| EP | 0701001 | 3/1996 |
| FR | 2598260 | 10/1987 |
| GB | 2017105 | 3/1979 |
| JP | 63230086 | 9/1988 |
| JP | 2215399 | 8/1990 |
| JP | 6294796 | 10/1994 |
| JP | 8290377 | 11/1996 |
| WO | 8402579 | 7/1984 |
| WO | 8603840 | 7/1986 |
| WO | 8909282 | 10/1989 |
| WO | 8909406 | 10/1989 |
| WO | 8910786 | 11/1989 |
| WO | 8911270 | 11/1989 |
| WO | 8912694 | 12/1989 |
| WO | 9001564 | 2/1990 |
| WO | 9003382 | 4/1990 |
| WO | 9007582 | 7/1990 |
| WO | 9014148 | 11/1990 |
| WO | 9015883 | 12/1990 |
| WO | 9106678 | 5/1991 |
| WO | 9113075 | 9/1991 |
| WO | 9115600 | 10/1991 |
| WO | 9203575 | 3/1992 |
| WO | 9207879 | 5/1992 |
| WO | 9210092 | 6/1992 |
| WO | 9213629 | 8/1992 |
| WO | 9213969 | 8/1992 |
| WO | 9215712 | 9/1992 |
| WO | 9306925 | 4/1993 |
| WO | 9309668 | 5/1993 |
| WO | 9320236 | 10/1993 |
| WO | 9400562 | 1/1994 |
| WO | 9411529 | 5/1994 |
| WO | 9411530 | 5/1994 |
| WO | 9411735 | 5/1994 |
| WO | 9416101 | 7/1994 |

| | | |
|---|---|---|
| WO | 9421822 | 9/1994 |
| WO | 9504524 | 2/1995 |
| WO | 9507361 | 3/1995 |
| WO | 9513538 | 5/1995 |
| WO | 9515001 | 6/1995 |
| WO | 9530773 | 11/1995 |
| WO | 9531429 | 11/1995 |
| WO | 9619587 | 6/1996 |
| WO | 9629431 | 9/1996 |
| WO | 9632504 | 10/1996 |
| WO | 9636731 | 11/1996 |
| WO | 9636732 | 11/1996 |
| WO | 9636986 | 11/1996 |
| WO | 9636987 | 11/1996 |
| WO | 9637630 | 11/1996 |
| WO | 9703499 | 1/1997 |
| WO | 9708306 | 3/1997 |
| WO | 9716699 | 5/1997 |
| WO | 9720194 | 6/1997 |
| WO | 9733000 | 9/1997 |
| WO | 9737041 | 10/1997 |
| WO | 9742348 | 11/1997 |
| WO | 9743617 | 11/1997 |
| WO | 9803684 | 1/1998 |
| WO | 9812355 | 3/1998 |
| WO | 9820019 | 5/1998 |
| WO | 9820020 | 5/1998 |
| WO | 9820166 | 5/1998 |
| WO | 9820200 | 5/1998 |
| WO | 9826095 | 6/1998 |
| WO | 9854751 | 12/1998 |
| WO | 9912040 | 3/1999 |
| WO | 9914375 | 3/1999 |

OTHER PUBLICATIONS

Burlingame et al., Anal. Chem., 70:647R–716R, 1988.

Database CIN bei STN; AN(27)31:35339Bzu: "Mass spectrometry used to find mass of large intact nucleic acids," Chem. Eng. News. Jul. 13, 1998 (199980713) 76(28): p.55.

Eckerson et al. "Analysis of Proteins by Direct–Scanning Infrared–MALDI Mass Spectrometry after 2D–PAGE Separation and Electroblotting," Anal. Chem. 69: 2888–2892 (1997).

Good et al. "Antisense inhibition of gene expression in bacteria by PNA targeted to mRNA," Nature Biotechnology 16: 355–8 (1998).

Good et al. "Inhibition of translation and bacterial growth by peptide nucleic acid targeted to ribosomal RNA," Proc. Natl. Acad. Sci. USA 95: 2073–6 (1998).

Good et al. "Review: Progress in Developing PNA as a Gene–Targeted Drug," Antisense & Nucleic Acid Drug Development 7: 431–7 (1997).

Hyrup, B. and P.E. Nielsen. "Review Article: Peptide Nucleic Acids (PNA): Synthesis, Properties, and Potenial Applications," Bioorganic & Medicinal Chemistry 4(1): 5–23 (1996).

Karas et al. "Matrix Dependence of Metastable Fragmentation of Glycoproteins in MALDI TOF Mass Spectrometry," Anal. Chem. 67: 675–679 (1995).

Nielsen et al. "Sequence–Selective Recognition of DNA by Strand Displacement with a Thymine–Substituted Polyamide," Science 254: 1497–1500 (1991).

Griffin et al. "Genetic analysis by peptide nucleic acid affinity MALDI–TOF mass spectrometry," Nature Biotechnology 15: 1368–72 (1997).

Jiang–Baucom et al. "DNA Typing of Human Leukocyte Antigen Sequence Polymorphisms Nucleic Acid Probes and MALDI–TOF Mass Spectrometry," Analytical Chemistry 69: 4894–8 (1997).

Anderson et al., Preparation of a cell–free protein–synthesizing system from wheat germ, Meth. Enzymol. 101:635–645 (1983).

Eperon, I. C., Rapid preparation of bacteriophage DNA for sequence anlaysis in sets of 96 clones, using filtration, Anal. Biochem 156:406–412 (1986).

Erickson and Blobel, Cell–free translation of messenger RNA in a wheat germ system, Meth. Enzymol. 96:38–50 (1982).

Hopert et al., Specificity and sensitivity of polymerase chain reaction (PCR) in comparison with other methods for the detection of mycoplasma contamination in cell lines, J. Immunol. Methods 164:91–100 (1993).

Köster et al., Some improvements in the synthesis of DNA of biological interest, Nucl Acids Res 7:39–59 (1980).

Köster et al., Well–defined insoluble primers for the enzymatic synthesis of oligo– and polynucleotides, Hoppe–Seyler's Z. Physiol. Chem. 359:11579–1589 (1978).

Matthews, et al., "Analytical strategies for the use of DNA probes", Analytical Biochemistry 169:1–25 (1988).

Melton et al., Efficient in vitro synthesis of biologically active RNA and RNA hybridization probes from plasmids containing a bacteriophage SP6 promoter, Nucl. Acids Res. 12:7035–7056 (1984).

Seela and Kehne, Palinddromic octa– and dodecanucleotides containing 2'–deoxytubercidin: Synthesis, hairpin formation, and recognition by the endodeoxyribonuclease EcoRI, Biochemistry 26:2232–2238 (1987).

Tam et al., Biological availability and nuclease resistance resistance extend the in vitro activity of a phosphorothioate–3'hydroxypropylamine oligonucleotide, Nucl. Acids Res. 22:977–986 (1994).

Zubay, In vitro synthesis of protein in microbial systems, Ann. Rev. Genet. 7:267–287 (1973).

Chemistry of Biomolecules.

Bunin et al., The combinatorial synthesis and chemical and biological evaluation of a 1,4–benzodiazepine library, Proc. Natl. Acad. Sci. U.S.A. 91:4708–4712 (1994).

Bannwarth, Solid–phase synthesis of oligodeoxynucleotides containing phosphoramidate internucleotide linkages and their specific chemical cleavage, Helvetica Chimica Acta 71:1517–1527 (1988).

Chen et al., "Analogous" organic synthesis of small–compound libraries: validation of combinatorial chemistry in small–molecule synthesis, J. Am. Chem. Soc. 116:2661–2662 (1994).

Ecker and Crooke, Combinatorial drug discovery: which methods will produce the greatest value?, BioTechnology 13:351360 (1995).

Ellison et al. Epitope–tagged Ubiquitin, J. Biol. Chem. 266:21150–21157 (1991).

Lin et al. Modified RNA sequence pools for in vitro selection, Nucl. Acids Res. 22:5229–5234 (1994).

Mateucci et al., Synthesis of deoxyoligonucleotides on a polymer support, J. A. Chem. Soc. 103:3185–3191, 1981.

Mizusawa, et al., "Improvement of the dideoxy chain termination method of DNA sequencing by use of deoxy–7–deazaguanosine triphosphate in place of dGTP", Nucleic Acids Res. 14(3):1319–1325 (1986).

Narang et al., Improved phosphotriester method for the synthesis of gene fragments, *Meth. Enzymol.* 68:90–98 (1979).

Newton et al., "The production of PCR products with 5' single–stranded tails using primers that incorporate novel phosphoramidite intermediates", *Nucl. Acids. Res.* 21:1155–1162 (1993).

Pagratis et al., Potent 2'–amino–, and 2'–fluoro–2'deoxyribonucleotide RNA inhibitors of keratinocyte growth factor, *Nature Biotechnol.* 15:68–73 (1997).

Rink, "Solid–phase synthesis of protected peptide fragments using a trialkoxy–diphenyl–methlester resin", *Tetrahedron Lett.* 28:3787–3790 (1987).

Tong et al., Solid–phase method for the purification of DNA sequencing reactions, *Anal. Chem.* 64:2672–2677, (1992).

Wiedmann M. et al., Ligase chain reaction (LCR)—overview and applications, *PCR Methods Appl.* 3(4):S51–S64 (1994).

Biopolymer Diagnostics.

Beck et al., Chemiluminescent detection of DNA: application for DNA sequencing and hybridization, *Nucl Acids Res* 17:5115–5123 (1989).

Jurinke et al., Application of nested PCR and mass spectrometry for DNA–based virus detection: HBV–DNA detected in the majority of isolated anti–HBc positive sera, *Genetic Analysis* 14:97–102 (1998).

Kozal et al., "Extensive polymorphisms observed in HIV–1 clade B protease gene using high–density oligonucleotide arrays", *Nature Medicine*, 2(7):753–759 (1996).

Kuppuswamy, et al., "Single nucleotide primer extension to detect gentic diseases: experimental application to hemophilia B (factor IX) and cystic fibrosis genes", *Proc. Natl. Acad. Sci. USA* 88:1143–1147 (1991).

Lamture et al., "Direct detection of nucleic acid hybridization on the surface of a charge coupled device", *Nucl. Acids Res.* 22:2121–2125 (1994).

Landegren et al., "DNA Diagnostics—Molecular techniques and automation", *Science* 242:229–237 (1988).

Li et al., "Analysis of single mammalian cell lysates by mass spectrometry", *J. Am. Chem. Soc.* 118:11662–11663 (1996).

Little et al., Detection of RET proto–oncogene codon 634 mutations using mass spectrometry, *J. Mol Med.* 75:745–750 (1997).

Little et al., Identification of apolipoprotein E polymorphisms using temperature cycled primer oligo base extension and mass spectrometry, *Short Communiation.*

Wain–Hobson et al., Nucleotide sequence of the AIDS virus, LAV, *Cell* 40:9–17 (1985).

Walker et al., Multiplex strand displacement amplification (SDA) and detection of DNA sequences from *Mycobacterium tuberculosis* and other mycobacteria, *Nucleic Acids Res.* 22(13):2670–2677 (1994).

Yang, et al., "Detection of hepatitis B virus in plasma using flow cytometric analyses of polymerase chain reaction–amplified DNA incorporating digoxigenin–11 –dUTP", *Blood* 81(4):1083–1088 (1993).

Genetics & Disease.

Anker et al., Tetranucleotide repeat polymorphism at the human thyroid peroxidase (hTPO) locus, *Hum. Mol. Genet.* 1:137 (1992).

Barany F., Genentic disease detection and DNA amplification using cloned thermostable ligase, *Proc. Natl. Acad. Sci.* 88:189–193 (1991).

Beckmann et al., Survey of human and rat microsatellites, *Genomics* 12:627–631 (1992).

Brook et al., Molecular basis of myotonic dystrophy: expansion of a trinucleotide (CTG) repeat at the 3' end of a transcript encoding a protein kinase family member, *Cell* 68:799–808 (1992).

Edwards et al., Pentanucleotide repeat length polymorphism at the human CD4 locus, *Nucl. Acids Res.* 19:4791 (1991).

Ferrie et al., Development, multiplexing, and application of ARMS tests for common mutations in the CFTR gene, *Am. J. Hum. Genet.* 51:251–262 (1992).

Fu et al., Variation of the CGG repeat at the fragile X site reslts in genetic instability: resolution of the Sherman paradox, *Cell* 67:1047–58 (1991).

Gust et al., Tazomonic classification of Hepatitis A virus *Intervirology* 20:1–7 (1983).

Guyader, et al., "Genome organization and transactivation of the human immunodeficiency virus type 2", *Nature* 326:662–669 (1987).

Hirst et al., Genotype prediction in the fragile X syndrome, *J. Med. Genet.* 28:824–29 (1991).

Jeffreys et al., Hypervariable 'minisatellite' regions in human DNA, *Nature* 314:67–73 (1985).

Kremer et al., Mapping of DNA instability at the fragile X to a trinucleotide repeat sequence p(CCG)n, *Science* 252:1711–14 (1991).

La Spada et al., ndrogen receptor gene mutations in X–linked spinal and bulbar muscular atrophy, *Nature* 352:77–79 (1991).

Litt et al., Dinucleotide repeat polymorphism at the D11S35 locus, *Nucl. Acids Res.* 18:5921 (1990).

Litt et al., Dinucleotide repeat polymorphism at the D6S89 locus, *Nucl. Acids Res.* 18:4301 (1990).

Lopez–Galindez, et al., "Characerization of genetic variation and 3'–azido–3'–deoxythymidine–resistance mutations of human immunodeficiency virus by the RNase A mismatch cleavage method", *Proc. Natl. Acad. Sci, USA* 88:4280–4284 (1991).

Luty et al., Five polymorphic microsatellite VNTRs on the human X chromosome, *Am. J. Hum. Genet.* 46:776–783 (1990).

Luty et al., Dinucleotide repeat polymorphism at the D14S45 locus, *Nucl. Acids Res.* 19:4308 (1991).

Mahadevan et al., Myotonic dystrophy mutation: an unsable CTG repeat in the 3' untranslated region of the gene, *Science* 255:1253–55 (1992).

Miyazaki, et al., The first Japanese cse of Hb Santa Ana, an unstable abnormal hemoglobin, identified rapidly by electrospray ionization mass spectrometry. *Internal Medicine* 36:365–370 (1997).

Nakamura et al., ariable number of tandem repeat (VNTR) markers for human gene mapping, *Science* 235:1616–1622 (1987).

Nikiforov et al. "Genetic Bit Analysis: a solid phase method for typing single nucleotide polymorphisms" *Nucleic Acids Research*, 22(20):4167–4175 (1994).

Nishimura et al., A tetranucleotide repeat for the F13B locus, *Nucl. Acids Res.* 20:1167 (1992).

Ploos van Amstel et al., Tetranucleotide repeat polymorphism inthe vWF gene, *Nucl. Acids Res.* 18:4957 (1990).

Polymeropoulos et al., Tetranucleotide repeat polymorphism at the human aromatase cytochrome P–450 gene (CYP19), *Nucl. Acids Res.* 19:195 (1991).

Polymeropoulos et al., Trinucleotide repeat polymorphism at the human met–tRNA–i gene 1 (TRMI), *Nucl. Acids Res.* 19:4306 (1991).

Polymeropoulos et al., Trinucleotide repeat polymorphism at the human c–fes/fps proto–oncogene (FES), *Nucl. Acids Res.* 19:4018 (1991).

Polymeropoulos et al., *Nucl. Acids Res.* 18:7468 (1990).

Saiki, et al., "Genetic analysis of amplified DNA with immobilized sequence–specific oligonucleotide probes", *Proc. Natl. Acad. Sci. USA* 86:6230–6234 (1989).

Tautz, Hypervariability of simple sequences as a general source for polymorphic DNA markers, *Nucl. Acids Res.* 17:6463–6471 (1989).

Weber et al., Abundant class of human DNA polymorphisms which can be typed using the polymerase chain reaction, *Am. J. Hum. Genet.* 44:388–396 (1989).

Zhang et al., "Single–base mutational analysis of cancer and genetic diseases using membrane bound modified oligonucleotides", *Nucl. Acids Res.* 19:3929–3933 (1991).

Zuliani et al., Tetranucleotide repeat polymorphism in the LPL gene, *Nucl. Acids Res.* 18:4958 (1990).

General Sequencing of Biomolecules.

Arlinghaus et al., "Applications of resonance ionization spectroscopy for semiconductor, environmental and biomedical analysis, and for DNA sequencing", *SPIE*, vol. 1435, *Opt. Methods Ultrasensitive Detect. Anal. Tech. Appl.* pp. 26–35 (1991).

Bains, Setting a sequence to sequence a sequence, *Biotechnology* 10:757–758 (1992).

Broude, Natalia E. et al., "Enhanced DNA sequencing by hybridization (streptavidin/biotin/stacking interaction/T4 DNA ligase/DNA polymerase)", *Proc. Natl. Acad. Sci.*, 91:3072–3076 (1994).

Chait and Kent, Weighing naked proteins: practical, high–accuracy mass measurements of peptides and proteins, *Science* 257:1885–1804 (1992).

Charkrabarti et al., Sequence of Simian Immunodeficiency Virus from Macaque and its Relationship to Other Human and Simian Retroviruses, Nature 328:543–547 (1987).

Chen and Seeburg, Supercoil sequencing: A fast and simple method for sequencing plasmid DNA, *DNA* 4(2):165–170 (1985).

Church et al., "Multiplex DNA Sequencing", *Science* 240:185–188 (1988).

Drmanac, et al., "Sequencing of megabase plus DNA by hybridization: theory of the method", *Genomics* 4:114–128 (1989).

Frank and Köster, DNA chain length and the influence of base composition on electrophoretic mobility of oligodeoxyribonucleotides in polyacrylamide–gels, *Nucl. Acids Res.* 6:2069–2087 (1979).

Fu et al., A DNA sequencing strategy that requires only five bases of known terminal sequence for priming, *Proc. Natl. Acad. Sci. USA* 92:10162–10166 (1995).

Fu et al., Sequencing double–stranded DNA by strand displacement, *Nucl Acids Res* 25:677–679 (1997).

Fu et al., A DNA sequencing strategy which requires only five bases of known terminal sequence for priming, Paper presented, Genome Mapping and Sequencing, Cold Spring Harbor Laboratory.

Higuchi et al., Kinetic PCR analysis: Real–time monitoring of DNA amplification reactions, *Bio/Technology* 11:1026–1030 (1993).

Higuchi et al., A general method of in vitro preparation and mutagenesis of DNA fragments: Study of protein and DNA interactions, *Nucleic Acids Res.* 16:7351–7367 (1988).

Hultman et al., Direct solid phase sequencing of genomic and plasmid DNA using magnetic beads as solid support, *Nucl. Acids Res.* 17:4937–4946 (1989).

Hyman, A new method of sequencing DNA, *Anal. Biochem.* 174:423–436 (1988).

Innis et al., DNA sequencing with *Thermus aquaticus* DNA polymerase and direct sequencing of polymerase chain reaction–amplified DNA, *Proc. Natl. Acad. Sci. USA* 85:9436–9440 (1988).

Jett et al., "High–Speed DNA Sequencing: An Approach Based Upon fluorescence Detection of Single Molecules", *J. Bio Strut & Dynam.* 7(2):301–09 (1989).

Ji et al., Two–dimensional electrophoretic analysis of proteins expressed by normal and cancerous human crypts: Application of mass spectrometry to peptide–mass fingerprinting, *Electrophoresis* 15:391–405 (1994).

Khrapko et al., An oligonucleotide hybridization approach to DNA sequencing, *FEB* 256(1,2):118–122 (1989).

Khrapko et al., "A method for DNA sequencing by hybridization with oligonucleotide matrix", *J. DNA Seq. and Mapping* 1:375–388 (1991).

Köster, et al., "Oligonucleotide synthesis and multiplex DNA sequencing using chemiluminescent detection", *Nucleic Acids Research*, Symposium Series No. 24, 318–321 (1991).

Labeit et al., Laboratory methods: A new method of DNA sequencing using deoxynucleoside α–thiotriphophates, *DNA* 5:173–177 (1986).

Lawrance et al., Megabase–scale mapping of the HLA gene complex by pulsed field gel electrophoresis, *Science* 235:1387–1389 (1987).

Little et al., "Mass spectrometry from miniaturized arrays for full comparative DNA analysis", *Nature Med* 3(12):1413–1416 (1997).

Marshall and Hodgson, "DNA chips: An array of possibilities", *Nature Biotechnology* 16:27–31 (1998).

Martin, "New technologies for large–genome sequencing", *Genome* 31:1073–1080 (1989).

Maxam and Gilbert, Sequencing end–labeled DNA with base–specific chemical cleavages, *Methods in Enzymology* 65:499–560 (1980).

Nakamaye et al., "Direct sequencing of polymerase chain reaction amplified DNA fragments through the incorporation of deoxymucleoside α–thiotriphosphates", *Nucleic Acids Res.* 16(12):9947–9959 (1988).

O'Donnell et al., "MassArray as an Enabling Technology for the Industrial–Scale Analysis of DNA", *Genetic Engineering News* 17(21) (1997).

O'Donnell–Maloney et al., The development of microfabricated arrays for DNA sequencing and analysis, *TIBTECH* 14:401–407 (1996).

O'Donnell–Maloney et al., Microfabrication and array technologies for DNA sequencing and diagnostics, *Genetic Analysis: Biomolecular Engineering* 13:151–157 (1996).

Ornstein et al., Sequencing DNA using $^{35}$S–labeling: A troubleshooting guide, *Biotechniques* 3:476–483 (1985).

Prome et al., Use of combined mass spectrometry methods for the characterization of a new variant of human hemoglobin: The double mutant hemoglobin villeparisis beta 77(EF1), *J. American Society for Mass Spect* 7(2):163–167 (1996).

Raftery, et al., Characterization of mutant recombinant S100 protein using electrospray ionization mass spectrometry. *Rapid Comm. Mass Spec.* 11:405–409 (1997).

Ratner et al., Complete nucleotide sequence of the AIDS virus, HTLV–III, *Nature* 313:227–284 (1985).

Sanger et al., DNA sequencing with chain–terminating inhibitors, *Proc. Natl. Acad. Sci.* 74:5463–67 (1977).

Smith et al., Fluorescence detection in automated DNA sequence analysis, *Nature* 321:674–679 (1986).

Stahl, et al., "Solid phase DNA sequencing using the biotin–avidin system", *Nucleic Acids Res.* 16(7):3025–3039 (1988).

Strezoska, et al., "DNA sequencing by hybridization: 100 bases read by a non–gel–based method", *Proc. Natl. Acad. Sci. USA* 88:10089–10093 (1991).

Swerdlow and Gesteland, Capillary gel electrophoresis for rapid, high resolution DNA sequencing, *Nucleic Acids Res.* 18(6):1415–1419 (1990).

Tabor and Richardson, DNA sequence analysis with a modified bacteriophage T7 DNA polymerase, *Proc. Natl. Acad. Sci.* 84:4767–4771 (1987).

Automation.

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal chem* 69:4540–4546 (1997).

Moini et al., "A Moving Belt Device to Couple High–Performance Liquid Chromatography and Chemical Reaction Interface Mass Spectrometry", *Bio Mass Spect* 20:308–312 (1991).

Roberts and Paterson, Efficient translation of tobacco mosaic virus RNA and rabbit globin 93 RNA in a cell–free system from commercial wheat germ, *Proc. Natl. Acad Sci., USA* 70:2330–2334 (1973).

Ruppert et al., "Preparation of plasmid DNA as Sequencing Templates in a Microtiter Plate Format", Paper presented, Cold Spring Harbor Laboratory, N.Y. May 10–14, 1995.

Ruppert et al., "A rapid and high throughput method for plasmid isolations", Presented: Automation in Mapping and DNA Sequencing Conference, Aug. 31—Sep. 2 1994.

Ruppert et al., A filtration method for plasmid isolation using microtiter filter plates, *Anal. Biochem.* 230:130–134 (1995).

Spirin et al., A continuous cell–free translation system capable of producing polypeptides in high field, *Science* 242:1162–64 (1988).

Trainor, "DNA Sequencing, Automation, and the Human Genome", *Anal. Chem.* 62:418–426 (1990).

Zimmermann et al., Automated preparation and purification of M13 templates for DNA sequencing, *Meth. Mol. Cell. Biol.* 1:29–34 (1989).

Fluid Dispensing.

Clark et al., Experimenting in picoliter microvials, *CHEMTECH* 28:20–25 (1998).

Wallace, "Ink–jet based fluid microdispensing in biochemical applications", Microfab Technologies, Inc., Laboratory Automation News, 1(5):6–9 (1996).

Mass Spectrometry Design.

Alimplev et al., Laser desorption mass spectrometry from frozen water solutions using a 3.28 μm YAG/OPO laser system, Proceedings from the 44th ASMS Conference on Mass Spectrometry, p. 644.

Berkenkamp et al., Infrared MALDI–MS of large nucleic acids, Proceedings of the 46th ASMS Conference on Mass Spectrometry and Allied Topics, Orlando, Florida, May 31–Jun. 4, 1998.

Berkenkamp et al., Water as a matrix in infrared MALDI–MS, Proceedings of the 43rd ASMS Conference on Mass Spectrometry and Allied Topics, p. 1247, Atlanta, Georgia, May 1995.

Berkenkamp et al., Performance of infrared matrix–assisted laser desorption/ionization mass spectrometry with lasers emitting in the 3 μm wavelength range, *Rapid Commun. Mass Spectrom.* 11:1399–1406 (1997).

Berkenkamp et al., Infrared MALDI mass spectrometry of large nucleic acids, *Science* 281:260–2 (1998).

Berkenkemp et al., Ice as a matrix for IR–matrix–assisted laser desorption/ionization: mass spectra from a protein single crystal, *Proc. Natl. Acad. Sci. USA* 93:7003–7007 (1996).

Caldwell et al., Mid–infrared matrix assisted laser desorption ionization with a water/glycerol matrix, *Applied Surface Science* 127–129:242–247 (1998).

Eckerskorn et al., High–sensitivity peptide mapping by micro–LC with on–line membrane blotting and subsequent detection by scanning–IR–MALDI mass spectrometry, *J of Protein Chem* 16(5):349–362 (1997).

Ehring et al., Photochemical versus thermal mechanisms in matrix–assisted laser desorption/ionization probed by back side desorption, *Rapid Comm in Mass Spect* 10:821–824 (1996).

Kambara, Characteristics of molecular secondary ion mass spectrometry, *Springer Ser. Chem. Phys.* 36:357–362 (1984).

Li et al., Pulsed laser desorption method for volatilizing thermally labile molecules for supersonic jet spectroscopy, *Rev. Sci. Instrum.* 59:557–561 (1988).

Nelson et al., "Volatilization of High Molecular Weight DNA by Pulsed Laser Ablation of Frozen Aqueous Solutions", *Science* 246:1585–1587 (1989).

Pierce ImmunoTechnology Catalog, p. 57 (1993).

Pierce Catalog, pp. T123–T154, 1994.

Smith et al., Capillary Zone electrophoresis–mass spectrometry using an electrospray ionization interface, *Anal. Chem.* 60:436–441 (1988).

Spengler et al., Fundamental aspects of postsource decay in matrix–assisted laser desorption mass spectrometry, *J. Phys. Chem.* 96:9678–9684 (1992).

Takayama, *Org. Mass Spectrom*.26:1123–1124 (1991).

Wolter et al., Influence of the matrix on the analysis of small oligoribonucleotides by fast atom bombardment mass spectrometry, *J. Mass Spectorm.* 30:485–491 (1995).

Yamashita et al., Electrospray ion source. Another variation on the free–jet theme, *J. Phys. Chem.* 88:4451–4459, (1984).

Yoshida et al., Detection of high mass molecular ions by laser desorption time–of–flight mass spectrometry, *Shitsuryo Bunseki* 36:59–69 (1988).

Zhang et al., Exploring infrared wavelength matrix–assisted laser desorption/ionization of proteins with delayed–extraction time–of–flight mass spectrometry, *J. Am. Soc. Mass Spectrom.* 9:879–884 (1998).

Labeling Biomolecules.

Agrawal et al., Efficient methods for attaching non–radioactive labels to the 5' ends of synthetic oligodeoxyribonucleotides, *Nucleic Acids Res.* 14:6227–6245 (1986).

Beaucage et al., The synthesis of modified oligonucleotides by the phosphoramidite approach and their applications, *Tetrahedron* 49:6123–6194 (1993).

Beck et al., Applications of dioxetane chemiluminescent probes to molecular biology, *Anal. Chem.* 62:2258–2270 (1990).

Connolly, B. A., "Oligonucleotides containing modified bases", *Oligonucleotides and Analogues, A Practical Approach*, Edited by F. Eckstein, Oxford University Press, Ch. 7, pp. 40–45 (1991).

Eckstein and Goody, Synthesis and properties of diastereoisomers of adenosine 5'-(O-1-thiotriphosphate) and adenosine 5'-(O-2-thiotriphosphate), *Biochemistry* 15(8):1685–1691 (1976).

Eckstein, Nucleoside phosphorothioates, *Ann. Rev. Biochem.* 54:367–402 (1985).

Eckstein (ed.), *Oligonucleotides and Analogues*, IRL Press, Oxford (1991).

Eckstein, F., Phosphorothioate analogues of nucleotides, *Accounts Chem. Res.* 12:204–210 (1979).

Eggers et al., "A microchip for quantitative detection of molecules utilizing luminescent and radioisotope reporter groups", *Bio Techniques* 17:516–524 (1994).

Hobbs and Eckstein, A general method for the synthesis of 2'–azido–2'deoxy–and 2'–amino–2'–deoxyribofuranoxyl purines, *J. Org. Chem.* 42:714–719 (1976).

Hsiung et al., A new simpler photoaffinity analogue of peptidyl rRNA, *Nucl Acids Res* 1:1753–1762 (1974).

Jellinek et al., Potent 2'amino–2'–deoxypyrimidine RNA inhibitors of basic fibroblast growth factor, *Biochemistry* 34:11363–11372 (1995).

Köster et al., N–acyl protecting groups for deoxynucleotides: A quantitative and comparative study, *Tetrahedron* 37:363–369 (1981).

Manoharan et al., A 2'–O–thiol tether in the ribose moiety of nucleic acids for conjugation chemistry, *Gene*, 149:147–156 (1994).

Olejnik et al., "Photocleavable biotin phosphoramidite for 5'–end–labeling, affinity purification and phosphorylation of synthetic oligonucleotides", *Nucleic Acids Res.* 24:351–366 (1996).

*Oligonucleotides and Analogues: A Practical Approach*, Eckstein, ed., Oxford University Press Ch. 3, pp. 49–59, 137–139, 255–259 (1991).

Sasaki et al., Introduction of an azide group into some uridine derivatives via 2',3'–benzoxonium and 2',3'–azidonium intermediates, *J. Org. Chem.* 41:3138–3143 (1976).

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res.* 23(9):1570–1575 (1995).

Singh et al., Oligonucleotides, part 5+: synthesis and fluorescence studies of DNA oligomers d(AT)$_5$ containing adenines covalently linked at C–8 with dansyl fluorophore, *Nucleic Acids Res.* 18(11):3339–3345 (1990).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Slim et al., Configurationally defined phosphorothioate––containing oligoribonucleotides in the study of the mechanism of cleavage of hammerhead ribozymes, *Nucleic Acids Res.* 19:1183–1188 (1991).

Sproat et al., The synthesis of protected 5'amino–2', 5'–dideoxyribonucleoside–3'–O–phosphoroamidites; applications of 5'–amino–oligodeoxyribonucleotides, *Nucleic Acids Res.* 15:6181–6196 (1987).

Sproat et al., The synthesis of protected 5'–mercapto–2', 5'dideoxyribonucleoside–3'–O–phosphoroamidites; uses of 5'mercapto–olideoxyribonucleotides, *Nucleic Acids Res.* 15:4837–4848 (1987).

Wellhöner et al., Uptake and concentration of bioactive macromolecules by K562 cells via the transferrin cycle utilizing an acid–labile transferrin conjugate, *J. Biol. Chem.* 256:4309–4314, (1991).

Zuckermann et al., Efficient methods for attachment of thiol specific probes to the 3'–ends of synthetic oligodeoxyribonucleotides, *Nucleic Acids Research*, 15:13, 5305–5321 (1987).

Linkers & Supports.

Alderton et al., Magnetic bead purification of M13 DNA sequencing templates, *Anal. Biochem.* 201:166–169 (1992).

Arshady, Reza; Review: Beaded Polymer Supports and Gels, I. Manufacturing Techniques; Journal of Chromatography, 586 (1991); pp. 181–197.

Arshady, Reza, Beaded polymer supports and gels: II. Physico–chemical criteria and functionalization, *Journal of Chromatography*, 586:199–219 (1991).

Batista–Viera et al., A new method for reversible immobilization of thiol biomolecules bsed on solid–phase bound thiolsulfonte groups, *App. Biochem and Biotech*,31:175–195 (1991).

Batra et al., Insertion of constant region domains of human IgG1 into CD4–PE40 increases its plasma half–life, *Mol. Immunol.* 30:379–386 (1993).

Brown, et al, "A single–bead decode strategy using electrospray ionization mass spectrometry and a new photolabile linker: 3–amino–3–(2–nitrophenyl) propionic acid", *Mol. Diversity* 1:4–12(1995).

Chrisey et al., Fabrication of patterned DNA surfaces, *Nucl. Acids. Res.* 24:3040–3047 (1996).

Chrisey et al., Covalent attachment of synthetic DNA to self–assembled monlayer films, *Nucl. Acids Res.* 24:3031–3039 (1996).

Damha, Masad J. et al., An improved procedure for derivatization of controlled–pore glass beads for solid–phase oligonucleotide synthesis; *Nucleic Acids Research* 18(13):3813–3821 (1990).

DeWitt et al., "Diversomers": An approach to nonpeptide, nonoligomeric chemical diversity, *Proc. Natl. Acad. Sci. U.S.A.* 90:6909–6913 (1993).

Fattom et al., Comparative immunogenicity of conjugates composed of the *Staphylococcus aureus* type 8 capsular polysaccharide bound to carrier proteins by adipic acid dihydrazide or N–succinimidyl–3–(2–pyridyldithio)propionate, Infect. Immun. 60:584–589 (1992).

Fujita et al., Surprising lability to biotin–streptavidin bond during transcription of biotinylated DNA bound to paramagnetic beads, *BioTechniques* 14:608–617 (1993).

Ghosh, et al., "Covalent attachment of oligonucleotides to solid supports", *Nuc. Acids. Res.* 15)13):5353–5372 (1987).

Gildea et al., A versatile acid–labile linker for modification of synthetic biomolecules, *Tetrahedron Letters* 31:7095–7098 (1990).

Goldmacher et al, Photoactivation of toxin conjugates, *Bioconjugate Chem.* 3:104–107, (1992).

Hale, Irreversible, oriented immobilization of antibodies to cobalt–iminodiacetate resin for use as immunoaffinity media, *Analytical Biochem.* 231:46–49 (1995).

Hayashi, et al., "Immobilization of Thiol Proteases onto porous poly(vinyl alcohol) beads", *Polymer Journal*, 25(5):489–497 (1993).

Hazum et al., A photocleavable protecting group for the thiol function of cysteine, *Pept., Proc. Eur. Pept. Symp., 16th*, Brunfeldt, K (Ed), pp. 105–110 (1981).

Heermann, et al., "Liquid–phase hybridization and capture of hepatitis B virus DNA with magnetic beads and fluorescence detection of PCR product", *J. of Virol. Methods* 50:43–58 (1994).

Hornes and Korsnes, Magnetic DNA hybridization of oligonucleotide probes attached to superparamagnetic beads and their use in the isolation of Poly(A) mRNA from eukaryotic cells, *GATA* 7:145–150, (1990).

III et al., A COOH–terminal peptide confers regiospecific orientation and facilittes atomic force microscopy of an $IgG_1$, *Biophys. J.* 64:919–924 (1993).

Kennedy et al. (1983) *Solid Phase Biochemistry, Analytical and Synthetic Aspects*, Scouten, ed., pp. 253–391.

Köster et al., Polymer support oligonucleotide synthesis—$XV^{1, 2}$, *Tetrahedron* 40:102–112 (1984).

Leznoff, The use of insoluble polymer supports in general organic synthesis, *Ace. Chem. Res.* 11:327 (1978).

Loetscher et al., Immobilization of monoclonal antibodies for affinity chromatography using a chelating peptide, *J. Chromatography* 595:113–199 (1992).

Lund, Vera et al., "Assessment of methods for covalent binding of nucleic acids to magnetic beads, dynabeads, and the characteistics of the bound nucleic acids in hybridization reactions", *Nucleic Acids Res.* 16(22) (1988).

McCray and Trentham, "Properties and uses of photoreactive caged compounds", *Annu. Rev. Biophys. Biophys. Chem.* 18:239–270 (1989).

Nikiforov and Rogers, "The use of 96–well polystyrene plates for DNA hybridization–based assays: An evaluatin of different approaches to oligonucleotide immobilization", *Anal. Biochm.* 227:201–209 (1995).

O'Donnell et al., High–density, covalent attachment of DNA to silicon wafers for analysis by MALDI–TOF mass spectrometry, *Analytical Chemistry* 69:2438–2443 (1997).

Padwa et al., Photoclimination of a β–Keto sulfide with a low–lying π–π* triplet state, *J. Org. Chem.* 41:3550–3552 (1971).

Pon, Richard T. et al.; Research Report: Derivatization of Controlled Pore Glass Beads for Solid Phase Oligonucleotide Synthesis; BioTechniques vol. 6, No. 8 (1988); pp. 768–770, 773–775.

Rasmussen et al., "Covalent immobilization of DNA onto polystyrene microwells: The molecules ar eonly bound at the 5' end", *Anal. Biochem.* 198:138–142 (1991).

Rothschild et al., A versatile acid–labile linker for modification of synthetic biomolecules, *Nucl. Acids Res.* 24:351–66 (1996).

Running and Urdea, "A procedure for productive coupling of synthetic oligonucleotides to polystyrene microtiter wells for hybridization capture", *Biotechniques* 8:276–277 (1990).

Senter et al., Novel photocleavable protein crosslinking reagents and their use in the preparation of antibody–toxin conjugates, Photochem. Photobiol. 42:231–237, (1985).

Sinha et al., Polymer support oligonucleotides synthesis XVIII: Use of B–cyanoethyl–N, N–dialkylamino–/N–morpholino phosphoramidite of deoxynucleosides for the synthesis of DNA fragments simplifying deprotection and isolation of final product, *Nucleic Acids Res.* 12:4539 (1984).

Smith et al., Kinetically inert Co(III) linkage through an engineered metal binding site: specific orientation of recombinant human papillomavirus type 16 E7 protein on a solid support, *Methods: A Companion to Methods in Enz.* 4:73–78 (1992).

Sucholeiki, Solid–phase photochemical C–S bonc cleavage of thioethers–A new approach to the solid–phase production on non–peptide molecules, *Tetrahedron Lttrs.* 35:7307–7310 (1994).

Thuong and Asseline, Oligonucleotides attached to intercalators, photoreactive and cleavage agents, *Oligonucleotides and Analogues: A Practical Approach*, Eckstein, edr., Oxford University Press Ch. 12, pp. 283–308 (1991).

Vedejs et al., A method for mild photochemical oxidation; conversion of phenacyl sulfides into carbonyl compounds, *J. Org. Chem.* 49:573–575 (1984).

Wang, Solid phase synthesis of protected peptides via photolytic cleavage of the α–methylphenacyl ester anchoring linkage, *J. Org. Chem.* 41(20):3258–3261 (1976).

Waters et al., Multiple sample PCR amplification and electrophoretic analysis on a microchip, *Anal. Chem.* 70:5172–5176 (1998).

Wong, Ch. 12: Conjugation of proteins to solid matrices, *Chemistry of Protein Conjugation and Cross Linking* 12:295–317 (1993).

Woolley et al., Functional integration of PCR amplification and capillary electrophoresis in a microfabricated DNA analysis device, *Anal. Chem.* 68:4081–4086 (1996).

Yen et al., Synthesis of water–soluble copolymers containing photocleavable bonds, *Makromol. Chem.* 190:69–82 (1989).

Zuckermann et al., Efficient method for the preparation of peptoids [oligo(N–substituted glycines)] by submonomer solid–phase synthesis, *J. Am. Chem. Soc.* 114:10646–10647 (1992).

MALDI of Biomolecules.

Bornsen et al., Influence of solvents and detergents on matrixj–assisted laser desorption/ioniation mass spectrometry measurements of proteins and oligonucleotides, *Rapid Comm. Mass. Spectrom.* 11:603–609 (1997).

Chan et al., Matrix–assisted laser desorption/ionization using a liquid matrix: formation of high–mass cluster ions from proteins, *Org. Mass Spectrom.* 27:53–56 (1992).

Cornett et al., Liquid mixtures for matrix–assisted laser desorptioin, 65:2608–2613 (1993).

Cramer et al., Analysis of phospho– and glycopolypeptides with infrared matrix–assisted laser desorption and ionization, *Anal. Chem.* 70:4939–4944 (1998).

Fu et al., Sequencing exons 5 to 8 of the p53 gene by MALDI–TOF mass spectrometry, *Nat Biotechnol* 16:381–4 (1998).

Fu et al., Efficient preparation of short DNA sequence ladders potentially suitable for MALDI–TOF DNA sequencing, *Genetic Analysis* 12:137–142 (1996).

Gruić–Sovulj I. et al., Matrix–assisted laser desorption/ionisation mass spectrometry of transfer ribonucleic acids isolated from yeast, *Nucleic Acids Res.* 25(9):1859–61 (1997).

Haglund et al., Marix–assisted laser–desorption mass spectrometry of DNA using an infrared free–electron laser, *SPIE* 1854:117–128 (1993).

Hillenkamp, MALDI–MS with other wavelengths: options, potentials and limitations, Proceedings of the 46th ASMS Conference on Mass Spectrometry and Allied Topics, Oraldno, Florida, p. 796, May 31–Jun. 4, 1998.

Hillenkamp et al., Matrix Assisted UV–Laser Desorption/Ionization: A New Approach to Mass Spectrometry of Large Biomolecules, *Biological Mass Spectrometry*, Editors: A. L. Burlingame and J. A. McCloskey, Elsevier Science Publishers, B. V., Amsterdam, pp. 49–61 (1989).

Hillenkamp and Karas, Matrix–assisted laser desorption/ionization mass spectrometry of biopolymers, *Anal. Chem* 63(24):1193–1203 (1991).

Hillenkamp, et al., Matrix assisted UV–laser desorption/ionization: A new approtach to mass spectrometry of large biomolecules, *In Biological Mass Spectrometry* (Burlingame and McCloskey, eds.), Elseveir, Amsterdam (1989).

Hunter et al., Frozen–solution MALDI mass spectrometry studies of DNA, *Proc. SPIE–Int. Soc. Opt. Eng.* 2680:384–389 (1996).

Huth–Fehre et al., Matrix–assisted laser desorption mass spectrometry of oligodeoxythymidylic acids, *Rapid Comm in Mass Spect* 6:209–213 (1992).

Jespersen et al., *Mass Spectrom. in Biol Sci*, Burlingame, ed. p. 217 (1996).

Juhasz et al., Applications of delayed extraction matrix–assisted laser desorption ionization time–of–flight mass spectrometry to oligonucleotide analysis, *Analy Chem* 68:941–946 (1996).

Jurinke et al., Analysis of ligase chain reaction products via matrix–assisted laser desorption/ionization time–of–flight –mass spectrometry, *Analy Biochem* 237:174–181 (1996).

Jurinke et al., Recovery of nucleic acids from immobilized biotin–streptavidin complexes using ammonium hydroxide and applications in MALDI–TOF mass spectrometry, *Anal. Chem.* 69:904–910 (1997).

Jurinke et al., Detection of hepatitis B virus DNA in serum samples via nested PCR and MALDI–TOF mass spectrometry, *Genetic Analysis* 13:67–71 (1996).

Kim et al., Investigation of porphyrins and metalloporphyrins by liquid matrix–assisted laser desorption mass spectrometry, *Mikrochim. Acta* 113:101–111 (1994).

Kirkepar et al., Matrix Assisted Laser Desorption/Ionization Mass Spectrometry of Enzymatically Synthesized RNA up to 150 kDa, Nucl. Acids Res. 22:3866–3870 (1994).

Kirpekar et al., "7–deaza purine bases offer a higher ion stability in the analysis of DNA by matrix–assisted laser desorption/ionization mass spectrometry" *Rapid Commun. Mass Spectrom.* 9:525–531 (1995).

Kirpekar et al., DNA sequence analysis by MALDI mass spectrometry, *Nucleic Acids Res.* 26:2554–9 (1998).

Kussman et al., Matrix–assisted Laser Desorption /Ionization Mass Spectrometry Sample Preparation Techniques Designed for Various Peptide and Protein Analytes, *J. Mass Spectrom.* 32:593–601 (1997).

Li et al., "High–Resolution MALDI Fourier Transform Mass Spectrometry of Oligonucleotides", *Anal Chem.* 68(13):2090–2096 (1996).

Little et al., Direct detection of synthetic and biologically generated double–stranded DNA by MALDI–TOF MS, *J. Mass Spec* 17:1–8 (1997).

Liu et al., Use of a nitrocellulose film substrate in matrix–assisted laser desorption/ionization mass spectrometry for DNA mapping and screening, *Anal. Chem.* 67:3482–3490 (1995).

Nordhoff et al., Direct mass spectrometric sequencing of low–picomole amounts of oligodeoxynucleotides iwth up to 21 bases by matrix–assisted laser desorption/ionization mass spectrometry, *J. Mass Spectrom.* 30:99–112 (1995).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial 181–197* (1992).

Pieles et al., Matrix–assisted laser desorption ionization time–of–flight mass spectrometry: a powerful tool for the mass and sequence analysis of natural and modified oligonucleotides, *Nucleic Acids Res.* 21:3191–3196 (1993).

Ross et al., Analysis of short tandem repeat polymorphisms in human DNA by matrix assisted laser desorption/ionization mass spectrometry, *Anal. Chem.* 69:3966–3972 (1997).

Shaler et al., "Effect of Impurities on the matrix–Assisted Laser Desorption Mass Spectra of Single–Stranded Oligodeoxynucleotides", *Anal. Chem.* 68:576–579 (1996).

Shaler et al., "Analysis of enzymatic DNA sequencing reactions by matrix–assisted laser desorption/ionization time–of–flight mass spectrometry", *Rapid Commun Mass Spectrom* 9(10):942–947 (1995).

Siegert et al., Matrix–assisted laser desorption/ionization time–of–flight mass spectrometry for the detection of polymerase hain reaction products containing 7–deasapurine moieties, *Anal. Biochem.* 243:55–65 (1996).

Tang et al., Detection of 500–nucleotide DNA by laser desorption mass spectrometry, *Rapid Commun. Mass Spectrom.* 8:727–730 (1994).

Tang et al., Matrix–assisted laser desorption/ioniation of restriction enzyme–digested DNA, *Rapid Commun. Mass Spectrom.* 8:183–186 (1994).

Tang et al., "Matrix–assisted laser desorption/ionization mass spectrometry of immobilized duplex DNA proes", *Nucleic Acids Research* 23:3126–3131 (1995).

Tang, et al., Improving mass resolution in MALDI/TOF analysis of DNA.

Tsarbopoulos et al., Comparative mapping of recombinant proteins and glycoproteins by plasma desorption and matrix–assisted laser desorption/ionization mass spectrometry, *Anal. Chem..* 66:2062–2070 (1994).

Vorm et al., Improved resolution and very high sensitivity in MALDI TOF of matrix surfaces made by fast evaportion, *Anal. Chem.* 66:3281–3287 (1994).

Williams et al., p–Nitroaniline/glycerol: a binary liquid matrix for matrix–assisted laser desorption/ionization analysis, *Eur. Mass. Spectrom.* 4:379–383.

Wu et al., Matrix–assisted Laser Desorption Time–of–flight Mass Spectrometry of Oligonucleotides Using 3–Hydroxypicolinic Acid as an Ultraviolet–sensitive Matrix, *Rapid Comm Mass Spec* 7:142–146 (1993).

Wu et al., Time–of–Flight Mass Spectrometry of Underivatized Single–Stranded DNA Oligomers by Matrix–Assisted Laser Desorption, *Anal. Chem.* 66:1637–1645 (1994).

Yau et al., Threshold fluences for productin of positive and negative ions in matirx–assisted laser desorption/ionisation using liquid and solid matrices, *Chem. Phys. Lett.* 202:93–100 (1993).

IR MALDI of Biomolecules.

Berkenkamp et al., *Proc. Natl. Acad. Sci. USA* 93:7003 (1996).

Berkenkamp et al., *Rapid Comm. Mass Spectrom.* 11:1399–1406 (1997).

Gruic–Sovolj et al., Detection of noncovalent tRNA–aminoacyl–tRNA synthetase complexes by matrix–assisted laser desorption/ionization mass spectrometry, *J. of Biol. Chem.* 1997, 272, 32084–91.

Hillenkamp et al., MALDI–MS in the infrared: a critical evaluation, Proceedings of the 43rd ASMS Conference on Mass Spectrometry and Allied Topics, p. 357, Atlanta, Georgia, May 1995.

Jespersen et al. (1996) p. 217 in *Mass Spectrom. in Biol. Sci*, Burlingame, Ed.).

Kirpekar et al., Double stranded DNA analysed by UV–and IR–MALDI–MS, Proceedings of the 46th ASMS Conference on Mass Spectrometry and Allied Topics, p. 1004, Orlando, Florida, May 31–Jun. 4, 1998.

Lecchi et al. *J. Am. Soc. Mass Spectrom.* 1995, 6, 972–75.

Menzel et al., New developments in IR–MALDE–MS with a TEA–$CO_2$–Laser, Proceedings of the 46th ASMS Conference on Mass Spectrometry and Allied Topics, p. 797, Orlando, Florida, May 31–Jun. 4, 1998.

Menzel et al., IR–MALDI–MS in the 3$\mu$m wavelength region with lasers of different pulse width, Proceeding of the 46th ASMS Conference on Mass Spectrometry and Allied Topics, Orlando, Florida, p. 922, May 31–Jun. 4, 1998.

Niu, et al., Direct comparison of infrared and ultraviolet wavelength matrix–assisted laser desorption/ionization mass spectrometry of proteins, *J Am Soc Mass Spectrom* 9:1–7 (1998).

Nordhoff et al., Ion stability of nucleic acids in infrared matrix–assisted laser desorption/ionization mass spectrometry, *Nuc Acids Res. 21*:3347–3357 (1993).

Nordhoff et al., Comparison of IR– and UV–matrix–assisted laser desorption/ionization mass spectrometry of oligodeoxynucleotides, *Nuc Acids Res* 22(13):2460–2465 (1994).

Nordhoff et al., Matrix–assisted laser desorption/ionization mass spectrometry of nucleic acids with wavelength in the ultraviolet and infrared, *Rapid Comm in Mass Spectorm.* 6:771–776 (1992).

Overberg et al, *Rapid Commun. Mass Spectrom.*, 1990, 4, 293–296.

Overberg et al., Matrix–assisted laser desorption of large biomolecules with a TEA–$CO_2$–laser, *Rapid Comm in Mass Spectro* 5(3):128–131 (1991).

Overberg et al., Matrix–assisted infrared–laser (2.94 um) desorption/ionization mass spectrometry of large biomolecules, *Rapid Comm in Mass Spectrom.* 4:293 (1990).

*Protein LabFax*, ed., N.C. Price; Bios Scientific Publ. pp. 273–276 (1996).

Sadeghi, et al., Compact tunable Cr:LiSAF laser for infrared matrix–assisted laser desorption/ionization, *Rapid Comm. Mass Spectrom.* 11:393–397 (1997).

Siegel et al., Determination of distribution and loading values for calicheamicin derivatives conjugated to antibodies by matrix–assisted infrared–laser desorption/ionization mass spectrometry, Proceedings of the 42nd ASMS Conference on Mass Spectrometry, p. 967, May 29–Jun. 3, 1994.

Siegel et al., Calicheamicin derivatives conjugated to monoclonal antibodies: determination of loading values and distributions by infrared and UV matrix–assisted laser desorptioin/ionization mass spectrometry and electrospray ionization mass spectrometry, *Anal. Chem.* 69:2716–2726 (1997).

Strupat et al., Infrared–matrix–assisted laser desorption/ionization mass spectrometry (IR–MALDI–MS) of proteins electroblotted onto polymer membranes after SDS–PAGE separtion, *Mass Spectrometry in the Biological Sciences* Burlingame and Carr, eds. Humana Press, pp. 203–216 (1995).

Strupat et al., Matrix–assisted laser desorption ionization mass spectrometry of proteins electroblotted after polyacrylamide gel electrophoresis, *Anal. Chem.* 66:464–470 (1994).

Sutton et al., The analysis of myocardial proteins by infrared and ultravilet laser desorption mass spectrometry, *Electrophoresis* 18:424–431 (1997).

Vestal et al., Delayed extraction matrix–assisted laser desorption time–of–flight mass spectrometry, *Rapid Commun. Mass Spectrom.* 9:1044–1050 (1995).

Mass Spectroscopy of Biomolecules.

Aberth et al., Secondary ion mass spectrometry with cesium ion primary beam and liquid target matrix for analysis of bioorganic compounds, *Anal. Chem.* 54:2029–2034 (1982).

Andersen, et al., Electrospray ionization and matrix assisted laser desorption/ionization mass spectrometry: Powerful analytical tools in recombinant protein chemistry, *Nature Biotech.* 14:449–457 (1996).

Ardey, Electrospray mass spectrometry, *Spectroscopy Europe, 4*:10–20 (1992).

Bai et al., Procedures for detection of DNA by matrix–assisted laser desorptioin/ionization mass spectrometry using a modified nation film substrate, *Rapid Comm. Mass Spectrom* 9:1172–1176 (1995).

Bains, DNA sequencing by mass spectrometry: Outline of a potential future application, *Chimicaoggi* 9:13–16 (1991).

Barrell B., "DNA sequencing: present limitations and prospects for the future", *FASEB Journal* 5:40–45 (1991).

Braun et al., Detecting CFTR gene mutations by using primer oligo base extension and mass spectrometry, *Clinical Chemistry* 43:1151–1158 (1997).

Braun et al., "Improved Analysis of Microsatellites Using Mass Spectrometry", *Genomics* 46:18–23 (1997).

Brennan et al., New methods to sequence DNA by mass spectrometry, *SPIE*, vol. 1206, *New Technol. Cytom. Mol. Biol.* pp. 60–77 (1990).

Chen et al., Trapping, detection, and mass determination of coliphage T4 DNA ions of $10^8$ Da by electrospray ionization fourier transorm ion cyclotron resonance mass spectrometry, *Anal. Chem..* 67:1159–1163 (1995).

Covey, et al., The determination of protein, oligonucleotide and peptide molecular weights by ion–spray mass spectrometry, *Rapid Comm. Mass Spectrom.* 2:249–256 (1988).

Crain, Mass spectrometric techniques in nucleic acid research, *Mass Spectrom. Rev.* 9:505–554 (1990).

Dass et al., Particle beam induced reactions between peptides and liquid matrices, *Anal. Chem.* 60:2723–2729 (1988).

Edmonds et al., Thermospray liquid chromatography–mass spectrometry of nucleosides and of enzymatic hydrolysates of nucleic acids, *Nucleic Acids Research 13*:8197–8206 (1985).

Fenn, et al., Electrospray ionization for mass spectrometry of large biomolecules, *Science* 246:64–71 (1989).

Ferstenau and Benner, Molecular weight determination of megadalton DNA electrospray ions using charge detection time–of–flight mass spectrometry, *Rapid Commun. Mass Spectrom.* 9:1528–1538 (1995).

Fuerstenau & Brenner, Molecular weight determination of megadalton DNA electrospray ions using charge detection time–of–flight mass spectrometry, *Rapid Comm. Mass Spectrom.* 9:1159–1163 (1995).

Ganem et al., Detection of oligonucleotide duplex forms by ion–spray mass spectrometry, *Tetrahedron Letters* 34:1445–1448, (1993).

Gross et al., Investigations of the mestable decay of DNA under ultraviolet matrix–assisted laser desorption/ionization conditions with post–source–decay analysis and hydrogen/deuterium exchange, *J Amer Soc for Mass Spect* 9:866–878 (1998).

Grotjahn et al., Sequencing of oligodeoxyribonucleotides by negative FAB–MS, *Int. J. Mass. Spectrom. Ion Phys.* 46:439–442 (1983).

Grotjahn, Oligonucleotide sputtering from liquid matrices, Springer Proc. Phys. 9:118–125 (1986).

Harada et al., Diethanolamine assisted secondary ion mass spectrometry of naturally occurring complex oligosaccharides, *Org. Mass Spectrom.* 17:386–391 (1982).

Hillenkamp and Ehring, Laser desorption mass specrometry Part 1: Basic mechanisms and techniques, *Mass Spectrometry in the Biological Sciences: A tutorial*, pp. 165–179 (1992).

Jacobson, et al. Applications of mass spectrometry to DNA sequencing, *GATA* 8:223–229 (1991).

Karas & Hillenkamp, Laser desorption ionization of proteins with molecular masses exceeding 10 000 daltons, *Anal. Chem.* 60:2299–3001 (1988).

Köster et al., "A strategy for rapid and efficient DNA sequencing by mass spectrometry", *Nature Bio* 14:1123–1128 (1996).

Kovacik et al., Liquid secondary ion mass spectrometry of methyl glycosides of oligosaccharides using matrices containing carboxamides, *Rapid Comm. Mass. Spectrom.* 10:1661–1667 (1996).

Laramee et al., Evidence for radical anion formation during liquid secondary ion mass spectrometry analysis of oligonucleotides and synthetic oligomeric analogues: a deconvolution algorithm for molecular ion region clusters, *Anal. Chem.* 61:2154–2160 (1989).

Limbach et al., Molecular mass measurement of intact ribonucleic acids via electrospray ionization quadrupole mass spectrometry, *J. Am. Soc. Mass Spectrom* 6:27–39 (1995).

Little et al., Verification of 50– to 100–mer DNA and RNA sequences with high–resolution mass spectrometry, *Proc. Natl. Acad. Sci. USA* 92:2318–2322 (1995).

McLaffery et al., High–resolution tandem FT mass spectrometry above 10 kDa, *Acc. Chem. Res.* 27:297–386 (1994).

Monforte and Becker, High–throughput DNA analysis by time–of–flight mass spectrometry, *Nature Medicine* 3:360–362 (1997).

Mosca et al., Mass spectrometry and DNA analysis, *Hemoglobin* 17(3):261–268 (1993).

Muddiman et al., Characterization of PCR products from Bacilli using electrospray ionization FTICR mass spectrometry, *Anal. Chem.* 68:3705–3715 (1996).

Murray, "DNA sequencing by mass spectrometry", *J. Mass. Spect.* 31:1203–1215 (1996).

Nelson et al., Time–of–flight mass spectrometry of nucleic acids by laser ablation and ionization from a frozen aqueous matrix, *Rapid Communications in Mass Spectrometry* 4:348–351 (1990).

Nordhoff, et al., Mass spectrometry of nucleic acids, *Mass Spectrom. Rev.* 15:67–138 (1977).

Pomerantz et al., Determination of oligonucleotide composition from mass spectrometrically measured molecular weight, *Am. Soc. Mass Spectrom.* 4:204–09 (1993).

Ross and Belgrader, Analysis of short tandem repeat polymorphisms in human DNA by matrix–assisted laser desorption/ionization mass spectrometry, *Anal. Chem.* 69:3966–3972 (1997).

Schram, Karl H., "Mass Spectrometry of Nucleic Acid Components", *Bio Appl of Mass Spect.* 34:203–287 (1990).

Siuzdak, The emergence of mass spectrometry in biochemical research, *Proc. Natl. Acad. Sci. USA* 91:11290–11297 (1994).

Smith R. D., New Developments in Biochemical Mass Spectrometry: Elecrospray Ionization, *Anal. Chem.* 62:882–899 (1990).

Spengler et al., *J. Phys. Chem.* 96:9678 (1992).

Stults and Marsters, *Rapid Comm. Mass Spectrom.* 5:359–363 (1991).

Sunner et al., Graphite surface–assisted laser desorption/ionization time–of–flight mass spectrometry of peptides and proteins from liquid solutions, *Anal. Chem.* 67:4335–4342 (1995).

Tomer et al., "Coaxial Continuous Flow Fast Atom Bombardment for Higher–Molecular–Weight Peptides: Comparison with Static Fast Atom Bombardment and electrospray Ionization", *Bio Mass Spect* 20:783–788 (1991).

Valaskovic et al., Attomole–sensitivity electrospray source for large–molecule mass spectrometry, *Anal. Chem.* 67:3802–3805 (1995).

Valaskovic et al., "Attomole protein characterization by capillary electrophoresis–mass spectrometry", *Science* 273:1199–1202 (1996).

Williams, Time of flight mass spectrometry of DNA laser–ablated from frozen aqueous solutions: applications to the Human Genome Project, *Intl. J. Mass Spectrom. and Ion Processes* 131:335–344 (1994).

Wolter et al., Negative ion FAB mass spectrometric analysis of non–charged key intermediated in oligonucleotide synthesis: rapid identification of partially protected dinucleoside monophosphates, *Biomedical Environmental Mass Spectrometry* 14:111–116 (1987).

Yates, III, Mass spectrometry and the age of the proteome, *J. Mass Spec.* 33:1–19 (1998).

Liquid Matrix & Mass Spectroscopy.

Dale et al., Graphite/liquid matrices for laser desorption/ioniation mass spectrometry, *Anal. Chem.* 68:3321–3329 (1996).

Fabris et al., Massive cluster impact ionization on a four sector tandem mass spectrometer, *J. Mass Spect.* 30:140–143 (1995).

Jiang et al., The liquid matrix effects for determination of oligosaccharides by LSIMS, *Chin. Sci. Bull.* 37:1431–1435.

Kolli et al., A new matrix for matrix–assisted laser desorption/ionization of magnetic sector instruments with point detectors, *Rapid Commun. Mass Spectrom* 10:923–926 (1996).

Other.

Certified English translation of European patent 0412883A1, Fast screening and/or identification of a single base on a nucleic acid sequence, including applications.

Certified English translation of Japanese patent 6–294796, Nucleic acid analysis method.

Database WPI, Derwent Publication #199018, citing German Patent No. 3930312, Nucleic acid sequencing—involving amplification–denaturation cycles in presence of deoxy –nucleoside alpha–thio–triphosphate.

Database WPI, Derwent Publications #198942, citing International PCT Application No. WO 89/09406 published Oct. 05, 1989, Immobilisation of sustances—on crystalline protein membrane having layer of identical protein mols.

Database WPI, Derwent Publications #199703, citing Japanese Patent No. 8290377 published Nov. 05, 1996, Micro –manipulation appts. —comprises fluid–filled micro–pipette, piezoelectric element contacted with fluid via diaphragm, and power source for piezoelectric element.

Databse WPI, Derwent Publication, AN88–311964, JP63230086 A 880926 DW8844, Carry immobilise physiological active substance comprise bind chain form di sulphide compound epoxy group latex contain polymer particle.

Database WPI, Derwent Publication #003843590, citing German Patent No. 3221681, Mass spectrometer with external specimen holder—is exp. for vaporising and ionising sample and has thin polymer foil providing vacuum at entry window.

Database WPI, Derwent Publication #198749, citing French Patent No. 2597260, Sample inroduction system for mass spectrometry—has table carrying sample series inserted in spectrometer chamber and rotated to present each to source inturn.

Database WPI, Derwent Publication #198822, citing European Patent No. 269520 A, New HIV–2 retrovirus causing AIDS—and new antigenic proteins, antibodies and complementary nucleic acid sequences.

Database WPI, Derwent Publication #199043, citing German Patent No. 4011991, Simultaneous sequencing of several DNA samples—by cloning into separate vectors, electrophoretic sepn. etc.

Database WPI, Derwent Publication #199015, citing European Patent No. 0360677, Identification of sub–units incomplex moles.—by mass spectrometry, especially in nucleic acid sequencing.

Database WPI, Derwent Publication AN90–302767, Japanese Patent, JP2215399 A, Method detect DNA single strand combination DNA prime correspond base sequence forming replica.

Sequenom Reports On Use of Its DNA MassArray™Technology to Analyze Genes Associated with Alzheimer's Disease and Arteriosclerosis, Press Release: Sep. 22, 1997, http://www.sequenom.com/pressrelease.htm.

Sequenom Signs Agreement With Bruker–Franzed Analytik to Develop Mass Spectrometer for DNA Massarray Analysis, Press Release: Jan. 12, 1998, http://www.sequenom.com/pressrelease.htm.

Sequenom Advances the Industrial Genomics Revolution with the Launch of Its DNA MassArray™Automated Process Line, Press Release: Sep. 28, 1998, http://www.sequenom.com/pressrelease/92898.html.

Sequenom Uses DNA MassArray™to Sequence Section of Human Cancer–Related p53 Gene, Press Release: Mar. 27, 1998, http://www.sequenom.com/pressreleases/32798.html.

Sequenom Reports DNA MassArray™Technology More Sensitive Than Electrophoretic Methods in Detecting Gene Mutations, Press Release: Dec. 15, 1997, http://www.sequenom.com/pressrelease.htm.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:1:

CGCCTGAGTA GTACGTTCGC                                     20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:2:

GCGGTGTGTA CAAGACCCGA                                     20

INFRARED MATRIX-ASSISTED LASER DESORPTION/IONIZATION MASS SPECTROMETRIC ANALYSIS OF MACROMOLECULES

RELATED APPLICATIONS

For U.S. purposes, this application is a continuation-in-part of U.S. application Ser. No. 09/074,936, filed May 7, 1998, to Franz Hillenkamp, entitled "IR-MALDI Mass Spectrometry of Nucleic Acids Using Liquid Matrices." Where permitted the subject matter this application is herein incorporated by reference in its entirety.

FIELD OF THE INVENTION

The disclosed processes relate generally to the field of genomics, proteomics and molecular medicine, and more specifically to processes of using infrared matrix assisted laser desorption-ionization mass spectrometry to analyze, or otherwise detect the presence of or determine the identity of a biological macromolecule.

BACKGROUND OF THE INVENTION

In recent years, the molecular biology of a number of human genetic diseases has been elucidated by the application of recombinant DNA technology. More than 3000 diseases are known to be of genetic origin (Cooper and Krawczak, "Human Genome Mutations" (BIOS Publ. 1993)), including, for example, hemophilias, thalassemias, Duchenne muscular dystrophy, Huntington's disease, Alzheimer's disease and cystic fibrosis, as well as various cancers such as breast cancer. In addition to mutated genes that result in genetic disease, certain birth defects are the result of chromosomal abnormalities, including, for example, trisomy 21 (Down's syndrome), trisomy 13 (Patau syndrome), trisomy 18 (Edward's syndrome), monosomy X (Turner's syndrome) and other sex chromosome aneuploidies such as Klinefelter's syndrome (XXY).

Other genetic diseases are caused by an abnormal number of trinucleotide repeats in a gene. These diseases include Huntington's disease, prostate cancer, spinal cerebellar ataxia 1 (SCA-1), Fragile X syndrome (Kremer et al., *Science* 252:1711–14 (1991); Fu et al., *Cell* 67:1047–58 (1991); Hirst et al., *J. Med. Genet.* 28:824–29 (1991)); myotonic dystrophy type I (Mahadevan et al., *Science* 255:1253–55 (1992); Brook et al., *Cell* 68:799–808 (1992)), Kennedy's disease (also termed spinal and bulbar muscular atrophy (La Spada et al., *Nature* 352:77–79 (1991)), Machado-Joseph disease, and dentatorubral and pallidoly-usian atrophy. The aberrant number of triplet repeats can be located in any region of a gene, including a coding region, a non-coding region of an exon, an intron, or a regulatory element such as a promoter. In certain of these diseases, for example, prostate cancer, the number of triplet repeats is positively correlated with prognosis of the disease.

Evidence indicates that amplification of a trinucleotide repeat is involved in the molecular pathology in each of the disorders listed above. Although some of these trinucleotide repeats appear to be in non-coding DNA, they clearly are involved with perturbations of genomic regions that ultimately affect gene expression. Perturbations of various dinucleotide and trinucleotide repeats resulting from somatic mutation in tumor cells also can affect gene expression or gene regulation.

Additional evidence indicates that certain DNA sequences predispose an individual to a number of other diseases, including diabetes, arteriosclerosis, obesity, various autoimmune diseases and cancers such as colorectal, breast, ovarian and lung cancer. Knowledge of the genetic lesion causing or contributing to a genetic disease allows one to predict whether a person has or is at risk of developing the disease or condition and also, at least in some cases, to determine the prognosis of the disease.

Numerous genes have polymorphic regions. Since individuals have any one of several allelic variants of a polymorphic region, each can be identified based on the type of allelic variants of polymorphic regions of genes. Such identification can be used, for example, for forensic purposes. In other situations, it is crucial to know the identity of allelic variants in an individual. For example, allelic differences in certain genes such as the major histocompatibility complex (MHC) genes are involved in graft rejection or graft versus host disease in bone marrow transplantation. Accordingly, it is highly desirable to develop rapid, sensitive, and accurate methods for determining the identity of allelic variants of polymorphic regions of genes or genetic lesions.

Several methods are used for identifying allelic variants or genetic lesions. For example, the identity of an allelic variant or the presence of a genetic lesion can be determined by comparing the mobility of an amplified nucleic acid fragment with a known standard by gel electrophoresis, or by hybridization with a probe that is complementary to the sequence to be identified. Identification only can be accomplished, however, if the nucleic acid fragment is labeled with a sensitive reporter function, for example, a radioactive ($^{32}$P, $^{35}$S), fluorescent or chemiluminescent reporter. Radioactive labels can be hazardous and the signals they produce can decay substantially over time. Non-radioactive labels such as fluorescent labels can suffer from a lack of sensitivity and fading of the signal when high intensity lasers are used. Additionally, labeling, electrophoresis and subsequent detection are laborious, time-consuming and error-prone procedures. Electrophoresis is particularly error-prone, since the size or the molecular weight of the nucleic acid cannot be correlated directly to its mobility in the gel matrix because sequence specific effects, secondary structures and interactions with the gel matrix cause artifacts in its migration through the gel.

Applications of mass spectrometry in the biosciences have been reported (see *Meth. Enzymol.*, Vol. 193, *Mass Spectrometry* (McCloskey, ed.; Academic Press, NY 1990); McLaffery et al., *Acc. Chem. Res.* 27:297–386 (1994); Chait and Kent, *Science* 257:1885–1894 (1992); Siuzdak, *Proc. Natl. Acad. Sci., USA* 91:11290–11297 (1994)), including methods for mass spectrometric analysis of biopolymers (see Hillenkamp et al. (1991) *Anal. Chem.* 63:1193A–1202A) and for producing and analyzing biopolymer ladders (see, International Publ. WO 96/36732; U.S. Pat. No. 5,792,664).

Mass spectrometry has been used for the analysis of nucleic acids (see, for example, Schram, *Mass Spectrometry of Nucleic Acid Components, Biomedical Applications of Mass Spectrometry* 34:203–287 (1990); Crain, *Mass Spectrom. Rev.* 9:505–554 (1990); Murray, *J. Mass Spectrom. Rev.* 31:1203 (1996); Nordhoff et al., *Mass Spectrom. Rev.* 15:67–138 (1997); U.S. Pat. No. 5,547,835; U.S. Pat. No. 5,605,798; PCT Application Publication No. WO94/16101; PCT Application Publication No. WO 96/29431).

The so-called "soft ionization" mass spectrometric methods, including Matrix-Assisted Laser Desorption/Ionization (MALDI) and ElectroSpray Ionization (ESI), allow intact ionization, detection and mass determination of large molecules, i.e., well exceeding 300 kDa in mass (Fenn et al., *Science* 246:64–71 (1989); Karas and Hillenkamp, *Anal. Chem.* 60:2299–3001 (1988)). MALDI mass spectrometry (MALDI-MS; reviewed in Nordhoff et al., *Mass Spectrom. Rev.* 15:67–138 (1997)) and ESI-MS have been used to analyze nucleic acids. Nucleic acids are very polar biomolecules that are difficult to volatilize and, therefore, there has been an upper mass limit for clear and accurate resolution.

ESI has been used for the intact desorption of large nucleic acids even in the megaDalton mass range (Ferstenau and Benner, *Rapid Commun. Mass Spectrom.* 9:1528–1538 (1995); Chen et al., *Anal. Chem.* 67:1159–1163 (1995)). Mass assignment using ESI is very poor and only possible with an uncertainty of about 10%. The largest nucleic acids that have been accurately mass determined by ESI-MS are a 114 base pair double stranded PCR product (Muddiman et al., *Anal. Chem.* 68:3705–3712 (1996)) of about 65 kDA in mass and a 120 nucleotide *E.coli* 5S rRNA of about 39 kDa in mass (Limbach et al., *J. Am. Soc. Mass Spectrom.* 6:27–39 (1995)). Furthermore, ESI requires extensive sample purification.

MALDI-MS requires incorporation of the macromolecule to be analyzed in a matrix, and has been performed on polypeptides and on nucleic acids mixed in a solid (i.e., crystalline) matrix. In these methods, a laser is used to strike the biopolymer/matrix mixture, which is crystallized on a probe tip, thereby effecting desorption and ionization of the biopolymer. In addition, MALDI-MS has been performed on polypeptides using the water of hydration (i.e., ice) or glycerol as a matrix. When the water of hydration was used as a matrix, it was necessary to first lyophilize or air dry the protein prior to performing MALDI-MS (Berkenkamp et al. (1996) *Proc. Natl. Acad. Sci. USA* 93:7003–7007). The upper mass limit for this method was reported to be 30 kDa with limited sensitivity (i.e., at least 10 pmol of protein was required). Infrared MALDI-MS of proteins reportedly consumes 100–1000 times more material per spectrum as compared to UV MALDI-MS and, in combination with matrices such as glycerol, can tend to form adducts which broaden the peaks on the high mass side (Hillenkamp et al. (1995) 43rd ASMS Conference on Mass Spectrometry and Allied Topics, p. 357). Furthermore, although IR-MALDI MS appeared to provide increased mass resolution due to less metastable fragmentation as compared to UV-MALDI MS, this decrease in metastable decay has been reported to be accompanied by an increase in fragmentation.

UV-MALDI-MS is limited in the size of biological macromolecules that can be analyzed. For example, it is difficult to analyze nucleic acid molecules much larger than about 100 nucleotides (100-mer) by UV-MALDI-MS.

Accordingly, despite the effort to apply mass spectrometry methods to the analysis of nucleic acid molecules, limitations remain due, in part, to physical and chemical properties of nucleic acids. For example, the polar nature of nucleic acid biopolymers makes them difficult to volatilize.

Analysis of large DNA molecules using UV-MALDI-MS has been reported (Ross and Belgrader, *Anal. Chem.* 69:3966–3972 (1997); Tang et al., *Rapid Commun. Mass Spectrom.* 8:727–730 (1994); Bai et al., *Rapid Commun. Mass Spectrom.* 9:1172–1176 (1995); Liu et al., *Anal. Chem.* 67:3482–3490 (1995); Siegert et al., *Anal. Biochem.* 243:55–65 (1997)). Based on these reports, it is clear that analysis of nucleic acids exceeding 30 kDa in mass (approximately a 100-mer) by UV-MALDI-MS becomes increasingly difficult with a current upper mass limit of about 90 kDa (Ross and Belgrader, *Anal. Chem.* 69:3966–3972 (1997)). The inferior quality of the DNA UV-MALDI spectra has been attributed to a combination of ion fragmentation and multiple salt formation of the phosphate backbone. Since RNA is considerably more stable than DNA under UV-MALDI conditions, the accessible mass range for RNA is up to about 150 kDa (Kirpekar et al., *Nucl. Acids Res.* 22:3866–3870 (1994)).

Nucleic acids in solid matrices (mostly succinic acid and, to a lesser extent, urea and nicotinic acid) have been analyzed by IR-MALDI (Nordhoff et al., *Rapid Commun. Mass Spectrom.* 6:771–776 (1992); Nordhoff et al., *Nucl. Acids Res.* 21: 3347–3357 (1993); Nordhoff et al., *J. Mass Spec.* 30:99–112 (1995)). Nordhoff et al. (1992) initially reported that a 20-mer of DNA and an 80-mer of RNA were about the uppermost limit for resolution. Nordhoff et al. (1993) later provided distinct spectra for a 26-mer of DNA and a 104-mer of tRNA and reported that reproducible signals were obtained for RNA up to 142 nucleotides. Nordhoff et al. (1995) also reported a substantially better spectra for the analysis of a 40-mer by UV-MALDI with the solid matrix, 3-hydroxy picolinic acid, than by IR-MALDI with succinic acid, but that IR-MALDI resulted in a substantial degree of prompt fragmentation.

Analysis of macromolecules in a biological sample, for example, can provide information as to the condition of the individual from which the sample was obtained. For example, nucleic acid analysis of a biological sample obtained from an individual can be useful for diagnosing the existence of a genetic disease or chromosomal abnormality, a predisposition to a disease or condition, or an infection by a pathogenic organism, or can provide information relating to identity, heredity or compatibility. Since mass spectrometry can be performed relatively quickly and is amenable to automation, improved methods for obtaining accurate mass spectra for biological macromolecules, particularly for larger nucleic acid molecules larger than about 90 kDa for DNA and 150 kDA for RNA are needed.

Accordingly, a need exists for methods to detect and characterize biological macromolecules such as nucleic acid molecules, including methods to detect genetic lesions in a nucleic acid molecule. There is a need for accurate, sensitive, precise and reliable methods for detecting and characterizing biological macromolecules, particularly in connection with the diagnosis of conditions, diseases and disorders. Therefore it is an object herein to provide processes that satisfy these needs and provide additional advantages.

SUMMARY OF THE INVENTION

Processes for the determination of the mass or identity of biological macromolecules using infrared matrix assisted laser desorption/ionization (IR-MALDI) mass spectrometry and a liquid matrix are provided. In particular, infrared matrix assisted laser desorption/ionization (IR-MALDI) mass spectrometry of nucleic acids, including DNA and RNA, in a liquid matrix are provided. The liquid matrix (liquid at room temperature, one atmosphere pressure) is an IR-absorbing biocompatible material, such as a polyglycol, particularly glycerol, that can form a glass or vitreous solid. The use of IR-MALDI and this liquid matrix can be employed in any method, particularly diagnostic methods and sequencing methods, heretofore performed with UV-MALDI. Such methods, particularly diagnostic methods for nucleic acids and proteins, include, but are not limited to, those described in U.S. Pat. Nos. 5,547,835, 5,691,141, 5,605,798, 5,622,824, 5,777,324, 5,830,655, 5,700,642, allowed U.S. application Ser. Nos. 08/617,256, 08/746,036, 08/744,481, 08/744,590, 08/647,368, published International PCT application Nos. WO 96/29431, WO 99/12040, WO 98/20019, WO 98/20166, WO 98/20020, WO 97/37041, WO 99/14375, WO 97/42348, WO 98/54751 and WO 98/26095.

In practicing an embodiment of the method for nucleic acid analyses, a composition for IR-MALDI containing the nucleic acid and a liquid matrix is deposited onto a substrate, which, generally, is a solid support, to form a homogeneous, transparent thin layer of nucleic acid mixture. This mixture is illuminated with infrared radiation so that the nucleic acid solution is desorbed and ionized, thereby emitting ion particles, which are analyzed using a mass analyzer to determine the mass of the nucleic acid. Preferably, sample preparation and deposition are performed using an automated device.

Methods for detecting the presence or absence of a biological macromolecule in a sample using IR-MALDI mass spectrometry are also provided herein. In a particular embodiment, a composition for IR-MALDI containing the biological macromolecule and a matrix is illuminated with infrared radiation, desorbed and ionized, thereby emitting ion particles, which are analyzed to determine whether the nucleic acid is present.

Methods for detecting the presence or absence of a nucleic acid in a sample using IR-MALDI mass spectrometry are also provided herein. In a particular embodiment, a composition for IR-MALDI containing the sample and a liquid matrix is illuminated with infrared radiation, desorbed and ionized, thereby emitting ion particles which are analyzed to determine whether the nucleic acid is present.

Liquid matrices for use in the processes disclosed herein have a sufficient absorption at the wavelength of the laser to be used in performing desorption and ionization and are a liquid at room temperature (20° C.) and can form a vitreous or glass solid. The liquid is intended to be used in any IR MALDI format and at any temperature, typically about −200° C. to 80° C., preferably −60° C. to about 40° C., suitable for such formats.

For absorption purposes, the liquid matrix can contain at least one chromophore or functional group that strongly absorbs infrared radiation. Preferred functional groups include nitro, sulfonyl, sulfonic acid, sulfonamide, nitrile or cyanide, carbonyl, aldehyde, carboxylic acid, amide, ester, anhydride, ketone, amine, hydroxyl, aromatic rings, dienes and other conjugated systems.

Among the preferred liquid matrices are substituted or unsubstituted (1) alcohols, including glycerol, sugars, polysaccharides, 1,2-propanediol, 1,3-propanediol, 1,2-butanediol, 1,3-butanediol, 1,4-butanediol and triethanolamine; (2) carboxylic acids, including formic acid, lactic acid, acetic acid, propionic acid, butanoic acid, pentanoic acid and hexanoic acid, or esters thereof; (3) primary or secondary amides, including acetamide, propanamide, butanamide, pentanamide and hexanamide, whether branched or unbranched; (4) primary or secondary amines, including propylamine, butylamine, pentylamine, hexylamine, heptylamine, diethylamine and dipropylamine; and (5) nitriles, hydrazine and hydrazide. The liquids do not crystallize, but rather can form a glass or vitreous phase when subjected to drying, cooling or other conditions leading to a transition from the liquid phase. Materials of relatively low volatility are preferred to avoid rapid evaporation under conditions of vacuum during the IR-MALDI processes.

Preferably, a liquid matrix for use herein is miscible with a nucleic acid compatible solvent. As noted, it is also preferable that the liquid matrix is vacuum stable, i.e., has a low vapor pressure, so that the sample does not evaporate quickly in the mass analyzer. Preferably the liquid has an appropriate viscosity to facilitate dispensing of microliter to nanoliter volumes of matrix, either alone or mixed with a nucleic acid compatible solvent. Mixtures of different liquid matrices and additives to such matrices may be desirable to confer one or more of the properties described above. Such mixtures can contain two liquid matrix materials (i.e.,. binary mixtures), three (tertiary mixtures) or more.

A nucleic acid/matrix composition for IR-MALDI is deposited as a thin layer on a substrate, which preferably is contained with a vacuum chamber. Preferred substrates for holding the nucleic acid/matrix solution can be solid supports, for example, beads, capillaries, flat supports, pins or wafers, with or without filter plates. Preferably the temperature of the substrate can be regulated to cool the nucleic acid/matrix composition to a temperature that is below room temperature.

Preferred infrared radiation is in the mid-IR wavelength region from about 2.5 $\mu$m to about 12 $\mu$m. Particularly preferred sources of radiation include CO, $CO_2$ and Er lasers. In certain embodiments, the laser can be an optic fiber laser, or the laser radiation can be coupled to the mass spectrometer by fiber optics.

In a further preferred embodiment, the ion particles generated by infrared irradiation of the analyte in the liquid matrix are extracted for analysis by the mass analyzer in a delayed fashion prior to separation and detection in a mass analyzer. Preferred separation formats include linear or reflector, with linear and nonlinear fields, for example, curved field reflectron; time-of-flight (TOF); single or multiple quadrupole; single or multiple magnetic sector; Fourier transform ion cyclotron resonance (FTICR); or ion trap mass spectrometers.

Processes of using IR-MALDI mass spectrometry to identify the presence of a target nucleic acid in a biological sample are provided. Such a process can be performed, for example, by amplifying nucleic acid molecules in the biological sample; contacting the amplified nucleic acid molecules with a detector oligonucleotide, which can hybridize to a target nucleic acid sequence present among the amplified nucleic acid molecules; preparing a composition for IR-MALDI, by mixing the product of the reaction with a liquid matrix, which absorbs infrared radiation; and identifying duplex nucleic acid molecules in the composition by IR-MALDI mass spectrometry, wherein the presence of duplex nucleic acid molecules identifies the presence of the target nucleic acid in the biological sample.

A process for identifying the presence of a target nucleic acid sequence in a biological sample also can be performed by amplifying nucleic acid molecules obtained from a biological sample; specifically digesting the amplified nucleic acid molecules using at least one appropriate nuclease, to produce digested fragments; hybridizing the digested fragments with complementary capture nucleic acid sequences, which are immobilized on a solid support and can hybridize to a digested fragment of a target nucleic acid to produce immobilized fragments; preparing a composition for IR-MALDI, containing the immobilized fragments and a liquid matrix, which absorbs infrared radiation; and identifying immobilized fragments by IR-MALDI mass spectrometry, thereby detecting the presence of the target nucleic acid sequence in the biological sample.

The presence of a target nucleic acid in a biological sample also can be identified by performing on nucleic acid molecules obtained from the biological sample, a first polymerase chain reaction using a first set of primers, which are capable of amplifying a portion of the nucleic acid containing the target nucleic acid; preparing a composition containing the first amplification product and a liquid matrix, which absorbs infrared radiation; and detecting the first amplification product in the composition by IR-MALDI mass spectrometry, thereby detecting the presence of the target nucleic acid in the biological sample. If desired, such a process can include, prior to preparing the composition for IR-MALDI, performing a second polymerase chain reaction on the first amplification product using a second set of primers that can amplify at least a portion of the first amplification product containing the target nucleic acid.

Also disclosed herein are compositions, particularly compositions for IR-MALDI, such compositions containing a biological macromolecule, which is suitable for analysis by IR-MALDI, and a liquid matrix, which absorbs infrared radiation. A biological macromolecule suitable for analysis by IR-MALDI can be, for example, a nucleic acid, a polypeptide or a carbohydrate, or can be a macromolecular complex such as a nucleoprotein complex, protein-protein complex, or the like. A composition for IR-MALDI as disclosed herein generally contains the biological macromolecule, for example, a nucleic acid, and the liquid matrix in a ratio of about $10^{-4}$ to $10^{-9}$, and can contain less than about 10 picomoles of biological macromolecule to be analyzed, for example, about 100 attomol to about 1 picomole (pmol) of the biological macromolecule. (For proteins, the analyte to matrix ratio is typically narrower ranging from about $2 \times 10^{-4}$ to $2 \times 10^{-5}$). A composition for IR-MALDI as disclosed herein also can contain an additive, which facilitates detection of the biological macromolecule by IR-MALDI, for example, an additive that improves the miscibility of the biological macromolecule in the liquid matrix. In one embodiment, a composition for IR-MALDI is deposited on a substrate, which can be a solid support such as a silicon wafer or other material providing a surface for deposition of a composition for IR-MALDI, for example, a stainless steel surface.

Processes for characterizing a biological macromolecule by IR-MALDI mass spectrometry are provided. For example, the mass of a biological macromolecule can be determined by preparing a composition for IR-MALDI containing the biological macromolecule to be analyzed and a liquid matrix, which absorbs infrared radiation; then analyzing the biological macromolecule in the composition by IR-MALDI mass spectrometry, thereby allowing a determination of the mass of the biological macromolecule.

A process as disclosed herein also can be used for detecting a target biological macromolecule by preparing a composition for IR-MALDI containing the target biological macromolecule and a liquid matrix, which absorbs infrared radiation, and performing IR-MALDI mass spectrometry on the composition to identify the target biological macromolecule in the composition, thereby detecting the target biological macromolecule. If desired, the target biological macromolecule can be present in or obtained from a biological sample. Accordingly, a process for identifying the presence of a target biological macromolecule in a biological sample, is provided. The presence of a target nucleic acid, for example, can be identified by preparing a composition for IR-MALDI, containing a biological sample containing nucleic acid molecules (or nucleic acid molecules isolated from the biological sample) and a liquid matrix, which absorbs infrared radiation; then analyzing the composition by IR-MALDI mass spectrometry, wherein detection of a nucleic acid molecule having a molecular mass of the target nucleic acid sequence identifies the presence of the target nucleic acid sequence in the biological sample.

Also provided is a process of using IR-MALDI mass spectrometry to identify an individual having a disease or a predisposition to a disease by detecting a characteristic of a biological macromolecule that is obtained from the individual and is associated with the disease or the predisposition. Such a process is particularly useful for identifying a genetic disease, or a disease associated with a bacterial infection, or a predisposition to such a disease, and also is useful for determining identity, heredity or compatibility.

The processes disclosed herein are suitable for analyzing one or more target biological macromolecules, particularly a large number of target biological macromolecules, for example, by depositing a plurality of compositions, each containing one or more target biological macromolecules, on a solid support, for example, a chip, in the form of an array. The disclosed processes are particularly suitable for multiplex analysis of a plurality of biological macromolecules contained in a single composition, including a liquid matrix, in which case each biological macromolecule in the plurality can be differentially mass modified to facilitate multiplex analysis. Accordingly, the processes disclosed herein are readily adaptable to high throughput assay formats.

Processes for obtaining information on a sequence of a nucleic acid molecule by determining the identity of a target polypeptide encoded by the nucleic acid molecule are provided. In practicing these methods, a target polypeptide (or mixture thereof) is prepared from a nucleic acid molecule encoding the target polypeptide; the molecular mass of the target polypeptide is determined by providing a mixture of the polypeptide with a liquid matrix, or in some embodiments, with water or succinic acid, and preforming IR-MALDI. The identity of the target polypeptide is determined by comparing the molecular mass of the target polypeptide with the molecular mass of a reference polypeptide of known identity. Information, such as the presence of a mutation, on a sequence of nucleotides in the nucleic acid molecule encoding the target polypeptide can thereby be obtained.

A biological macromolecule particularly suitable for analysis by a process of IR-MALDI mass spectrometry can be a nucleic acid, a nucleic acid analog or mimic, a triple helix, a polypeptide, a polypeptide analog or mimetic, a carbohydrate, a lipid or a proteoglycan, or can be a macromolecular complex such as a protein-protein complex or a nucleoprotein complex or other complexes. For analysis by a process as disclosed herein, a target biological macromolecule can be immobilized to a substrate, particularly a solid support, which can be, for example, a bead, a flat surface, a chip, a capillary, a pin, a comb, or a wafer, and can be any of various materials, including a metal, a ceramic, a plastic, a resin, a gel, and a membrane. Immobilization can be through a reversible linkage (i.e. an ionic bond, such as biotin/streptavidin), a covalent bond, such as a photocleavable bond or a thiol linkage or a hydrogen bond, and the linkage can be cleaved using, for example, a chemical process, an enzymatic process, or a physical process, including the IR-MALDI mass spectrometric analysis procedure.

A biological macromolecule to be analyzed can be conditioned prior to IR-MALDI mass spectrometric analysis, thereby improving the ability to analyze the particular biological macromolecule by IR-MALDI mass spectrometry, for example, by improving the resolution of the mass spectrum. A target biological macromolecule can be conditioned, for example, by ion exchange, by contact with an alkylating agent or trialkylsilyl chloride, or by incorporation of at least one mass modified subunit of the biological macromolecule. If desired, the biological macromolecule can be isolated prior to conditioning or prior to IR-MALDI mass spectrometric analysis.

A process for determining the identity of each target biological macromolecule in a plurality of target biological macromolecules, which can be fragments of a biological macromolecule, can be performed, for example, by preparing a composition for IR-MALDI containing a plurality of differentially mass modified target biological macromolecules and a liquid matrix, which absorbs infrared radiation; determining the molecular mass of each differentially mass modified target biological macromolecule in the plurality by IR-MALDI mass spectrometry; and comparing the molecular mass of each differentially mass modified target biological macromolecule in the plurality with the molecular mass of a corresponding known biological macromolecule. Where such a process is performed using a plurality of target biological macromolecules, each of which is a fragment of a larger biological macromolecule, the fragments can be prepared by contacting the biological macromolecules with at least one agent that cleaves a bond involved in the formation of the biological macromolecules, particularly a bond between monomer subunits of the biological macromolecule.

Processes for identifying one or more subunits in a biological macromolecule using IR-MALDI mass spectrometry also are provided, for example, processes for detecting a mutation in a nucleotide sequence. The identity of a target nucleotide can be identified, for example, by hybridizing a nucleic acid molecule containing the target nucleotide with a primer oligonucleotide that is complementary to the nucleic acid molecule at a site adjacent to the target nucleotide, to produce a hybridized nucleic acid molecule; contacting the hybridized nucleic acid molecule with a complete set of dideoxynucleosides or 3'-deoxynucleoside triphosphates and a DNA dependent DNA polymerase, so that only the dideoxynucleosides or 3'-deoxynucleoside triphosphate that is complementary to the target nucleotide is extended onto the primer; preparing a composition containing the extended primer and a liquid matrix, which absorbs infrared radiation; and detecting the extended primer in the composition by IR-MALDI mass spectrometry, thereby determining the identity of the target nucleotide.

A process for detecting the absence or presence of a mutation in a target nucleic acid sequence can be performed by hybridizing a nucleic acid molecule containing the target nucleic acid sequence with at least one primer, which has 3' terminal base complementarity to the target nucleic acid sequence, to produce a hybridized product; contacting the hybridized product with an appropriate polymerase enzyme and sequentially with one of the four nucleoside triphosphates, then preparing a composition containing the reaction product and a liquid matrix, which absorbs infrared radiation; and detecting the product in the composition by IR-MALDI mass spectrometry, wherein the molecular weight of the product indicates the presence or absence of a mutation next to the 3' end of the primer in the target nucleic acid molecule. A mutation in a nucleic acid molecule also can be detected, for example, by hybridizing the nucleic acid molecule with an oligonucleotide probe, to produce a hybridized nucleic acid, wherein a mismatch is formed at the site of a mutation; contacting the hybridized nucleic acid with a single strand specific endonuclease, then preparing a composition containing the reaction product and a liquid matrix, which absorbs infrared radiation; and analyzing the composition by IR-MALDI mass spectrometry, wherein the presence of more than one nucleic acid fragment in the composition indicates that the nucleic acid molecule contains a mutation.

A process for identifying the absence or presence of a mutation in a target nucleic acid sequence also can be performed, for example, by performing at least one hybridization on a nucleic acid molecule containing the target nucleic acid sequence with a set of ligation educts and a DNA ligase; preparing a composition containing the reaction product and a liquid matrix, which absorbs infrared radiation; and analyzing the composition by IR-MALDI mass spectrometry. Using such a process, the detection of a ligation product in the composition identifies the absence of a mutation in the target nucleic acid sequence, whereas the detection only of the set of ligation educts in the composition identifies the presence of a mutation in the target nucleic sequence. A process of detecting the presence of a ligation product, as disclosed above, also can be useful for detecting a target nucleotide or a target nucleic acid by performing at least one hybridization on a nucleic acid molecule containing the target nucleotide with a set of ligation educts and a thermostable DNA ligase; preparing a composition containing the reaction product and a liquid matrix, which absorbs infrared radiation; and identifying a ligation product in the composition by IR-MALDI mass spectrometry, thereby detecting the presence of a target nucleotide in the nucleic acid sequence.

Processes for determining a subunit sequence of a biological macromolecule also are provided. A subunit sequence of at least one species of target biological macromolecule, i, can be determined, for example, by contacting the species of target biological macromolecule with one or more agents sufficient to cleave each bond involved in the formation of the target biological macromolecule, to produce a set of nested biological macromolecule fragments, then preparing a composition containing at least one biological macromolecule fragment of the set and a liquid matrix, which absorbs infrared radiation; and determining the molecular mass of the at least one biological macromolecule fragment by IR-MALDI mass spectrometry; and repeating these steps until the molecular mass of each biological macromolecule fragment in the set has been determined, thereby determining the subunit sequence of the species of target biological macromolecule. Such a process is particularly suitable for multiplex analysis of a plurality of i+1 species of target biological macromolecules, wherein each species of target biological macromolecule is differentially mass modified such that a biological macromolecule fragment of each species of target biological macromolecule can be distinguished from a biological macromolecule of each different species by IR-MALDI mass spectrometry.

Processes for determining the nucleotide sequence of at least one species of nucleic acid are provided. Such a process can be performed by synthesizing complementary nucleic acids, which are complementary to the species of nucleic acid to be sequenced, starting from an oligonucleotide primer and in the presence of chain terminating nucleoside triphosphates, to produce four sets of base-specifically terminated complementary polynucleotide fragments; preparing a composition for IR-MALDI, containing the four sets of polynucleotide fragments and a liquid matrix, which absorbs infrared radiation; determining the molecular weight value of each polynucleotide fragment by IR-MALDI mass spectrometry; and determining the nucleotide sequence of the species of nucleic acid by aligning the molecular weight values according to molecular weight. Such a process is particularly suitable to multiplex analysis of a plurality of i+1 species of nucleic acids, which can be sequenced concurrently using i+1 primers, wherein one of the i+1 primers is an unmodified primer or a mass modified primer and the other i primers are mass modified primers, and wherein each of the i+1 primers can be distinguished from the other by IR-MALDI mass spectrometry.

A sequence of a target nucleic acid also can be determined by hybridizing at least one partially single stranded target nucleic acid to one or more nucleic acid probes, each probe containing a double stranded portion, a single stranded portion, and a determinable variable sequence within the single stranded portion, to produce at least one hybridized target nucleic acid, then preparing a composition containing the hybridized target nucleic acid and a liquid matrix, which absorbs infrared radiation; and determining a sequence of the hybridized target nucleic acid by IR-MALDI mass spectrometry based on the determinable variable sequence of the probe to which the target nucleic acid hybridized. If desired, the steps of the process can be repeated a sufficient number of times to determine an entire sequence of a target nucleic acid and, where a plurality of target nucleic acids are to be sequenced, the one or more nucleic acid probes can be immobilized in an array. If desired, the hybridized target nucleic acid can be ligated to the determinable variable sequence prior to preparing the composition for IR-MALDI.

A process for determining the sequence of a target biological macromolecule also can be performed by generating at least two biological macromolecule fragments from the target biological macromolecule, then preparing a composition containing the biological macromolecule fragments and a liquid matrix, which absorbs infrared radiation; and analyzing the biological macromolecule fragments in the composition by IR-MALDI mass spectrometry, thereby determining the sequence of the target nucleic acid molecule. Such a process is particularly useful for ordering two or more portions of a biological macromolecule sequence within a larger sequence.

Also, provided are compositions for IR-MALDI that contain a liquid matrix, which absorbs infrared radiation, and a biological macromolecule. In particular, the biological macromolecule and the liquid matrix are present in a ratio of about $10^{-4}$ to $10^{-9}$ biological macromolecule to liquid matrix in the composition. Also provided are these compositions in which the biological macromolecule is present in an amount less than about picomoles of biological macromolecule, preferably about 100 attomoles to about 1 picomole of biological macromolecule. The compositions can further include an additive that facilitates detection of the nucleic acid by IR-MALDI. Supports (or substrates) on which the compositions are deposited are provided.

BRIEF DESCRIPTION OF THE DRAWINGS

FIG. 1A shows ultraviolet matrix assisted laser desorption ionization (UV-MALDI) and detection by a linear time-of-flight (TOF) instrument using delayed extraction and a 3 hydroxypicolinic acid (3HPA) matrix (sum of 20 single shot mass spectra); FIG. 1B shows UV-MALDI reflectron (ref) TOF spectrum, using delayed extraction and a 3HPA matrix (sum of 25 single shot mass spectra); FIG. 1C shows IR-MALDI-refTOF spectrum, using delayed extraction and a glycerol matrix, (sum of single shot mass spectra).

FIG. 2A—a synthetic DNA 21-mer (sum of 10 single shot spectra); FIG. 2B—a DNA mixture containing a restriction enzyme products of a 280-mer (87 kDA), a 360-mer (112 kDa), a 920-mer (285 kDa) and a 1400-mer (433 kDa) (sum of 10 single shot spectra); FIG. 2C—DNA mixture; restriction enzyme products of a 130-mer (approximately 40 kDa), a 640-mer (198 kDa) and a 2180-mer (674 kDa) (sum of 20 single shot spectra); FIG. 2D—an RNA 1206-mer (approximately 387 kDa) (sum of 15 single shot spectra). Ordinate scalings are intercomparable.

FIGS. 3A to 3C show the spectra of a 515-mer double stranded PCR DNA product. Total amounts of sample were loaded, as follows: FIG. 3A—300 fmol (single shot spectrum); FIG. 3B—3 fmol (single shot spectrum; FIG. 3C—300 attomol (sum of 25 single shot spectra). Obtained using an IR-MALDI refTOF, wherein the laser emitted at a wavelength of 2.94 $\mu$m using a glycerol matrix.

DETAILED DESCRIPTION OF THE INVENTION

Definitions

Figure 1:
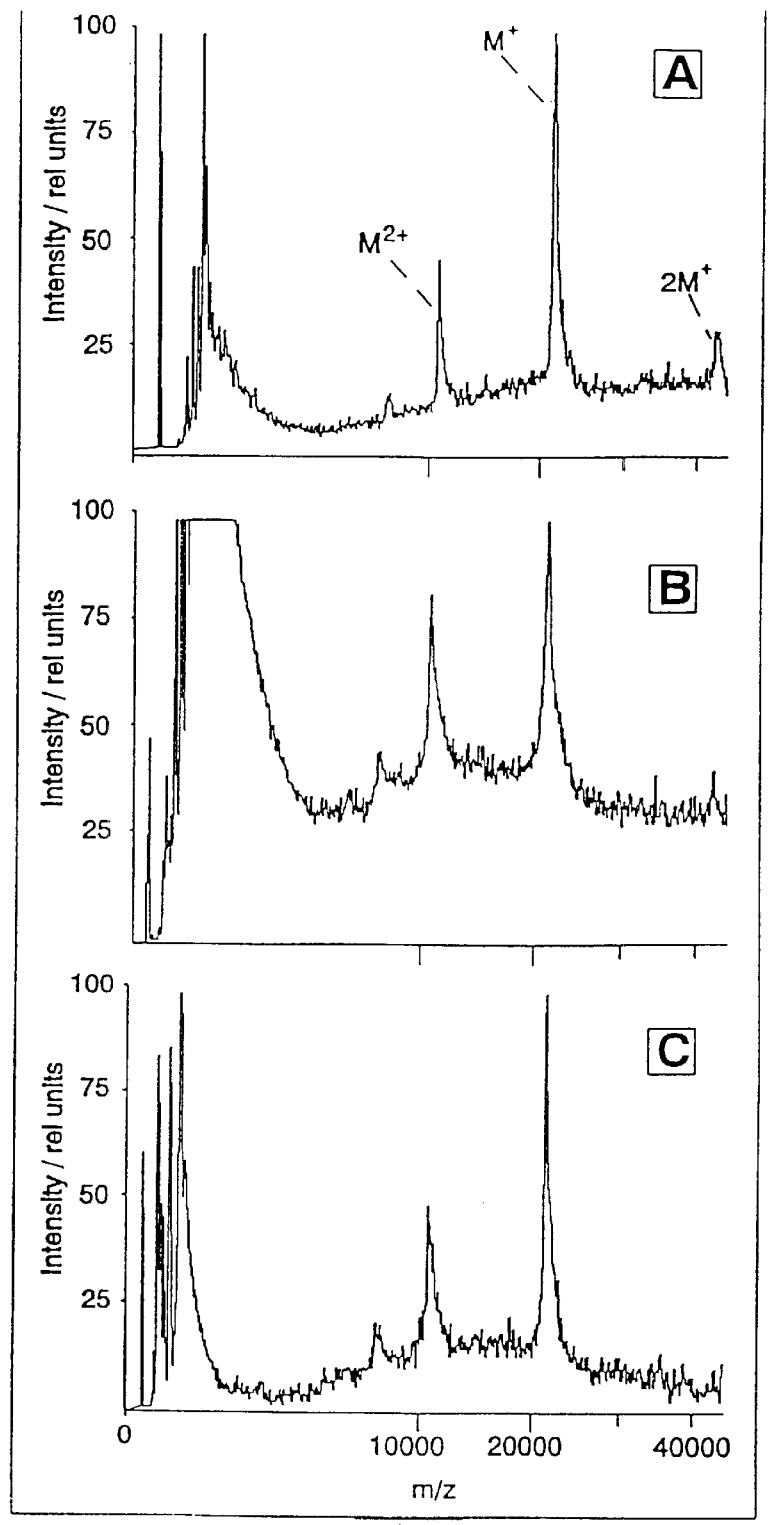
FIGS. 1A to 1C show mass spectra of a synthetic DNA 70-mer.

All patents, patent applications and publications cited herein are incorporated herein by reference. The meaning of certain terms and phrases used in the specification and claims are provided below. Unless defined otherwise, all technical and scientific terms used herein have the same meaning as is commonly understood by one of skill in the art to which the subject matter belongs.

As used herein, a biological macromolecule refers to a molecule, which typically may be found in a biological source. Biological macromolecules include biopolymers, which are molecules containing monomeric subunits, which subunits can be the same or different. Macromolecules thus include molecules, such as peptides, proteins, small organics, oligonucleotides or monomeric units of the peptides, organics, nucleic acids and other macromolecules. A monomeric unit refers to one of the constituents from which the resulting molecule is built. Thus, monomeric units include, nucleotides, amino acids, and pharmacophores from which small organic molecules are synthesized.

Biopolymers are well known in the art and include, for example, nucleic acids, polypeptides, and carbohydrates, which are naturally occurring molecules. For purposes of the present disclosure, however, a biological macromolecule such as a biopolymer also can be a synthetic molecule that is based on or derived from a naturally occurring molecule or can be a macromolecular complex such as a nucleoprotein complex, protein-protein complex, or the like. When such a molecule is a biopolymer, it contains at least one molecule containing monomeric subunits in association with a second molecule, which may or may not comprise monomeric subunits. Thus, a biopolymer can be, for example, a nucleic acid sequence containing a bond other than a phosphodiester bond between two or more nucleotides; or a polypeptide containing one or more mass modified amino acids; or a DNA binding protein in association with a nucleic acid sequence containing the DNA binding protein recognition site or a variant thereof. The monomeric subunits of a biopolymer can be, for example, the four nucleotides that generally comprise DNA, or the twenty amino acids that generally comprise a polypeptide, or the various sugars that comprise carbohydrates, or derivatives, analogs or mimetics of such naturally occurring monomer subunits. Other biological macromolecules include lipids, glycopolypeptides, phoshpopolypeptides, peptidoglycans, oligo-nucleotides, polysaccharides, peptidomimetics, peptide analogs; nucleic acid analogs and other nucleic acid structures including triple helices.

As used herein, large biological macromolecules with reference to proteins refer to proteins that are approximately larger than bovine serum albumin (i.e., greater than about 65 kD).

As used herein, analyze means to identify or detect a target molecule in a sample or determination of physical or determining identifying structural characteristics, such as the presence or absence of a mutation or mass of the nucleotide, or any method in which a property of a biological macromolecule is assessed using IR MALDI.

As used herein, the term "biological sample" refers to any material obtained from a living source, for example, an animal such as a human or other mammal, a plant, a bacterium, a fungus, a protist or a virus. The biological sample can be in any form, including a solid material such as a tissue, cells, a cell pellet; a biological fluid such as urine, blood, saliva, amniotic fluid, exudate from a region of infection or inflammation; a mouth wash containing buccal cells; a cell extract, or a biopsy sample.

As used herein, the term "polymorphism" refers to the coexistence, in a population, of more than one form of an allele. A polymorphism can occur in a region of a chromosome not associated with a gene or can occur, for example, as an allelic variant or a portion thereof of a gene. A portion of a gene that exists in at least two different forms, for example, two different nucleotide sequences, is referred to as a "polymorphic region of a gene." A polymorphic region of a gene can be localized to a ingle nucleotide, the identity of which differs in different alleles, or can be several nucleotides long. Of particular interest herein, polymorphisms, referred to as single nucleotide polymorphism (SNPs) that arise by virtue of change in single nucleotide base.

As used herein, the term "liquid dispensing system" means a device that can transfer a predetermined amount of liquid to a target site. The amount of liquid dispensed and the rate at which the liquid dispensing system dispenses the liquid to a target site, which can contain a reaction mixture, can be adjusted manually or automatically, thereby allowing a predetermined volume of the liquid to be maintained at the target site. Preferred dispensing systems are designed to dispense nano-liter volumes (i.e., volumes between about 1 and 100 nanoliters) of material. Such systems are known (see, e.g., published International PCT application No. WO 98/20200, which is based on allowed U.S. application Ser. No. 08/787,639, U.S. Pat. No. 6.024,925, as well as U.S. application Ser. No. 08/786,988).

As used herein, the term "liquid" is used to mean a non-solid, non-gaseous material, at room temperature and 1 atm. pressure, which can contain one or more solid or gaseous materials dissolved or suspended or otherwise mixed therein.

As used herein, the term "target site" refers to a specific locus on a solid support that can contain a liquid.

A solid support contains one or more target sites, which can be arranged randomly or in ordered array or other pattern. In particular, a target site restricts growth of a liquid to the "z" direction of an xyz coordinate. Thus, a target site can be, for example, a well or pit, a pin or bead, or a physical barrier that is positioned on a surface of the solid support, or combinations thereof such as beads on a chip, chips in wells, or the like. A target site can be physically placed onto the support, can be etched on a surface of the support, can be a "tower" that remains following etching around a locus, or can be defined by physico-chemical parameters such as relative hydrophilicity, hydrophobicity, or any other surface chemistry that allows a liquid to grow primarily in the z direction. A solid support can have a single target site, or can contain a number of target sites, which can be the same or different, and where the solid support contains more than one target site, the target sites can be arranged in any pattern, including, for example, an array, in which the location of each target site is defined.

As used herein, the term "target biological macromolecule" refers to any biological macromolecule of interest, including a fragment of a biological macromolecule, that is to be analyzed by IR-MALDI mass spectrometry. For example, a target biological macromolecule can be a nucleic acid such as a gene or an mRNA, or a relevant portion of a nucleic acid such as a restriction fragment or deletion fragment of the nucleic acid. A target nucleic acid can be a polymorphic region of a chromosomal nucleic acid, for example, a gene, or a region of a gene potentially having a mutation. Target nucleic acids include, but are not limited to, nucleotide sequence motifs or patterns specific to a particular disease and causative thereof, and to nucleotide sequences specific as a marker of a disease but not necessarily causative of the disease or condition. A target nucleic acid also can be a nucleotide sequence that is of interest for research purposes, but that may not have a direct connection to a disease or that may be associated with a disease or condition, although not yet proven so.

A target biological macromolecule also can be a polypeptide, or a relevant portion thereof, that is subjected to IR-MALDI mass spectrometry, for example, for identifying the presence of a polymorphism or a mutation. A target polypeptide can be encoded by a nucleotide sequence encoding a protein, which can be associated with a specific disease or condition, or a portion of a protein, or can be encoded by a nucleotide sequence that normally does not encode a translated polypeptide. A target polypeptide also can be encoded, for example, from a sequence of dinucleotide repeats or trinucleotide repeats or the like, which can be present in chromosomal nucleic acid, for example, a coding or a non-coding region of a gene, for example, in the telomeric region of a chromosome. A target polypeptide can be obtained from a naturally occurring protein or can be prepared from a nucleic acid by an in vitro method.

The identity of a target biological macromolecule can be determined by comparison of the molecular mass or sequence with that of a corresponding known biological macromolecule.

As used herein, the term "corresponding known biological macromolecule" means a biological macromolecule having a known characteristic, which can be any relevant characteristic including, for example, the mass or charge, the fragmentation pattern following treatment with a fragmenting agent, the tissue or cell type in which the biological macromolecule normally is found in nature, or the like. A corresponding known biological macromolecule generally is used as a control for comparison to a second biological macromolecule, particularly a target biological macromolecule. By comparing the spectra of a target biological macromolecule with a corresponding known biological macromolecule, information about the target biological macromolecule can be obtained.

As used herein, a corresponding known biological macromolecule can have substantially the same subunit sequence as the target biological macromolecule, or can be substantially different. For example, where a target polypeptide is an allelic variant that differs from a corresponding known polypeptide by a single amino acid difference, the amino acid sequences of the polypeptides will be the same except for the single difference. In comparison, where a mutation in a nucleic acid encoding the target polypeptide changes, for example, the reading frame of the encoding nucleic acid or introduces or deletes a STOP codon, the sequence of the target polypeptide can be substantially different from that of the corresponding known polypeptide.

With respect to a nucleic acid, a target nucleic acid can be, for example, a DNA molecule that is obtained from a subject, such as prostate cancer patient and includes the polymorphic region that demonstrates amplification of a trinucleotide sequence associated with prostate cancer, and the corresponding known nucleic acid can be the same polymorphic region from a subject that does not have prostate cancer. Depending on the amount of amplification, the target nucleic acid can be substantially larger than the corresponding known nucleic acid. A target nucleic acid also can be a polymorphism or a mutated gene, which can alter the phenotype of a subject as compared to a subject not having the polymorphism or the mutated gene, and a corresponding known nucleic acid can be the nucleotide sequence of an allele that is present in the majority of subjects in a relevant population.

A target biological macromolecule can be a fragment of a larger biological macromolecule and can be produced by contacting the larger biological macromolecule with an appropriate fragmenting agent.

As used herein, the term "fragmenting agent" means a physical, chemical or biochemical agent that, upon contacting a biological macromolecule, breaks the biological macromolecule into at least two separate portions. In general, a fragmenting agent is specific for a particular type of biological macromolecule, for example, a peptidase, which cleaves a polypeptide; a nuclease, which cleaves a nucleic acid molecule; or a glycosidase, which cleaves a carbohydrate. Non-specific fragmenting agents also are well known and include, for example, physical agents such as ionizing radiation or sonication. Contacting a biological macromolecule with a fragmenting agent produces fragments of the biological macromolecule.

As used herein, the term "fragment," when used with reference to a biological macromolecule, means a portion of the biological macromolecule that has a lower molecular mass than the entire biological macromolecule. A fragment of a biological macromolecule can be one or more of the subunits that comprise the biological macromolecule, or can be portions of the biological macromolecule lacking one or more subunits, including deletion fragments.

A fragment of a polypeptide, for example, generally is produced by specific chemical or enzymatic degradation of the polypeptide. Where chemical or enzymatic cleavage occurs in a sequence specific manner, the production of fragments of a polypeptide is defined by the primary amino acid sequence of the polypeptide. Fragments of a polypeptide can be produced, for example, by contacting the polypeptide, which can be immobilized to a solid support, with a chemical agent such as cyanogen bromide, which cleaves a polypeptide at methionine residues, or hydroxylamine at high pH, which can cleave an Asp-Gly peptide bond; or with a peptidase, for example, an endopeptidase such as trypsin, which cleaves a polypeptide at Lys or Arg residues, or an exopeptidase such as carboxypeptidase, which produces one or more free amino acids, which have been released from the carboxy terminus of the polypeptide, and deletion fragments of the polypeptide that lacks the one or more amino acids.

The term "deletion fragment" refers to a fragment of a biological macromolecule that remains following sequential cleavage of a subunit from a terminus of the biological macromolecule. The term "nested set of deletion fragments" refers to a population of deletion fragments that results from sequential cleavage of subunits from a biological macromolecule. A nested set of deletion fragments generally contains at least one deletion fragment that terminates in each subunit of at least a portion of the biological macromolecule, thereby allowing sequencing of the biological macromolecule. Thus, as many as N deletion fragments can be produced from a biological macromolecule, where "N" is the number of subunits in the biological macromolecule, although fewer than N deletion fragments can be produced. It should be recognized that a "nested set" of nucleic acid fragments also can be produced, for example, by performing a chain-terminating polymerase reaction such as a dideoxy sequencing method.

In comparison to the production of deletion fragments using a fragmenting agent that cleaves a biological macromolecule from a terminus, treatment of a biological macromolecule with a fragmenting agent that recognizes specific sites in the biological macromolecule results of the production in M+1 fragments of the biological macromolecule, where "M" is the number of specific cleavage sites in the biological macromolecule. For example, treatment of a polypeptide having four internal and interspersed methionine residues with cyanogen bromide results in the production in five fragments of the polypeptide.

Fragments of nucleic acids, carbohydrates, or other biological macromolecules also can be produced. For example, exonucleases, including DNAses and RNAses, and endonucleases, including restriction endonucleases, can be used to produce fragments of a nucleic acid molecule (see Sambrook et al., *Molecular Cloning: A laboratory manual* (Cold Spring Harbor Laboratory Press 1989), listing nucleic acid fragmenting agents). The choice of a nuclease to produce nucleic acid fragments will depend on the process being performed and the characteristics of the nucleic acid molecule, for example, whether it is DNA or RNA and whether, if DNA, it contains recognition sites, if necessary, for action by the nuclease. Similarly, fragments of carbohydrates can be produced using enzymes such as exoglycosidases or endoglycosidases, for example, amylases, which can produce fragments of carbohydrates containing $\alpha$-1,4-glycosydic bonds (see U.S. Pat. No. 5,821,063).

A nested set of deletion fragments of a target biological macromolecule can be produced using an agent that cleaves the biological macromolecule from a terminus.

As used herein, the term "agent that cleaves a biological macromolecule unilaterally from a terminus" refers to a physical, chemical or biological agent for sequentially removing subunits from one end of a biological macromolecule. A biological agent that cleaves a biological macromolecule unilaterally from a terminus is exemplified by an exopeptidase such as carboxypeptidase Y, which sequentially cleaves amino acids from the carboxyl terminus of a polypeptide (see U.S. Pat. No. 5,792,664; International Publ.

WO 96/36732), or by an exonuclease such as exonuclease III, which sequentially cleaves nucleotides from the 3'-hydroxyl terminus of a double stranded DNA (see International Publ. WO 94/21822). A physical agent is exemplified by a light source, for example, a laser, which can cleave a terminal subunit from a biological macromolecule, particularly where the subunit is bound to the biological macromolecule through a photolabile bond. A chemical agent is exemplified by phenylisothiocyanate (Edman's reagent), which, in the presence of an acid, cleaves an amino terminal amino acid from a polypeptide.

As used herein, the residues of naturally occurring α-amino acids are the residues of those 20 α-amino acids found in nature that are incorporated into protein by the specific recognition of the charged tRNA molecule with its cognate mRNA codon in humans.

As used herein, non-naturally occurring amino acids refer to amino acids that are not genetically encoded. Preferred such non-naturally occurring amino acids herein include those with unsaturated side chains.

As used herein, the term "polypeptide" means at least two amino acids, or amino acid derivatives, which can be mass modified amino acids or non-naturally-occurring amino acids, that are linked by a peptide bond, which can be a modified peptide bond. Exemplary polypeptides include, but are not limited to, native proteins, gene products, protein conjugates, mutant or polymorphic polypeptides, post-translationally modified proteins, genetically engineered gene products including products of chemical synthesis, in vitro translation, cell-based expression systems, including fast evolution systems involving vector shuffling, random or directed mutagenesis and peptide sequence randomization, oligopeptides, antibodies, enzymes, receptors, regulatory proteins, nucleic acid-binding proteins, hormones, or protein products of a display method such as phage or bacterial display methods.

A polypeptide can be translated from a nucleotide sequence that is at least a portion of a coding sequence, or from a nucleotide sequence that is not naturally translated due, for example, to its being in a reading frame other than the coding frame or to its being an intron sequence, a 3' or 5' untranslated sequence, or a regulatory sequence such as a promoter. A polypeptide also can be chemically synthesized and can be modified by chemical or enzymatic methods following translation or chemical synthesis. The terms "protein," "polypeptide" and "peptide" can be used interchangeably herein when referring to a translated nucleic acid, for example, a gene product, although "peptides" generally are smaller than "polypeptides" and "proteins" often can have post-translational modifications.

As used herein, the term "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA, such as PNA, and can contain, for example, one or more nucleotide analogs or a covalent linkage (backbone) other than a phosphodiester bond, for example, a thioester bond, a phosphotriester bond, or a peptide bond (peptide nucleic acid; PNA; see, for example, Tam et al., *Nucl. Acids Res.* 22:977–986 (1994); Ecker and Crooke, *BioTechnology* 13:351360 (1995)); triple helices are also contemplated. The nucleic acid can be single-stranded, double-stranded, or a mixture thereof. For purposes herein, unless specified otherwise, the nucleic acid is double-stranded or it is apparent from the context. Nucleotide analogs are commercially available and methods of preparing polynucleotides containing such nucleotide analogs are well known (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997)).

A nucleic acid can be single stranded or double stranded, including, for example, a DNA-RNA hybrid. A nucleic acid also can be a portion of a longer nucleic acid molecule, for example, a portion of a gene containing a polymorphic region. The molecular structure of a nucleic acid, for example, a gene or a portion thereof, is defined by its nucleotide content, including deletions, substitutions or additions of one or more nucleotides; the nucleotide sequence; the state of methylation; or any other modification of the nucleotide sequence. Although a nucleic acid contains two or more nucleotides or nucleotide analogs linked by a covalent bond, including single stranded or double stranded molecules, it should be recognized that a "fragment" of a nucleic acid, which can be produced as discussed above, can be as small as a single nucleotide. The terms "polynucleotide" and "oligonucleotide" also are used herein to mean two or more nucleotides or nucleotide analogs linked by a covalent bond, although oligonucleotides such as PCR primers generally are less than about fifty to one hundred nucleotides in length.

As used herein, the phrase "determining the identity of a target biological macromolecule" refers to determining at least one characteristic of the biological macromolecule, which can be a nucleic acid, polypeptide or other biological macromolecule. Determining the identity of a biological macromolecule can include, for example, determining the molecular mass or charge of the biological macromolecule; or determining the identity of at least one subunit, or of a subunit sequence of the biological macromolecule; or determining a particular pattern of fragments of the biological macromolecule. For example, where the biological macromolecule is a nucleic acid, determining the identity of the target nucleic acid can include determining at least one nucleotide of the target nucleic acid, or determining the number of nucleotide repeats present in a sequence of tandem nucleotide repeats. Similarly, where the target biological macromolecule is a polypeptide, determining the identity of the target polypeptide can include determining at least one amino acid, or a particular pattern of peptide fragments of the target polypeptide, for example, following treatment of the polypeptide with an endopeptidase. Determining the identity of a target biological macromolecule is performed by subjecting the target biological macromolecule, if necessary, to a particular reaction, as appropriate; preparing a composition containing target biological macromolecule or reaction product thereof and a liquid matrix, which absorbs IR radiation; and analyzing the target biological macromolecule or reaction product thereof by IR-MALDI mass spectrometry.

The terms "infrared radiation" and "infrared wavelength" refer to electromagnetic wavelengths that are longer than those of red light in the visible spectrum and shorter than radar waves, generally wavelengths within the range of about 760 nm to about 50 μm. An appropriate infrared wavelength can be generated using a laser, as disclosed herein.

As used herein, the term "liquid matrix" means a material that has a sufficient absorption at the wavelength of the laser to be used in performing desorption and ionization (i.e. an IR emitting laser) and that is a liquid at room temperature (about 20° C., 1 atm). The contemplated liquids are those that can form vitreous solids or glasses in the solid state as opposed to a crystalline structure, such as that which forms when a matrix such as picolinic acid or 3HPA is dried. Vitreous solids and glasses do not form solid crystalline heterogenous structures, but rather retain properties of liquids that derive from their lack of ordered structure. In addition, such liquid matrices form a homogenous layer when applied to the surface of a substrate or support. Thus, for purposes herein, liquid matrices are relatively nonvolatile materials that are biocompatible, particularly compatible with nucleic acids and/or proteins, and include, but are not limited to, alcohols, including glycols and polyols, such as glycerol, sugars, such as sucrose, mannose, galactose, and other sugars as well as polymeric sugars, ethylene glycol, propylene glycol, trimethylolpropane, pentaerythritol, dextrose, methylglycoside or sorbitol. sucrose, mannose and other such materials that in the solid state can form glasses rather than crystalline structures. Also included is "glassy" water, which state occurs under conditions in which very small volumes, i.e., submicroliters, particular nanoliters or less, are dispensed. Other liquid matrices include, but are not limited to triethanolamine, lactic acid, 3-nitrobenzylalcohol, diethanolamine, DMSO, -nitrophenyloctylether (3-NPOE), 2,2'dithiodiethanol, tetraethyleneglycol, dithiothreitol/erytritol (DTT/DTE), 2,3-dihydroxy-propyl-benzyl ether, α-tocopherol, and thioglycerol. Other suitable "liquid" matrices are set forth below.

For absorption purposes, the liquid matrix can contain at least one chromophore or functional group that strongly absorbs infrared radiation. Examples of appropriate functional groups include nitro, sulfonyl, sulfonic, acid, sulfonamide, nitrile or cyanide, carbonyl, aldehyde, carboxylic acid, amide,-ester, anhydride, ketone, amine, hydroxyl, aromatic rings, dienes and other conjugated systems. A liquid matrix, which absorbs IR radiation, including a composition containing a biological macromolecule to be analyzed by IR-MALDI and a liquid matrix, can contain an additive that facilitates IR-MALDI analysis of the biological macromolecule.

As used herein, appropriate viscosity, refers to the viscosity for dispensing glass-type liquid matrices and means that it can be dispensed as a small volume and evenly distribute over a small surface area in an thin layer.

As used herein, the term "additive" means a material that facilitates IR-MALDI analysis of a biological macromolecule. For example, an additive can facilitate solubility of the biological macromolecule in a composition containing a liquid matrix. An additive also can be a compound or compounds that have a high extinction coefficient (E) at the laser wavelength used for desorption and ionization, for example, dinitrobenzenes or polyenes. Additives also include compounds that alter the ionic strength of the matrix/sample mixture or the matrix. Exemplary salt additives include, but are not limited to, ammonium salts and salts of amines. Exemplary salt additives for this purpose include $NH_4$-acetate and Tris-HCl.

Where the biological macromolecule to be analyzed by IR-MALDI is a nucleic acid, for example, an additive can be a compound that acidifies the liquid matrix, thereby inducing dissociation of double stranded nucleic acids or denaturing a secondary structure of a nucleic acid such as tRNA or other single stranded nucleic acid. An additive also can minimize salt formation between the matrix and the biological macromolecule and can be, for example, a material that conditions the biological macromolecule. When it is desirable to analyze or detect a double-stranded nucleic acid by IR-MALDI, the additive can be a substance that stabilizes the double-stranded molecule or reduces denaturation of the double-stranded nucleic acid, but that is generally compatible with mass spectrometric analysis. Such additives include, but are not limited to, salts. Preferred salt additives include ammonium salts and salts of amines. Exemplary salt additives for this purpose include $NH_4$-acetate and Tris-HCl.

The matrix can be treated by further purification to remove other organic contaminants, including harmful derivatives and other by-products of the production process.

A biological macromolecule or fragment thereof, particularly a target biological macromolecule, can be conditioned prior to IR-MALDI mass spectrometry.

As used herein, the term "conditioned" or "conditioning," when used in reference to a biological macromolecule, means that the biological macromolecule is modified so as to decrease the amount of IR radiation required to ionize or volatilize the biological macromolecule, to minimize the likelihood of undesirable fragmentation of the biological macromolecule, or to increase the resolution of a mass spectrum of the biological macromolecule or fragments thereof. Resolution of a mass spectrum of a target biological macromolecule or fragment thereof can be increased by conditioning the biological macromolecule prior to performing IR-MALDI mass spectrometry. Conditioning can be performed at any stage prior to IR-MALDI mass spectrometry, particularly while the biological macromolecule is immobilized to a substrate. Conditioning includes any process that achieves these results, and includes, but is not limited to, subjecting the macromolecule to ion exchange or other process that provides for a uniform charge distribution, mass modification, modification of the phosphodiester backbone of a nucleic acid, removal of negative charge from the phosphodiester backbone, cation exchange, further purification, and any other such process known to those of skill in the art to achieve conditioning.

Conditioning of a biological macromolecule will depend, in part, on the biochemical nature of the biological macromolecule. For example, a biological macromolecule can be conditioned by treatment with a cation exchange material or an anion exchange material, which reduces the charge heterogeneity of the biological macromolecule, thereby eliminating peak broadening due to heterogeneity in the number of cations (or anions) bound to the target biological macromolecule. A polypeptide, for example, can be conditioned by treatment with an alkylating agent such as alkyliodide, iodoacetamide, iodoethanol, or 2,3-epoxy-1-propanol, which prevents the formation of disulfide bonds. Such alkylating agents also can be used to condition a nucleic acid by transforming the monothiophosphodiester bonds to phosphotriester bonds. A polypeptide also can be conditioned by converting charged amino acid side chains to uncharged derivatives by contact with trialkylsilyl chlorides, which also can be used to condition a nucleic acid by transforming phosphodiester bonds to uncharged derivatives. Biological macromolecules also can be conditioned by incorporating modified subunits that are more stable than the corresponding unmodified subunits, for example, the substitution of N7- or N9-deazapurine nucleotides in a target nucleic acid, thereby minimizing the likelihood of fragmentation of the biological macromolecule.

The processes disclosed herein provide methods for analyzing a plurality of biological macromolecules in one or a few samplings, for example, by multiplex analysis.

As used herein, the term "multiplex" refers to simultaneously determining the identity of at least two target biological macromolecules by IR-MALDI mass spectrometry. For example, where a population of different target biological macromolecules are present in an array on a microchip or other substrate, multiplexing can be used to determine the identity of a plurality of target biological macromolecules. Multiplexing can be performed, for example, by differentially mass modifying each different biological macromolecule of interest, then using IR-MALDI mass spectrometry to determine the identity of each different biological macromolecule. Multiplex analysis provides the advantage that a plurality of target biological macromolecules can be identified in as few as a single IR-MALDI mass spectrum, as compared to having to perform a separate mass spectrometric analysis for each individual target biological macromolecule.

"Multiplexing" can be achieved by several different methodologies. For example, several mutations can be simultaneously detected on one target sequence by employing corresponding detector (probe) molecules (e.g. oligonucleotides or oligonucleotide mimetics). The molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities into the detector oligonucleotide. Mass modifying moieties can be attached, for instance, to either the 6'-end of the oligonucleotide, to the nucleobase (or bases), to the phosphate backbone, and to the 2'-position of the nucleoside (nucleosides) or/and to the terminal 3'-position. Examples of mass modifying moieties include, for example, a halogen, an azido, or of the type, XR, wherein X is a linking group and R is a mass-modifying functionality. The mass-modifying functionality can thus be used to introduce defined mass increments into the oligonucleotide molecule.

The mass-modifying moiety, M, can be attached either to the nucleobase, in case of, for example, $c^7$-deazanucleosides also to C-7, to the triphosphate group at the alpha phosphate, or to the 2'-position of the sugar ring of the nucleoside triphosphate. Furthermore, the mass-modifying functionality can be added so as to affect chain termination, such as by attaching it to the 3'-position of the sugar ring in the nucleoside triphosphate. As another exemplary embodiment, various mass-modifying functionalities, R, other than oligo/polyethylene glycols, can be selected and attached via appropriate linking chemistries, X. A simple mass-modification can be achieved by substituting H for halogens like F, Cl, Br and/or I, or pseudohalogens such as SCN, NCS, or by using different alkyl, aryl or aralkyl moieties such as methyl, ethyl, propyl, isopropyl, t-butyl, hexyl, phenyl, substituted phenyl, benzyl, or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass-modification can be obtained by attaching homo- or heteropeptides through the nucleic acid molecule (e.g. detector (D)) or nucleoside triphosphates. One example useful in generating mass-modified species with a mass increment of 57 is the attachment of oligoglycines, e.g. mass-modifications of 74 (r=1, m=0), 131 (r=1, m=2), 188 (r=1, m=3), 245 (r=1, m=4) are achieved. Simple oligoamides also can be used, e.g., mass-modifications of 74 (r=1, m=0), 88 (r=2, m=0), 102 (r=3, m=0), 116 (r=4, m=0), etc. are obtainable. The mass modifications serve, not only to aid in multiplexing, but to enhance or aid in resolving mass spectrometry of fragments (i.e., mass modification aids in "conditioning" the nucleic acids for analysis. Other chemistries can be used in the mass-modified compounds, as for example, those described in *Oligonucleotides and Analogues, A Practical Approach*, F. Eckstein, editor, IRL Press, Oxford, 1991 and are known to those of skill in the art of mass spectrometry.

As used herein, the term "plurality," when used in reference to biological macromolecules, means two or more biological macromolecules, each of which has a different subunit sequence. The difference in sequences can be due to a naturally occurring variation among the sequences, for example, to an allelic variation in a nucleotide or an encoded amino acid, or can be due to the introduction of particular modifications into various sequences, for example, the differential incorporation of mass modified nucleotides or amino acids into each nucleic acid or polypeptide, respectively, in the plurality.

The processes as disclosed herein can be performed using an isolated biological macromolecule.

As used herein, the term "isolated" means that a biological macromolecule is substantially separated from macromolecules normally associated with the biological macromolecule in its natural state. An isolated nucleic acid molecule, for example, is substantially separated from the cellular material normally associated with it in a cell or, as relevant, can be substantially separated from bacterial or viral material; or from culture medium where produced by recombinant DNA techniques; or from chemical precursors or other chemicals where the nucleic acid is chemically synthesized. In general, an isolated nucleic acid molecule, which can be a fragment of a larger nucleic acid, is at least about 50% enriched with respect to its natural state, and generally is about 70% to about 80% enriched, particularly about 90% or 95% or more. Preferably, an isolated nucleic acid constitutes at least about 50% of a sample containing the nucleic acid, and can be at least about 70% or 80% of the material in a sample, particularly at least about 90% to 95% or greater of the sample.

Similarly, an isolated polypeptide can be identified based on its being enriched with respect to materials it naturally is associated with or its constituting a fraction of a sample containing the polypeptide to the same degree as defined above, i.e., enriched at least about 50% with respect to its natural state or constituting at least about 50% of a sample containing the polypeptide. An isolated polypeptide, for example, can be purified from a cell that normally expresses the polypeptide or can be produced using recombinant DNA methodology, and can be a fragment of a larger polypeptide.

A biological macromolecule can be isolated using a reagent that interacts specifically with the biological macromolecule or with a tag attached to the biological macromolecule. For example, a target polypeptide can be isolated using a reagent that interacts specifically with the target polypeptide, with a peptide tag (i.e. peptide that can serve to specifically bind to a reagent, such as a column) fused to the target polypeptide, or with a peptide tag conjugated to the target polypeptide.

As used herein, the term "reagent" means a ligand or a ligand binding molecule that interacts specifically with a particular ligand binding molecule or ligand, respectiyvely. The term "tag peptide" or "peptide tag" is not to be confused with a mass tag, and is used herein to mean a peptide, for which a reagent is available. The term "tag" refers more generally to any molecule, for which a reagent is available and, therefore, includes a tag peptide.

As used herein, reagent can be an antibody that interacts specifically with an epitope of a target biological macromolecule, for example, a polypeptide, or with an epitope of a tag attached to the target biological macromolecule. For example, a reagent can be an anti-myc epitope antibody, which can interact specifically with a myc epitope fused to a target polypeptide. A reagent also can be, for example, a metal ion such as nickel ion or cobalt ion, which interacts specifically with a polyhistidine tag peptide; or zinc, copper or, for example, a zinc finger domain, which interacts specifically with a polyarginine or polylysine tag peptide; or a molecule such as avidin, streptavidin or a derivative thereof, which interacts specifically with a tag such as biotin or a derivative thereof (see International Publ. WO 97/43617, which describes, for example, methods for dissociating biotin compounds, including biotin and biotin analogs conjugated (biotinylated) to a polypeptide, from biotin binding compounds, including avidin and streptavidin, using amines, particularly ammonia).

A tag such as biotin also can be incorporated into a target nucleic acid, thereby allowing isolation of the target nucleic acid using a reagent such as avidin or streptavidin. In addition, a target nucleic acid can be isolated by hybridization to reagent containing a complementary nucleic acid sequence, which can be immobilized to a solid support such as beads, for example, magnetic beads, if desired.

The term "interacts specifically," when used in reference to a reagent and a target biological macromolecule sequence or a tag to which the reagent binds, indicates that binding occurs with relatively high affinity. As such, a reagent has an affinity of at least about $1 \times 10^6$ $M^{-1}$, generally, at least about $1 \times 10^7$ $M^{-1}$, and, in particular, at least about $1 \times 10^8$ $M^{-1}$, for the particular biological macromolecule sequence or tag. A reagent the interacts specifically, for example, with a particular tag peptide primarily binds the tag peptide, regardless of whether other unrelated molecules are present and, therefore, is useful for isolating the tag peptide, including a target polypeptide fused to the tag peptide, from a sample containing the target polypeptide, for example, from an in vitro translation reaction. Similarly, a reagent complementary nucleic acid sequence that interacts specifically with a target nucleic acid selectively binds the target nucleic acid, but not unrelated nucleic acid molecules.

A hybridizing nucleic acid sequence, which generally is an oligonucleotide, is at least nine nucleotides in length, such sequences being particularly useful as primers for the polymerase chain reaction (PCR), and can be at least fourteen nucleotides in length or, if desired, at least seventeen nucleotides in length, such nucleotide sequences being particularly useful as hybridization probes, as well as for PCR. It should be recognized that the conditions required for specific hybridization of an oligonucleotide, for example, a PCR primer, with a nucleic acid sequence, for example, a target nucleic acid, depends, in part, on the degree of complementarity shared between the sequences, the GC content of the hybridizing molecules, and the length of the antisense nucleic acid sequence, and that conditions suitable for obtaining specific hybridization can be calculated based on readily available formulas or can be determined empirically (Sambrook et al., *Molecular Cloning: A laboratory manual* (Cold Spring Harbor Laboratory Press 1989); Ausubel et al., *Current Protocols in Molecular Biology* (Green Publ., NY 1989)).

It can be advantageous in performing a disclosed process to immobilize a biological macromolecule, for example, a target nucleic acid or target polypeptide, on a a substrate, particularly a solid support, such as a bead, microchip, glass or plastic capillary, or any surface, particularly a flat surface, which can contain a structure such as wells, pins or the means by which the target macromolecule is constrained at a site. A biological macromolecule can be conjugated to a solid support by various means, including, for example, by a streptavidin or avidin to biotin interaction; a hydrophobic interaction; by a magnetic interaction using, for example, functionalized magnetic beads such as DYNABEADS, which are streptavidin coated magnetic beads (Dynal Inc.; Great Neck N.Y.); by a polar interaction such as a "wetting" association between two polar surfaces or between oligo/polyethylene glycol; by the formation of a covalent bond such as an amide bond, a disulfide bond, a thioether bond, or the like; through a crosslinking agent; and through an acid-labile or photocleavable linker (see, for example, Hermanson, *Bioconjugate Techniques* (Academic Press 1996)). In addition, a tag can be conjugated to biological macromolecule of interest, particularly to a target biological macromolecule.

As used herein, the term "conjugated" or "immobilized" refers to an attachment, which can be a covalent attachment or a noncovalent attachment, that is stable under defined conditions. As disclosed herein, a biological macromolecule can be immobilized to a substrate, or a first substrate can be conjugated to second substrate. Immobilization of a biological macromolecule to a substrate can be direct or can be indirect through a linker, and can reversible or irreversible. A reversible immobilization can be reversed either by cleaving the attachment, for example, using light to cleave a photocleavable bond, or by subjecting the attachment to conditions that reverse the bond, for example, reducing conditions, which reverse a disulfide linkage.

As used herein, the term "substrate" or "solid support" means a flat surface or a surface with structures, to which a functional group, including a biological macromolecule containing a reactive group, can be conjugated. The term "surface with structures" means a substrate that contains, for example, wells, pins or the like, to which a functional group, including a biological macromolecule containing a reactive group, can be attached. Numerous examples of solid supports (substrates) are disclosed herein or otherwise known in the art.

A process as disclosed herein can be used to identify a subject that has or is predisposed to a disease or condition. As used herein, the term "disease" has its commonly understood meaning of a pathologic state in a subject. For purposes of the present disclosure, a disease can be due, for example, to a genetic mutation, a chromosomal defect or an infectious organism. The term "condition," which is to be distinguished from conditioning of a biological macromolecule, is used herein to mean any state of a subject, including, for example, a pathologic state or a state that determines, in part, how the subject will respond to a stimulus. The condition of a subject can be determined, in part, by determining a characteristic of the subject's genotype, which can provide an indication as to how the subject will respond, for example, to a graft or to treatment with a particular medicament; or by detecting a particular biological macromolecule in a biological sample obtained from the subject, for example, expression of a carbohydrate associated with a particular disease. Accordingly, reference to a subject being predisposed to a condition can indicate, for example, that the subject has a genotype indicating that the subject will not respond favorably to a particular medicament or that the subject will reject a particular graft.

Reference herein to an allele or an allelic variant being "associated" with a disease or condition means that the particular genotype is characteristic, at least in part, of the genotype exhibited by a population of subjects that have or are predisposed to the disease or condition. For example, an allelic variant such as a mutation in the BRCA1 gene is associated with breast cancer, and an allelic variant such as a higher than normal number of trinucleotide repeats in a particular gene is associated with prostate cancer. The skilled artisan will recognize that an association of an allelic variant with a disease or condition can be identified using well known statistical methods for sampling and analysis of a population.

As used herein, compositions include mixtures of materials and as well as solutions.

Except as otherwise disclosed, the practice of the processes described herein employs conventional techniques of cell biology, cell culture, molecular biology, transgenic biology, microbiology, recombinant DNA, and immunology, which are within the skill of the art and described, for example, in *DNA Cloning*, Volumes I and II (D. N. Glover, ed., 1985); *Oligonucleotide Synthesis* (M. J. Gait, ed., 1984); Mullis et al., U.S. Pat. No: 4,683,194; *Nucleic Acid Hybridization* (Hames and Higgins, eds., 1984); *Transcription and Translation* (Hames and Higgins eds., 1984); *Culture of Animal Cells* (R. I. Freshney; Alan R. Liss, Inc., 1987); *Immobilized Cells and Enzymes* (IRL Press, 1986); B. Perbal, *A Practical Guide to Molecular Cloning* (1984); *Gene Transfer Vectors For Mammalian Cells* (Miller and Calos, eds.; Cold Spring Harbor Laboratory 1987); *Methods In Enzymology*, Vols. 154 and 155 (Wu et al., eds., Academic Press, NY), *Immunochemical Methods In Cell And Molecular Biology* (Mayer and Walker, eds.; Academic Press London, 1987); *Handbook Of Experimental Immunology*, Volumes I to IV (Weir and Blackwell, eds., 1986); *Manipulating the Mouse Embryo* (Cold Spring Harbor Laboratory press, Cold Spring Harbor N.Y., 1986).

PROCESSES AND COMPOSITIONS FOR USE WITH IR MALDI

The processes and compositions disclosed herein allow the detection, identification or characterization of biological macromolecules, including nucleic acids, polypeptides, and carbohydrates, as well as macromolecular complexes such as protein complexes and nucleoprotein complexes, by infrared (IR) matrix assisted laser desorption/ionization (MALDI) mass spectrometry. A composition for IR-MALDI is provided, the composition being a composition containing at least a biological macromolecule to be analyzed by IR-MALDI mass spectrometry and a liquid matrix, which absorbs IR radiation. Such a composition, which can be deposited on a substrate, is useful for determining a characteristic of a biological macromolecule by IR-MALDI mass spectrometry.

Processes for analyzing a target biological macromolecule using IR-MALDI mass spectrometry also are provided, including, for example, processes for detecting a target biological macromolecule in a sample, particularly a biological sample; processes for determining the identity of a biological macromolecule such as the presence of a mutation or other genetic change in a nucleic acid or of an amino acid change in a polypeptide encoded by a nucleic acid having a genetic change; and processes for determining a sequence of a biological macromolecule. The processes disclosed herein allow the analysis by IR-MALDI mass spectrometry of one or more target biological macromolecules, either in separate, but related processes such as a high throughput process, where the biological macromolecules can be analyzed serially, or can be arranged in an array on a silicon wafer, for example, and analyzed in parallel; or in a single process using a multiplex format, where each biological macromolecule in a plurality is differentially identifiable, for example, due to differential mass modification of the biological macromolecules.

The disclosed processes and compositions are based, in part, on the finding that high resolution mass spectra of large nucleic acid molecules (DNA and RNA) can be obtained by desorbing and ionizing the nucleic acids in a liquid matrix using a laser that emits in the infrared electromagnetic wavelength. Accordingly, a process is provided for performing IR-MALDI mass spectrometry, containing mixing a nucleic acid composition with a liquid matrix to form a matrix/nucleic acid composition and depositing the composition onto a substrate to form a homogeneous, thin layer of matrix/nucleic acid composition. The nucleic acid containing substrate then can be illuminated with IR radiation of an appropriate -wavelength to be absorbed by the matrix, so that the nucleic acid is desorbed and ionized, thereby emitting ion particles that can be extracted (separated) and analyzed by a mass analyzer to determine the mass of the nucleic acid. A process for analyzing a nucleic acid by mass spectrometry can be performed by depositing a composition containing the nucleic acid and a liquid matrix on a substrate, to form a homogeneous, thin layer of a nucleic acid/liquid matrix composition; illuminating the substrate containing the deposited composition with an infrared laser, so that the nucleic acid is desorbed and ionized; and mass separating and detecting the ionized nucleic acid using an appropriate mass separation and analysis format.

Processes are provided for analyzing a target biological macromolecule, particularly a target nucleic acid, by preparing a composition containing the target biological macromolecule and a liquid matrix, which absorbs IR radiation, and analyzing the target biological macromolecule in the composition by IR-MALDI mass spectroscopy. The various processes disclosed herein allow a determination of the molecular mass of a target biological macromolecule, the detection or identification of a target biological macromolecule, which can be present in a biological sample, or the determination of a subunit sequence of a target biological macromolecule. Depending on the source of the target biological macromolecule, a process as disclosed herein can be useful, for example, for determining whether an individual has a disease or a predisposition to a disease, or for determining heredity, identity or compatibility of an individual (see International Publ. WO 98/20019).

A target biological macromolecule, for example, a target nucleic acid molecule, can be obtained from a subject, particularly from a cell or tissue in the subject or from a biological fluid, i.e., a biological sample. A target biological macromolecule can be a target nucleic acid molecule, or can be a target polypeptide, which can be obtained, for example, by in vitro translation of an RNA molecule encoding the target polypeptide; or by in vitro transcription of a nucleic acid encoding the target polypeptide, followed by translation, which can be performed in vitro or in a cell, where the nucleic acid to be transcribed is obtained from a subject. The processes disclosed herein provide fast and reliable methods for identifying or obtaining information about the target biological macromolecule.

Exemplary Advantages of IR-MALDI in the Detection of Target Molecules Obtained from Biological Samples Biological samples containing a target molecule which have undergone some purification still are likely to contain extraneous contaminants (i.e., materials other than the target molecule) that are not present in a pure sample of target molecule. For example, extraneous proteins and salts may be present in partially purified preparations thereby making such preparations in reality "mixtures" as opposed to pure samples. Accordingly, mass resolution, accuracy, sensitivity and the signal-to-noise ratio become very critical parameters in mass spectrometric methods designed to detect the presence of a target molecule obtained from a biological sample. The mass spectrometric technique must be able to clearly resolve the target molecule, which may not be present in significant quantities, from the contaminant materials.

Thus, the fact that a particular mass spectrometric method may be used to measure the mass of a relatively pure biological molecule is no guarantee that it will be applicable to the detection of target molecules obtained from a biological sample. Furthermore, because of the inherent differences in the various types of mass spectrometric methods (e.g., ESI and MALDI using different lasers and/or matrices), the fact that one mass spectrometric technique may be useful in the detection of target molecules obtained from a biological sample is no guarantee that another type would also be suitable for this purpose. Additionally, the fact that a particular mass spectrometric method or set of conditions may be used to detect one particular type of target molecule, from a biological sample does not guarantee that it can be used effectively to detect another type of target molecule from a biological sample. For example, even different sizes and types of a single class of target molecule (e.g., single-stranded vs. double-stranded DNA) from a biological sample may or may not be detected by different mass spectrometric methods and conditions, just as completely different classes of target molecules, e.g., nucleic acids vs. proteins, from a biological sample may or may not be detected by different mass spectrometric methods and conditions.

A comparison of proteins and nucleic acids reveals several differences that directly impact their amenability to analysis by mass spectrometry. For example, nucleic acids are typically more susceptible to fragmentation than proteins due to losses of nucleobases as a result of the labile N-glycosidic bond between the different bases and the deoxyribose moiety and to depurination. Spectra of nucleic acids reveal a greater tendency toward adduct formation than those of proteins. Furthermore, the relative ease of desorption/ionization appears to be greater for proteins as compared to nucleic acids since proteins tend to fold into defined structures whereas nucleic acids have less tertiary structure than proteins.

As disclosed herein, IR-MALDI mass spectrometry has been found to be effective and advantageous in methods of detection of target molecules, particularly large target molecules, obtained from biological samples. This has been due in part to the recognition of the significance of defining the optimal parameters (for example, the particular combinations of laser, wavelength, matrix, additive, pulse width, beam profile, temperature and/or fluence) that provide the level of resolution, sensitivity, signal-to-noise level, etc., required to detect a target molecule obtained from a biological sample.

For example, shorter pulse widths can be used in IR-MALDI mass spectrometric detection of target molecules, particularly employing lasers with optoelectronic switches. Typically, pulse widths less than about 90 ns, and generally about 80 ns, may be used in IR-MALDI mass spectrometric detection methods.

In addition, lower electric field strength for ion extraction can be used in IR-MALDI mass spectrometric detection of target molecules. Field strengths of about less than 1000 V/mm to about 200 V/mm may typically be used in IR-MALDI mass spectrometric detection of target molecules. Furthermore, the single-shot ion signals are a factor of 3–5 times more intense than those obtained with UV-MALDI mass spectrometry, and fewer shots may be required to obtain an adequate signal-to-noise ratio.

With these improvements, the choice of laser fluence (energy per unit area on the sample) can be much less critical. Whereas in order to avoid risking substantial ion fragmentation in UV-MALDI mass spectrometry it is necessary to restrict fluence to values between $H_0$ and 1.5 $H_0$, in the disclosed IR-MALDI mass spectrometric methods for detecting target molecules, it is possible to use fluence values of up to 3 $H_0$ or 5 $H_0$, particularly when glycerol is used as a matrix.

In addition, glycerol, when used as a matrix in IR-MALDI mass spectrometry has been found to be particularly tolerant to contaminants such as salts, buffers, detergents, etc. in the sample being analyzed for the presence or absence of a target molecule. This has been surprisingly advantageous in the detection of target polypeptides, particularly large polypeptides, by IR-MALDI mass spectrometry using glycerol as a matrix because polypeptides obtained from biological samples can contain such contaminants. Such contaminants, for instance, salts, can interfere with UV-MALDI measurement of polypeptides using more traditional acidic solid state matrices. Accordingly, less purification of target molecules from biological samples is required in preparing a sample for analysis by IR-MALDI using a glycerol matrix than by UV-MALDI.

For a glycerol matrix, when used in IR-MALDI mass spectrometric methods, the molar ratio of analyte-to-matrix is much less critical than it is for crystalline matrices. Analyte-to-matrix ratios in the range of about $5 \times 10^{-3}$ and $1 \times 10^{-6}$ can be employed in IR-MALDI mass spectrometric detection of target molecules without substantial degradation of the ion signal. This is particularly advantageous in the analysis of biological samples when the concentration of target molecule may not be known.

With these improved conditions and other conditions and methods as described herein, clear ion signals for even large, e.g., greater than 500 kDa proteins and greater than 700 kDa nucleic acids, target molecules from biological samples are obtainable using IR-MALDI mass spectrometry. Thus, the detection of target molecules, particularly large target molecules, obtained from biological samples notoriously difficult to analyze due to the presence of mixtures, contaminants, impurities is made possible by IR-MALDI mass spectrometry and further is made amenable to automation as desired in large-scale diagnostic and screening procedures.

COMPOSITIONS FOR IR-MALDI ANALYSIS OF BIOLOGICAL MACROMOLECULES

Compositions, which are suitable for IR-MALDI, are provided herein. Such a composition referred to herein as a "composition for IR-MALDI," is a liquid mixture containing a biological macromolecule, which is to be analyzed by IR-MALDI, and a liquid matrix, which absorbs infrared radiation. A biological macromolecule suitable for analysis by IR-MALDI can be, for example, a nucleic acid, a polypeptide or a carbohydrate, or can be a macromolecular complex such as a nucleoprotein complex, protein-protein complex, a polysaccharide, an oligosaccharide, such as dextrans and dextrins, lipids, lipopolysaccharides and other macromolecules.

A composition for IR-MALDI contains the biological macromolecule, for example, a nucleic acid, and the liquid matrix, generally in a ratio of about $10^{-4}$ to $10^{-9}$. The composition for IR-MALDI can contain less than about 10 picomoles of biological macromolecule to be analyzed, for example, about 100 attomol to about 1 picomole (pmol) of the biological macromolecule. A composition for IR-MALDI also can contain an additive, which facilitates detection of the biological macromolecule by IR-MALDI. For example, an additive can improve the miscibility of the biological macromolecule in the liquid matrix. For example, a composition can contain a nucleic acid as the biological macromolecule to be analyzed by IR-MALDI and glycerol as the liquid matrix. The liquid matrix can be treated with a cation exchange material prior to mixing with the nucleic acid, if desired, to reduce alkali salt formation with the phosphate backbone.

A composition for IR-MALDI can be deposited on a substrate, for example, a solid support such as a silicon wafer, a bead, or other support know to those of skill in the art, thereby providing a solid support having deposited thereon a composition for IR-MALDI.

In particular, the solid support can be a silicon wafer and a plurality of compositions for IR-MALDI can be deposited on the wafer in an addressable array. If desired, a composition for IR-MALDI can contain two or more different biological macromolecules to be analyzed, provided the biological macromolecules are differentially identifiable due, for example, to mass modification.

Liquid Matrices

As defined above, a liquid matrix refers to a material that is compatible with the macromolecule of interest, absorbs IR, and can form a glass (rather than a crystalline structure). A liquid matrix has a sufficient absorption at the wavelength of the laser to be used in performing desorption and ionization and is a liquid (not a solid or a gas) at room temperature (one atmosphere pressures).

In addition, for purposes herein in performing IR-MALDI, contemplated matrices in embodiments for methods of diagnosis and detection of proteins and nucleic acids also can include materials that form crystalline structures. Such materials include, but are not limited to, water, ice and succinic acid and picolinic acid and other acids. These types of materials include those that do form ordered structures when cooled, dried and/or are under pressure. These types of matrices are contemplated for use in detection methods of proteins using IR MALDI. When succinic acid is dispensed on a selected substrate (or support) for IR MALDI, preferably, nucleic acid should be added prior to dispensing. For other matrices that are dried on the substrate, nucleic acids can be added to the dried matrix material.

For absorption purposes, the liquid matrix can contain at least one chromophore or functional group that strongly absorbs infrared radiation. Examples of appropriate functional groups include nitro, sulfonyl, sulfonic acid, sulfonamide, nitrile or cyanide, carbonyl, aldehyde, carboxylic acid, amide, ester, anhydride, ketone, amine, hydroxyl, aromatic rings, dienes and other conjugated systems.

Preferred liquid matrices, include but are not limited to, substituted or unsubstituted (1) alcohols, preferably non-volatile liquids (or liquids of low volatility), including glycols, such as glycerol, 1,2-propanediol or 1,3-propanediol, 1,2-butanediol, 1,3-butanediol, 1,4-butanediol and triethanolamine, sucrose, mannose and other polyols; (2) carboxylic acids including formic acid, lactic acid, acetic acid, propionic acid, butanoic acid, pentanoic acid and hexanoic acid, and esters thereof; (3) primary or secondary amides, including acetamide, propanamide, butanamide, pentanamide and hexanamide, whether branched or unbranched; (4) primary or secondary amines, including propylamine, butylamine, pentylamine, hexylamine, heptylamine, diethylamine and dipropylamine; (5) nitriles, hydrazine and hydrazide.

Particularly preferred compounds contain eight or fewer carbon atoms. For example, particularly preferred carboxylic acids and amides contain six or fewer carbon atoms, preferred amines contain about three to about seven carbons and preferred nitriles contain eight or fewer carbons. Compounds that are unsaturated to any degree can contain a larger number of carbons, since unsaturation confers liquid properties on a compound. Although the particular compound used as a liquid matrix must contain a functional group, the matrix preferably is not so reactive that it fragments or otherwise damages the nucleic acid to be analyzed.

An appropriate liquid matrix should be miscible with a nucleic acid compatible solvent. Preferably, the liquid matrix also should have an appropriate viscosity, for example, typically less than or equal to about 1.5 s/m$^2$, preferably in the range of about 1 s/M$^2$ to about 2 s/m$^2$, which is the viscosity of glycerol at room temperature, to facilitate dispensing of microliter or nanoliter volumes of matrix alone or mixed with a nucleic acid compatible solvent.

For use herein, a liquid matrix also should have an appropriate survival time in the vacuum of the analyzer, typically having a pressure in the range of about 10$^{-10}$ mbars, to allow the analysis to be completed. Liquids having an appropriate survival time are "vacuum stable," a property that is strictly a function of the vapor pressure of the matrix, which, in turn, is strongly dependent on the sample temperature. Preferred matrices have a low vapor pressure at room temperature such that less than about fifty percent of the sample in a mass analyzer having a back pressure less than or equal to 10$^{-5}$ mbars evaporates in the time needed for the analysis of all samples introduced, for example, about 10 minutes to about 2 hours. For a single sample, for example, the analysis may be performed in minutes, whereas, for multiple samples, the analysis may require hours for completion.

Glycerol, for example, can be used as a matrix at room temperature and in a vacuum for about 10 to 15 minutes. If glycerol is to be used for analyzing multiple samples in a single vacuum, the vacuum may need to be cooled to maintain the sample at a temperature in the range of about −50° C. to about −100° C. (about 173° K. to about 223° K.) for the time required to complete the analysis. Colder temperatures can also be used, including as low as about −200° C. Triethanolamine, in contrast, has a much lower vapor pressure than glycerol and can survive in a vacuum for at least about one hour, even at room temperature.

Mixtures of different liquid matrices and additives to such matrices may be desirable to confer one or more of the properties described above. For example, an appropriate liquid matrix can contain a small amount of a composition containing an IR absorbing chromophore and a greater amount of an IR invisible (nonabsorbing) material, in which, for example, the nucleic acid is soluble. It also may be useful to use a matrix that is "doped" with a small amount of a compound or compounds having a high extinction coefficient (E) at the laser wavelength used for desorption and ionization, for example, dinitrobenzenes or polyenes. An additive that acidifies the liquid matrix also may be added to dissociate double stranded nucleic acids or to denature secondary structure of nucleic acids such as tRNA or other RNA. Additional additives may be helpful for minimizing salt formation between the matrix and the phosphate backbone of the nucleic acid. For example, the additive can contain an ammonium salt or ammonium loaded ion exchange bead, which removes alkali ions from the matrix. Alternatively, the liquid matrix can be distilled prior to mixture with the nucleic acid composition, to minimize salt formation between the matrix and the phosphate backbone of the nucleic acid.

The liquid matrix also can be mixed with an appropriate volume of water or other liquid to control sample viscosity and rate of evaporation. Since all of the water is evaporated during mass analysis, an easily manipulated volume, for example, 1 μl, can be useful for sample preparation and transfer, but still result in a very small volume of liquid matrix. As a result, only small volumes of nucleic acid sample are required to yield about $10^{-16}$ to about $10^{-12}$ moles (about 100 attomol to about 1 pmol) of nucleic acid in the final liquid matrix droplet.

As disclosed herein, when glycerol is used as a matrix, the final analyte-to-glycerol molar ratio (concentration) should be in the range of about $10^{-4}$ to $10^{-9}$, depending on the mass of the nucleic acid, which can range up to about $10^4$ Daltons to about $10^6$ Daltons or greater, and the total amount of nucleic acid available. For example, for the sensitivity test disclosed herein, the relatively high concentration of nucleic acid used was measured by standard UV spectrophotometry. Practically speaking, the appropriate amount of nucleic acid generated, for example, from a PCR or transcription reaction generally is known. The large range specified indicates that the actual amount of nucleic acid analyzed is not very critical. Typically, a greater amount of nucleic acid results in a better spectrum. There may be instances where the nucleic acid sample requires dilution.

Other liquid matrices include, but are not limited to triethanolamine, lactic acid, 3-nitrobenzylalcohol, diethanolamine, DMSO, nitrophenyloctylether (3-N POE), 2,2'dithiodiethanol, tetraethyleneglycol, dithiotreitol/erythritol (DTT/DTE), 2,3-dihydroxy-propyl-benzyl ether, α-tocopherol, and thioglycerol.

IMMOBILIZATION OF A BIOLOGICAL MACROMOLECULE TO A SOLID SUPPORT OR SUBSTRATE

For IR-MALDI mass spectrometric analyses, a target biological macromolecule or other biological macromolecule of interest can be immobilized to a substrate, particularly a solid support, in order to facilitate manipulation of the biological macromolecule. Solid supports are well known in the art and include any material used as a solid support for linking nucleic acids, proteins, carbohydrates, or the like (see, for example, International Publ. WO 98/20019).

The substrate can be selected to be impervious to the conditions of IR-MALDI mass spectrometric analyses, and can be functionalized for the immobilization of biological macromolecules or can be further associated with a second solid support, if desired. Where a substrate, for example, a bead is to be conjugated to a second solid support, biological macromolecules can be immobilized on the functionalized bead before, during or after it is conjugated to the second support.

A biological macromolecule can be conjugated directly to a solid support or can be immobilized indirectly through a functional group present either on the support, or a linker attached to the support, or the biological macromolecule or both. For example, a polypeptide can be immobilized to a solid support through a hydrophobic, hydrophilic or ionic interaction between the support and the polypeptide. Although such a method can be useful for certain manipulations such as for conditioning of the biological macromolecule prior to IR-MALDI mass spectrometry, such a direct interaction is limited in that the orientation of the biological macromolecule is not known and can be random based on the position of the interacting subunits, for example, hydrophobic amino acids in a polypeptide. Thus, a polypeptide or other biological macromolecule generally is immobilized in a defined orientation by conjugation through a functional group on either the solid support or the biological macromolecule or both.

A biological macromolecule can be modified by adding an appropriate functional group to a terminus of the biological macromolecule, for example, to the 5' or 3' end of a nucleic acid, or to the carboxyl terminus or amino terminus of a polypeptide, or to a reactive group in the biological macromolecule, for example, to a reactive group of a nucleotide or to the phosphodiester backbone of a nucleic acid, or to a reactive side chain of an amino acid or to the peptide backbone of a polypeptide. A naturally occurring nucleotide in a nucleic acid or a naturally occurring amino acid in a polypeptide also can contain a functional group suitable for conjugating the polypeptide to the solid support. For example, a cysteine residue present in the polypeptide can be used to immobilize the polypeptide to a substrate containing a sulfhydryl group, for example, a solid support having cysteine residues attached thereto, through a disulfide linkage. Other bonds that can be formed between two amino acids, for example, include monosulfide bonds between two lanthionine residues, which are non-naturally occurring amino acids that can be incorporated into a polypeptide; a lactam bond formed by a transamidation reaction between the side chains of an acidic amino acid and a basic amino acid, such as between the γ-carboxyl group of Glu (or β-carboxyl group of Asp) and the ε-amino group of Lys; or a lactone bond produced, for example, by a crosslink between the hydroxy group of Ser and the γ-carboxyl group of Glu (or β-carboxyl group of Asp). Thus, a solid support can be modified to contain a desired amino acid residue, for example, a Glu residue, and a polypeptide having a Ser residue, particularly a Ser residue at the carboxyl terminus or amino terminus, can be conjugated to the solid support through the formation of a lactone bond. It should be recognized, however, that the support need not be modified to contain the particular amino acid, for example, Glu, where it is desired to form a lactone-like bond with a Ser in the polypeptide, but can be modified, instead, to contain an accessible carboxyl group, thus providing a function corresponding to the γ-carboxyl group of Glu.

A biological macromolecule can be modified to facilitate immobilization to a solid support, for example, by incorporating a chemical or physical moiety at an appropriate position in the biological macromolecule, generally at a terminus of the biological macromolecule. The artisan will recognize, however, that such a modification, for example, the incorporation of a biotin moiety, can affect the ability of a particular reagent to interact specifically with the biological macromolecule and, accordingly, will consider this factor, if relevant, in selecting how best to modify a biological macromolecule of interest.

In one aspect of the processes provided herein, a polypeptide of interest can be covalently conjugated to a solid support and the immobilized polypeptide can be used to capture a target polypeptide, which binds to the immobilized polypeptide. The target polypeptide then can be released from immobilized polypeptide by ionization or volatilization for IR-MALDI mass spectrometry, whereas the covalently conjugated polypeptide remains-bound to the support.

Accordingly, a process as disclosed herein can utilize IR-MALDI to determine the identity of polypeptides that interact specifically with a polypeptide of interest. For example, the identity of target polypeptides obtained from one or more biological samples that interact specifically with a immobilized polypeptide of interest can be determined, or the identity of binding proteins such as antibodies that bind to the immobilized polypeptide antigen of interest, or receptors that bind to an immobilized polypeptide ligand of interest, or the like can be determined. Such a process can be useful, for example, for screening a combinatorial library of modified target polypeptides such as modified antibodies, antigens, receptors, hormones, or other polypeptides to determine the identity of those target polypeptides that interact specifically with the immobilized polypeptide.

A solid support can be selected based on advantages that it can provide. For example, a solid support can provide a relatively large surface area, thereby allowing immobilization of a relatively large number of biological macromolecules. A solid support such as a bead can have any three dimensional structure, including a surface to which a biological macromolecule, functional group, or other molecule can be attached.

A substrate also can be modified to facilitate immobilization of a biological macromolecule. A thiol-reactive functionality is particularly useful for immobilizing a polypeptide to a solid support (International Publ. WO 98/20166). A thiol-reactive functionality can rapidly react with a nucleophilic thiol moiety to produce a covalent bond, for example, a disulfide bond or a thioether bond. A variety of thiol-reactive functionalities are known in the art, including, for example, haloacetyls such as iodoacetyl; diazoketones; epoxy ketones; α- and β-unsaturated carbonyls such as α-enones and β-enones; and other reactive Michael acceptors such as maleimide; acid halides; benzyl halides; and the like. A free thiol group of a disulfide, for example, can react with a second free thiol group by disulfide bond formation, including by disulfide exchange. Reaction of a thiol group or other functional group can be prevented temporarily by blocking with an appropriate protecting group (see Greene and Wuts, *Protective Groups in Organic Synthesis* 2nd ed. (John Wiley & Sons 1991)).

A thiol-reactive functionality such as 3-mercaptopropyltriethoxy-silane can be used to functionalize a silicon surface with thiol groups. The amino functionalized silicon surface then can be reacted with a heterobifunctional reagent such as N-succinimidyl (4-iodacetyl) aminobenzoate (SIAB; Pierce; Rockford Ill.). If desired, the thiol groups can be blocked with a photocleavable protecting group, which then can be selectively cleaved, for example, by photolithography, to provide portions of a surface activated for immobilization of a polypeptide of interest. Photocleavable protecting groups are known in the art (see, for example, International Publ. WO 92/10092; McCray et al., *Ann. Rev. Biophys. Biophys. Chem.* 18:239–270 (1989)) and can be selectively deblocked by irradiation of selected areas of the surface using, for example, a photolithography mask.

Solid Supports (Substrates)

The solid support is any known to those of skill in the art as matrix for performing synthetic reactions and assays. It can be fabricated from silicon, glass, silicon-coated materials, metal, a composite, a polymeric material such as a plastic, a polymer-grafted material, such as a metal-grafted polymer, or other material as disclosed herein. This material can be further functionalized, as necessary, for example, chemically, to enhance or permit linkage of molecules or other particles, such as cells or cell membranes or viral envelopes or other such biological materials, of interest. The surface of a support can be modified, such as by radiation grafting of a suitable polymer on the surface and derivatization thereof to render it suitable for binding capturing a molecule or particle, such as a cell. The support may also include beads linked thereto (see, copending allowed U.S. application Ser. No. 08/746,036, U.S. Pat. No. 5,900,481, copendin U.S. application Ser. No. 08/933,792, U.S. Pat. No. 6,133,436 and International application No. PCT/US97/20194, which claims priority to the U.S. applications). It may also include dendrite trees of captured material, or combinations of such additional components. A solid support can have one or more target sites, each of which can contain or retain a volume of a liquid.

By way of example, a solid support can be a flat surface such as a glass fiber filter, a glass surface, a silicon or silicon dioxide surface, a composite surface, or a metal surface, including a steel, gold, silver, aluminum or copper surface, a plastic material, including polyethylene, polypropylene, polyamide or polyvinylidenedifluoride, which further can be in the form of multiwell plate or a membrane: can be in the form of a bead (or other geometry) or particle, such as a silica gel, a controlled pore glass, a magnetic or cellulose bead, which can be in a pit of a flat surface such as a wafer, for example, a silicon wafer; or can be a pin, including an array of pins suitable for combinatorial synthesis or analysis (see, e.g., International PCT application No. WO98/20019), comb, microchip. The skilled artisan will recognize that various factors, including the size and shape of the support and the chemical and physical stability of the support to the conditions to which it will be exposed, will be considered in selecting a particular solid support for use in a disclosed system or method.

Also contemplated is the use of the end of a fiber optic cable or plate as a substrate or support (see, e.g., U.S. Pat. No. 5,826,214, which describes embodiments in which the electromagnetic radiation is delivered via a fiber optic cable, which can abut against a thin transparent plate on which the specimen or resides).

A solid support contains one or more target sites, which can contain a volume of a liquid. A target site can be, for example, a well, pit, channel, or other depression, with or without rims, on the surface of a solid support; can be a pin, bead or other material, which can be positioned on a surface of a solid support; or can be a physical barrier such as a cylinder, cone or other such barrier positioned on a surface of a solid support.

A target site also can be, for example, a reservoir or reaction chamber, which is attached to a solid support (see, for example, Walters et al., *Anal. Chem.* 70:5172–5176 (1998)). In addition, a target site can be etched, for example, on a surface of a silicon wafer using a photolithographic method (see, for example, Woolley et al. (*Anal. Chem.* 68:4081–4086 (1996)). Photolithography allows the construction of very small target sites, including wells or towers, and, for example, has been used in combination with wet chemical-etching to construct "picoliter vials" on microchips (Clark et al. *CHEMTECH* 28:20–25 (1998)).

A support also can be a glass or silicon surface containing wells having a very thin base that is transparent to electromagnetic radiation of a desired wavelength, such as laser light, thereby permitting measurement of parameters, such as volume, or an excitation wavelength for fluorescence measurement.

A target site also can be defined by physico-chemical parameters such as hydrophilicity, hydrophobicity, the presence of acidic or basic groups, groups capable of forming a salt bridge, or any surface chemistry that allows a liquid to grow primarily in the z direction. For example, where the liquid to be placed on a target site is water or an aqueous composition, the target site can be defined by a hydrophilic area surrounded by a hydrophobic area on the surface of a solid support, or by a series of rows, alternately having less hydrophobic rows and more hydrophobic rows, whereby the aqueous mixture is constrained to the less hydrophobic rows. With respect to such a target site, the aqueous composition is dispensed, for example, onto the hydrophilic area, and is constrained from spreading from the target site due to the adjacent and surrounding hydrophobic area. Conversely, where the liquid is a nonpolar liquid, it is dispensed onto a hydrophobic region and is constrained in that region due to an adjacent hydrophilic region or a region or that is less hydrophobic that the region to which the liquid is applied.

A solid support can have a single target site, or can contain a number of target sites, for example, 2 sites, 10 sites, 16 sites, 100 sites, 144 sites, 384 sites, 1000 sites, or more, all or some of which can be the same or can be different. Where a solid support contains more than one target site and, therefore, can contain, for example, more than one reaction mixture, the characteristics that define each target site serve not only to constrain a reaction mixture, but also to prevent intermingling of different reaction mixtures or other liquids on the support. In addition, where a solid support contains more than one target site, the target sites can be arranged in any pattern, for example, in a line, a spiral, concentric circles, rows, or an array of rows and columns. Furthermore, the location of each target site of a number of target sites on a support can be defined. The availability of such addressable target sites on a solid support allows multiple reactions to be performed in parallel and is convenient, for example, for performing multiplex reactions, for including control reactions with test reactions such that all are performed under identical conditions, for performing a similar reaction under different conditions, or for performing different reactions.

Thus, any substrate on which the nucleic acid/liquid matrix can be deposited and retained for desorption and ionization of the nucleic acid can be used in a process provided herein. Preferred substrates include, but are not limited to beads, for example, silica gel, controlled pore glass, magnetic, cross-linked dextrans, such as those sold under the tradename Sephadex (Pharmacia) and agarose gel, such as gels sold under the tradename Sepharose (Pharmacia), which is a hydrogen bonded polysaccharide-type agarose gel (epichlorhydrins), or cellulose; capillaries; flat supports, for example, filters, plates or membranes made of glass, metal surfaces such as steel, gold, silver, aluminum, copper or silicon, or plastic such as polyethylene, polypropylene, polyamide or polyvinylidene fluoride; pins, for example, arrays of pins suitable for combinatorial synthesis or analysis of beads in pits of flat surfaces such as wafers, with or without filter plates.

Preferably the selected substrate and format are amenable to miniaturization, such as the chips that retain the deposited material by virtue of hydrophobic or hydrophilic interaction, described above, in which the target site can be defined by a hydrophilic area surrounded by a hydrophobic area on the surface of a solid support (or the converse).

Preferably, nucleic acid samples are prepared and deposited as a thin layer, for example, a monolayer to about a 100 μm layer, preferably between about 0.1 μm and about 100 μm, more preferably 1 μm to 10 μm, onto a substrate manually or using an automated device, so that multiple samples can be prepared and analyzed on a single sample support plate with only one transfer into the vacuum of the analyzer and requiring only a relatively short period of time for analysis. Appropriate automated sample handling systems for use in the instant process are described, for example, in U.S. Pat. Nos. 5,705,813; 5,716,825; and 5,498,545 and co-pending U.S. application Ser. No. 09/285,481, as well as allowed U.S. application Ser. No. 08/787,639, U.S. Pat. No. 6,024,925 and published International PCT application WO 98/20166.

Immobilization and Activation

Numerous methods have been developed for the immobilization of proteins, nucleic acids and other biomolecules onto solid or liquid supports [see, e.g., Mosbach (1976) *Methods in Enzymology* 44; Weetall (1975) *Immobilized Enzymes, Antigens, Antibodies, and Peptides*; and Kennedy et al. (1983) *Solid Phase Biochemistry, Analytical and Synthetic Aspects*, Scouten, ed., pp. 253–391; see, generally, *Affinity Techniques. Enzyme Purification: Part B. Methods in Enzymology*, Vol. 34, ed. W. B. Jakoby, M. Wilchek, Acad. Press, N.Y. (1974); *Immobilized Biochemicals and Affinity Chromatography, Advances in Experimental Medicine and Biology*, vol. 42, ed. R. Dunlap, Plenum Press, N.Y. (1974)].

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art [see, e.g., the PIERCE CATALOG, ImmunoTechnology Catalog & Handbook, 1992–1993, which describes the preparation of and use of such reagents and provides a commercial source for such reagents; and Wong (1993) *Chemistry of Protein Conjugation and Cross Linking*, CRC Press; see, also DeWitt et al. (1993) *Proc. Natl. Acad. Sci. U.S.A.* 90:6909; Zuckermann et al. (1992) *J. Am. Chem. Soc.* 114:10646; Kurth et al. (1994) *J. Am. Chem. Soc.* 116:2661; Ellman et al. (1994) *Proc. Natl. Acad. Sci. U.S.A.* 91:4708; Sucholeiki (1994) *Tetrahedron Lttrs.* 35:7307; and Su-Sun Wang (1976) *J. Org. Chem.* 41:3258; Padwa et al. (1971) *J. Org. Chem.* 41:3550 and Vedejs et al. (1984) *J. Org. Chem.* 49:575, which describe photosensitive linkers]

To effect immobilization, a composition of the protein or other biomolecule is contacted with the support material such as any described herein, alumina, carbon, an ion-exchange resin, cellulose, glass or a ceramic. Fluorocarbon polymers have been used as supports to which biomolecules have been attached by adsorption [see, U.S. Pat. No. 3,843,443; Published International PCT Application WO/86 03840].

A large variety of methods are known for attaching biological molecules, including proteins and nucleic acids, molecules to solid supports [see. e.g., U.S. Pat. No. 5,451,683]. Such linkages may be effected through covalent bonds, ionic bonds and other interactions. The linkages may be reversible or labile to certain conditions, such as particular EM frequencies.

For example, U.S. Pat. No. 4,681,870 describes a method for introducing free amino or carboxyl groups onto a silica support. These groups may subsequently be covalently linked to other groups, such as a protein or other anti-ligand, in the presence of a carbodiimide. Alternatively, a silica support may be activated by treatment with a cyanogen halide under alkaline conditions. The anti-ligand is covalently attached to the surface upon addition to the activated surface. Another method involves modification of a polymer surface through the successive application of multiple layers of biotin, avidin and extenders [see, e.g., U.S. Pat. No. 4,282,287]; other methods involve photoactivation in which a polypeptide chain is attached to a solid substrate by incorporating a light-sensitive unnatural amino acid group into the polypeptide chain and exposing the product to low-energy ultraviolet light [see, e.g., U.S. Pat. No. 4,762,881].

Oligonucleotides have also been attached using a photochemically active reagents, such as a psoralen compound, and a coupling agent, which attaches the photoreagent to the substrate [see, e.g., U.S. Pat. No. 4,542,102 and U.S. Pat. No. 4,562,1571. Photoactivation of the photoreagent binds a nucleic acid molecule to the substrate to give a surface-bound probe.

Covalent binding of the protein or other biomolecule or organic molecule or biological particle to chemically activated solid support supports such as glass, synthetic polymers, and cross-linked polysaccharides is a more frequently used immobilization technique. The molecule or biological particle may be directly linked to the support or linked via linker, such as a metal [see, e.g., U.S. Pat. No. 4,179,402; and Smith et al. (1992) *Methods: A Companion to Methods in Enz.* 4:73–78]. An example of this method is the cyanogen bromide activation of polysaccharide supports, such as agarose. The use of perfluorocarbon polymer-based supports for enzyme immobilization and affinity chromatography is described in U.S. Pat. No. 4,885,250]. In this method the biomolecule is first modified by reaction with a perfluoroalkylating agent such as perfluorooctylpropylisocyanate described in U.S. Pat. No. 4,954,444. Then, the modified protein is adsorbed onto the fluorocarbon support to effect immobilization.

The activation and use of supports are well known and may be effected by any such known methods [see, e.g., Hermanson et al. (1992) *Immobilized Affinity Ligand Techniques*, Academic Press, Inc., San Diego]. For example, the coupling of the amino acids may be accomplished by techniques familiar to those in the art and provided, for example, in Stewart and Young, 1984, *Solid Phase Synthesis*, Second Edition, Pierce Chemical Co., Rockford.

Molecules may also be attached to supports through kinetically inert metal ion linkages, such as Co(III), using, for example, native metal binding sites on the molecules, such as IgG binding sequences, or genetically modified proteins that bind metal ions [see, e.g., Smith et al. (1992) *Methods: A Companion to Methods in Enzymology* 4, 73 (1992); III et al. (1993) *Biophys J.* 64:919; Loetscher et al. (1992) *J. Chromatography* 595:113–199; U.S. Pat. No. 5,443,816; Hale (1995) *Analytical Biochem.* 231:46–49].

Other suitable methods for linking molecules and biological particles to solid supports are well known to those of skill in this art [see, e.g., U.S. Pat. No. 5,416,193]. These linkers include linkers that are suitable for chemically linking molecules, such as proteins and nucleic acid, to supports include, but are not limited to, disulfide bonds, thioether bonds, hindered disulfide bonds, and covalent bonds between free reactive groups, such as amine and thiol groups. These bonds can be produced using heterobifunctional reagents to produce reactive thiol groups on one or both of the moieties and then reacting the thiol groups on one moiety with reactive thiol groups or amine groups to which reactive maleimido groups or thiol groups can be attached on the other. Other linkers include, acid cleavable linkers, such as bismaleimidoethoxy propane, acid labile-transferrin conjugates and adipic acid dihydrazide that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) *Molecular Immunol.* 30:379–386). Presently preferred linkages are direct linkages effected by adsorbing the molecule or biological particle to the surface of the support. Other preferred linkages are photocleavable linkages that can be activated by exposure to light [see, e.g., Goldmacher et al. (1992) *Bioconj. Chem.* 3:104–107, which linkers are herein incorporated by reference]. The photocleavable linker is selected such that the cleaving wavelength that does not damage linked moieties. Photocleavable linkers are linkers that are cleaved upon exposure to light [see, e.g., Hazum et al. (1981) in *Pept., Proc. Eur. Pept. Symp.*, 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages]. The selected linker will depend upon the particular application and, if needed, may be empirically selected.

Linkers

A biological macromolecule can be immobilized directly to a substrate or can be immobilized through a linking moiety or moieties. Immobilization can be effected by any desired linkage including covalent linkages, ionic linkages, physical linkages, and any other linkages known. The linkage can be reversible and/or cleavable. Any linker known to those of skill in the art to be suitable for immobilizing a nucleic acid, polypeptide, carbohydrate or other biological macromolecule to a substrate, either directly or through a spacer, can be used (see International Publ. WO 98/20019). Among preferred linkers are those that are cleave or otherwise release upon exposure to IR.

A biological macromolecule can be immobilized directly to a support through a linker or can be immobilized through a variable spacer. In addition, the conjugation can be directly cleavable, for example, through a photocleavable linkage such as a streptavidin or avidin to biotin interaction, which can be cleaved by a laser, or indirectly through a photocleavable linker (U.S. Pat. No. 5,643,722) or an acid labile linker, heat sensitive linker, enzymatically cleavable linker or other such linker. Accordingly, a linker can provide a reversible linkage such that it is cleaved under defined conditions such as during the IR-MALDI mass spectrometry procedure. Such a linker can be, for example, a photocleavable bond such as a charge transfer complex or a labile bond formed between relatively stable organic radicals.

A linker (L) on a biological macromolecule can form a linkage, which generally is a temporary linkage, with a second functional group (L') on the solid support. Furthermore, where the biological macromolecule has a net negative charge, or is conditioned to have such a charge, the linkage can be formed with L' being, for example, a quaternary ammonium group. In this case, the surface of the solid support carries a negative charge that repels the negatively charged biological macromolecule, thereby facilitating desorption of the biological macromolecule for IR-MALDI mass spectrometric analysis. Desorption can occur due to the heat created by the IR radiation or, where L' is a chromophore, by specific absorption of IR radiation by the chromophore.

A linkage (L–L') can be, for example, a disulfide bond, which is chemically cleavable by mercaptoethanol or dithioerythrol; a biotin/streptavidin linkage, which can be photocleavable; a heterobifunctional derivative of a trityl ether group, which can be cleaved by exposure to acidic conditions (see Köster et al., *Tetrahedron Lett.* 31:7095 (1990)); leuvinyl-mediated linkage, which can be cleaved under almost neutral conditions with a hydrazinium/acetate buffer; an arginine-arginine or a lysine-lysine bond, either of which can be cleaved by an endopeptidase such as trypsin; a pyrophosphate bond, which can be cleaved by a pyrophosphatase; or a ribonucleotide bond, which can be cleaved using a ribonuclease or by exposure to alkali condition.

The functionalities, L and L', can also form a charge transfer complex, thereby forming a temporary L–L' linkage. The IR laser energy can be tuned to the corresponding energy of the charge-transfer wavelength and specific desorption from the solid support can be initiated. It will be recognized that several combinations of L and L' can serve this purpose and that the donor functionality can be on the solid support or can be coupled to the biological macromolecule to be detected or vice versa, provided a liquid matrix, which absorbs IR radiation, also is present.

Selectively cleavable linkers that are particularly useful in a process as disclosed herein include photocleavable linkers, acid cleavable linkers, acid-labile linkers, and heat sensitive linkers. Acid cleavable linkers include, for example, bis-maleimideothoxy propane, adipic acid dihydrazide linkers (Fattom et al., *Infect. Immun.* 60:584–589 (1992)), and acid labile transferrin conjugates that contain a sufficient portion of transferrin to permit entry into the intracellular transferrin cycling pathway (Welhöner et al., *J. Biol. Chem.* 266:4309–4314 (1991)). Photocleavable linkers also include the linkers described in WO 98/20019.

Linkers suitable for chemically linking polypeptides, for example, to supports, include disulfide bonds, thioether bonds, hindered disulfide bonds, and covalent bonds between free reactive groups such as amine and thiol groups.

Agents useful for creating linkages include, for example, dimaleimide, dithio-bis-nitrobenzoic acid (DTNB), N-succinimidyl-S-acetyl-thioacetate (SATA), N-succinimidyl-3-(2-pyridyidithiol propionate (SPDP), succinimidyl 4-(N-maleimidomethyl)cyclohexane-1-carboxylate (SMCC) 6-hydrazino nicotimide (HYNIC). Appropriate linkers, which can be crosslinking agents, for use for conjugating a polypeptide to a solid support include a variety of agents that can react with a functional group present on a surface of the support, or with the polypeptide, or both. Useful crosslinking agents include agents containing homobifunctional or heterobifunctional groups. Useful bifunctional crosslinking agents include, but are not limited to, N-succinimidyl(4-iodoacetyl) aminobenzoate (SIAB), dimaleimide, dithio-bis-nitrobenzoic acid (DTNB), N-succinimidyl-S-acetyl-thioacetate (SATA), N-succinimidyl-3-(2-pyridyidithio) propionate (SPDP), succinimidyl 4-(N-maleimidomethyl)cyclohexane-1-carboxylate (SMCC) and 6-hydrazino-nicotimide (HYNIC).

A crosslinking agent also can be used to form a selectively cleavable bond between a biological macromolecule and a solid support. For example, a photolabile crosslinker such as 3-amino-(2-nitrophenyl)-propionic acid (Brown et al., *Molec. Divers.* 4–12 (1995); Rothschild et al., *Nucl. Acids Res.* 24:351–66 (1996); U.S. Pat. No. 5,643,722) can be employed as a means for cleaving a polypeptide from a solid support. Other crosslinking reagents are well known in the art (see, for example, Wong, *Chemistry of Protein Conjugation and Cross-Linking* (CRC Press 1991); Hermanson, *Bioconjugate Techniques* (Academic Press 1996)).

Hydroxyester linkers, including, for example, hydroxyacetate (glycolate), $\alpha$-, $\beta$-, $\gamma$-, ..., $\omega$-hydroxyalkanoates, $\omega$-hydroxy(polyethylene-glycol)COOH, hydroxybenzoates, hydroxyarylalkanoates and hydroxyalkylbenzoates, can be useful for immobilizing a biological macromolecule. Photocleavable linkers also are useful for immobilizing a biological macromolecule; methods of preparing such linkers are provided in International Publ. WO 98/20019. In addition, a bifunctional trityl linker can be attached to a solid support, for example, to the 4-nitrophenyl active ester on a resin such as a Wang resin, through an amino group or a carboxyl group on the resin via an amino resin. Using a bifunctional trityl approach, the solid support can require treatrnent with a volatile acid such as formic acid or trifluoroacetic acid to ensure that the biological macromolecule can be removed. In such a case, the biological macromolecule can be deposited as a beadless patch at the bottom of a well of a solid support or on the flat surface of a solid support. After addition of a matrix composition, the biological macromolecule can be desorbed during IR-MALDI mass spectrometry.

Hydrophobic trityl linkers also can be exploited as acid-labile linkers by using a volatile acid or an appropriate matrix composition, which is acidic or contains an additive that renders the liquid matrix acidic, to cleave an amino linked trityl group from the biological macromolecule. Acid lability also can be changed. For example, trityl, monomethoxytrityl, dimethoxytrityl or trimethoxytrityl can be changed to the appropriate p-substituted, or more acid-labile trityalmine derivatives.

Other linkers, include, for example, Rink amide linkers (Rink, *Tetrahedron Letters* 28:3787 (1976)), tritylchloride linkers (Leznoff, *Ace. Chem. Res.* 11:327 (1978)), Merrifield linkers (Bodansky et al., *Peptide Synthesis* 2d ed., Academic Press; New York, 1986); trityl linkers (U.S. Pat. Nos. 5,410,068 and 5,612,474); and amino trityl linkers (U.S. Pat. No. 5,198,531).

Other linkers include acid cleavable linkers such as bis-maleimidoethoxy propane, acid labile transferrin conjugates and adipic acid dihydrazide linkers that can be cleaved in more acidic intracellular compartments; photocleavable cross linkers that are cleaved by IR, visible or UV light, RNA linkers that are cleavable by ribozymes or other RNA enzymes, and linkers such as the various domains, including $C_H1$, $C_H2$, and $C_H3$, from the constant region of human $IgG_1$ (see, Batra et al., *Mol. Immunol.* 30:379–386 (1993)). Combinations of any linkers also can be useful, for example, a linker that can be cleavable under IR-MALDI mass spectrometric conditions such as a silyl linkage or photocleavable linkage can be combined with a linker such as an avidin biotin linkage, which is not cleaved under IR-MALDI mass spectrometry conditions but can be cleaved under other conditions.

A biological macromolecule of interest can be immobilized to a solid support such as a bead. In addition, a first solid support such as a bead also can be conjugated to a second solid support, which can be a second bead or other substrate, by any suitable means. In particular, any of the conjugation methods and means disclosed herein with reference to conjugation of a biological macromolecule to a solid support also can be applied for conjugation of a first support to a second support, where the first and second solid supports can be the same or different. Furthermore, use of bifunctional linkers allows for orthogonal cleavage of a biological macromolecule from a support, or of a first support from a second.

It should be recognized that any of the binding members disclosed herein or otherwise known in the art can be reversed with respect to the examples provided herein. Thus, biotin, for example, can be incorporated into either a biological macromolecule or a solid support and, conversely, avidin or other biotin binding moiety would be incorporated into the support or the polypeptide, respectively. Other specific binding pairs contemplated for use herein are exemplified by hormones and their receptors, enzymes and their substrates, a nucleotide sequence and its complementary sequence, an antibody and the antigen to which it interacts specifically, and other such pairs known to those skilled in the art.

A target biological macromolecule, particularly each target biological macromolecule in a plurality of target biological macromolecules, can be immobilized to a solid support prior to mass modifying, conditioning, or otherwise manipulating the biological macromolecule. In particular, the solid support can be a flat surface, or a surface with a structure such as wells, such that each of the target biological macromolecules in the plurality can be positioned in an array, each at a particular address. In general, a target biological macromolecule is immobilized to the solid support through a cleavable linker such as an acid labile linker, a chemically cleavable linker or a photocleavable linker. Following a reaction of the target biological macromolecule in a disclosed process, undesirable reaction products can be washed from the reaction and the remaining immobilized target biological macromolecule can be released, for example, by chemical cleavage or photocleavage, as appropriate, and can be analyzed by IR-MALDI mass spectrometry. It should be recognized, however, that manipulation of a biological macromolecule, for example, by mass modification prior to performing a chemical or enzymatic degradation or other reaction can influence the rate or extent of the reaction. Accordingly, the skilled artisan will know that the influence of conditioning, mass modification, or the like on the extent of a reaction should be characterized prior to initiating a process.

In some cases, it can be useful to immobilize a particular target biological macromolecule to a support through both termini of the biological macromolecule, for example, the amino terminus and the carboxyl terminus of a polypeptide using, for example, a chemically cleavable linker at one terminus and a photocleavable linker at the other end. In this way, the target biological macromolecule, which can be immobilized, for example, in an array in wells, can be contacted, for example, with one or more agents that cleave at least one bond linking the monomer subunits in the biological macromolecule, the internal biological macromolecule fragments then can be washed from the wells, along with the agent and any reagents in the well, leaving one biological macromolecule fragment of the target biological macromolecule immobilized to the solid support through the chemically cleavable linker and a second biological macromolecule fragment, from the opposite end of the target biological macromolecule, immobilized through the photocleavable linker. Each fragment then can be further manipulated using a process as disclosed herein or can be analyzed by IR-MALDI mass spectrometry following sequential cleavage of the fragments, for example, after first cleaving the chemically cleavable linker, then cleaving the photocleavable linker. Such a process provides a convenient means of analyzing both termini of a biological macromolecule, thereby facilitating analysis of the target biological macromolecule.

Immobilization of a target biological macromolecule at both termini can be performed by modifying both ends of the biological macromolecule, for example, one terminus being modified to allow formation of a chemically cleavable linkage with the solid support and the other terminus being modified to allow formation of a photocleavable linkage with the solid support. Alternatively, the biological macromolecules can be split into two portions, one portion being modified at one terminus allow formation, for example, of a chemically cleavable linkage, and the second portion being modified at the other terminus to allow formation, for example, of a photocleavable linkage. The two populations of modified biological macromolecules then can be immobilized, together, on a solid support containing the appropriate functional groups for completing immobilization.

IR-MALDI MASS SPECTROMETRIC ANALYSIS OF BIOLOGICAL MACROMOLECULES

The processes disclosed herein are useful for analyzing a biological macromolecule by subjecting a composition containing the biological macromolecule and a liquid matrix, which absorbs IR radiation, to IR-MALDI mass spectrometry. Depending on the process selected, the presence of a biological macromolecule can be detected, for example, in a biological sample; or a particular biological macromolecule can be identified, for example, by comparison to a corresponding known biological macromolecule, or by determining its molecular mass or at least a part of its subunit sequence (see, for example, U.S. Pat. Nos. 5,503,980; 5,547,835; 5,605,798; and 5,691,194; see, also, International Publs. WO 94/16101; WO 94/21822, WO 96/29431; WO 97/37041; WO 97/42348; and WO 98/20019).

Mass Spectrometric Analysis Using an IR Laser

The support containing a sample can be placed in a vacuum chamber of a mass analyzer to identify or detect the nucleic acid in the sample. Preferably, the mass analyzer can maintain the temperature of a sample at a preselected value, for example, a temperature in the range of at least about −200° C. to about 80° C., preferably at least about −60° C. to about 40° C., more preferably −200° C. to about 20° C., and most preferably about −60° C. to about 20° C., during sample preparation, disposition and/or analysis. For example, improved spectra may be obtained, in some instances, by cooling the sample to a temperature below room temperature during sample preparation or mass analysis. Further, as described above, the vacuum stability of a matrix may be increased by cooling. Alternatively, it may be useful to heat a sample to denature double stranded nucleic acids into single strands or to decrease the viscosity during sample preparation.

Desorption and ionization of the sample is performed in the mass analyzer using infrared radiation. Preferred infrared wavelengths include the mid-IR wavelength region, from about 2.5 µm to about 12 µm. Preferred sources of infrared radiation are CO lasers, which emit at about 6 µm; $CO_2$ lasers, which emit at about 9.2 µm to 11 µm; Er lasers, with any of a variety of crystals, for example, Er-YAG (yttrium-aluminum-garnet), Er-YILF or Er-YSGG, emitting at wavelengths about 3 µm; and optical paramagnetic oscillator lasers emitting in the range of about 2.5 µm to about 12 µm.

Pulse Duration, Field Strength and Other Parameters

Solid state Erbium lasers with pulse widths around 100 ns can be used for infrared Matrix-Assisted Laser Desorption/Ionization mass spectrometry (IR-MALDI MS) [Overberg et al, *Rapid Commun. Mass Spectrom.*, 1990, 4, 293–296; Berkenkamp et al., *Rapid Commun. Mass Spectrom.*, 1997, 11, 1399–1406]. Optical parametric oscillators (OPO) with pulse durations of a few nanoseconds may also be used in IR-MALDI MS. The fixed pulse width of the OPO systems of a few nanoseconds is determined by the pump laser. The pulse duration and/or size of the irradiated area (spot size) can be varied to generate multiple charged ions. A preferred pulse duration is in the range of about 100 picoseconds (psec) to about 500 nanoseconds (ns).

An Er:YAG- and an OPO laser were used to investigate pulse width and wavelength dependence of IR-MALDI-MS in the 5–200 ns pulse width and 3 µm wavelength region. For laser pulse durations from 90 to 185 ns an Er:YAG laser (Spektrum GmbH, Berlin, Germany, wavelength λ=2.94 µm) was used. The pulse duration was varied by changing the Q-switch delay time. For the Nd:YAG pumped OPO laser (Mirage 3000B, Continuum, Santa Clara, Calif., USA) the pulse width was fixed at 6 ns, whereas this system is tunable from 2.2 µm to 4.0 µm. The wavelength scale was calibrated to an accuracy of ±5 nanometers. An in-house-built TOF instrument with a linear (2.2 m) and a reflectron port (3.5 m equivalent flight length) was used. The mass spectrometer can be operated with static or delayed ion extraction. Special optics were implemented to permit a rapid interchange of the two laser beams. A 150 µm pinhole was illuminated by the central part of the Gaussian beams and imaged onto the sample to ensure a homogeneous and equal sample illumination for both lasers. All spectra were obtained under identical instrumental conditions and from identical samples.

Results: a) To a first approximation the threshold fluences for the generation of Cytochrome C mass spectra were independent of the pulse duration in the range of 6 to 185 ns.

| Laser System | $H_0/J\ m^{-2}$ | | |
|---|---|---|---|
| | Succinic acid | Thiourea | Glycerol |
| OPO (τ = 6 ns) | 3564 ± 695 | 2053 ± 296 | 4186 ± 143 |
| Er:YAG (τ = 98 ns) | 4304 ± 538 | 3433 ± 127 | 4992 ± 118 |
| Er:YAG (τ = 185 ns) | 4591 ± 532 | 3398 ± 398 | 4941 ± 730 |

For the OPO-systems the threshold fluences were consistently and statistically significantly lower by up to a factor of 1.5 as compared to the Er:YAG laser. H$_0$wever, the irradiances of ~50 MW/cm² (τ=6 ns) for the OPO system and of ~2 MW/cm² (τ=18.5 ns) for the Er:YAG laser differ by a factor of ~25. It is, therefore, concluded, that the desorption in IR-MALDI is governed by the deposited energy per unit volume, rather than the peak power or irradiance for pulse durations up to 200 ns.

b) Within the experimental error, mass resolution for signals of peptides, desorbed out of a succinic acid matrix, was observed to be independent of the pulse width within the range of 6–100 ns for static and delayed ion extraction. For longer pulses up to 200 ns and static ion extraction the resolution decreased by up to a factor of two. In the analysis of the influence of laser pulse widths on the peak resolution of Gramicidin S, an optimal resolution of m/Δm=11000 was observed for 6 ns OPO laser pulses with delayed ion extraction, as well as for 100 ns Erbium laser pulses in the linear mode of the mass spectrometer.

c) For the 6 ns pulses an increase in the abundance of multiply charged ions and a decrease of signals of oligomers was observed, as compared to 100 ns pulses.

d) The threshold fluence for the generation of IR-MALDI spectra was determined in the wavelength range from 2.6 µm to 3.6 µm for several solid and liquid matrices with the OPO laser system. They were compared to the corresponding transmission spectra of the matrices [Merke, R., Langenbucher, F., *Infrared Spectra*, Heyden & Co., Freiburg, 1964]. A clear correlation between the threshold fluences for succinic acid and glycerol on their (inverse) transmission was observed in a study of the influence of laser wavelength A on the threshold fluence $H_0$ of cytochrome C. For glycerol the double peak structure is clearly reproduced. A similar behavior was observed for triethanolamine. For succinic acid the threshold fluence follows the absorption spectrum in the range of 3.2–3.6 µm. The surprisingly low threshold fluence between 2.8 and 3.2 µm seems to reflect the strong absorption of residual water in the succinic acid microcrystals.

Field strengths typically less than 1000 V/mm, preferably as low as 200 V/mm, particularly for proteins, are used.

A preferred spot size is in the range of about 50 µm in diameter to about 1 mm. IR-MALDI can be matched with an appropriate mass analyzer, including linear (lin) or reflector (ref), with linear and nonlinear fields, for example, curved field reflectron, time-of-flight (TOF); single or multiple quadrupole, single or multiple magnetic sector, Fourier transform ion cyclotron resonance or ion trap. Preferably, detection is performed using a linTOF or a refTOF mode instrument in positive or negative ion modes, so that the ions are accelerated through a total potential difference of about 3 kV to about 30 kV in the split extraction source using static or delayed ion extraction (DE). TOF mass spectrometers separate ions according to their mass-to-charge ratio by measuring the time it takes generated ions to travel to a detector. The technology behind TOF mass spectrometers is described for example in U.S. Pat. Nos. 5,627,369; 5,625, 184; 5,498,545; 5,160,840 and 5,045,694.

Delayed extraction with delay time ranging from about 50 nsec to about 5 psec may improve the mass resolution of some nucleic acids, for example, nucleic acids in the mass range of from about 30 kDa to about 50 kDa, using either a liquid or solid matrix. For delayed extraction, conditions are selected to permit a longer optimum extraction delay and hence a longer residence time, which results in increased resolution (see, e.g., Juhasz et al., *Anal. Chem.* 68:941–946 (1996); Vestal et al., *Rapid Commun. Mass Spectrom.* 9:1044–1050 (1995); see, also, U.S. Pat. Nos. 5,777,325; 5,742,049; 5,654,545; 5,641,959; 5,654,545; and 5,760,393, for descriptions of MALDI and delayed extraction protocols). In delayed ion extraction, a time delay is introduced between the formation of the ions and the application of the accelerating field. During the time lag, the ions move to new positions according to their initial velocities. By properly choosing the delay time and the electric fields in the acceleration region, the time of flight of the ions can be adjusted so as to render the flight time independent of the initial velocity to the first order.

ANALYSIS OF NUCLEIC ACIDS BY IR-MALDI

Methods and processes for sequencing, diagnosis and detection of nucleic acids using UV MALDI have been developed and are known to those of skill in the art (see, e.g., U.S. Pat. Nos. 5,605,798, 5,830,655, 5,700,642, allowed U.S. application Ser. No. 08/617,256, U.S. Pat. No. 6,043,031 published International PCT application Nos. WO 96/29431, WO 98/20019, WO 99/14375, WO 97/03499, WO 98/26095 and others).

Processes of using IR-MALDI to analyze a nucleic acid in a liquid matrix are provided. Nucleic acids to be analyzed according to a process provided herein can include any single stranded or double stranded polynucleotide such as DNA, including genomic DNA and cDNA; RNA; or an analog of RNA or DNA, as well as nucleotides or nucleosides and any derivative thereof. Nucleic acids can be of any size ranging from single nucleotides or nucleosides to tens of thousands of base pairs. For analysis herein, preferred nucleic acids contain about one thousand nucleotides or less.

Nucleic acids may be obtained from a biological sample, which can be any material obtained from any living source, including a human, animal, plant, bacterium, fungus, protist or virus, using any of a number of procedures that are well known in the art. A particular isolation procedure for obtaining a nucleic acid from a biological sample can be selected as appropriate for the particular biological sample. For example, freeze-thaw or alkaline lysis procedures can be useful for obtaining nucleic acid molecules from solid materials; heat and alkaline lysis procedures can be useful for obtaining nucleic acids from blood (Rolff et al., *PCR: Clinical Diagnostic and Research* (Springer Verlag 1994)).

Prior to being mixed with a liquid matrix, the particular nucleic acid to be analyzed may be further processed to yield a relatively pure, isolated nucleic acid sample. For example, a standard ethanol precipitation may be performed on a restriction enzyme digested DNA. Alteratively, PCR products may require primer removal prior to analysis. Likewise, RNA strands can be separated from the molar excess of premature termination products always present in in vitro transcription reactions.

SEQUENCING

Exemplary Formats and Strategies

Any sequencing strategy known to those of skill in the art, including Sanger, exonuclease and hybridization methods can be adapted for use with IR MALDI methods provided herein, by liquid matrices and IR MALDI. For example, a Sanger sequencing strategy assembles the sequence information by analysis of the nested fragments obtained by base-specific chain termination via their different molecular masses, which can be determined using IR-MALDI. Further increases in throughput, if needed can be obtained by conditioning the nucleic acid fragments, such as by introducing mass modifications into the oligonucleotide primer, the chain-terminating nucleoside triphosphates and/or the chain-elongating nucleoside triphosphates, as well as using integrated tag sequences that allow multiplexing by hybridization of tag specific probes with mass differentiated molecular weights.

Exonuclease-based sequencing protocols can also be performed. These methods, which include those described in U.S. Pat. No. 5,622,824 adapted for use with IR-MALDI, involve a direct sequencing approach and can begin wit DNA fragments cloned into conventional cloning vectors. The DNA is by means of protection, specificity of enzymatic activity, or immobilization, unilaterally degraded in a stepwise manner via exonuclease digestion and the nucleotides or derivatives detected by mass spectrometry. Prior to the enzymatic degradation, sets of ordered deletions that span the whole sequence of the cloned DNA fragment are created. In this manner, mass-modified nucleotides can be incorporated using a combination of exonuclease and DNA/RNA polymerase. This permits either multiplex mass spectrometric detection, or modulation of the activity of the exonuclease so as to synchronize the degradative process.

Methods for sequencing by hybridization include methods of positional sequencing by hybridization (see, e.g., U.S. Pat. No. 5,503,980, 5,795,714 and 5,631,134). Briefly, sequencing by hybridization refers to methods of sequencing a nucleic acid by hybridizing that nucleic acid with a set of nucleic acid probes containing random, but determinable sequences within the single stranded portion adjacent to a double stranded portion where the single stranded portion of the set preferably comprises every possible combination of sequences over a predetermined range. Hybridization occurs by complementary recognition of the single stranded portion of a target with the single stranded portion of the probe and is thermodynamically favored by the presence of adjacent double strandedness of the probe. In particular, a method for determining a nucleotide sequence of a nucleic acid target by hybridization includes the steps of creating a set of nucleic acid probes, wherein each probe is preferably about 14–50 nucleotides in length and has a double stranded portion, a single stranded portion, and a variable sequence within the single stranded portion that is determinable; hybridizing the target that is at least partly single stranded to one or more of the nucleic acid probes; and determining the nucleotide sequence of the target that is hybridized to the single stranded portion of any probe. To detect the probes the target can be labeled with a first detectable label at a terminal site and a second different detectable label at an internal site. The labels are selected to be detectable by IR mass spectrometry.

Examples of the Above Formats

In one exemplary direct sequencing embodiment, the method of sequencing obtaining multiple nucleic acid copies of the target nucleic acid, where the multiple copies contain at least one mass modified nucleotide, corresponding to one of the four possible nucleotide bases; cleaving the multiple nucleic acid copies from a first end to a second end with an exonuclease having an activity, which is inhibited by the mass-modified nucleotide, thereby generating base terminated nucleic acid fragments; identifying the nested nucleic acid fragments by IR-MALDI; and (iv) determining the sequence of the target nucleic acid from the identified nested nucleic acid fragments.

In all formats, the nucleic acids can be immobilized, including in array formats. Immobilization can be effected with linkers that are cleavable, such as by the IR radiation emitted by the IR laser. The linkages can be reversible or irreversible.

Thus, processes for determining a subunit sequence of a target biological macromolecule also are provided. A sequence of a target biological macromolecule can be determined by contacting the biological macromolecule with an agent that cleaves the biological macromolecule unilaterally from a terminus of the biological macromolecule, to produce a nested set of deletion fragments; preparing a composition containing the nested set of biological macromolecule fragments and a liquid matrix, which absorbs infrared radiation; determining the molecular weight value of each biological macromolecule fragment in the composition by IR-MALDI mass spectrometry; and determining the sequence of the nucleic acid from the molecular weight values of the biological macromolecule fragments in the set.

A sequence of a target nucleic acid, for example, can be determined by subjecting the target nucleic acid to exonuclease digestion for various periods of time to produce a nested set of deletion fragments containing the target nucleic acid sequence (see International Publ. WO 94/21822), then analyzing the nested set of deletion fragments by IR-MALDI. Similarly, a sequence of a target polypeptide can be determined by subjecting the polypeptide to an exopeptidase, which can be a carboxypeptidase such as carboxypeptidase Y, carboxypeptidase P, carboxypeptidase A, carboxypeptidase G or carboxypeptidase B; or an aminopeptidase such as alanine aminopeptidase, leucine aminopeptidase, pyroglutamate peptidase, dipeptidyl peptidase and microsomal peptidase; or a chemical polypeptide fragmenting agent such as phenylisothiocyanate, for various periods of time to produce a nested set of fragments of the biological macromolecule, which can be analyzed by IR-MALDI mass spectrometry to determine the sequence of the target biological macromolecule (see, also, *Protein LabFax*, pages 273–276 (ed., N. C. Price; Bios Scientific Publ., 1996); listing polypeptide fragmenting agents). Exonucleases, exopeptidases and exoglycosidases are well known in the art (see, for example, U.S. Pat. No. 5,821,063), as are methods of modifying the activity of such agents (see, for example, U.S. Pat. No. 5,792,664; International Publ. WO 96/36732).

A sequence of a target biological macromolecule also can be determined by treating the biological macromolecule with an agent that cleaves the biological macromolecule unilaterally from a terminus, in a time-limited manner, and identifying the released monomer subunits by IR-MALDI mass spectrometry. If desired, degradation of a target biological macromolecule can be performed in a reactor apparatus (see International Publ. WO 94/21822), in which the biological macromolecule can be free in composition and the agent that cleaves can be immobilized, or in which the agent that cleaves can be free in composition and the biological macromolecule can be immobilized. At time intervals or as a continuous stream, the reaction mixture containing released subunits is transported from the reactor for analysis by IR-MALDI mass spectrometry. Prior to IR-MALDI mass spectrometric analysis, the released subunits can be transported to a reaction vessel for conditioning, which can be by mass modification.

A sequence of a target biological macromolecule also can be determined by generating at least two biological macromolecule fragments from the target biological macromolecule; preparing a composition containing the biological macromolecule fragments and a liquid matrix, which absorbs infrared radiation; and analyzing the biological macromolecule fragments in the composition by IR-MALDI mass spectrometry, thereby determining the sequence of the target nucleic acid molecule. In particular, such a process can be useful for determining the order of subunit sequences within a large biological macromolecule sequence (see International Publ. WO 98/20019).

A process of determining the subunit sequence of at least one species of target biological macromolecule, i, also is provided. Such a process can be performed, for example, by contacting the species of target biological macromolecule with one or more agents sufficient to cleave each the bonds between each monomer subunit in the target biological macromolecule, to produce a nested set of deletion fragments; preparing a composition containing at least one biological macromolecule fragment of the set and a liquid matrix, which absorbs infrared radiation; and determining the molecular mass of the at least one biological macromolecule fragment by IR-MALDI mass spectrometry; and repeating these steps until the molecular mass of each biological macromolecule fragment in said set has been determined, thereby determining the subunit sequence of the species of target biological macromolecule. Such a process is particularly suitable for multiplex analysis of a plurality of i+1 species of target biological macromolecules. For multiplex analysis, each species of target biological macromolecule can be differentially mass modified such that a biological macromolecule fragment of each species of target biological macromolecule can be distinguished from every other biological macromolecule species by IR-MALDI mass spectrometry.

A process of determining the nucleotide sequence of at least one species of nucleic acid also is provided. Such a process can be performed by synthesizing complementary nucleic acids, which are complementary to the species of nucleic acid to be sequenced, starting from an oligonucleotide primer and in the presence of chain terminating nucleoside triphosphates, to produce four sets of base-specifically terminated complementary polynucleotide fragments; preparing a composition for IR-MALDI that contains four sets of polynucleotide fragments and a liquid matrix, which absorbs infrared radiation; determining the molecular weight value of each polynucleotide fragment by IR-MALDI mass spectrometry; and determining the nucleotide sequence of the species of nucleic acid by aligning the molecular weight values according to molecular weight. The process is particularly suitable to multiplex analysis of a plurality of i+1 species of nucleic acids, which can be sequenced concurrently using i+1 primers. For multiplex analysis, one of the i+1 primers is an unmodified primer or a mass modified primer, and the other i primers are mass modified primers, such that each of the i+1 primers can be distinguished from every other primer by IR-MALDI mass spectrometry.

A sequence of a target nucleic acid also can be determined by hybridizing at least one partially single stranded target nucleic acid to one or more nucleic acid probes, each probe containing a double stranded portion, a single stranded portion, and a determinable variable sequence within the single stranded portion, to produce at least one hybridized target nucleic acid; preparing a composition containing the hybridized target nucleic acid and a liquid matrix, which absorbs infrared radiation; and determining a sequence of the hybridized target nucleic acid by IR-MALDI mass spectrometry based on the determinable variable sequence of the probe to which the target nucleic acid hybridized (U.S. Pat. No. 5,503, 980). Optionally, a hybridized target nucleic acid can be ligated to the determinable variable sequence. If desired, the steps of the process can be repeated a sufficient number of times to determine an entire sequence of a target nucleic acid. Where a plurality of target nucleic acids are to be sequenced, the one or more nucleic acid probes can be immobilized in an array.

IR-MALDI mass spectrometry also can be used to determine a nucleic acid sequence by analyzing a target polypeptide encoded by the nucleic acid. Since the mass of a polypeptide is only about 10% of the mass of its encoding nucleic acid, the translated polypeptide can be more amenable to mass spectrometric detection. In addition, IR-MALDI mass spectrometric detection of polypeptides can yield analytical signals of high sensitivity and resolution (see Berkenkamp et al., *Rapid Commun. Mass Spectrom.* 11:1399–1406 (1997)).

Oligonucleotide sizing, fingerprinting and sequencing using IR-MALDI mass spectrometry and immobilized cleavable primers IR-MALDI mass spectrometry can also be used, in conjunction with the immobilized cleavable primers described in U.S. Pat. No. 5,830,655 and U.S. Pat. No. 5,700,642 or other such primers, to determine the size of a primer extension product. In one specific embodiment, a method for determining the size of a primer extension product is provided. It includes the steps of (a) hybridizing a primer with a target nucleic acid, where the primer (i) is complementary to the target nucleic acid; (ii) has a first region containing the 5' end of the primer, and (iii) has a second region containing the 3' end of the primer, where the 3' end is capable of serving as a priming site for enzymatic extension and where the second region contains a selected cleavable site; (b) extending the primer enzymatically to generate a polynucleotide mixture containing an extension product composed of the primer and an extension segment; (c) cleaving the extension product at the cleavable site to release the extension segment; and (d) sizing the extension segment by IR-MALDI mass spectrometry with a liquid matrix, whereby the cleaving is effective to increase the read length of the extension segment relative to the read length of the product of (b).

In one embodiment, the target nucleic acid contains an immobilization attachment site and is thereby immobilized by attachment to a solid support. The target nucleic acid can be immobilized prior to the extending. Also preferably, the target nucleic acid is immobilized prior to the cleaving. Further more preferably, the product of (b) from the immobilized target nucleic acid is separated prior to the cleaving step.

In another embodiment, the cleavable site is a nucleotide capable of blocking 5' to 3' enzyme-promoted digestion, and where the cleaving is carried out by digesting the first region of the primer with an enzyme having a 5' to 3' exonuclease activity. In another embodiment, the cleavable site is located at or within about five nucleotides from the 3' end of the primer. More preferably, the second region of the primer is a single nucleotide that also contains the cleavable site, such as, but are not limited to, a ribonucleotide, dialkoxysilane, 3'-(S)-phosphorothioate, 5'-(S)-phosphorothioate, 3'-(N)-phosphoramidate, 5'-(N)phosphoramidate, uracil or ribose. The enzyme for extending the primer in step (b) can be a DNA polymerase.

In yet another embodiment, the extending is carried out in the presence of a nucleotide containing (i) an immobilization attachment site and (ii) a releasable site, which is thereby incorporated into the extension segment. More preferably, a further step of immobilizing the extension segment at the immobilization attachment site and releasing the extension segment at the releasable site prior to the sizing by IR-MALDI mass spectrometry is included.

In another specific embodiment, a method for determining the size of a primer extension product is provided, which method comprises (a) hybridizing a primer with a target nucleic acid, where the primer (i) is complementary to the target nucleic acid; (ii) has a first region containing the 5' end of the primer, and an immobilization attachment site, where the immobilization attachment site of the primer is composed of a series of bases complementary to an intermediary oligonucleotide, and (iii) has a second region containing the 3' end of the primer, where the 3' end is capable of serving as a priming site for enzymatic extension and where the second region contains a selected cleavable site, (b) extending the primer enzymatically to generate a polynucleotide mixture containing an extension product composed of the primer and an extension segment; (c) cleaving the extension product at the cleavable site to release the extension segment, where prior to the cleaving the primer is immobilized by specific hybridization of the immobilization attachment site to the intermediary oligonucleotide bound to a solid support; and (d) sizing the extension segment by IR-MALDI mass spectrometry with a liquid matrix, whereby the cleaving is effective to increase the read length of the extension segment relative to the read length of the product of (b).

In still another specific embodiment, a method for determining the size of a primer extension product is provided that includes (a) combining first and second primers with a target nucleic acid, under conditions that promote hybridization of the primers to the nucleic acid, generating primer/nucleic acid complexes, where the first primer (i) has a 5' end and a 3' end, (ii) is complementary to the target nucleic acid, (iii) has a first region containing the 5' end of the first primer and (iv) has a second region containing the 3' end of the first primer, where the 3' end is capable of serving as a priming site for enzymatic extension and where the second region contains a cleavable site, and where the second primer (i) has a 5' end and a 3' end, (ii) is homologous to the target nucleic acid, (iii) has a first segment containing the 3' end of the second primer, and (iv) has a second segment containing the 5' end of the second primer and an immobilization attachment site; (b) converting the primer/nucleic acid complexes to double-stranded fragments in the presence of a DNA polymerase and deoxynucleoside triphosphates; (c) amplifying the primer-containing fragments by successively repeating the steps of (i) denaturing the double-stranded fragments to produce single-stranded fragments, (ii) hybridizing the single stranded fragments with the first and second primers to form strand/primer complexes, (iii) generating amplification products from the strand/primer complexes in the presence of DNA polymerase an deoxynucleoside triphosphates, and (iv) repeating steps (i) to (iii) until a desired degree of amplification has been achieved; (d) immobilizing amplification products containing the second primer via the immobilization attachment site; (e) removing non-immobilized amplified fragments; (f) cleaving the immobilized amplification products at the cleavable site, to generate a mixture including a double-stranded product; (g) denaturing the double-stranded product to release the extension segment; and (h) sizing the extension segment by IR-MALDI mass spectrometry with a liquid matrix, whereby the cleaving is effective to increase the read length of the extension segment relative to the read length of the amplified strand-primer complexes of (c).

In another embodiment, the method for determining the size of a includes the steps of (a) hybridizing a primer with a target nucleic acid, where the primer (i) is complementary to the target nucleic acid; (ii) has a first region containing the 5' end of the primer and an immobilization attachment site, and (iii) has a second region containing the 3' end of the primer, where the 3' end is capable of serving as a priming site for enzymatic extension and where the second region contains a selected cleavable site, (b) extending the primer enzymatically to generate a polynucleotide mixture containing an extension product composed of the primer and an extension segment; (c) cleaving the extension product at the cleavable site to release the extension segment, where prior to the cleaving the primer is immobilized at the immobilization attachment site; and (d) sizing the extension segment by IR-MALDI mass spectrometry with a liquid matrix, whereby the cleaving is effective to increase the read length of the extension segment relative to the read length of the product of (b). The enzyme for extending the primer in step (b) can be a DNA polymerase.

In one embodiment, the cleavable site is located at or within about five nucleotides from the 3' end of the primer. More preferably, the second region of the primer is a single nucleotide that also contains the cleavable site, such as, but are not limited to, a ribonucleotide, dialkoxysilane, 3'-(S)-phosphorothioate, 5'-(S)phosphorothioate, 3'-(N)-phosphoramidate, 5'-(N)phosphoramidate, or ribose.

In another embodiment, a further step of washing the immobilized product prior to the cleaving step is included. In another embodiment, the primer is immobilized on a solid support by attachment at the immobilization attachment site to an intervening spacer arm bound to the solid support. More preferably, the intervening spacer arm is six or more atoms in length. The immobilization attachment site preferably occurs as a substituent on one of the bases or sugars of the DNA primer. In another embodiment, the immobilization attachment site is biotin or digoxigenin. In another embodiment, the primer is immobilized on a solid support, including, but are not limited to, glass, silicon, polystyrene, aluminum, steel, iron, copper, nickel or gold.

In another embodiment, the method for determining the size of a primer includes the steps of: (a) combining first and second primers with a target nucleic acid under conditions that promote the hybridization of the primers to the nucleic acid, thus generating primer/nucleic acid complexes, where the first primer (i) is complementary to the target nucleic acid; (ii) has a first region containing the 5' end of the primer and an immobilization attachment site, and (iii) has a second region containing the 3' end of the primer, where the 3' end is capable of serving as a priming site for enzymatic extension and where the second region contains a cleavable site, and where the second primer is homologous to the target nucleic acid; (b) converting the primer/nucleic acid complexes to double-stranded fragments in the presence of a suitable polymerase and all four dNTPs; (c) amplifying the primer-containing fragments by successively repeating the steps of (i) denaturing the double-stranded fragments to produce single-strand fragments, (ii) hybridizing the single strands with the primers to form strand/primer complexes, (iii) generating double-stranded fragments from the strand/primer complexes in the presence of DNA polymerase and all four dNTPs, and (iv) repeating steps (i) to (iii) until a desired degree of amplification has been achieved; (d) denaturing the amplified fragments to generate a mixture including a product composed of the first primer and an extension segment; (e) immobilizing amplified fragments containing the first primer, utilizing the immobilization attachment site, and removing non-immobilized amplified fragments; (f) cleaving the immobilized fragments at the cleavable site to release the extension segment; and (g) sizing the extension segment by IR-MALDI mass spectrometry with a liquid matrix, whereby the cleaving is effective to increase the read length of the extension segment relative to the read length of the product of (d).

In another embodiment, a method for determining a single base fingerprint of a target DNA sequence is provided. The method includes the steps of (a) hybridizing a primer with a target DNA, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a selected cleavable site; (b) extending the primer with an enzyme in the presence of a dideoxynucleoside triphosphate corresponding to the single base, to generate a polynucleotide mixture of primer extension products, each product containing a primer and an extension segment; (c) cleaving the extension products at the cleavable site to release the extension segments, where prior to the cleaving the primers are immobilized at the immobilization attachment sites; (d) sizing the extension segments by IR-MALDI mass spectrometry with a liquid matrix, whereby the cleaving is effective to increase the read length of any given extension segment relative to the read length of its corresponding primer extension product of (b), and (e) determining the positions of the single base in the target DNA by comparison of the sizes of the extension segments.

In another embodiment, a method for an adenine fingerprint of a target DNA sequence by (a) hybridizing a primer with a DNA target, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a selected cleavable site; (b) extending the primer with an enzyme in the presence of deoxyadenosine triphosphate (dATP), deoxythymidine triphosphate (dTTP), deoxycytidine triphosphate (dCTP), deoxyguanosine triphosphate (dGTP), and deoxyuridine triphosphate (dUTP), to generate a polynucleotide mixture of primer extension products containing dUTP at positions corresponding to dATP in the target, each product containing a primer and an extension segment; (c) treating the primer extension. products with uracil DNA-glycosylase to fragment specifically at dUTP positions to produce a set of primer extension degradation products; (d) washing the primer extension degradation products, where prior to the washing, the primer extension degradation products are immobilized at the immobilization attachment sites, each immobilized primer extension degradation product containing a primer and an extension segment, where the washing is effective to remove non-immobilized species; (e) cleaving the immobilized primer extension degradation products at the cleavable site to release the extension segments; (f) sizing the extension segments by IR-MALDI mass spectrometry with a liquid matrix, whereby the cleaving is effective to increase the read length of any given extension segment relative to the read length of its corresponding primer extension degradation product; and (g) determining the positions of adenine in the target DNA by comparison of the sizes of the released extension segments.

In another specific embodiment, a method for determining the DNA sequence of a target DNA sequence is provided, which method comprises (a) hybridizing a primer with a target DNA, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a cleavable site, (b) extending the primer with an enzyme in the presence of a first of four different dideoxynucleotides to generate a mixture of primer extension products each product containing a primer and an extension segment; (c) cleaving at the cleavable site to release the extension segments, where prior to the cleaving the primers are immobilized at the immobilization attachment sites; (d) sizing the extension segments by IR-MALDI mass spectrometry with a liquid matrix, whereby the cleaving is effective to increase the read length of the extension segment relative to the read length of the product of (b), (e) repeating steps (a) through (d) with a second, third, and fourth of the four different dideoxy nucleotides, and (f) determining the DNA sequence of the target DNA by comparison of the sizes of the extension segments obtained from each of the four extension reactions.

In yet another specific embodiment, a method for determining the DNA sequence of a target DNA sequence is provided, which method comprises (a) hybridizing a primer with a target DNA, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a cleavable site, (b) extending the primer with an enzyme in the presence of a first of four different deoxynucleoside α-thiotriphosphate analogs (dNTPαS) to generate a mixture of primer extension products containing phosphorothioate linkages, (c) treating the primer extension products with a reagent that cleaves specifically at the phosphorothioate linkages, where the treating is carried out under conditions producing limited cleavage, resulting in the production of a group of primer extension degradation products, (d) washing the primer extension degradation products, where prior to the washing, the primer extension degradation products are immobilized at the immobilization attachment sites, each immobilized primer extension degradation product containing a primer and an extension segment, where the washing is effective to remove non-immobilized species, (e) cleaving at the cleavable site to release the extension segments, (f) sizing the extension segments by IR-MALDI mass spectrometry with a liquid matrix, whereby the cleaving is effective to increase the read length of any given extension segment relative to the read length of its corresponding primer extension degradation product, (g) repeating steps (a) through (f) with a second, third, and fourth of the four different dNTPαSs, and (h) determining the DNA sequence of the target DNA by comparison of the sizes of the extension segments obtained from each of the four extension reactions. More preferably, the reagent of step (c) is exonuclease, 2-iodoethanol, or 2,3-epoxy-1-propanol.

DIAGNOSIS AND DETECTION

Diagnostics

Using a process as disclosed herein, accurate (at least about 1% accurate) masses of a DNA sample can be obtained for at least about 2000-mer DNA (masses of at least about 650 kDa) and at least about 1200-mer RNA (masses of at least about 400 kDa; see Example 1). In addition, signals of single stranded, as well as double stranded, nucleic acids can be obtained in the spectra (see FIG. 3). The improved accuracy for measuring the mass of DNA by IR-MALDI mass spectrometry (accuracy of at least about 1%) is far superior to that provided by standard agarose gel sizing of nucleic acids (accuracy of about 5%). The accuracy of mass determination of RNA by IR-MALDI mass spectrometry (accuracy of at least about 0.5%) is even more significant, since an accurate size determination of RNA by gel analysis is difficult, if not impossible, in part because of the absence of suitable size markers and of a sufficiently suitable gel matrix.

In addition to the extension in mass range obtained using a process as disclosed herein, there is a dramatic decrease in the amount of analyte needed for preparation of the sample for mass spectrometry, down to the low femtomole (fmol) or attomole (attomol) range, even with an essentially simple preparation method. Also, by using a liquid matrix rather than a solid matrix, the ion signals generated are more reproducible from shot to shot. Use of a liquid matrix also facilitates sample dispensation, for example, onto various fields of a chip array. Furthermore, by using a liquid matrix in conjunction with IR-MALDI mass spectrometry, essentially all sample left on the target after IR-MALDI analysis can be retrieved for further use.

DIAGNOSIS AND DETECTION

A process of determining the molecular mass of a target biological macromolecule by IR-MALDI mass spectrometry is provided. Such a process can be performed, for example, by preparing a composition for IR-MALDI containing the biological macromolecule to be analyzed and a liquid matrix, which absorbs infrared radiation; and analyzing the biological macromolecule in the composition by IR-MALDI mass spectrometry (see Example 1; see, also, Berkenkamp et al., *Rapid Commun. Mass Spectrom.* 11:1399–1406 (1997); Berkenkamp et al., *Science* 281:260–262 (1998)). The molecular mass of the target biological macromolecule is determined by running, in parallel or in a separate spectrum, one or more control biological macromolecules having known molecular masses, and comparing the spectrum produced by the target spectrum with the spectrum of the control biological macromolecules. A control biological macromolecule, which can be a corresponding known biological macromolecule, generally is of the same type of molecule as the target biological macromolecule, for example, each is a nucleic acid or each is polypeptide. The control biological macromolecule need not be the same type of molecule as a target biological macromolecule in order to determine the molecular mass of the target biological macromolecule (see Example 1).

IR-MALDI mass spectrometry also can be used for detecting a target biological macromolecule by preparing a composition containing a biological macromolecule and a liquid matrix, which absorbs infrared radiation; and performing IR-MALDI mass spectrometry on the composition to identify the target biological macromolecule in the composition, thereby detecting the target biological macromolecule. If desired, the target biological macromolecule can be present in or isolated from a biological sample. Accordingly, a process for identifying the presence of a target biological macromolecule in a biological sample also is provided.

The presence of a target biological macromolecule, for example, a nucleic acid in a biological sample can be identified by preparing a composition for IR-MALDI, containing a biological sample containing nucleic acid molecules (or nucleic acid molecules isolated from the biological sample) and a liquid matrix, which absorbs infrared radiation; then analyzing the composition by IR-MALDI mass spectrometry. Detection of a nucleic acid molecule having a molecular mass of the target nucleic acid sequence identifies the presence of the target nucleic acid sequence in the biological sample. The molecular mass of the target biological macromolecule can be determined by comparison to a control spectrum, or can be determined based on the spectrum produced by a corresponding known biological macromolecule. Alternatively, a sequence of the biological macromolecule can be determined, thereby identifying the presence of the biological macromolecule.

Since the processes disclosed herein allow a characterization of a target biological macromolecule obtained from a biological sample, IR-MALDI mass spectrometry can be used to identify an individual having a disease or condition, or a predisposition to a disease or condition, by detecting a characteristic of a target biological macromolecule that is associated with the disease or the condition. Such a process can be performed, for example, by preparing a composition for IR-MALDI, containing the biological macromolecule, which is obtained from an individual to be tested, and a liquid matrix, which absorbs infrared radiation; and analyzing the biological macromolecule, or a relevant portion of the biological macromolecule, in the composition by IR-MALDI mass spectrometry. A determination of a particular mass of the target biological macromolecule identifies the individual as having the disease or condition or a predisposition to the disease or condition. Such a process is particularly useful for identifying a genetic disease, or a disease associated with a bacterial infection, or a predisposition to such a disease, and also is useful for determining identity, heredity or compatibility. Additional processes disclosed herein also are useful for such a diagnosis, for example, by determining the sequence of the target biological macromolecule obtained from the individual or by comparison of the target biological macromolecule with a corresponding known biological macromolecule.

The disclosed processes using IR-MALDI are suitable to analyzing more than one sample of biological macromolecule, particularly a large number of samples, for example, by depositing a plurality of compositions, each containing one or more biological macromolecules, on a solid support such as a chip, in the form of an array, if desired. In addition, the disclosed processes are suitable for multiplex analysis of a plurality of biological macromolecules contained in one or a few compositions containing a liquid matrix. Each biological macromolecule in a plurality can be differentially mass modified, for example, to facilitate multiplex analysis. Accordingly, the processes are readily adaptable to high throughput assay formats.

A biological macromolecule particularly suitable for analysis by a process of IR-MALDI can be a nucleic acid, a polypeptide, a carbohydrate, or a proteoglycan, or can be a macromolecular complex such as a protein-protein complex or a nucleoprotein complex. For analysis, a target biological macromolecule can be immobilized to a substrate, particularly a solid support, which can be, for example, a bead, a flat surface, a chip, a capillary, a pin, a comb, or a wafer, and can be any of various materials, including a metal, a ceramic, a plastic, a resin, a gel, and a membrane. For example, the solid support can be a silicon wafer or a stainless steel flat surface. Since the processes as disclosed herein are particularly useful for analyzing a large number of target biological macromolecules in high throughput assays, it can be particularly useful to immobilize a plurality of target biological macromolecules in an array on a solid support. Immobilization can be through a reversible linkage such as a photocleavable bond or a thiol linkage or a hydrogen bond, and the linkage can be cleaved using, for example, a chemical process, an enzymatic process, or a physical process, including during the mass spectrometric analysis procedure.

Where a target biological macromolecule is a nucleic acid, for example, the target nucleic acid can be immobilized by hybridization (hydrogen bonding) between a complementary capture nucleic acid molecule, which is immobilized to the solid support, and a portion of the nucleic acid molecule containing the target nucleic acid. It should be recognized, however, that, for some processes disclosed herein, at least a portion of the sequence containing the target nucleic acid should be distinct from the hybridizing portion of the target nucleic acid when immobilization is through hybridization to a capture nucleic acid, for example, where a detector oligonucleotide is to be hybridized to a sequence of the target nucleic acid.

Where the target biological macromolecule is a polypeptide, it can be immobilized to a solid support by binding to a reagent, which is conjugated to the solid support and specifically interacts with at least a portion of the target polypeptide or with a tag attached to the target polypeptide. Such a reagent can be, for example, an antibody that binds an epitope of the target polypeptide, or can be, for example, nickel ion, which binds to a polyhistidine sequence tag contained in the target polypeptide. A tag peptide such as a polyhistidine tag can be incorporated conveniently into a target polypeptide that is produced, for example, by an in vitro transcription or translation method.

A biological macromolecule to be analyzed can be conditioned prior to IR-MALDI mass spectrometric analysis. Conditioning improves the ability to analyze a particular biological macromolecule by IR-MALDI mass spectrometry, for example, by improving the resolution of the mass spectrum. If desired, the biological macromolecule can be isolated prior to conditioning or prior to mass spectrometric analysis.

A target biological macromolecule can be conditioned, for example, by ion exchange, by contact with an alkylating agent or a trialkylsilyl chloride, or by incorporating at least one mass modified subunit into the biological macromolecule. For example, where the biological macromolecule is a nucleic acid, the target nucleic acid can be conditioned by phosphodiester backbone modification such as by cation exchange; by incorporating at least one nucleotide such as an N7-deazapurine nucleotide, an N9-deazapurine nucleotide, or a 2'-fluoro-2'-deoxynucleotide, each of which can reduce sensitivity of a nucleic acid to depurination; by incorporation of at least one mass modified nucleotide; or by hybridization of a tag probe to a portion of a nucleic acid molecule containing the target nucleic acid (see U.S. Pat. No. 5,547,835).

A process for determining the identity of each target biological macromolecule in a plurality of target biological macromolecules can be performed, for example, by preparing a composition containing a plurality of differentially mass modified target biological macromolecules and a liquid matrix, which absorbs infrared radiation; determining the molecular mass of each differentially mass modified target biological macromolecule in the plurality by IR-MALDI mass spectrometry; and comparing the molecular mass of each differentially mass modified target biological macromolecule in the plurality with the molecular mass of a corresponding known biological macromolecule or fragment thereof. Where such a process is performed using a plurality of target biological macromolecules that are fragments of a biological macromolecule, the fragments can be prepared by contacting the biological macromolecules with at least one fragmenting agent that cleaves a bond involved in the formation of the biological macromolecules, particularly a bond between monomeric subunits of the biological macromolecule, to produce the fragment target biological macromolecules.

A target nucleic acid to be analyzed by IR-MALDI mass spectrometry can be in a biological sample and, if desired, can be amplified prior to analysis, then analyzed directly by IR-MALDI mass spectrometry. Alternatively, the amplified nucleic acid molecules can be contacted with a detector oligonucleotide, which can hybridize to a target nucleic acid sequence present in an amplified nucleic acid; a composition for IR-MALDI can be prepared by mixing the product of the reaction with a liquid matrix, which absorbs infrared radiation; and IR-MALDI mass spectrometry can be performed. Detection of duplex nucleic acid molecules, which form by hybridization of the detector oligonucleotide and an amplified target nucleic acid, identifies the presence of the target nucleic acid in the biological sample.

Amplification of nucleic acid molecules, including a target nucleic acid molecule, can be performed using well known methods and commercially available kits. Amplification can utilize a polymerase, which can be a thermostable polymerase, such as Taq DNA polymerase, AmpliTaq FS DNA polymerase, Deep Vent (exo–) DNA polymerase, Vent DNA polymerase, Vent (exo⁻) DNA polymerase, Deep Vent DNA polymerase, Thermo Sequenase, exo(–) *Pseudococcus furiosus* (Pfu) DNA polymerase, AmpliTaq, Ultman, 9 degree Nm, Tth, Hot Tub, *Pyrococcus furiosus* (Pfu) or *Pyrococcus woesei* (Pwo) DNA polymerase. Amplification processes include the polymerase chain reaction (Newton and Graham, PCR (BIOS Publ. 1994)); nucleic acid sequence based amplification; transcription-based amplification system, self-sustained sequence replication; Q-beta replicase based amplification; ligation amplification reaction; ligase chain reaction (Wiedmann et al., *PCR Meth. Appl.* 3:57–64 (1994); Barany, *Proc. Natl. Acad. Sci., USA* 88, 189–93 (1991)); strand displacement amplification (Walker et al., *Nucl. Acids Res.* 22:2670–77 (1994)); and variations of these methods, including, for example, reverse transcription PCR (RT-PCR; Higuchi et al., *Bio/Technology* 11:1026–1030 (1993)), and allele-specific amplification.

Where a nucleotide sequence of the target nucleic acid is amplified by PCR, well known reaction conditions are used. The minimal components of an amplification reaction include a template DNA molecule; a forward primer and a reverse primer, each of which is capable of hybridizing to the template DNA molecule or a nucleotide sequence linked thereto; each of the four different nucleoside triphosphates or appropriate analogs thereof; an agent for polymerization such as DNA polymerase; and a buffer having the appropriate pH, ionic strength, cofactors, and the like. Generally, about 25 to 30 amplification cycles, each including a denaturation step, an annealing step and an extension step, are performed, but fewer cycles can be sufficient or more cycles can be required depending, for example, on the amount of the template DNA molecules present in the reaction. Examples of PCR reaction conditions are described in U.S. Pat. No. 5,604,099.

A nucleic acid sequence can be amplified using PCR as described in U.S. Pat. No. 5,545,539, which provides an improvement of the basic procedure for amplifying a target nucleotide sequence by including an effective amount of a glycine-based osmolyte in the amplification reaction mixture. The use of a glycine-based osmolyte improves amplification of sequences rich in G and C residues and, therefore, can be useful, for example, to amplify trinucleotide repeat sequences such as those associated with Fragile X syndrome (CGG repeats) and myotonic dystrophy (CTG repeats).

The presence of a target nucleic acid sequence in a biological sample also can be identified by specifically digesting nucleic acid molecules, which can be amplified nucleic acid molecules, containing the target nucleic acid with at least one appropriate nuclease; hybridizing the digested nucleic acid fragments with complementary capture nucleic acid sequences, which are immobilized on a solid support and can hybridize to a digested fragment of a target nucleic acid; preparing a composition for IR-MALDI, containing the immobilized fragments and a liquid matrix, which absorbs infrared radiation; and identifying immobilized fragments by IR-MALDI mass spectrometry (see International Pubis. WO 96/29431 and WO 98/20019). The detection of nucleic acid fragments that were immobilized by hybridization to the complementary capture nucleic acid sequences identifies the presence of the target nucleic acid sequence in the biological sample. Immobilization of the nucleic acid fragments can be reversed prior to performing IR-MALDI or as a consequence of IR-MALDI mass spectrometry, for example, due to cleavage of an IR cleavable linkage during IR-MALDI.

The presence of a target nucleic acid in a biological sample also can be identified by performing on nucleic acid molecules obtained from the biological sample, a first polymerase chain reaction using a first set of primers, which are capable of amplifying a portion of the nucleic acid containing the target nucleic acid; preparing a composition containing the first amplification product and a liquid matrix, which absorbs infrared radiation; and detecting the first amplification product in the composition by IR-MALDI mass spectrometry, thereby detecting the presence of the target nucleic acid in the biological sample. Such a process can include, prior to performing IR-MALDI, a second polymerase chain reaction on the first amplification product using a second set of primers, which are capable of amplifying at least a portion of the first amplification product containing the target nucleic acid (International Publ. WO 98/20019).

Processes for determining the identity of a subunit in a biological macromolecule, for example, for detecting a mutation in a nucleotide sequence, also are provided. The identity of a target nucleotide can be determined by hybridizing a nucleic acid molecule containing the target nucleotide with a primer oligonucleotide that is complementary to the nucleic acid molecule at a site adjacent to the target nucleotide; contacting the hybridized nucleic acid molecule with a complete set of dideoxynucleosides or 3'-deoxynucleoside triphosphates and a DNA dependent DNA polymerase, so that only the dideoxynucleoside or 3'-deoxynucleoside triphosphate that is complementary to the target nucleotide is extended onto the primer; preparing a composition containing the extended primer and a liquid matrix, which absorbs infrared radiation; and detecting the extended primer in the composition by IR-MALDI mass spectrometry. The identity of the target nucleotide is determined based on the dideoxynucleoside or 3'-deoxynucleoside triphosphate present in the extended primer, as determined by IR-MALDI mass spectrometry.

The absence or presence of a mutation in a target nucleic acid sequence also can be determined by hybridizing a nucleic acid molecule containing the target nucleic acid sequence with at least one primer, which has 3' terminal base complementarity to the target nucleic acid sequence; contacting the hybridized nucleic acid with an appropriate polymerase enzyme and sequentially with one of the four nucleoside triphosphates; preparing a composition containing the reaction product and a liquid matrix, which absorbs infrared radiation; and detecting the product in the composition by IR-MALDI mass spectrometry. Based on the molecular weight of the product, the presence or absence of a mutation next to the 3' end of the primer in the target nucleic acid molecule can be determined (International PCT application No. WO 98/20019).

A mutation in a target nucleic acid molecule also can be detected by hybridizing the target nucleic acid molecule with an oligonucleotide probe, to produce a hybridized nucleic acid, wherein a mismatch is formed at the site of a mutation; contacting the hybridized nucleic acid with a single strand specific endonuclease; preparing a composition containing the reaction product and a liquid matrix, which absorbs infrared radiation; and analyzing the composition by IR-MALDI mass spectrometry. The oligonucleotide probe used in this process has the sequence expected in a normal (unmutated) nucleic acid sequence corresponding to the target nucleic acid. The detection by IR-MALDI mass spectrometry of more than one nucleic acid fragment in the composition indicates that a mismatch was present in the hybridization product formed between the target nucleic acid and the oligonucleotide probe and, therefore, that the target nucleic acid molecule contains a mutation (International Publ. WO 98/20019).

The absence or presence of a mutation in a target nucleic acid sequence also can be identified by performing at least one hybridization of a nucleic acid molecule containing the target nucleic acid sequence with a set of ligation educts and a DNA ligase; preparing a composition for IR-MALDI containing the reaction product and a liquid matrix, which absorbs infrared radiation; and analyzing the composition by IR-MALDI mass spectrometry. Using such a process, the detection of a ligation product in the composition identifies the absence of a mutation in the target nucleic acid sequence, whereas the detection only of the set of ligation educts in the composition identifies the presence of a mutation in the target nucleic sequence.

A process of detecting the presence of ligation product by IR-MALDI mass spectrometry, as disclosed above, also can detect the presence of a target nucleic acid by performing at least one hybridization on a nucleic acid molecule containing the target nucleic acid with a set of ligation educts and a thermostable DNA ligase; preparing a composition containing the reaction product and a liquid matrix, which absorbs infrared radiation; and identifying a ligation product in the composition by IR-MALDI mass spectrometry. The formation of a ligation product indicates the presence of the target nucleic acid.

A process as disclosed herein also provides a means of using IR-MALDI mass spectrometry to determine the identity of a target polypeptide by comparing the masses of defined peptide fragments of the target polypeptide with the masses of corresponding peptide fragments of a corresponding known polypeptide. Such a process can be performed, for example, by obtaining the target polypeptide by in vitro translation, or by in vitro transcription followed by translation of a nucleic acid encoding the target polypeptide; contacting the translated polypeptide with at least one fragmenting agent that cleaves at least one peptide bond in the polypeptide; preparing a composition for IR-MALDI containing the peptide fragments and a liquid matrix, which absorbs IR radiation; determining the molecular mass of at least one of the peptide fragments by IR-MALDI mass spectrometry; and comparing the molecular mass of the peptide fragments with the molecular mass of peptide fragments of a corresponding known polypeptide. The masses of the peptide fragments of a corresponding known polypeptide either can be determined in a parallel reaction with the target polypeptide, wherein the corresponding known polypeptide also is contacted with the agent; can be compared with known masses for peptide fragments of a corresponding known polypeptide contacted with the particular cleaving agent; or can be obtained from a database of polypeptide sequence information using algorithms that determine the molecular mass of peptide fragment of a polypeptide. Such a process is particularly useful, for example, for identifying mutations and, therefore, for screening for certain genetic disorders, for example, a single base mutation that introduces a STOP codon into an open reading frame of a gene, since such a mutation results in premature protein truncation; or a change in the encoded amino acid in an allelic variant of a polymorphic gene, for example, a single base change that results in an amino acid change of alanine to glycine, since polypeptides containing the different amino acids can be distinguished based on their masses.

A process of using IR-MALDI to analyze a target polypeptide to obtain information regarding the encoding nucleic acid can be used for identifying the presence of nucleotide repeats, particularly an abnormal number of nucleotide repeats, by determining the identity of a target polypeptide encoded by such repeats. An abnormal number of nucleotide repeats can be identified by using IR-MALDI mass spectrometry to compare the mass of a target polypeptide with that of a corresponding known polypeptide.

A target polypeptide can be obtained by translating an RNA molecule encoding the target polypeptide in vitro. If desired, the RNA molecule can be obtained by in vitro transcription of a nucleic acid encoding the target polypeptide. Translation of a target polypeptide can be effected by directly introducing an RNA molecule encoding the polypeptide into an in vitro translation reaction or by introducing a DNA molecule encoding the polypeptide into an in vitro transcription/translation reaction or into an in vitro transcription reaction, then transferring the RNA to an in vitro translation reaction.

In vitro transcription and in vitro translation kits are well known in the art and commercially available. In vitro translation systems include eukaryotic cell lysates such as rabbit reticulocyte lysates, rabbit oocyte lysates, human cell lysates, insect cell lysates and wheat germ extracts. Such lysates and extracts can be prepared or are commercially available (Promega Corp.; Stratagene, La Jolla Calif.; Amersham, Arlington Heights Ill.; and GIBCO/BRL, Grand Island N.Y.). In vitro translation systems generally contain macromolecules such as enzymes; translation, initiation and elongation factors; chemical reagents; and ribosomes. Mixtures of purified translation factors, as well as combinations of lysates or lysates supplemented with purified translation factors such as initiation factor-1 (IF-1), IF-2, IF-3 (alpha or beta), elongation factor T (EF-Tu) or termination factors, also can be used for mRNA translation in vitro. If desired, incubation can be performed in a continuous manner, whereby reagents are flowed into the system and nascent polypeptides removed or left to accumulate, using a continuous flow system as described by Spirin et al. (*Science* 242:1162–64 (1988)). Such a process can be desirable for large scale production of nascent polypeptides.

An in vitro translation reaction using a reticulocyte lysate, for example, can be carried out by mixing ten pl of a reticulocyte lysate with spermidine, creatine phosphate, amino acids, HEPES buffer (pH 7.4), KCl, MgAc and the RNA to be translated, and incubated for an appropriate time, generally about one hour at 30° C. The optimum amount of MgAc for obtaining efficient translation varies from one reticulocyte lysate preparation to another and can be determined using a standard preparation of RNA and a concentration of MgAc up to about 1 mM. The optimal concentration of KCl also can vary depending on the specific reaction. For example, 70 mM KCl generally is optimal for translation of capped RNA, whereas 40 mM generally is optimal for translation of uncapped RNA.

A wheat germ extract can be prepared as described by Roberts and Paterson (*Proc. Natl. Acad. Sci., USA* 70:2330–2334 (1973)) and can be modified as described by Anderson (*Meth. Enzymol.* 101:635 (1983)), if desired. The protocol also can be modified according to manufacturing protocol L418 (Promega Corp.). Generally, wheat germ extract is prepared by grinding wheat germ in an extraction buffer, followed by centrifugation to remove cell debris. The supernatant is separated by chromatography from endogenous amino acids and from plant pigments that are inhibitory to translation. The extract also is treated with micrococcal nuclease to destroy endogenous mRNA, thereby reducing background translation to a minimum. The wheat germ extract contains the cellular components necessary for protein synthesis, including tRNA, rRNA and initiation, elongation and termination factors. The extract can be optimized further by the adding an energy generating system such as phosphocreatine kinase and phosphocreatine; MgAc is added at a level recommended for the translation of most mRNA species, generally about 6.0 to 7.5 mM magnesium (see, also, Erickson and Blobel *Meth. Enzymol.* 96:38 (1982)), and can be modified, for example, by adjusting the final ion concentrations to 2.6 mM magnesium and 140 mM potassium, and the composition to pH 7.5 (U.S. Pat. No. 4,983,521). Translation in wheat germ extract also can be performed as described in U.S. Pat. No. 5,492,817.

For determining the optimal in vitro translation conditions or the extent of the reaction, translation of mRNA in an in vitro system can be monitored, for example, by mass spectrometric analysis. Monitoring also can be performed, for example, by adding one or more radioactive amino acids such as $^{35}$S-methionine and measuring incorporation of the radiolabel into the translation products by precipitating the proteins in the lysate such as with TCA and counting the amount of radioactivity present in the precipitate at various times during incubation. The translation products also can be analyzed by immunoprecipitation or by SDS-polyacrylamide gel electrophoresis (see, for example, Sambrook et al., *Molecular Cloning: A laboratory manual* (Cold Spring Harbor Laboratory Press 1989); Harlow and Lane, *Antibodies: A laboratory manual* (Cold Spring Harbor Laboratory Press 1988)). A labeled non-radioactive amino acid also can be incorporated into a nascent polypeptide. For example, the translation reaction can contain a mis-aminoacylated tRNA (U.S. Pat. No. 5,643,722). A non-radioactive marker can be mis-aminoacylated to a tRNA molecule and the tRNA amino acid complex is added to the translation system. The system is incubated to incorporate the non-radioactive marker into the nascent polypeptide and polypeptides containing the marker can be detected using a detection method appropriate for the marker. Mis-aminoacylation of a tRNA molecule also can be used to add a marker to the polypeptide in order to facilitate isolation of the polypeptide. Such markers include, for example, biotin, streptavidin and derivatives thereof (U.S. Pat. No. 5,643, 722).

In vitro transcription and translation reactions also can be performed simultaneously using, for example, a commercially available system such as the Coupled Transcription/Translation System (Promega Corp, catalog #L4606, #4610 or #4950). Coupled transcription and translation systems using RNA polymerases and eukaryotic lysates are described in U.S. Pat. No. 5,324,637. Coupled in vitro transcription and translation also can be carried out using a prokaryotic system such as a bacterial system, for example, E.coli S30 cell-free extracts (Zubay, *Ann. Rev. Genet.* 7:267 (1973)).

A target polypeptide also can be obtained from a host cell transformed with and expressing a nucleic acid encoding the target polypeptide. The nucleic acid encoding the target polypeptide can be amplified, for example, by PCR, inserted into an expression vector, and the expression vector introduced into a host cell suitable for expressing the polypeptide encoded by the target nucleic acid. Host cells can be eukaryotic cells, particularly mammalian cells such as human cells, or prokaryotic cells, including, for example, *E.coli*. Eukaryotic and prokaryotic expression vectors are well known in the art and can be obtained from commercial sources. Following expression in the host cell, the target polypeptide can be isolated using methods as disclosed herein. For example, if the target polypeptide is fused to a polyhistidine tag peptide, the target polypeptide can be purified by affinity chromatography on a chelated nickel ion column.

A target polypeptide can be produced from an amplified nucleic acid encoding the target polypeptide. Where a target polypeptide is produced, for example, from an amplified nucleic acid, it can be useful to operably link one or more transcription or translation regulatory elements to the nucleic acid or encoded polypeptide. Thus, a forward or reverse PCR primer can contain, if desired, a nucleotide sequence of a promoter, for example, a bacteriophage promoter such as an SP6, T3 or T7 promoter. Amplification of a nucleic sequence using such a primer produces an amplified nucleic acid operably linked to the promoter, i.e., the promoter is situated in the amplified nucleic acid such that it performs the function of a promoter. Such a nucleic acid can be used in an in vitro transcription reaction to transcribe the amplified target nucleic acid sequence.

A primer, for example, the forward primer, also can contain regulatory sequence elements necessary for translation of an RNA in a prokaryotic or eukaryotic system. In particular, where it is desirable to perform a translation reaction in a prokaryotic translation system, a primer can contain an operably linked prokaryotic ribosome binding sequence (Shine-Dalgarno sequence), which is located downstream of a promoter sequence and about 5 to 10 nucleotides upstream of the initiation codon.

A primer also can contain an initiation (ATG) codon, or complement thereof, as appropriate, located downstream of a promoter, if present, such that amplification of the target nucleic acid results in an amplified target sequence containing an operably linked ATG codon, which is in frame with the desired reading frame. The reading frame can be the natural reading frame or can be any other reading frame. Where the target polypeptide is not a naturally occurring polypeptide, operably linking an initiation codon to the nucleic acid encoding the target polypeptide allows translation of the target polypeptide in the desired reading frame.

A primer, generally the reverse primer, also can contain a sequence encoding a STOP codon in one or more of the reading frames, to assure proper termination of the target polypeptide. Further, by incorporating into the reverse primer sequences encoding three STOP codons, one into each of the three possible reading frames, optionally separated by several residues, additional mutations that occur downstream (3') of a mutation that otherwise results in premature termination of a polypeptide can be detected.

A forward or reverse primer also can contain a nucleotide sequence, or the complement of a nucleotide sequence (if present in the reverse primer), encoding a second polypeptide. The second polypeptide can be a tag peptide, which interacts specifically with a particular reagent, for example, an antibody. A second polypeptide also can have an unblocked and reactive amino terminus or carboxyl terminus.

The fusion of a tag peptide to a target polypeptide or other polypeptide of interest allows the detection and isolation of the polypeptide. A target polypeptide encoded by a nucleic acid linked in frame to a sequence encoding a tag peptide can be isolated from an in vitro translation reaction mixture using a reagent that interacts specifically with the tag peptide, then the isolated target polypeptide can be subjected to IR-MALDI mass spectrometry, as disclosed herein. It should be recognized that an isolated target polypeptide fused to a tag peptide or other second polypeptide is in a sufficiently purified form to allow IR-MALDI mass spectrometric analysis, since the mass of the tag peptide will be known and can be considered in the determination.

Numerous tag peptides and the nucleic acid sequences encoding such tag peptides, which aids in isolating of anything linked thereto, generally contained in a plasmid, are known and are commercially available (NOVAGEN). Any peptide can be used as a tag, provided a reagent such as an antibody that interacts specifically with the tag peptide is available or can be prepared and identified. Frequently used tag peptides include a myc epitope, which includes a 10 amino acid sequence from c-myc (see Ellison et al., *J. Biol. Chem.* 266:21150–21157 (1991)); the pFLAG system (International Biotechnologies, Inc.); the pEZZ-protein A system (Pharmacia); a 16 amino acid peptide portion of the *Haemophilus influenza* hemagglutinin protein; a GST polypeptide; and a polyhistidine peptide, which generally contains about four to twelve or more contiguous His residues, for example, His-6, which contains six His residues. Reagents that interact specifically with a tag peptide also are known in the art and are commercially available and include antibodies and various other molecules, depending on the tag, for example, metal ions such as nickel or cobalt ions, which interact specifically with a His-6 peptide; or glutathione, which can be conjugated to a solid support such as agarose and interacts specifically with GST.

A second polypeptide also can be designed to serve as a mass modifier of the target polypeptide encoded by the target nucleic acid. Accordingly, a target polypeptide can be mass modified by translating an RNA encoding the target polypeptide operably linked to a mass modifying amino acid sequence, where the mass modifying sequence can be at the amino terminus or the carboxyl terminus of the fusion polypeptide. Modification of the mass of the polypeptide derived from such a recombinant nucleic acid is useful, for example, when several polypeptides are analyzed in a single IR-MALDI mass spectrometric analysis, since mass modification can increase resolution of a mass spectrum and allow for analysis of two or more different target polypeptides by multiplexing.

Tagged Peptides

Polypeptides can be modified by addition of a peptide or polypeptide fragment to the target polypeptide. For example, a target polypeptide can be modified by translating the target polypeptide to include additional amino acids, such as polyhistidine, polylysine or polyarginine. These modifications serve to aid in purification, identification, and immobilization (and also in IR mass spectrometry). Modifications can be added post-translationally or can be encoded by a recombinant nucleic acid containing a sequence of nucleics that encode the target polypeptide.

Where a plurality of target polypeptides is to be differentially mass modified, each target polypeptide in the plurality can be mass modified, for example, using a different polyhistidine sequence, for example, His-4, His-5, His-6, and so on. The use of such a mass modifying moiety provides the further advantage that the moiety acts as a tag peptide, which can be useful, for example, for isolating the target polypeptide attached thereto. Accordingly, the disclosed processes permit multiplexing to be performed on a plurality of polypeptides, and, therefore, are useful for determining the amino acid sequences of each of a plurality of polypeptides, particularly a plurality of target polypeptides.

Primers for amplification can be selected such that the amplification reaction produces a nucleic acid that, upon transcription and translation, results in a non-naturally occurring polypeptide, for example, a polypeptide encoded by an open reading frame that is not a reading frame encoding a naturally occurring polypeptide. Accordingly, by appropriate primer design, in particular, by including an initiation codon in the desired reading frame and, if present, downstream of a promoter in the primer, a polypeptide produced from a target nucleic acid can be encoded by one of the two non-coding frames of the nucleic acid. Such a method can be used to shift out of frame STOP codons, which prematurely truncate a protein and exclude relevant amino acids, or to make a polypeptide containing an amino acid repeat more soluble. Primers useful for effecting the modifications disclosed herein can be obtained from commercial sources or can be synthesized using, for example, the phosphotriester method (see Narang et al., Meth. Enzymol. 68:90 (1979); U.S. Pat. No. 4,356,270; see, also U.S. Pat. Nos. 5,547,835; 5,605,798; and 5,622,824).

A non-naturally occurring target polypeptide also can be encoded by a 5' or 3' non-coding region of an exonic region of a nucleic acid; by an intron; or by a regulatory element such as a promoter sequence that contains, in one of the six frames (3 frames per strand), at least a portion of an open reading frame. In these situations, one primer for amplification of the target nucleic acid contains a promoter and an initiation codon, such that the amplified nucleic acid can be transcribed and translated in vitro. Thus, a method for determining the identity of a target polypeptide, as disclosed herein, permits the determination of the identity of a nucleotide sequence located in any region of a chromosome, provided a polypeptide of at least 2 amino acids, generally at least 3 or 4 amino acids, particularly at least 5 amino acids, is encoded by one of the six frames of the polynucleotide. Accordingly, a process as disclosed herein can be used to determine a nucleotide sequence of an unknown nucleic acid directly, or indirectly by comparing the amino acid sequence of a polypeptide encoded by the unknown nucleic acid with the amino acid sequence of a polypeptide encoded by a corresponding known nucleic acid. Where the nucleotide sequence is determined based on the amino acid sequence of an unknown polypeptide, the determined nucleotide sequence of the unknown polynucleotide can be the same as a naturally occurring nucleotide sequence encoding the polypeptide, or can be different from the naturally occurring sequence due to degeneracy of the genetic code.

The method designated primer oligo base extension (PROBE) can be used herein. This method uses a single detection primer followed by an oligonucleotide extension step to give products, which can be readily resolved by IR-MALDI mass spectrometry. The products differ in length by a number of bases specific for a number of repeat units or for second site mutations within the repeated region. The method is advantageously used for example, for determining identity, identifying mutations, familial relationship, HLA compatability and other such markers, using PROBE-MS analysis of microsatellite DNA. In a preferred embodiment, the method includes the steps of:

a) obtaining a biological sample from two individuals;

b) amplifying a region of DNA from each individual that contains two or more microsatellite DNA repeat sequences c) ionizing volatilizing the amplified DNA;

d) detecting the presence of the amplified DNA and comparing the molecular weight of the amplified DNA.

Different sizes are indicative of non-identity (i.e. wild-type versus mutation), non-heredity or non-compatibility; similar size fragments indicate the possibility identity, of familial relationship, or HLA compatibility. More than one marker may be examined simultaneously, primers with different linker moieties are used for immobilization.

Another method loop-primer oligo base extension, designated LOOP-PROBE, for detection of mutations especially predominant disease causing mutations or common polymorphisms can also be used in the IR-MALDI formats provided herein. In a particular embodiment, this method for detecting target nucleic acid in a sample, includes the steps of:

a) amplifying a target nucleic acid sequence, such as β-globin, in a sample, using (i) a first primer whose 5'-end shares identity to a portion of the target DNA immediately downstream from the targeted codon followed by a sequence that introduces a unique restriction endonuclease site, such as CfoI in the case of β-globin, into the amplicon and whose 3'-end primer is self-complementary; and (ii) a second downstream primer that contains a tag, such as biotin, for immobilizing the DNA to a solid support, such as streptavidin beads;

c) immobilizing the double-stranded amplified DNA to a solid support via a linker moiety;

d) denaturing the immobilized DNA and isolating the non-immobilized DNA strand;

e) annealing the intracomplementary sequences in the 3'-end of the isolated non-immobilzed DNA strand, such that the 3'-end is extendable by a polymerase, which annealing can be performed, for example, by heating then and cooling to about 37° C., or other suitable method;

f) extending the annealed DNA by adding DNA polymerase, 3 dNTPs/1 ddNTP, whereby the 3'-end of the DNA strand is extended by the DNA polymerase to the position of the next ddNTP location (i.e., to the mutation location);

g) cleaving the extended double stranded stem loop DNA with the unique restriction endonuclease and removing the cleaved stem loop DNA i) (optionally adding a matrix, particularly a liquid matrix as defined herein) ionizing/volatizing the extended product; and j) detecting the presence of the extended target nucleic acid, whereby the presence of a DNA fragment of a mass different from wild-type is indicative of a mutation at the target codon(s).

This method eliminates one specific reagent for mutation detection compared other methods of MS mutational analyses, thereby simplifying the process and rendering it amenable to automation. Also, the specific extended product that is analyzed is cleaved from the primer and is therefore shorter compared to the other methods. In addition, the annealing efficiency is higher compared to annealing of an added primer and should therefore generate more product. The process is compatible with multiplexing and various detection schemes (eq., single base extension, oligo base extension and sequencing). For example, the extension of the loop-primer can be used for generation of short diagnostic sequencing ladders within highly polymorphic regions to perform, for example, HLA typing or resistance as well as species typing.

Genotying and Phenotyping

A process for determining the identity of an allelic variant of a polymorphic region of a gene, particularly a human gene, also is provided. Allelic variants can differ in the identity of a single nucleotide or base pair, for example, by substitution of one nucleotide; in two or more nucleotides or base pairs; or in the number of nucleotides due, for example, to additions or deletions of nucleotides or of trinucleotide repeats; or due to chromosomal rearrangements such as translocations. Specific allelic variants of polymorphic regions are associated with specific diseases and, in some cases, correlate with the prognosis of the disease.

Also provided is a process for determining the genetic nature of a phenotype or for identifying a predisposition to that phenotype. For example, it can be determined whether a subject has a predisposition to a specific disease or condition, i.e., whether the subject has, or is at risk of developing, a disease or condition associated with a specific allelic variant of a polymorphic region of a gene. Such a subject can be identified by determining whether the subject carries an allelic variant associated with the specific disease or condition. Furthermore, if the disease is a recessive disease it can be determined whether a subject is a carrier of a recessive allele of a gene associated with the specific disease or condition.

Numerous diseases or conditions have been genetically linked to a specific gene and, more particularly, to a specific mutation or genetic lesion of a gene. For example, hyperproliferative diseases such as cancers are associated with mutations in specific genes. Such cancers include breast cancer, which has been linked to mutations in BRCA1 or BRCA2. Mutant alleles of BRCA1 are described, for example, in U.S. Pat. No. 5,622,829. Other genes such as tumor suppressor genes, which are associated with the development of cancer when mutated, include, but are not limited to, p53 (associated with many forms of cancer); Rb (retinoblastoma); WT1 (Wilm's tumor) and various proto-oncogenes such as c-myc and c-fos (see Thompson and Thompson, *Genetics in Medicine* 5th ed.; Nora et al., *Medical Genetics* 4th ed. (Lea and Febiger, eds.).

A process as disclosed herein also can be used to detect DNA mutations that result in the translation of a truncated polypeptide, as occurs, for example, with BRCA1 and BRCA2. In one embodiment, translation of nucleic acid regions containing such a mutation results in a truncated polypeptide, which easily can be differentiated from the corresponding non-truncated polypeptide by IR-MALDI mass spectrometry.

A process as disclosed herein also can be used to genotype a subject, for example, a subject being considered as a recipient or a donor of an organ or a bone marrow graft. For example, the identity of MHC alleles, particularly HLA alleles, in a subject can be determined. The information obtained using such a method is useful because transplantation of a graft to a recipient having different transplantation antigens than the graft can result in rejection of the graft and can result in graft versus host disease following bone marrow transplantation.

The response of a subject to medicaments can be affected by variations in drug modification systems such as the cytochrome P450 system, and susceptibility to particular infectious diseases can be influenced by genetic status. Genes involved in pharmacogenetics are well known (Nora et al., *Medical Genetics* 4th ed. (Lea and Febiger, eds.)). Thus, the identification of particular allelic variants can be used to predict the potential responsiveness of a subject to specific drug or the susceptibility of a subject to an infectious disease.

Some polymorphic regions may not be related to any disease or condition. For example, many loci in the human genome contain a polymorphic short tandem repeat (STR) region. STR loci contain short, repetitive sequence elements of 3 to 7 base pairs in length. It is estimated that there are 200,000 expected trimeric and tetrameric STRs, which are present as frequently as once every 15 kb in the human genome (see, e.g., International Publ. WO 92/13969; Edwards et al., *Nucl. Acids Res.* 19:4791 (1991); Beckmann et al., *Genomics* 12:627–631 (1992)). Nearly half of these STR loci are polymorphic, providing a rich source of genetic markers. Variation in the number of repeat units at a particular locus is responsible for the observed polymorphism reminiscent of variable nucleotide tandem repeat (VNTR) loci (Nakamura et al., *Science* 235:1616–1622 (1987)); and minisatellite loci (Jeffreys et al., *Nature* 314:67–73 (1985)), which contain longer repeat units, and microsatellite or dinucleotide repeat loci (Luty et al., *Nucl. Acids Res.* 19:4308 (1991); Litt et al., *Nucl. Acids Res.* 18:4301 (1990); Litt et al., *Nucl. Acids Res.* 18:5921 (1990); Luty et al., *Am. J. Hum. Genet.* 46:776–783 (1990); Tautz, *Nucl. Acids Res.* 17:6463–6471 (1989); Weber et al., *Am. J. Hum. Genet.* 44:388–396 (1989); Beckmann et al., *Genomics* 12:627–631 (1992)).

Polymorphic STR loci and other polymorphic regions of genes are extremely useful markers for human identification, paternity and maternity testing, genetic mapping, immigration and inheritance disputes, zygosity testing in twins, tests for inbreeding in humans, quality control of human cultured cells, identification of human remains, and testing of semen samples, blood stains and other material in forensic medicine. Such loci also are useful markers in commercial animal breeding and pedigree analysis and in commercial plant breeding. Traits of economic importance in plant crops and animals also can be identified through linkage analysis using polymorphic DNA markers.

STR loci can be amplified by PCR using specific primer sequences identified in the regions flanking the tandem repeat to be targeted. Allelic forms of these loci are differentiated by the number of copies of the repeat sequence contained within the amplified region. Examples of STR loci include pentanucleotide repeats in the human CD4 locus (Edwards et al., *Nucl. Acids Res.* 19:4791 (1991)); tetranucleotide repeats in the human aromatase cytochrome P-450 gene (CYP19; Polymeropoulos et al., *Nucl. Acids Res.* 19:195 (1991)); tetranucleotide repeats in the human coagulation factor XIII A subunit gene (F13A1; Polymeropoulos et al., *Nucl. Acids Res.* 19:4306 (1991)); tetranucleotide repeats in the F13B locus (Nishimura et al., *Nucl. Acids Res.* 20:1167 (1992)); tetranucleotide repeats in the human c-les/fps, proto-oncogene (FES; Polymeropoulos et al., *Nucl. Acids Res.* 19:4018 (1991)); tetranucleotide repeats in the LFL gene (Zuliani et al., *Nucl. Acids Res.* 18:4958 (1990)); trinucleotide repeat polymorphisms at the human pancreatic phospholipase A-2 gene (PLA2; Polymeropoulos et al., *Nucl. Acids Res.* 18:7468 (1990)); tetranucleotide repeats polymorphism in the VWF gene (Ploos et al., *Nucl. Acids Res.* 18:4957 (1990)); and tetranucleotide repeats in the human thyroid peroxidase (hTPO) locus (Anker et al., *Hum. Mol. Genet.* 1:137 (1992)).

Diagnosis of Genetic diseases and Infectious Diseases

Depending on the target biological macromolecule to be detected, the disclosed processes allow the diagnosis, for example, of a genetic disease or chromosomal abnormality; a predisposition to or an early indication of a gene influenced disease or condition such as obesity, atherosclerosis, diabetes or cancer; or an infection by a pathogenic organism, including a virus, bacterium, parasite or fungus; or provide information relating to identity or heredity based, for example, on an analysis of mini-satellites and micro-satellites, or to histocompatibility based, for example, on HLA phenotyping. Accordingly, processes are provided for detecting genetic lesions that are characterized, for example, by an abnormal number of trinucleotide repeats, which can range from less than 10 to more than 100 additional trinucleotide repeats relative to the number of repeats, if any, in a gene in a non-affected individual, by using IR-MALDI mass spectrometry to analyze an encoding target nucleic acid or an encoded target polypeptide, as disclosed herein.

Diseases associated with genetic lesions characterized by nucleotide repeats include, for example, Huntington's disease, prostate cancer, SCA-1, Fragile X syndrome (Kremer et al., *Science* 252:1711–14 (1991); Fu et al., *Cell* 67:1047–58 (1991)); Hirst et al., *J. Med. Genet.* 28:824–29 (1991))), myotonic dystrophy type I (Mahadevan et al., *Science* 255:1253–55 (1992); Brook et al., *Cell* 68:799–808 (1992)), Kennedy's disease (also termed spinal and bulbar muscular atrophy; La Spada et al., *Nature* 352:77–79 (1991)); Machado-Joseph disease, and dentatorubral and pallidolyusian atrophy. The abnormal number of triplet repeats can be located in any region of a gene, including a coding region, a non-coding region of an exon, an intron, or a promoter or other regulatory element. For example, the expanded trinucleotide repeat associated with myotonic dystrophy occurs in the 3' untranslated region (UTR) of the MtPK gene on chromosome 19. In some of these diseases, for example, prostate cancer, the number of trinucleotide repeats is positively correlated with prognosis of the disease such that a higher number of trinucleotide repeats correlates with a poorer prognosis.

Hence, the process for detecting nucleic acids by IR-MALDI mass spectrometry can be useful, for example, for diagnosing the existence of any one of the more than 3000 known genetic diseases (Cooper and Krawczak, "Human Genome Mutations" (BIOS Publ. 1993)), including hemophilias, thalassemias, Duchenne muscular dystrophy, Huntington's disease, Alzheimer's disease and cystic fibrosis, or other genetic disease to be identified. In addition, the processes can be useful for diagnosing certain birth defects that are the result of chromosomal abnormalities such as trisomy 21 (Down's syndrome), trisomy 13 (Patau syndrome), trisomy 18 (Edward's Syndrome), monosomy X (Turner's syndrome) and other sex chromosome aneuploidies such as Klinefelter's syndrome (XXY). The processes also can be used to detect certain DNA sequences that may predispose an individual to any of a number of diseases, including, for example, diabetes, arteriosclerosis, obesity, various autoimmune diseases and cancers such as colorectal, breast, ovarian, prostate and lung cancer, or that render an individual suitable or unsuitable for a particular medical treatment.

Alternatively, the processes can be used to detect nucleic acids that are characteristic of viruses, bacteria, fungi or other infectious organisms, which have nucleic acid sequences that are different from the sequences normally contained in the host cell. The processes also can be used to detect characteristic nucleic acid sequences that provide information relating to identity, heredity or compatibility.

Disease-causing viruses that infect humans and animals and that may be detected by a disclosed process include, but are not limited to, Retroviridae (e.g., human immunodeficiency viruses such as HIV-1 (also referred to as HTLV-III, LAV or HTLV-III/LAV; Ratner et al., *Nature* 313:227–284 (1985); Wain Hobson et al., *Cell* 40:9–17 (1985)), HIV-2 (Guyader et al., *Nature* 328:662–669 (1987); European Patent Publication No. 0 269 520; Chakrabarti et al., *Nature* 328:543–547 (1987); European Patent Application No. 0 655 501), and other isolates such as HIV-LP (International Publ. WO 94/00562); Picornaviridae (eq., polioviruses, hepatitis A virus, (Gust et al., *Intervirology* 20:1–7 (1983)); enteroviruses, human coxsackie viruses, rhinoviruses, echoviruses); Calcivirdae (e.g. strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae; Hepadnaviridae (Hepatitis B virus); Parvoviridae (most adenoviruses); Papovaviridae (papilloma viruses, polyoma viruses); Adenoviridae (most adenoviruses); Herpesviridae (herpes simplex virus type 1 (HSV-1) and HSV-2, varicella zoster virus, cytomegalovirus, herpes viruses; Poxviridae (variola viruses, vaccinia viruses, pox viruses); Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, i.e., Hepatitis C); Norwalk and related viruses, and astroviruses.

Examples of infectious bacteria include *Helicobacter pyloris, Borelia burgdorferi, Legionella pneumophilia,* Mycobacteria sp. (e.g. *M. tuberculosis, M. avium, M. intracellulare, M. kansaii, M. gordonae), Staphylococcus aureus, Neisseria gonorrheae, Neisseria meningitidis, Listeria monocytogenes, Streptococcus pyogenes* (Group A Streptococcus), *Streptococcus agalactiae* (Group B Streptococcus), Streptococcus sp. (viridans group), *Streptococcus faecalis, Streptococcus bovis,* Streptococcus sp. (anaerobic species), *Streptococcus pneumoniae,* pathogenic Campylobacter sp., Enterococcus sp., *Haemophilus influenzae, Bacillus antracis, Corynebacterium diphtheriae,* Corynebacterium sp., *Erysipelothrix rhusiopathiae, Clostridium perfringens, Clostridium tetani, Enterobacter aerogenes, Klebsiella pneumoniae, Pasturella multocida,* Bacteroides sp., *Fusobacterium nucleatum, Streptobacillus moniliformis, Treponema pallidium, Treponema pertenue,* Leptospira, and *Actinomyces israelli.*

Examples of infectious fungi include but are not limited to *Cryptococcus neoformans, Histoplasma capsulatum, Coccidioides immitis, Blastomyces dermatitidis, Chlamydia trachomatis, Candida albicans.* Other infectious organisms include protists such as *Plasmodium falciparum* and *Toxoplasma gondii.*

Releasable Mass-Label Molecules

IR-MALDI MS may be used in conjunction with mass-label molecules for the detection and identification of target molecules. Releasable mass-label molecules have been described in PCT Application Publication No. WO 98/26095, which is incorporated in its entirety by reference herein. In these methods, the target molecule is linked to a mass-label through an element that is specific for the target. The target is "indirectly" detected after release of the mass-label from the target molecule and detection of the mass-label by IR-MALDI MS. The mass value of the label identifies and characterizes the element specific for the target. Thus, detection of the mass-label, instead of the target molecule itself, is indicative of the presence of the target molecule in a sample.

Any of the methods of performing IR-MALDI mass spectrometry as described herein may be used to detect the mass label. For example, the mass label may be mixed with any of the matrices as described herein and subjected to IR-MALDI mass spectrometry. In particular embodiments, the mass label is mixed with a glycerol matrix prior to performing IR-MALDI mass spectrometry.

The mass label is contained within a release tag compound which further contains one or more reactive groups and one or more release groups. The reactive group reacts with the target molecule. The mass label is linked, or attached, to the reactive group via a releasable attachment. Typically, the mass label is released from all or a part of the reactive group prior to mass spectral analysis. This releasable attachment typically occurs through the use of a release group which may be the linkage between the mass label and the reactive group or which may comprise a portion or all of the reactive group or which may be contained within the reactive group.

Typical target molecules include polynucleotides, gene sequences, mutations within a gene or protein sequence, toxins, metals, receptors, antigens, ligands, polypeptides, carbohydrates and lipids.

The Mass Label

The mass label (also referred to as a tag) may be any compound that may be detected by mass spectrometry and includes synthetic polymers and biopolymers. Synthetic polymers include polyethylene glycol, polyvinyl phenol, polypropylene glycol, polymethyl methacrylate, and derivatives thereof. Synthetic polymers typically contain monomer units including ethylene glycol, vinyl phenol, propylene glycol, methyl methacrylate, and derivatives and combinations thereof. Biopolymers include those comprising monomer units such as amino acids, non-natural amino acids, peptide mimics, nucleic acids, nucleic acid mimics and analogs, and saccharides and combinations thereof. In certain embodiments, the mass label has a molecular weight greater than about 500 Daltons. In some embodiments, the mass label may be nonvolatile (including involatile), whereas in other embodiments, volatile mass labels may be used. Other mass labels include heme groups, dyes, organometallic compounds, steroids, fullerenes, retinoids, carotenoids and polyaromatic hydrocarbons.

The Reactive Group

The reactive group refers to a group capable of reacting with the molecule whose presence is to be detected. For example, the reactive group may be a biomolecule capable of specific molecular recognition. Biomolecules capable of specific molecular recognition may typically be any molecule capable of specific binding interactions with unique molecules or classes of molecules, including but not limited to peptides, polypeptides, proteins and polynucleic acids. Polypeptides include peptides comprising two or more native or non-native amino acid monomers such as native proteins, gene products, protein conjugates, mutant or polymorphic polypeptides, post-translationally modified proteins, genetically engineered gene products including products of chemical synthesis, in vitro translation, cell-based expression systems, including fast evolution systems involving vector shuffling, random or directed mutagenesis and peptide sequence randomization, oligopeptides, antibodies, enzymes, receptors, regulatory proteins, nucleic acid-binding proteins, hormones, or protein products of a display method such as phage or bacterial display methods.

Nucleic acids include standard or naturally-occurring as well as modified/non-natural nucleic acids, often known as nucleic acid mimics or mimetics. Thus, nucleotides refer to both naturally-occurring and modified/non-naturally occurring nucleotides, including nucleoside tri-, di-, and mono-phosphates as well as monophosphate monomers present within polynucleic acid or oligonucleotide. A nucleotide may be a ribo, 2'-deoxy, 2',3'-deoxy as well as a vast array of other nucleotide mimics that are well known in the art. Mimics include chain-terminating nucleotides, such as 3'-O-methyl, halogenated base or sugar substitutions, alternative sugar structures including nonsugar, alkyl ring structures, alternative bases including inosine, deaza-modified, chi and psi linker-modified, mass label-modified, phosphodiester modifications or replacements including phosphorothioate, methylphosphonate, boranophosphate, amide, ester, ether and a basic or complete internucleotide replacement, including cleavage linkages such a photocleavable nitrophenyl moiety. These modifications are well known in the art and based on fundamental principles as described in Saenger (1983) *Principles of Nucleic Acid Structure*, Springer-Verlag, NY.

Polynucleic acids include molecules containing more than one nucleic acid. Polynucleic acids include lengths of two or more nucleotide monomers and encompass nucleic acids, oligonucleotides, oligos, polynucleotides, DNA, genomic DNA, mitochondrial DNA, copy DNA, bacterial DNA, viral DNA, viral RNA, RNA, message RNA, transfer RNA, ribosomal RNA, catalytic RNA, clones, plasmids, M13, P1, cosmid, bacteria artificial chromosome, yeast artificial chromosome, mammalian artificial chromosome, amplified nucleic acid, amplicon, PCR product and other types of amplified nucleic acid.

A reactive group may be an oligonucleotide having one or more nucleotides or oligonucleotide(s) added after hybridization of the reactive group to a complementary nucleic acid sequence. A nucleotide added after hybridization may have a chain-terminating modification, for example, a chain-terminating dideoxynucleotides. The added nucleotide may also contain a functional group capable of being immobilized on a solid support, for example, a biotin or digoxigenin. Generally, this functional group or binding group or moiety is capable of attaching or binding the tag compound to the solid support. The binding moiety may be attached to the added nucleotide or oligonucleotide directly through an intervening linking group or by specific hybridization to an intermediary oligonucleotide which is itself bound to a solid support. Binding moieties include functional groups for covalent bonding to a solid support, ligands that attach to the solid support via a high-affinity, noncovalent interaction (such as biotin with streptavidin), a series of bases complementary to an intermediary oligonucleotide which is itself attached to the solid support, as well as other means that are well-known to those of skill in the art, such as those described elsewhere herein and in PCT Application Publication Nos. WO96/37630, WO96/29431, WO98/20019, WO94/16101, WO 98/20166, each of which is incorporated in its entirety by reference herein.

The reactive group may also contain a nuclease blocking moiety which serves to block the digestion of the oligonucleotide by the nuclease, such as an exonuclease. Typical nuclease blocking moieties include phosphorothioate, alkylsilyldiester, boranophosphate, methylphosphonate and peptide nucleic acid.

The releasable Attachment

The mass label is linked, or attached, to the reactive group via a releasable attachment. The release group may be any labile group providing for such a releasable attachment. The release group may thus be a chemically cleavable linkage or labile chemical linkage. Such linkages may typically be cleaved by methods that are well known to those of skill in the art, such as by acid, base, oxidation, reduction, heat, light, or metal ion catalyzed, displacement or elimination chemistry. For example, the chemically cleavable linkage may contain a modified base, a modified sugar, a disulfide bond, a chemically cleavable group incorporated into the phosphate backbone, or a chemically cleavable linker. Some examples of these linkages are described in PCT Application Publication no. WO96/37630. Chemically cleavable groups that may be incorporated into the phosphate backbone are well known to those of skill in the art and may include dialkoxysilane, 3'-(S)-phosphorothioate, 5'-(S)-phosphorothioate, 3'-(N)-phosphoroamidate, or 5'-(N)-phosphoroamidate. The chemically cleavable linker may be a modified sugar, such as ribose, or the linkage may be a disulfide bond.

When the releasable attachment is contained within the reactive group, the release of the releasable attachment may be activated by a selective event. For example, the selective release can be mediated by an enzyme such as an exonuclease specific for double-stranded or single-stranded DNA. Generally, when the releasable attachment is contained within the reactive group, the reactive group contains within its structure the particular release group which will cause the mass label to disconnect from the tag component.

The release groups include groups or linkages cleavable by an enzyme. Enzymatically cleavable release groups include phosphodiester or amide linkages as well as restriction endonuclease recognition sites. Nucleases for cleaving release groups include exonucleases and restriction endonucleases. Typical exonucleases include exonucleases specific for both double-stranded and single-stranded polynucleic acids. Additionally, restriction endonucleases include Type IIS and Type II restriction endonucleases. The release group may be cleavable by a protease, including endoproteinases.

Furthermore, the reactive group may contain a nucleoside triphosphate or may be synthesized using mass-labeled nucleoside triphosphates. The labeled probes may include at least two unique mass labels.

Exemplary Release Tag Compounds

Exemplary release tag compounds include those in which the reactive group is a double-stranded oligonucleotide containing a restriction endonuclease recognition site, the releasable attachment contains a phosphodiester linkage capable of being cleaved by a restriction endonuclease and the mass label is one detectable by mass spectrometry. The reactive group may further include a modified nucleotide and the mass label may include a portion of the reactive group. Double-stranded oligonucleotides include not only two complementary strands hybridized to each other by hydrogen bonding interactions, but also include single strands of nucleotides wherein portions of the strand are single-stranded and portions are double-stranded. For example, portions or all of the reactive group may include a self-complementary oligonucleotide hairpin where part of the reactive group is complementary to another part of the reactive group. In this case, certain conditions allow the formation of a double-stranded duplex between these two portions of the reactive group. It is not necessary that all of the reactive group be double-stranded; release tag compounds containing single-stranded regions are also included.

Further exemplary release tag compounds include those in which the reactive group is a double-stranded oligonucleotide, the releasable attachment is a chemically cleavable release group and the mass label is one detectable by mass spectrometry. In this instance, the releasable attachment is typically located within the reactive group. Cleavage at the chemically cleavable release group is generally inhibited in this aspect by the presence of a double-stranded oligonucleotide at the release group. Chemically cleavable release groups, such as 3'-(S)-phosphorothioate, 5'-(S)-phosphorothioate, 3'-(N)-phosphoroamidate, 5'-(N)-phosphoroamidate or ribose may be employed with these embodiments. A portion of the reactive group may be rendered single-stranded at the release group by hybridization of a portion of the reactive group to a target nucleic acid.

A set of release tags (i.e., a group of two or more release tag compounds) may also be used for detecting a target nucleic acid. In this instance, the target nucleic acid typically contains more than one release tag compound. Each release tag compound includes a reactive group, a releasable attachment and a mass label. The reactive group may be an oligonucleotide including a variable region and an invariant region, the releasable attachment is a release group and the mass label is one detectable by mass spectrometry. The invariant and variable regions react with the target nucleic acid. Generally, each release tag compound of the set will be different from all other members of the group. That is, each member will include a different combination of reactive group, release group and mass label. Typically, the mass label of at least one member of the set may identify a specific sequence within the variable region. In some instances, the mass label for each member of the set may uniquely identify each different sequence within the variable region. In other instances, a combination of the mass labels of two or more release tag compounds may identify each different sequence within the variable region.

Preparation of Mass-label Probes

Methods of producing mass-labeled probes include combining nucleoside or amino acid monomers with at least one mass-labeled monomer under conditions that allow for polymerization. The polymerization may be mediated, for example, by an enzyme or by chemical synthesis. Synthetic methods for preparing the mass-label probes are essentially those for standard peptide and DNA synthesis.

Methods for Detecting Target Molecules using Mass-labeled Probes

Generally, one method for detecting a target molecule includes obtaining a plurality of probes, each probe including a reactive group, a release group and a mass label as described herein and in PCT Application Publication No. WO98/26095. Typically, each probe within the plurality contains a unique mass-label. Next, a sample that may or may not contain the target molecule is contacted with the plurality of probes under conditions suitable to allow for the formation of probe:target molecule complexes. The mass label is released from the probe and the mass of the mass-label is determined by IR-MALDI mass spectrometry. In a preferred embodiment, the mass label is mixed with a liquid matrix in preparation for IR-MALDI mass spectrometric analysis. A particularly preferred liquid matrix is glycerol. Typically, the mass is indicative of a specific target molecule. In this way, the target molecule can be identified according to the unique combination of mass labels.

In another method for detecting a target molecule, the target molecule is amplified, using any method known by one of skill in the art, to produce an amplified target molecule. The amplified target molecule is then hybridized with a probe such as described herein and in PCT Application Publication No. WO98/26095 to produce probe:amplified target molecule complexes. The mass label on the amplified target molecule complexes are then released and the mass of the mass label is determined by IR-MALDI mass spectrometric analysis. In a preferred embodiment, the mass label is mixed with a liquid matrix in preparation for IR-MALDI mass spectrometric analysis. A particularly preferred liquid matrix is glycerol. The amplified target molecule may also be immobilized onto a solid support, and any probe not part of a probe:amplified target molecule complex is removed by washing.

Multiplexing methods are also provided wherein the target molecule is contacted with a plurality of probes. Each reactive group of the probe may be associated with a unique mass label or it may be associated with a unique set of mass labels. Thus a target molecule may be detected by the mass spectral detection of a particular mass label or a particular set of mass labels. Mass spectral detection is accomplished using IR-MALDI mass spectrometry. In a preferred embodiment, the mass label or labels are mixed with a liquid matrix prior to performing IR-MALDI mass spectrometry. A particularly preferred liquid matrix is glycerol. Where a set of mass labels is employed, the set of mass labels may be attached to the same probe. Alternatively, each member of the set may be attached to a different probe.

In another method for detecting a target molecule, the following steps are included: (a) obtaining a probe including a reactive group, a release group and a nonvolatile mass label; (b) contacting a target molecule with the probe to produce probe:target molecule complexes; (c) selectively releasing the mass label from the probe:target molecule complexes to produce released mass labels; and (d) determining the mass of the released mass labels by IR-MALDI mass spectrometry. In a further method, prior to step (d), the mass label is mixed with a liquid matrix, preferably glycerol.

In another method for detecting a target molecule, the following steps are included: (a) obtaining a probe including a reactive group, a release group and a mass label; (b) contacting a target molecule with the probe to produce probe:target molecule complexes; (c) releasing the mass label from the probe:target molecule complexes to produce released mass labels; and (d) determining the mass of the released mass labels by IR-MALDI mass spectrometry. In a further method, prior to step (d), the mass label is mixed with a liquid matrix, preferably glycerol.

A method for multiplexing the detection of a target molecule includes: (a) obtaining a plurality of probes, each probe including a reactive group, a release group, and a mass label; (b) contacting the target molecule with the plurality of probes to produce probe:target molecule complexes; (c) releasing the mass label from any probe belonging to the probe:target molecule complexes to produce released mass labels; and (d) determining the mass of any released mass label by IR-MALDI mass spectrometry. In this respect, each reactive group recognizing a specific target molecule is associated with a unique set of mass labels. A plurality of target molecules may also be detected with the plurality of probes. In a further embodiment, prior to step (d), the mass label is mixed with a liquid matrix, preferably glycerol.

A method for monitoring gene expression includes (a) obtaining a plurality of probes, each probe including a reactive group, a release group, and a mass label; (b) contacting a plurality of target nucleic acids with the plurality of probes to produce probe:target nucleic acid complexes; (c) selectively releasing the mass label from any probe belonging to the probe:target nucleic acid complex to produce released mass labels; and (d) determining the mass of any released mass label by IR-MALDI mass spectrometry. In a further embodiment, prior to step (d), the mass label is mixed with a liquid matrix, preferably glycerol. The target nucleic acids may be amplified prior to step (a).

A further method for detecting a target molecule includes: (a) amplifying one or more target nucleic acids to produce amplified nucleic acid products; (b) incorporating one or more molecules including a reactive group, a release group and a mass label into the amplified nucleic acid product during the amplification process; (c) selectively releasing the mass labels incorporated into the amplified nucleic acid products to produce released mass labels; and (d) determining the mass of the released mass labels by IR-MALDI mass spectrometry. In a further embodiment, prior to step (d), the mass label is mixed with a liquid matrix, preferably glycerol.

Another method for detecting a target molecule includes: (a) obtaining a probe comprising a reactive group, a release group and a mass label; (b) contacting the probe to a target nucleic acid molecule to produce probe:nucleic acid molecule complexes; (c) mass modifying the probe:nucleic acid molecule complexes by attaching a nucleotide or oligonucleotide to the probe to produce mass modified mass labels; (d) releasing the mass modified labels; and (e) determining the mass of the mass-modified labels by IR-MALDI mass spectrometry. In a further embodiment, prior to step (e), the mass label is mixed with a liquid matrix, preferably glycerol.

Methods for detecting single Nucleotide Polymorphisms (SNPS) Using Mass-labeled Molecules The methods utilizing mass-label molecules can also be used in the detection of single nucleotide polymorphisms (SNPs). Mass label probes may be prepared that hybridize immediately adjacent to a polymorphic site and a polymerase may then be used to add one base at the site of the polymorphism. For example, where a single probe is used, a mixture of the four chain-terminating triphosphates may be added, each with a unique mass label attached. In the homozygous SNP case only one of the four chain-terminating nucleotides may add to the end of the probe coupling the associated mass label to the probe. Approaches to releasing the mass label from the probe include, but are not limited to, the use of chemically labile functional groups linking the mass label to the terminating nucleotide, chemically labile functional groups within the backbone of the extended primer or the chain-termination nucleotide, or the use of an enzyme to cleave at one or more of the phosphodiester or glycosidic linkages within the primer extension product. In cases where the mass label release point is within the backbone of the extension product, the released mass label may include the terminal nucleotide or some mass-modified version thereof. In another version where the release point is internal to the primer extension product, the native chain-termination nucleotides themselves may serve as all or a portion of the mass labels since each base possesses a unique mass. In cases where the mass label is chemically cleaved from the probe, any unincorporated nucleotides may first be removed or washed away so that they are not visualized by the mass spectrometer.

Partitioning of the hybridized mass-labeled chain-terminating triphosphate may be done on the basis of mass differences, as labeled triphosphate hybridized to a target-hybridized probe will have a higher molecular weight than a labeled triphosphate that is not. The probe or target may also be attached to a solid-phase via a number of means including biotin/streptavidin or chemical coupling or UV cross-linking. A nuclease may also be used to digest the mass-labeled probe. Using a nuclease the mass-labeled chain-terminating nucleotide will be released as a monophosphate. The unincorporated mass-labeled chain-terminating nucleotides will remain as triphosphates, and the resulting mass shift to monophosphate will indicate which nucleotide was incorporated. This method relieves the necessity to remove unincorporated nucleotides prior to analysis.

Many SNPs may be detected simultaneously by multiplexing a large number of probes. Mass labels may be present to uniquely tag each of the probes that comprise the pool. The addition of a biotinylated chain-terminating nucleotide at the site of the point polymorphism may also be used to segregate the probe population depending on which probes incorporate a specific biotinylated chain-terminating nucleotide and which do not. As an example, the pool of mass-labeled probes with target may be divided into four reactions. The first reaction would contain only biotinylated dideoxy adenosine triphosphate, the second would contain only biotinylated dideoxy cytidine triphosphate, the third only biotinylated dideoxy guanidine triphosphate, and the fourth only biotinylated dideoxy thymidine triphosphate. Following a single base extension polymerase-dependent reaction in the presence of the proper nucleotide, the extended products are captured, washed and the mass labels are released for mass spectrometric analysis by IR-MALDI mass spectrometry. In the first reaction, only those mass-labeled probes that incorporate an A will be visualized. In the second reaction, only those mass-labeled probes that incorporated a C will be visualized. For the third and fourth reactions, probes that incorporated, respectively, a G or a T, will be visualized.

Another example of a mass change within a mass label is the case where the mass label is present at the 3' end of the probe. Following polymerase-dependent base extension, the mass label may be released, including the chain-terminating base addition as well as the penultimate base. Placement of the mass label and the release site may be at the other bases with a preference of placement near the 3' end. In all cases, the mass label should preferably be placed between the release group and the 3' end. In other embodiments, it may be preferred to perform what is effectively a short chain terminated sequencing reaction, where, in addition to dideoxynucleotides, some amount of normal deoxy nucleotides are present. Extension of the primer will result in a nested set of products, each being chain terminated by a dideoxynucleotide correlating to its complementary base on the template strand. In the preferred form, the mass label may be located within the primer near the 3' end which contains a chemical release group. Such a method offers a separate embodiment for short sequence reads as well as detection of one or more SNPs. All of the SNP detection methods may involve the use of mass-modified forms of the different nucleotides in order to enhance the mass difference between the different possible products.

SNPs may also be detected by the performance of a discriminating exonuclease event in the presence of matching and mismatching oligonucleotide probes. One example of this approach is to combine the use of releasable mass labels with nick translation PCR. In addition to its polymerase activity, Taq DNA polymerase has both 5' to 3' exonuclease and endonuclease activities. If a fully complementary oligonucleotide probe is placed in the path of polymerization, for example during nucleic acid amplification, the polymerase will attack the 5' end of the probe with its exonuclease activity, digesting the molecule until it is too small to remain hybridized. However, if the oligonucleotide is not perfectly complementary near the 5' end, e.g., a mismatch is present nearby, then the end of the probe will fray and be attacked by the endonucleolytic activity of the polymerase rather than the exonuclease activity. The nucleolytically cleaved product, preferably containing the mass label, will have a different final mass depending on whether or not a mismatch was present and how the nuclease cut in response to this mismatch. It has been demonstrated that the initiation of endonucleolytic activity can be influenced by the presence and placement of a mismatch within the hybridization probe. Selective placement of a mass label within the oligonucleotide probe relative to the expected mismatch site can be used to yield a differential signal depending on whether or not an actual mismatch is present. This assay can be extended to the simultaneous detection of multiple SNPs. Each of the probes targeting a particular SNP contains one of the four possible bases to complement the site of the polymorphism. The placement of the mass label is such that if the probe contains a perfect match to the template, the mass label will be released by the exonuclease activity of the Taq polymerase, primarily in a form that includes a single nucleotide. The other probes will create a mismatch and the endonuclease activity of the polymerase will initiate cutting of the probe in such a way that includes more than one nucleotide. The shift in mass of the mass label cleavage product is diagnostic of whether or not a mismatch has occurred.

Methods for Identifying Short Sequences Using Mass-labeled Probes

The mass-labeled probes may be used to identify short sequences. In particular, combinations of hybridization and enzymatic (polymerase or ligase) extension can be employed with the labeled probes to identify short sequence runs adjacent to a "priming" or anchoring region. There are several methods for doing this. In one method, a mixture of probes are synthesized containing two domains, a fixed sequence recognition domain, typically containing only one or a few sequences, and a randomized domain, comprising the full set (or some subset) of all possible sequences. The fixed sequence of the probe is used to target hybridization of the probe to a single site within a particular target nucleic acid. This target site is typically invariant. The sequence adjacent to the invariant sequence is variable and, depending on the particular target, can have any one of the total combinations of sequence. In order to probe for all possibilities, it is necessary to synthesize probes containing all the possible secondary domain sequence combinations. For example, if the second probe region is four bases in length, then 256 different probes need to be synthesized. The probes can be synthesized individually, each possessing a unique combination of mass labels as a releasable mass signature. Alternatively, the probes can be synthesized with unique mass signatures using a combinatorial synthesis method.

In order to increase the level of discrimination and extend the read length for the short sequence read it is possible to use an enzyme, such as a polymerase or ligase, to add a single nucleotide or oligonucleotide to the end of the variable region of the anchored probe, optionally including mass labels on the added nucleotide or oligonucleotide that can identify the sequence for these additions. Addition of bases by either enzyme places stricter requirements on the variable region being a perfect hybrid to enable enzymatic action. For polymerase the addition needs to be to the 3' end of the probe while ligation can occur at either the 3' or 5' end.

Methods for Detecting Mismatches Using Mass-labeled Probes

In one method for detecting mismatches, amplified nucleic acid product contains a double-stranded molecule containing a mismatch, and an exonuclease-blocking functionality at the 3' ends of the strands. Typically, this method may further include cleavage of at least one strand of the double-stranded molecule at the site of the mismatch and selective releasing of the mass label. Selective releasing of the mass label may typically be accomplished by digestion of the cleaved strand by a 3' to 5' exonuclease, such as exonuclease III. In selective releasing, a mass label is released from a probe which belongs to a probe:target molecule complex without releasing a mass label from a probe not belonging to such a complex without having to physically partition the two types of probes. The mismatch may be cleaved by an enzyme, such as mutHLS, T4 endonuclease VII, mutY DNA glycosylase, thymine mismatch DNA glycosylase or endonuclease V. The mismatch may also be cleaved by a chemical, such as $OsO_4$, $HONH_2$ or $KMnO_4$.

Analyzing DNA Tandem Nucleotide Repeat Alleles Using IR-MALDI Mass Spectrometry 1. Analyzing DNA Tandem Nucleotide Repeat Alleles IR-MALDI mass spectrometry can be used to analyze DNA tandem nucleotide repeat alleles and multiplex the identification of more than one DNA tandem nucleotide repeat regions from more than one DNA tandem nucleotide repeat loci. As noted above, methods using UV mass spectrometric methods for such analyses are known to those of skill in the art. These methods are modified herein for use with IR-MALDI.

In one embodiment, a method for analyzing DNA tandem nucleotide repeat alleles at a DNA tandem nucleotide repeat locus in a target nucleic acid by IR-MALDI is provided. This method includes the steps of extending a target nucleic acid using one or more primers to obtain a limited size range of nucleic acid extension products, where one or more primers are complementary to a sequence flanking the DNA tandem nucleotide repeat of the locus; and determining the mass of the nucleic acid extension products by IR-MALDI mass spectrometry with a liquid matrix.

In one embodiment, the 3' end of the one or more primers immediately flanks a DNA tandem nucleotide repeat region. In another embodiment, the one or more primers includes a sequence complementary to one, two or three tandem repeats of the DNA tandem nucleotide repeat locus or loci. In another embodiment, at least one primer inlcude a cleavable site. The cleavable site preferably includes a recognition site for a restriction endonuclease, an exonuclease blocking site, or a chemically cleavable site. In another embodiment, at least one primer is can be attached to a solid support. Means for attachment include biotin or digoxigenin.

In another embodiment, the extension of at least one primer is terminated using a chain termination reagent, such as a dideoxynucleotide triphospate. More than one target nucleic acids can be extended to produce more than one nucleic acid extension products, so that a plurality of nucleic acids can be analyzed. For example, in one embodiment, the mass of more than one DNA tandem nucleotide repeat allele at more than one DNA tandem nucleotide repeat loci are determined simultaneously. In another embodiment, the DNA tandem nucleotide repeat loci have overlapping allelic mass ranges. In another embodiment, the nucleic acid extension products have interleaving mass spectral peaks. In another preferred embodiment, at least one nucleic acid extension product contains a mass modified nucleotide.

In yet another preferred embodiment, the length of at least one nucleic acid extension product is reduced by cleaving the nucleic acid extension product at a cleavable site. More preferably, the cleavable site comprises a restriction endonuclease site, an exonuclease blocking site, or a chemically cleavable group.

2. Multiplexing the Identification of More Than One DNA Tandem Nucleotide Repeat Regions From More Than One DNA Tandem Nucleotide Repeat Loci Methods for multiplexing the identification of more than one DNA tandem nucleotide repeat region from more than one DNA tandem nucleotide repeat loci by mass spectrometry are provided. These methods include the steps of a) obtaining more than one nucleic acid extension products by extending one or more primers complementary to sequences flanking the DNA tandem nucleotide repeat regions; and b) determining the mass of the more than one nucleic acid extension products simultaneously by IR-MALDI mass spectrometry with a liquid matrix, where the nucleic acid extension products have overlapping allelic mass ranges.

In one embodiment, the 3' end of the one or more primers immediately flanks a DNA tandem nucleotide repeat region. In another embodiment, the one or more primers comprise a sequence complementary to up to one, two or three tandem repeat of the DNA tandem nucleotide repeat locus or loci. In another embodiment, the extension of at least one primer is terminated using a chain termination reagent, such as a dideoxynucleotide triphospate.

In yet another embodiment, at least one target nucleic acid extension product contains a mass modifying group. More preferably, the mass modifying group includes a mass modified nucleotide. Also more preferably, the mass modifying group comprises a nonstandard deoxyribonucleotide. In yet another embodiment, the cleavable site includes a recognition site for a restriction endonuclease, an exonuclease blocking site, or a chemically cleavable site. In yet another embodiment, the mass modifying group is incorporated during or after extension of the nucleic acid extension product.

In another embodiment, a method for multiplexing the identification of more than one DNA tandem nucleotide repeat regions from more than one DNA tandem nucleotide repeat loci by mass spectrometry is provided. This method includes the steps of obtaining more than one nucleic acid amplification products by amplifying two or more primers complementary to sequences flanking the DNA tandem nucleotide repeat regions; and determining the masses of more than one nucleic acid amplification products simultaneously by IR-MALDI mass spectrometry with a liquid matrix, where the nucleic acid extension products have overlapping allelic mass ranges.

In one such embodiment, the 3' end of the one or more primers immediately flanks a DNA tandem nucleotide repeat region. In another embodiment, the one or more primers include a sequence complementary to up to one, two or three tandem repeat of the DNA tandem nucleotide repeat locus or loci.

In still another embodiment, at least one nucleic acid amplification product contains a mass modifying group that preferably includes a mass modified nucleotide, such as a nonstandard deoxyribonucleotide. The mass modifying group is can be incorporated before, during or after amplification. In yet another embodiment, the cleavable site includes a recognition site for a restriction endonuclease, an exonuclease blocking site, or a chemically cleavable site.

3. Detecting Mutations in a Target Nucleic Acid Using IR-MALDI Mass Spectrometry As noted herein, IR-MALDI mass spectrometry can be used to detect mutations in a target nucleic acid. In one embodiment, a method for detecting mutations in a target nucleic acid is provided. The method includes obtaining from the target nucleic acid a set of nonrandom length fragments (NLFs) in single-stranded form, where the set includes NLFs derived from one of either the positive or the negative strand of the target nucleic acid or the set is a subset of single-stranded NLFs derived from the positive and the negative strand of the target nucleic acid; and then determining masses of the members of the set by IR-MALDI mass spectrometry with a liquid matrix.

In one embodiment, at least one member of the set of single-stranded NLFs optionally has one or more nucleotides replaced with mass-modified nucleotides. In another embodiment, the determining step optionally further includes using internal self-calibrants to provide improved mass accuracy. In another embodiment, the target nucleic acid is single-stranded and the obtaining step includes hybridizing the single-stranded target nucleic acid to one or more sets of fragmenting probes to form hybrid target nucleic acid/fragmenting probe complexes. The complexes contain at least one double-stranded region and at least one single-stranded region. The target nucleic acid molecule is then nonrandomly fragmented by cleaving the hybrid target nucleic acid/fragmenting probe complexes at every single-stranded region with at least one single-strand-specific cleaving reagent to form a set of NLFs. Preferably, the set of fragmenting probes leaves single-stranded gaps between double-stranded regions formed by hybridization of the set of fragmenting probes to the target nucleic acid. The hybridizing step can further include providing two sets of single-stranded target nucleic acid and separately hybridizing a first set of fragmenting probes to a first set of single-stranded target nucleic acid and a second set of fragmenting probes to a second set of single-stranded target nucleic acid, where the members of the second set of fragmenting probes include at least one single-stranded nucleotide sequence complementary to regions of the target nucleic acid that are not complementary to any nucleotide sequences in any members of the first set of fragmenting probes. Further, the members of the first set of fragmenting probes can include sequences of nucleotides that overlap with sequences of nucleotide of the members of the second set of fragmenting probes.

In yet another embodiment, the single-strand-specific cleaving reagent is a single-strand-specific endonuclease or a single-strand specific chemical cleaving reagent, such as, but are not limited to, reagents such as cleaving reagent is hydroxylamine, hydrogen peroxide, osmium tetroxide and potassium permanganate.

In another embodiment, where the target nucleic acid is single-stranded, a further step after the nonrandomly fragmenting step is included. This step involves hybridizing one or more of the NLFs to one or more capture probes, where the capture probes contain a single-stranded region complementary to at least one of the NLFs and a first binding moiety, binding the first binding moiety to a second binding moiety attached to a solid support, where the binding occurs either before or after the hybridizing of the NLFs to one or more capture probes, and isolating a set of single-stranded NLFs.

In another embodiment, where the target nucleic acid is single-stranded and fragmenting probes are used, the fragmenting probes include a single-stranded portion and a first binding moiety. The method further involves, after the nonrandomly fragmenting step, binding the first binding moiety to a second binding moiety attached to a solid support, and isolating the set of single-stranded NLFs.

In another embodiment, the obtaining step further includes nonrandomly fragmenting the target nucleic acid with one or more restriction endonucleases to form a set of NLFs; hybridizing one or more of the set of NLFs or a subset thereof to one or more oligonucleotide probes, where each of the oligonucleotide probes includes a nucleic acid comprising a single-stranded region and a first binding moiety, binding the first binding moiety to a second binding moiety attached to a solid support either before or after the hybridizing step; and isolating the set or subset of single-stranded NLFs. Preferably, all of the oligonucleotide probes include one of either full-length positive or full-length negative single strands of the target nucleic acid and a first binding moiety; or the binding between the first binding moiety and the second binding moiety is a covalent attachment; or one binding moiety is an antibody, a hormone, an inhibitor, a co-factor portion, a binding ligand, and a polynucleotide sequence, and the other binding moiety is a corresponding member of an antigen capable of recognizing the antibody, a receptor capable of recognizing the hormone, an enzyme capable of recognizing the inhibitor, a cofactor enzyme binding site capable of recognizing the co-factor portion, a substrate capable of recognizing the binding ligand, or a complementary polynucleotide sequence; or the isolating further comprises washing the set of NLFs bound to the solid support with a composition comprising volatile salts such as ammonium bicarbonate, dimethyl ammonium bicarbonate and trimethyl ammonium bicarbonate.

In another embodiment, where the target nucleic acid is single-stranded, the obtaining step further includes hybridizing the single-stranded target nucleic acid to one or more restriction site probes to form hybridized target nucleic acids having double-stranded regions where the restriction site probes have hybridized to the single-stranded target nucleic acid and at least one single-stranded region, nonrandomly fragmenting the hybridized target nucleic acids using one or more restriction endonucleases that cleave at restriction sites within the double-stranded regions. A further step after the nonrandomly fragmenting step can be included. This further step includes hybridizing the NLFs to one or more capture probes, where the capture probes comprise a single-stranded region complementary to at least one of the NLFs and a first binding moiety, binding the first binding moiety to a second binding moiety attached to a solid support, wherein the binding occurs either before or after the hybridizing of the NLFs to one or more capture probes, isolating a set of single-stranded NLFs. Also, preferably, the cleaved restriction site probes include a single-stranded region complementary to half of a restriction endonuclease site and a first binding moiety, and the method further includes, after the nonrandomly fragmenting step, binding the first binding moiety to a second binding moiety attached to a solid support, and isolating a set of single-stranded NLFs.

In another embodiment, where the target nucleic acid is single-stranded, the obtaining step further includes performing the method under conditions permitting folding of the single-stranded target nucleic acid to form a three-dimensional structure having intramolecular secondary and tertiary interactions; nonrandomly fragmenting the folded target nucleic acid with at least one structure-specific endonuclease to form a set of single-stranded NLFs, modifying either the target nucleic acid or the set of single-stranded NLFs such that members of the set of single-stranded NLFs include a single-stranded nucleotide sequence and at least one first binding moiety; binding the first binding moiety to a second binding moiety attached to a solid support; and isolating the set of single-stranded NLFs.

In another embodiment, where the target nucleic acid is single-stranded, the obtaining step also can include providing conditions permitting folding of the single-stranded target nucleic acid to form a three-dimensional structure having intramolecular secondary and tertiary interactions; nonrandomly fragmenting the folded target nucleic acid with at least one structure-specific endonuclease to form a set of single-stranded NLFs; hybridizing one or more of the set of NLFs to one or more capture probes, where the capture probes contain a single-stranded nucleotide sequence and a first binding moiety; binding the first binding moiety to a second binding moiety attached to a solid support either before or after the hybridizing step; and isolating a set of single-stranded NLFs. More preferably, the isolated set of single-stranded NLFs include any NLFs having a 5' and or 3' end of the target nucleic acid. Also preferably, the structure-specific endonuclease is T4 endonuclease VII, RuvC, MutY, or the endonucleolytic activity from the 5'-3' exonuclease subunit of thermo-stable polymerases.

In another embodiment, where the target nucleic acid is single-stranded, the obtaining step further includes hybridizing the single-stranded target nucleic acid to one or more wild type probes, nonrandomly fragmenting the target nucleic acid with one or more mutation-specific cleaving reagents that specifically cleave at any regions of nucleotide mismatch that form between the target nucleic acid and any of the wild type probes. More preferably, the nonrandomly fragmenting step further includes digesting the first set of nonrandom length fragments with one or more restriction endonucleases or cleaving the first set of nonrandom length fragments with one or more single-strand-specific cleaving reagents. Also preferably, members of the set of single-stranded NLFs comprise a single-stranded region and at least one first binding moiety; and the method includes, after the nonrandomly fragmenting step, binding the first binding moiety to a second binding moiety attached to a solid support; and isolating a set of single-stranded NLFs. Further, the obtaining step can further include hybridizing members of the set of NLFs to one or more capture probes, where the capture probes include a single-stranded portion and at least one first binding moiety; and the method includes binding the first binding moiety to a second binding moiety attached to a solid support, and isolating a set of single-stranded NLFs. The obtaining step can further include isolating a set of single-stranded NLFs containing any NLFs that have a 5' end of the target nucleic acid.

In another embodiment, a method for detecting mutations in a target nucleic acid is provided. The method includes the steps of nonrandomly fragmenting, preferably in a restriction buffer containing volatile salts, the target nucleic acid with one or more restriction endonucleases to form a set of double-stranded NLFs; and determining masses of the members of the set of double-stranded NLFs by IR-MALDI mass spectrometry with a liquid matrix.

In still another specific embodiment, a method for detecting mutations in a target nucleic acid is provide that includes the steps of nonrandomly fragmenting the target nucleic acid using one or more restriction endonucleases to form a first set of nonrandom length fragments (NLFs); hybridizing members of the first set of NLFs to a set of wild type probes; nonrandomly fragmenting one or more members of the set of NLFs with one or more mutation-specific cleaving reagents that specifically cleave at any regions of nucleotide mismatch that form between members of the first set of NLFs and complementary members of the set of wild type probes, where the nonrandomly fragmenting step forms a second set of NLFs; and determining masses of members of the second set of NLFs using IR-MALDI mass spectrometry with a liquid matrix. More preferably, the set of wild type probes obtained by nonrandomly fragmenting a wild type target nucleic acid are obtained using the same restriction endonucleases used to form the first set of NLFs. More preferably, the steps of nonrandomly fragmenting of the target nucleic acid and obtaining the set of wild type fragmenting probes are performed simultaneously in a single composition. Also more preferably, a further step before the determining step is included. This further step includes isolating the second set of NLFs, where the members of the second set include a double-stranded region and a first binding moiety; and binding the first binding moiety to a second binding moiety attached to a solid support. A further step before the determining step can be included. This step includes isolating the second sep of NLFs by hybridizing members of the second set of NLFs to one or more capture probes, where the capture probes include a single-stranded region and a first binding moiety; and binding the first binding moiety to a second binding moiety attached to a solid support.

In another embodiment, a method for detecting mutations in a target nucleic acid is provided that includes nonrandomly fragmenting the target nucleic acid in a composition containing one or more volatile salts to form a set of nonrandom length fragments (NLFs); and determining masses of members of the set of NLFs using IR-MALDI mass spectrometry with a liquid matrix.

In another embodiment, a method for decreasing background noise is provided. In this method, the sample is washed with a composition of volatile salts, which is then evaporated from the sample.

ANALYSIS OF DOUBLE-STRANDED NUCLEIC ACID USING IR-MALDI

IR-MALDI is advantageously used for analysis of double-stranded nucleic acids. It is shown herein, that for analysis of longer fragments, the liquid matrix should include a salt, such as salts of amines, including ammonium salts or other salts that are compatible with mass spectrometric analysis of nucleic acids (see, e.g., Nordhoff et al. *Mass Spectrom. Rev.* 1996, 15, 67–138), to raise the ionic strength.

As exemplified herein (EXAMPLES) double stranded DNA molecules ranging from 9 kDA to over 500 kDA were desorbed and analyzed by MALDI TOF mass spectrometry. IR-MALDI with glycerol as matrix yielded excellent results for larger double stranded DNA by adjusting the ionic strength through the addition of salts. Very little fragmentation and a routine sensitivity in the sub-picomole range were observed in IR-MALDI when double stranded analytes harboring 70 base pairs or more were probed. In the lower mass range (up to approx. 70 bp), UV-MALDI with 6-aza-2-thiothymine (ATT) as matrix was used. Essentially quantitative detection of the double stranded form was observed for a 70-mer. With larger fragments, UV-MALDI, however, was accompanied by significant fragmentation and a resulting reduced sensitivity and mass resolution.

Automated Analyses

The methods described herein may be used as part of automated processes. For example, U.S. application Ser. No. 09/285,481, provides a fully automated modular analytical system that integrates sample preparation, instrumentation, and analysis of biopolymer samples. The system integrates analytical methods of detection and analysis, e.g., mass spectrometry, radiolabeling, mass tags, chemical tags, fluorescence chemiluminescence, and the such labeling moieties, with robotic technology and automated chemical reaction systems to provide a high-throughput, accurate automated process line. The instrumentation and processes described herein may be performed and integrated into the automated process line or into any automated analysis system or protocol.

A fully automated modular analytical system integrates instrumentation to permit analysis of biopolymer samples. The samples include, but are not limited to, all biopolymers, e.g., nucleic acids, proteins, peptides and carbohydrates. The system integrates analytical methods of detection and analysis, em., mass spectrometry, radiolabeling, mass tags, chemical tags, fluorescence and chemiluminescence, with robotic technology and automated chemical reaction systems to provide a high-throughput, accurate Automated Process Line (APL).

Kits

Also provided herein are kits for performing IR-MALDI with a liquid matrix. The kits include a liquid and a support and optionally instructions for performing IR-MALDI as well as particular controls. The kits can also contain a support that comprises an array that includes at least one target biological macromolecule immobilized at a defined position on the array on a support.

The following examples are included for illustrative purposes only and are not intended to limit the scope of the invention.

EXAMPLE 1

MALDI Mass Spectrometric Analysis of Nucleic Acid Molecules Containing 70 to 2180 Nucleotides This example demonstrates that incorporation of nucleic acid molecules in a liquid matrix allows accurate mass determination of the nucleic acid molecules.

A. Materials and Methods

1. Samples

Synthetic oligodeoxynucleotides were obtained from Pharmacia Biotech (Uppsala, Sweden). The 70-mer was FPLC-purified by the supplier; smaller oligonucleotides were used without additional purification. Plasmid DNA was purified from *E. coli* strain DH5α by use of the Qiagen miniprep kit (QIAGEN GmbH; Hilden, Germany) according to the manufactures recommendations. Restriction enzymes were obtained from New England Biolabs GmbH (Schwalbach/Taunus, Germany); restriction enzyme digests of plasmid DNA were performed according to the supplier's protocols. Samples intended for MALDI mass spectrometric analysis were adjusted to 10 mM EDTA and 2 M $NH_4$ acetate, and precipitated with 2 volumes of ethanol. The pellet was washed once with 70% ethanol and dissolved in water to an approximate concentration of 0.5 pmol/μl.

The 1206 nucleotide in vitro transcript was synthesized and ethanol precipitated according to standard procedures (Kirpekar et al., *Nucl. Acids Res.* 22:3866–3870 (1994)), using the SeaI digested plasmid pBluescript KS+ as template for the T3 RNA polymerase (MBI Fermentas; Vilnius, Lithuania). A 10 μl Poros 50 R2 (PerSeptive Biosystems; Framingham, Mass.) reverse phase column was prepared and equilibrated with 3% acetonitrile/10 mM triethyl ammonium acetate (TEAA) as described elsewhere (Kussman et al., *J. Mass. Spectrom.* 32:593–6010 (1997)). The RNA sample was adjusted to 0.3 M TEAA and loaded onto the column. The column was washed with 200 μl 3% acetonitrile/10 mM TEAA, and the sample was eluted with 10 μl 25% acetonitrile/10 mM TEAA.

Subsequent to lyophilization, the eluate was dissolved in 5 μl water; the estimated sample concentration was 1 pmol/μl. A crude DNA preparation from mycoplasma-infected HeLa cells was made, and PCR was performed essentially as described (Hopert et al., *J. Immunol. Meth.* 164:91–100 (1993)) using the primers 5'-CGC CTG AGT AGT ACG TTC GC-3' (SEQ ID NO: 1) and 5'-GCG GTG TGT ACA AGA CCC GA-3' (SEQ ID NO: 2), and recombinant Taq DNA polymerase (MBI Fermentas). The PCR results in an approximately 515 bp DNA fragment originating from the 16S rRNA gene of mycoplasma (Hopert et al., *J. Immunol. Meth.* 64:91–100 (1993)), however, the precise length of the PCR product cannot be predicted because the species of the mycoplasma is unknown.

A reamplification by PCR was performed under identical conditions using the same primer set, and the final product was adjusted to 4 mM EDTA/2 M $NH_4$ acetate, and precipitated as described for the restriction enzyme digests. The pellet was dissolved in 200 μl water and purified over a Microcon-100 (Amicon GmbH; Witten, Germany) microconcentrator by three successive diafiltrations with 100 μl water as recommended by the manufacturer. The retentate was lyophilized and redissolved in water to a concentration of 0.6 pmol/μl as determined by UV spectrophotometry.

2. Sample Preparation

For IR-MALDI, glycerol was used as the matrix. The glycerol was incubated with an equal volume of a H+ cation exchange bead suspension (Dowex 50W-X8; Biorad AG; Munich, Germany) in order to reduce subsequent alkali salt formation of the nucleic acid backbone phosphates. Typically, 0.5 to 1 μl of glycerol was mixed with an equal amount of an aqueous analyte composition on the target to give a final analyte-to-glycerol molar ratio of the sample of about $10^{-4}$ to $10^{-7}$, depending on the mass of the analyte. The mixture was smeared evenly over an area of about 1 to 2 $mm^2$ to form a homogeneous, transparent thin layer on the stainless steel substrate. The water was evaporated off at a pressure of about $10^{-2}$–1 Pa before the sample was introduced into the mass spectrometer.

Samples for UV-MALDI mass spectrometry were prepared by on-target mixing of 1 μl of a $10^{-5}$ to $10^{-6}$ M aqueous analyte composition with 0.7 μl of a 50 g/l 3-hydroxypicolinic acid (3HPA) composition in 20% acetonitrile. About ten ammonium-loaded cation exchange beads were added to the samples before drying in a cool stream of air (Nordhoff et al., *Rapid Commun. Mass Spectrom.* 6:771–776 (1992)).

3. Instrumental

Experiments were performed using an in-house built MALDI single stage reflectron time-of-flight (refTOF) mass spectrometer of 3.5 m equivalent flight length (Berkenkamp et al., *Rapid Commun. Mass Spectrom.* 11:1399–1406 (1997)). The mass spectrometer also can be used in the linear TOF (linTOF) mode. Unless specifically mentioned, the experiments were carried out in reflectron—and positive ion mode.

Ions are accelerated through a total potential difference of about 16–25 kV in the split extraction source using either static or delayed ion extraction (DE). A venetian blind secondary electron multiplier (EMI 9643) with a conversion dynode, mounted 10 mm in front of the cathode (ion impact energy of about 20 to 40 kV, depending on ion mass) on a Chevron Micro-Channel plate (Galileo Co.; Sturbridgem Mass.) are used for ion detection. For high mass ions, the potential between the conversion dynode and the electron multiplier cathode is set to several thousand volts in order to increase the ion signal by making efficient use of the secondary ions. If maximum mass resolution is sought in the mass range up to several thousand Daltons, the potential between the two electrodes is kept below about 500 V in order to detect secondary electrons only and thereby avoid the time (and mass) dispersion of the secondary ions (see, for example, FIG. 2A). Signals are processed by a transient recorder with a time resolution of about 0.5 ns (LeCroy 9350). The digitized data are transferred to a PC for storage and further evaluation.

For IR-MALDI experiments, an Er-YAG-Laser emitting at 2.94 μm (Spectrum GmbH; Berlin, Germany; τ=80–90 ns, energy stability ca. ±2–4% from shot to shot) was used. A frequency tripled Nd-YAG laser, emitting in the UV at 35 nm (τz=6 ns) was used for direct comparison between IR-MALDI and UV-MALDI. Single laser pulses are focused to a spot diameter of approximately 150 μm (IR) or 100 μm (UV) on the sample under an angle of 45°. Samples are observed in situ with a CCD camera having about 5 μm resolution.

B. Results

UV-MALDI spectra of DNA having at least about 50 nucleotides and with a reasonable quality could be obtained only in the linTOF, DE mode. FIGS. 1A and 1B demonstrate the striking differences in spectra quality for the two modes of operation for a synthetic DNA 70-mer (approx. 21.5 kDA) and a 3HPA matrix (355 nm). The quality of the spectrum of FIG. 1B, obtained in reflectron mode is quite inferior to that of FIG. 1A in several respects. Signal intensity and signal-to-noise ratio are considerably degraded, as is the mass resolution, down to 15 (M/Δm; FWHM) from 65 in the spectrum of FIG. 1A. The saturated signal in the mass range below approximately 2000 Da in FIG. 2B reflects the increased laser fluence necessary to obtain analyte signals of the intensity shown. The loss in mass resolution is, for the most part, a result of the sloping low mass edge of the peaks, signaling abundant metastable small neutral lasses. Exact mass determination is severely compromised by the loss of spectral quality.

The IR-MALDI spectrum (refTOF, DE mode) of the same DNA 70-mer with glycerol as matrix is shown in FIG. 1C. The quality of this spectrum is comparable to UV-MALDI analysis obtained in the linear mode with respect to signal intensity and mass resolution (FIG. 1A). The base peak has a steeply rising low mass edge, demonstrating an essential absence of any metastable small neutral loss. This behavior was consistently observed for IR-MALDI of nucleic acid with glycerol as a matrix qualifying it as a very gentle desorption method forming ions of nucleic acids of high ion stability. This contrasts strikingly to the IR-MALDI spectra of nucleic acids obtained with succinic acid as matrix (see Nordhoff et al, *Nucl. Acids Res.* 21: 3347–3357 (1993), FIGS. 1d and e). The absence of literally all metastable neutral loss for the glycerol matrix was, therefore, a very unexpected result not anticipated based on prior experience.

Figure 2:
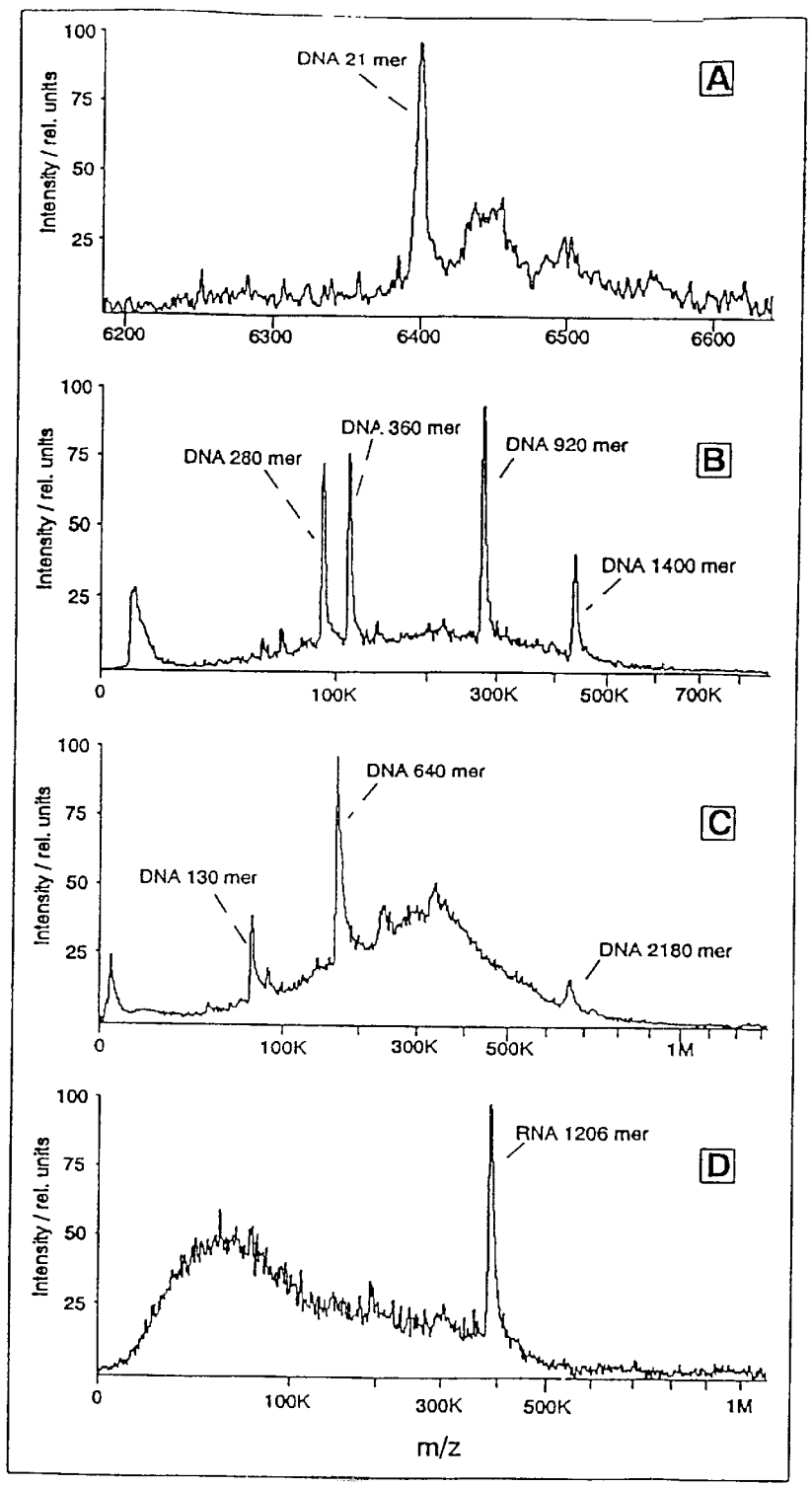
FIGS. 2A to 2D show IR-MALDI refTOF mass spectra using a 2.94 $\mu$m wavelength and a glycerol matrix. The spectra are as follows.

Analysis of nucleic acids by IR-MALDI mass spectrometry is useful for a broad mass range of nucleic acids, from small oligonucleotides to molecules having up to more than 2000 nucleotides (see FIG. 2). A refTOF IR-MALDI mass spectrum of a synthetic 21-mer DNA is shown in FIG. 2A. With delayed ion extraction, a mass resolution of 1050 (FWHM) was obtained, comparable to the resolution obtained with the instrument for proteins in this mass range. Several poorly resolved peaks on the high mass side of the analyte peak that appeared in the spectrum are detection artifacts of residual secondary ions generated at the conversion dynode, operated here in a mode to preferentially detect only secondary electrons in order to not degrade mass resolution by the ion detection system.

FIG. 2B demonstrates the high mass range with a restriction enzyme digest of a plasmid (pBluescript-KS+digested with Bgll and Rsal), yielding four fragments of 280 bp, 360 bp, 920 bp and 1,400 bp. All four signals represent single strands and are the composite signal of the two complementary strands. Very weak, if any, signals of the double stranded oligomers are apparent in this spectrum. The dissociation of the double strands in samples prepared with purified glycerol tentatively is attributed to an acidification by the H+ ion exchange resin. The mass resolution of all high mass ion signals is about 50 (FWHM) and appears to be relatively independent of the ion mass.

The IR-MALDI mass spectrum of FIG. 1C shows the upper mass limit measured so far for a restriction enzyme digest (130 bp, 640 bp and 2,180 bp). The signal of the 2,180 nucleotide single stranded fragment was obtained only after heating the restriction digest to a temperature of 95° C. for 5 minutes, apparently because such large DNA fragments do not get separated into single strands under the conditions used, in contrast to the DNA fragments up to 1400 bp. The relatively poor mass resolution of about 30 for the 2,180 nucleotide fragment in this spectrum and the strong background signals indicate an upper mass limit for IR-MALDI mass spectrometry of nucleic acids of approximately 700 kDa under the current conditions. Accordingly, the double stranded 2,180 nucleotide fragment was not observable.

IR-MALDI mass spectrometry of large RNA molecules also was possible, including a 1206 nucleotide RNA in vitro transcript (FIG. 2D). The increased ion stability for RNA compared to DNA, which is well documented for UV-MALDI, was not observed for IR-MALDI in the mass range examined. Large DNA ions, as well as large RNA ions, appeared to be of comparable stability, stable enough even for TOF analysis in the reflection mode. The large hump centered at about 50 kDa is believed to reflect impurities of the sample rather than metastable fragments. The comparably steep rise of the peak at the low mass side also testifies to a very limited loss of small neutrals such as single bases.

One advantage of glycerol as matrix is the superior shot to shot reproducibility and mass precision (200–400 ppm; see Nordhoff et al., *Nucl. Acids Res.* 21: 3347–3357 (1993)). These values, originally determined for proteins, are also valid for analysis of smaller oligonucleotides. Mass accuracy was mass dependent. Using an external 2 point calibration with angiotensin II (1047 Da) and bovine insulin (5743 Da), the mass of the 21-mer (6398 Da) was determined to within ±2 Da of the known mass, i.e., an accuracy of 0.003% (see FIG. 2A). The molecular mass of the 70-mer (theoretical mass 21517 Da) was determined to within ±25 Da, i.e., a mass accuracy of 0.1% from the spectrum of FIG. 1C, calibrated with cytochrome C oligomers (M+, 2M+, 3M+).

For each of the ten different samples of high mass DNA analyzed, the measured mass was within less than about 1% of the theoretical mass derived from the sequence (see, for example, FIGS. 2B and 2C). The average mass of the two single strands was used as the theoretical mass in the case of DNA restriction enzyme fragments. The masses of the two single strands never differed by more than about 1%. Only one large mass RNA was measured (FIG. 2D). The measured mass of this RNA was 388,270 Da, whereas the mass calculated from the gene sequence is 386,606 Da. Given that the sample most likely is a heterogeneous mixture of the species expected from the gene sequence, with less abundant products extended by one to three extra nucleotides (Melton et al., *Nucl. Acids Res.* 12:7035–7056 (1984)), the actual mass of the RNA sample is probably about 500 Da larger than that calculated from the sequence. It would appear, therefore, as though a mass accuracy of at least about 1% as observed for DNA also can be achieved for RNA.

For external 4 point calibrations of large DNA or RNA molecules with molecular masses between 100 and 400 kDa, either clusters of cytochrome C, for example, 10M+, 20M+, 30M+, 40M+, or multimers of an IgG monoclonal antibody, for example, 2M+3M+, 4M+, were used. For analytes exceeding 500 kDa the calibration with IgG monoclonal antibody was more exact. Mass calibration of unknown DNA fragments using DNA or RNA calibrants may be more desirable, resulting in more accurate mass determination.

Experiments to evaluate the sensitivity of IR-MALDI mass spectrometry of large nucleic acids with glycerol as matrix were carried out with a PCR product of an unknown sequence having approximately 515 nucleotides; the mass was measured to be 318,480 Da. For these measurements, glycerol, not subjected to ion exchange purification, was used. The spectra show dominant signals of the double stranded moiety. The dissociation of the double strands in samples prepared with purified glycerol tentatively is attributed to an acidification of the glycerol by the protons exchanged for the cations, although additional parameters may be involved in the double strand dissociation under IR-MALDI conditions.

Figure 3:
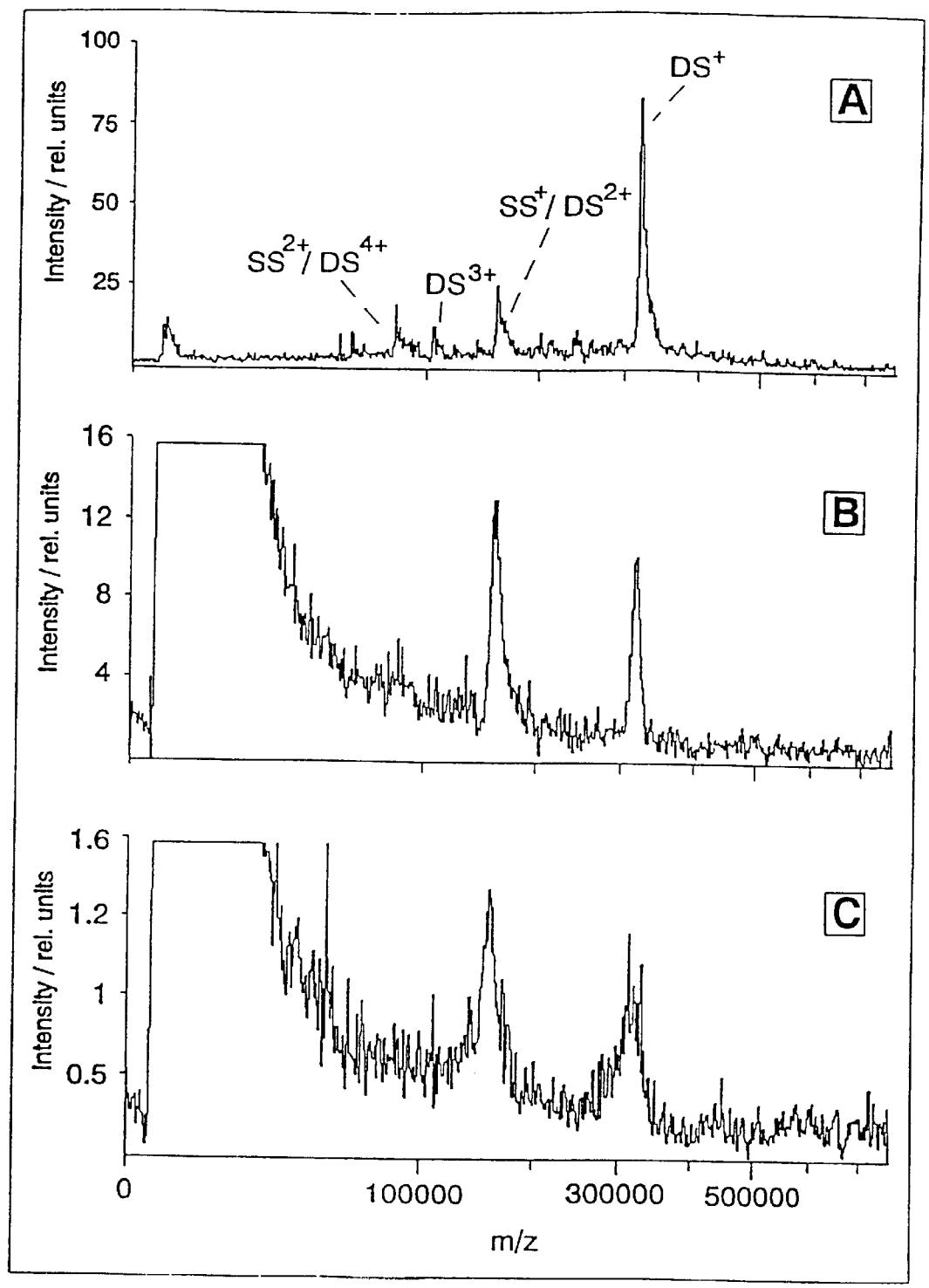

The starting concentration for the dilution experiment was 0.6 pmol/l as determined by UV spectrophotometry. The mass spectra were obtained by loading different amounts of sample onto the target (FIG. 3). For the single shot mass spectrum shown in FIG. 3A, 300 fmol of the PCR product was loaded. The quality of this spectrum, with a S/N ratio better than 100 and a mass resolution of 65 (FWHM) for the double strand, indicates that the analyte to matrix ratio (A/M) of about $10^{-3.1\ 7}$ is well suited for an analyte of this size (about 320 kDa).

The mass spectrum in FIG. 3B was obtained using a 3 fmol total load (A/M about $2\times10^{-9}$). A strong background signal dominated the low mass range. Total signal intensity, mass resolution (of about 25 FWHM for the ds-ion signal), and S/N-ratio were significantly degraded compared to FIG. 3A. Mass determination still was possible with an accuracy of about 1%. The spectrum in FIG. 3C was obtained from a very small sample volume, forming an approximately 270 μm diameter sample spot on the target and a total sample load of only 300 attomol (A/M about $8\times10^{-10}$). Such small sample volumes can be realized either by dispensing the small volumes using micropipettes (see, for example, Little, *Anal. Chem.* 69:4540–4546 (1997)), or by preparing the analyte in a standard microliter volume of a suitable glycerol/water mixture. In the latter case, the water is evaporated off prior to or upon insertion of the sample into the vacuum. The poor mass resolution of only about 10 classifies 300 attomol of analyte as the limit for the particular instrument and detection system used for a mass accuracy of better than about 3%. Compared to values reported for UV-MALDI mass spectrometry (Tang et al., Rapid Commun. Mass Spectrom. 8:727–730 (1994); see FIGS. 5 and 6), the sensitivity obtained here for IR-MALDI mass spectrometry demonstrates an improvement of at least about 2 to 3 orders of magnitude for nucleic acids of this size.

EXAMPLE 2

Performance of IR Matrix-assisted Laser Desorption/ionization Mass Spectrometry

The performance characteristics of two lasers emitting in the mid infrared, an Er-YAG (2.94 μm wavelength, 80–90 ms pulse width), and an Er-YSGG infrared laser (2.79 μm wavelength, 80 ns pulse width), in matrix-assisted laser desorption/lionization mass spectrometry (IR-MALDI-MS) of biological macromolecules, was studied. Glycerol and succinic acid were used as matrices. In IR-MALDI sample consumption per laser shot typically exceeds that of UV-MALDI by-about two orders of magnitude. Using glycerol as matrix, the reproducibility of the ion signals from shot to shot is comparable to the best values achieved in UV-MALDI. The same holds true for the precision and accuracy of the mass determination. For succinic acid all these values are significantly worse, due to the strong sample heterogeneity as typically found in dried droplet preparations. Metastable fragmentation is comparable for UV- and IR-MALDI in the law mass range, but is significantly less for the IR in the mass range above ca. 20 kDA, leading to an improved mass resolution and an extended high mass limit for IR-MALDI.

In this Example, results and performance data for IR-MALDI analysis obtained with ER lasers emitting at 2.94 μm and 2.79 μm, and the applicability of delayed extraction for an improved mass resolution, is presented. In particular, is demonstrated that the extent of metastable fragmentation is different for the mass resolution of high molecular mass analytes.

EXPERIMENTAL

The experiments were carried out with an in-house built, single stage reflectron TOF mass spectrometer of 3.5 m equivalent flight length. The mass spectrometer can also be used in linear mode. Unless specifically mentioned, the experiments reported here have been carried out in reflectron mode. In the split extraction source, ions are accelerated through total potential differences of 12–20 kV using either static or delayed extraction. In the delayed mode extraction, a maximum potential difference of 8kV can be switched; the minimum delay for ion extraction is 120 ns. No arcing was observed under these operation conditions in the positive or negative ion modes for any of the matrices used. A venetian blind secondary electron multiplier, (EMI R2362) with a conversion dynode, mounted 10 mm in front of the cathode (ion impact energy 20–27 kV, depending on ion mass), or a Chevron microchannel plate detector (Galileo Co., Sturbridge, Mass., USA), are used for ion detection. Signals were processed by a transient recorder with a time resolution of 2.5 ns (LeCroy 9450A) in the majority of the experiments. For the high mass-resolution experiments a LeCroy 9348La recorder with a time resolution of 0.5 ns was used. The data are transferred to a PC for storage and further evaluation. The instrument is equipped with two infrared lasers, one emitting at 2.94 μm (Er-YAG:Fa.Spectrum GmbH, Berlin, Germany: τ=80–90 ns, energy stability ca. ±2–4% from shot to shot) and a second radiating at 2.79 μm (Er-YSGG: Schwartz Electro Optics. USA: τ=80 ns; energy stability ca. ±2%). A frequency tripled Nd-YAG laser, emitting in the UV at 355 nm (τ=16 ns) is used for direct comparison between IR- and UV-MALDI. Single laser-pulses are focused to a spot diameter of ca. 200 μm (IR) and 100 μm (UV) on the sample under an angle of 45°. Samples are observed in situ with a CCD camera of ca. 5 μm resolution. The stainless steel substrate can be cooled with liquid nitrogen to a temperature of ca. 150–170 K. Its temperature is monitored by a thermocouple with an accuracy of ±5 K.

SAMPLE PREPARATION

A wide variety of small molecules can be used as matrices in IR-MALDI as described previously. Succinic acid (solid matrix) and glycerol (fluid or frozen, solid) were preferred. DHBs (2,5-dihydroxybenzoic acid mixed with 10% 2-hydroxy-5-methoxybenzoic acid), a common matrix in UV-MALDI also functions in IR-MALDI and was used for comparison in some cases. Additionally, mixtures of compounds, e.g. succinic acid/DBHs or succinic acid/TRIS (Tris-hydroxymethylaminomethane) were found suitable. Solid matrix samples were prepared using the standard dried droplet method by mixing ca. 1–3 μl of a $10^{-4}10^{-5}$ M aqueous analyte solution with 1–5 μL of a 30 μL matrix solution on the target and subsequently drying in a stream of cool air.

For glycerol, analytes were either dissolved directly at a concentration of 0.5–10 g/L, or the glycerol was mixed with an aqueous analyte solution to a final analyte-to-glycerol molar ration of $2\times10^{-4}$–$1\times10^{-5}$, depending on the mass of the analyte. A volume of typically 1 μL is applied to the stainless steel substrate and smeared out evenly over an area of ca. 3–4 mm$^2$ to form a homogeneous, transparent thin layer. If an aqueous analyte solution is mixed with the glycerol, the water must be evaporated off before sample introduction into the mass spectrometer, usually at a pressure of $10^{-2}$–1 Pa. Samples are either inserted directly into the mass spectrometer or are cooled down to a temperature of ca. 150–170 K in liquid nitrogen before insertion.

For the matrices investigated, IR-MALDI was found to be quite tolerant with respect to salts and buffers. Spectra of samples containing NaCl at concentrations of up to 200 mM, saccharose up to 20% (w/v) or Tris/HCl buffer up to 100 mM have, for example, been obtained without significant loss in spectral quality with succinic acid as well as glycerol.

RESULTS

Sample Consumption and Analytical Sensitivity

The analytical sensitivity of MALDI can be limited by either the minimal concentration of the analyte solution used for the analysis or the total amount of analyte available. For the actual measurement the total sample volume used for the preparation and the analyte-to-matrix ratio in the sample can be adjusted within certain limits to accommodate a given situation. In this section typical, as well as limiting, values for these quantities in IR-MALDI is presented and compared to the corresponding UV-MALDI values. As an introduction a few general differences between IR- and UV-MALDI will be discussed.

Given comparable laser spot sizes on the sample, 100–1000-times more material is desorbed by the IR as compared to the UV laser beam, because of the correspondingly smaller absorption coefficient and higher penetration depth of the radiation into the sample. Under the experimental conditions described here the single shot ion signals in the IR and UV typically were of comparable intensity. With that much more material ablated per laser pulse in IR-MALDI, the material is either primarily removed as larger clusters and small particles, as actually observed experimentally, and/or the ion yield is smaller by two to three orders of magnitude.

The intensity of low mass signals, the signal-to-noise ratio and mass resolution are the main criteria for the quality of recorded mass spectra. The optimal molar analyte-to-matrix ration on the target for the signal intensity and quality of spectra depends on the molecular mass of the analyte. For analytes with molecular masses below ca. 50 kDa a ratio of $2 \times 10^{-4}$–$2 \times 10^{-5}$ was found to be optimal. A ratio of $10^{-5}$ was found to work best for analytes with masses exceeding 50 kDa. Hence, in particular in the low mass range, the optimal analyte concentration in IR-MALDI exceeds that typically used in UV-MALDI by approximately one to two orders of magnitude. Spectra of reasonable quality can be obtained for analyte-to-matrix ratios down to $2 \times 10^{-6}$–$10^{-7}$, depending on molecular mass of the analyte. This corresponds to a sample consumption per laser shot of 1–50 fmol. In routine applications, spectra of IgG monoclonal antibodies (ca. 150 kDa) have been obtained with reasonable quality using $10^{-7}$ M aqueous solutions using either succinic acid or glycerol as matrix. This compares to values of only a few attomole in UV-MALDI.

The results demonstrated the attainable sensitivity for a lysozyme/glycerol preparation. Here, $5.5 \times 10^{-3}$ μL of a $1.2 \times 10^{-7}$ mol/L frozen glycerol solution, corresponding to a total amount of prepared lysozyme of ca. 0.7 fmol, were used for the preparation. This corresponds to a molar A/M-ratio of ca. $10^{-8}$. The frozen sample on the target had a diameter of about 1.5 times that of the laser spot on the sample. After the ten laser exposures summed for the spectrum some sample was still left on the target. Consequently, sample consumption of average was less than 70 attomol per single spectrum. However, when using such low A/M ratios the mass resolution is down at m/Δm=10–20. The signal-to-noise (S/N) ratio has also degraded substantially and the low mass background signals become excessive. For UV-MALDI a sample consumption in the high zeptomole range has been reported (see, Jespersen et al. (1996) p. 217 in *Mass Spectrom. in Biol. Sci*, Burlingame, Ed.).

In IR-MALDI there is also a pronounced dependence on the A/M ratio of the yield of (non-specific) analyte oligomers or multiply charged ions. These tendencies are more pronounced in IR- as compared to UV-MALDI. A mass spectrum of hen egg lysozyme from a preparation with a A/M-ration of $2 \times 10^{-4}$ was obtained. Homo-oligomers of lysozyme up to the 25th mer (ca. 500 kDA) were identified in this spectrum. Conversely, signals of multiply charged analyte ions become dominant in the spectra for A/M-ratios below a value of ca. $10^{-6}$ whereas oligomer signals decrease to values below the noise level. These trends have also been observed with succinic acid and the water of hydration as matrices ( ) Sadeghi (1997) *Rapid Commun. Mass. Spectrom.* 11:393), and are particularly pronounced for analytes with molecular masses exceeding 50 kDa. Given the observed high yield of analyte homo-oligomers, the details of the distribution in particular the most abundant oligomer signal, can be influenced significantly by changes in the ion extraction conditions, e.g. by using low (soft or mild) or high (hard or harsh) ion extraction fields in a two stage ion source. Low extraction fields will shift the distribution towards a higher degree of oligomerization. This observation is a strong indication of gas phase processes in the expanding desorption plume besides possibly reflecting differences in the acceptance of the spectrometer under different extraction conditions.

Reproducibility

For Er-YAG lasers presently used, the pulse shot-to-shot stability is ca. ±2%, a value quite comparable to that of the best UV lasers, and, thus, does not contribute substantially to signal variation. Laser energy fluctuations from shot to shot, therefore, play only a minor role with these lasers. Another source of signal variation from shot-to-shot is the sample homogeneity, which depends on the matrix and the preparation technique. Solid matrices such as succinic acid typically form heterogeneous microcrystalline patterns. High quality mass spectra can only be achieved from 'sweet spots'. For some matrices like DHB (2,5-dihydroxybenzoic acid mixed with 10% 2-hydroxy-5-methoxybenzoic acid) this is also true for UV-MALDI. In UV-MALDI 50–100 spectra can be obtained from any 'sweet spot', in contrast to only 3–4 spectra from a given 'sweet spot' in IR-MALDI, because of the much larger sample consumption per exposure.

Liquid matrices such as glycerol form very homogeneous layers and spectra of comparable quality can be obtained from all locations across the sample. Also, the surface of these liquid samples recovers after every laser shot and more than 500 spectra of almost identical quality can be obtained from the same spot of a typical penetration. The spectrum of hen egg lysozyme was obtained after more that 250 shots on the same location at a laser repetition rate of 2 Hz. No significant differences in signal intensity, mass resolution, or S/N ratio as well as oligomer distribution, were observed between the early and late exposures. As a result, reproducibility of IR-MALDI spectra was found to be comparable to, if not better than, that for UV-MALDI preparations if glycerol is used as matrix. For solid matrices such as succinic acid reproducibility of ion signals from shot to shot may become a problem and considerable experience of the operator is often required for good results.

Fragmentation

Fragmentation is also an important parameter in MALDI-MS. Generally the yield of so call 'prompt' fragments, generated during the desorption and ionization process on a time scale short compared to the ion extraction time, is very low in UV-as well as IR-MALDI. These fragments are detected at their true (fragment) mass in linear as well as reflecting time-of-flight (TOF) spectrometers. This is also true under delayed extraction with delay times of ca. 1 µs or less. In IR-MALDI, a somewhat increased yield for such prompt fragments of oligonucleotides has been observed but the overall yield was very low nonetheless. Metastable ion decay, on the microsecond to hundreds of microseconds time scale in the field free region of the TOF mass spectrometer is much more important. On the one hand it degrades mass resolution in reflectron (reTOF) instruments, but on the other hand it can be used for structural analysis in the post-source decay (PSD) mode. No significant differences between UV- and IR-MALDI have so far been found for the metastable fragmentation of peptides and proteins in the mass range up to ca. 20 kDa. For analytes with a molecular mass above 20 kDa a markedly different metastable fragmentation has been observed. reTOF spectra of an IgG monoclonal antibody (mouse, MW ca. 150 kDa) obtained with UV- (matrix: DHBs) and IR-MALDI (matrix: succinic acid; matrix: glycerol) were obtained. The base peak of the parent ion had a rather symmetrical shape in both IR-MALDI spectra, whereas it showed a strong tail on the low mass side in the UV-MALDI spectrum, testifying to a significant amount of metastable decay. The peak width full width at half maximum (FWHM) decreases from a value of 2000 Da in the UV spectrum to values of 1000 Da in the IR spectrum with succinic acid as matrix, and merely 700 Da if glycerol is used as matrix. It was also noticeable that the analyte signals ride on a substantially elevated baseline in the UV-MALDI spectrum which results from delayed fragmentations somewhere within the ion source. No such baseline distortions were observed in the IR-MALDI spectra if the desorption fluence remained within a range of ca. 1–1.5 times ion detection threshold fluence.

It has been reported in the literature that in UV-MALDI the degree of metastable decay increases significantly with degrading source back pressure. Two spectra of an IgG monoclonal antibody (mouse) were obtained with (a) UV- and (b) IR-MALDI at a source back pressure of $4\times10^{-3}$ Pa as compared to a back pressure of $4\times10^{-4}$ Pa used to obtain the spectra described above. The UV-MALDI spectrum exhibited signals with a substantially increased tailing to the low mass side, particularly visible for the oligomers $2M^-$ and $3M^{2-}$; whereas no such tailing was seen in the IR-MALDI spectrum.

Another observation is the dependence of metastable fragmentation on the analyte-to-matrix ratio. In reTOF UV-MALDI, too high a A/M-ratio will usually result in a degraded S/N ratio and a loss of mass resolution. This was shown in with spectra for cytochrome c and DHB as the matrix. A higher A/M-ratio of $10^{-3}$ used to obtain the spectrum, resulted in a strong, low-mass tail of the peaks, again stronger for the dimer as compared to the parent ion peak, but not seen in the spectrum obtained from a sample with an A/M ratio of $10^{-4}$ The IR-MALDI spectrum shown of the same sample used showed no such tailing, again indicating substantially less metastable fragmentation. For IR-MALDI of cytochrome c using the water of hydration as 'intrinsic' matrix the molar A/M ratio is even higher (ca. $5\times10^{-3}$), yet no significant metastable decay was observed (Berkenkamp et al. (1996) *Proc. Natl. Acad. Sci. U.S.A.* 93:7003), It is a generally held notion that collisions of ions with matrix neutrals in the plume and with residual gas molecules in the spectrometer are the major cause of metastable fragmentation (see, e.g., Spengler et al. (1992) *J. Phys. Chem.* 96:9678). Considering that much more material is desorbed in IR versus UV-MALDI, resulting presumably in a more extended plume, and that in addition proportionally more of the absorbed laser energy goes into the analyte molecule in the IR, the finding of much less metastable fragmentation in IR-MALDI under all the different conditions presented above was not expected. Contrary to intuition, IR-MALDI seems to be a milder method than UV-MALDI.

Accessible Mass Range

The lower degree of fragmentation gives IR-MALDI an advantage over UV-MALDI for the analysis of very high mass analytes, particularly when an ion mirror is used. Not only does this lead to stronger signals of large parent molecular ions, it also, and more importantly, allows the use of higher laser fluences up to about twice the ion detection threshold fluence without deterioration in spectral quality as would be the case in UV-MALDI under such conditions. This increases the high mass signals even further.

A spectrum of gramicidin-S-synthetase of mass 510 kDa, prepared in glycerol matrix from an aqueous solution containing 50 mM Tris/HCL, 18% (w/v) saccharose and 5 mM dithiothreitol, with a quite acceptable S/N ratio and mass resolution of $m/\Delta m=50$ was obtained. No signals of this analyte could be obtained with UV-MALDI under a variety of conditions tried.

A mass spectrum of an IgG monoclonal antibody (mouse) demonstrated that IR-MALDI in combination with a TOF mass analyzer, can be used for the analysis of biomolecules with molecular weights exceeding 1 MDa. Multiply charged ions of the 13-mer homo-oligomer of ca. 2 MDa mass could unambiguously be identified in the spectrum and signals of ions of other oligomers with m/z values as high as 900 000 were also clearly identified in the spectrum.

Mass resolution

Delayed ion extraction (DE) is used for enhanced mass resolution in UV-MALDI-TOF MS. It was not immediately clear whether DE would be as advantageous in IR-MALDI as well, considering the much higher desorbed sample amount and the possibly substantially different plume expansion dynamics. In fact, for peptides in the 1000 Da mass range, the mass resolution is only about 200 (FWHM), down from about 1000 for UV-MALDI under otherwise comparable conditions, indicating difference in the ion generation process. Nonetheless DE gave equal mass resolution for IR- and UV-MALDI within the accuracy of the measurement. This was demonstrated with a reTOF spectrum (sodiated gramicidin-s, MW 1164.5 Da) obtained with the Er-YAG laser at 2.94 µm and 80 ns pulse width and succinic acid as matrix. The mass resolution in this spectrum was 1000, corresponding to a width of the individual peaks of 3.5 ns, limited by the time resolution of the dual MCP detector (3.0 ns). Using a reTOF for Mellitin (2846 Da) a mass resolution of 9500 and one of 1500 for cytochrome c (12360 Da) were obtained. Thus an enhancement in resolution by factors of ca. 50 for peptides and of 4 for cytochrome c was achieved.

In the high mass range mass resolution in the linear TOF with static ion extraction at 20 kV is limited to a value of ca. 50, equal for IR- and UV-MALDI. In both cases the mass resolution is determined by the distribution of initial ion velocities and kinetic energies. Using DE the mass resolution could be improved by a factor of 3 to equal values of ca. 150 for IR- as well as UV-MALDI.

For analytes exceeding 50 kDa mass resolution in IR-MALDI can, however, be improved even more with a reTOF analyzer, in contrast to UV-MALDI. As demonstrated by the spectra discussed above (reTOF spectra of an IgG monoclonal antibody) the strongly decreased metastable fragmentation in IR-MALDI resulted in a peak width of only 700 Da for the parent ion peak of a monoclonal antibody desorbed with the IR-laser out of a glycerol matrix, compared to a peak width of ca. 2000 Da for the UV-MALDI spectrum. The peak width of 700 Da, corresponding to a resolution of about 200, was the best obtained for all experimental conditions tested. Using either a matrix other than glycerol, or an Er-YAG laser with a longer pulse width ($\geq 120$ ns instead of $\leq 90$ ns) or switching to the Er-YSGG laser at a wavelength of 2.79 $\mu$m and 80 ns pulse width, led to slightly larger peak widths. No significant improvement in mass resolution was observed for the IR-MALDI reTOF spectra using DE for large masses, in agreement with observations made in UV-MALDI. Electrospray mass spectra of an IgG monoclonal antibody show that the peak width of 700 Da reflects the peak envelope of the various glycosylation states of the molecule. The instrumental mass resolution has, therefore, been even somewhat higher. This assumption was supported by a spectrum of chondroitinase in which the peak of the singly charged dimer was observed at mass 224 kDa with a peak width of 700 Da, corresponding to a mass resolution of 300.

Mass Accuracy and Precision

Similar to the reproducibility of the intensity of ion signals in IR-MALDI, precision of the mass determination as given by the standard deviation of sequential measurements depends on the matrix (sample morphology) as well as on the shot-to-shot variation of the laser pulse energy.

For prompt ion extraction and solid matrices, such as succinic acid and dried droplet preparations, mass precision is typically 400–500 ppm for molecular weights up to 150 kDa. It is limited by the strong heterogeneity of the sample morphology and the need for a frequent change of the desorption location on the sample as described above. For prompt extraction and liquid matrices such as glycerol, forming very homogeneous layers, variations in total flight time resulting from variations of the laser pulse energy determines the precision of the mass determination. If, for example, the laser energy is raised intentionally from threshold ($I_0$) to $1.5 I_0$, an increase in flight time of ca. 0.1% for cytochrome c (total flight time ca. 253 $\mu$s) was observed. Thus for glycerol the precision of mass determination depends on the stability of laser output energy. For IR lasers of current design with glycerol as matrix, a precision of the mass determination of 200–400 ppm can be achieved up to a mass of approximately 150 kDa. For analytes below 30 kDa this precision is lower by about one order of magnitude than the values typically obtained in prompt extraction UV-MALDI. In the high mass regime, precision in IR-MALDI was found to be better by at least a factor of 2, most likely due to the enhanced mass resolution of IR-MALDI in this mass range.

The mass accuracy for prompt extraction IR-MALDI was determined by external calibration with 3 well known standards. (Low mass range: angiotensin (human), mellitin, bovine insulin; high mass range: cytochrome c (horse heart), apo-myoglobin (horse), subtilisin Carlsberg (*bacillus subtilis*)). In the mass range up to 30 kDa, 5 sum spectra of 15 single shots each were used to obtain the calibration factors from the calibration spectrum and the mass of the 'unknown' in the second spectrum. For both matrices, succinic acid and glycerol, the absolute mass accuracy has been found to be $10^2 - 5 \times 10^3$ ppm depending on molecular mass. For proteins up to 40 kDa the mass accuracy of 100–500 ppm is in good agreement with the previously described numbers for UV-MALDI (static extraction). For analytes exceeding 40 kDA accuracy is $1 - 5 \times 10^3$ ppm.

CONCLUSIONS

As judged by the lesser degree of metastable fragmentation compared to the UV, IR-MALDI appears to be the 'milder' of the two techniques for generating biomolecular ions. Glycerol or an equivalent material is the matrix of choice for many applications because of its superior reproducibility in comparison to solid matrices. Among the two lasers tested in this study, Er-YAG laser performs slightly better than Ef-YSGG laser for glycerol and-substantially better for succinic acid as matrix. The lesser metastable fragmentation makes IR-MALDI also particularly well suited for the analysis of high mass analytes in the reTOF mode. Delayed ion extraction works well with IR-MALDI, with results comparable to UV-MALDI.

EXAMPLE 3

Detection of Double-stranded DNA by IR-MALDI Mass Spectrometry

In this Example, the use of IR- and UV-MALDI-MS for the analysis of ds-DNA using glycerol and ATT, respectively, as matrices is described. This example shows that IR-MALDI can be used effectively as a diagnostic tool. IR-MALDI, using a glycol matrix, such as a glycerol matrix, yielded excellent results for larger double stranded DNA. These results were achieved adjusting the ionic strength through the addition of salts. Very little fragmentation and a routine sensitivity in the subpicomole range were observed in IR-MALDI when double stranded analytes harboring 70 base pairs or more were probed.

Double stranded DNA molecules ranging from 9 kDA to over 500 kDA were desorbed and analyzed by MALDI TOF mass spectrometry. IR-MALDI with glycerol as matrix yielded excellent results for larger double stranded DNA by adjusting the ionic strength through the addition of salts. Very little fragmentation and a routine sensitivity in the subpicomole range were observed in IR-MALDI when double stranded analytes harboring 70 base pairs or more were probed. In the lower mass range (up to approx. 70 bp), UV-MALDI with 6-aza-2-thiothymine as matrix was the ionization method of choice because it allowed specific double stranded complexes containing relatively few base pairs to be desorbed in intact form. In this mode an essentially quantitative detection of the double stranded form was observed for a 70-mer. The UV-MALDI was accompanied by a significant fragmentation and a resulting reduced sensitivity and mass resolution.

The methods described demonstrate that MALDI-MS, particular IR-MALDI, can be used for the analysis of large DNA/DNA and DNA-protein complexes.

Materials and Methods

Samples. The synthetic oligodeoxynucleotides were obtained from Pharmacia Biotech (Uppsala, Sweden). To form double stranded oligodeoxynucleotides, individual complementary single strands were mixed in a 1:1 ratio (typically 5–10 pmol/µl in water), heated to 75° C. for 2 minutes and cooled to 10° C. over 30 minutes. The synthetic oligodeoxynucleotides and their mixtures were adjusted to 5 mM EDTA and 2M $NH_4$ acetate, and precipitated with two volumes of 1:1 mixture of ethanol and 2-propanol. Samples were re-dissolved in water to concentration 10–20 pmol/µl.

The DNA plasmids pBR-322 and Bluescript KS+ were purified from *E.coli* cells by a Qiagen miniprep kit according to the supplier's protocol (Qiagen GmbH, Hilden, Germany), and subjected to restriction enzyme digests. The restriction enzymes were obtained from New England Biolabs GmbH (Schwalbach/Tannus, Germany), and used according to the supplier's suggestion except that the addition of bovine serum albumin was omitted in the case of EcoRV digest. The restriction enzyme digested DNA was adjusted to 5 mM EDTA and 2M $NH_4$ acetate, precipitated with 2 volumes of ethanol, and finally re-dissolved in water to approx. 0.5 pmol/µl. All restriction enzyme digests were verified by agarose gel electrophoresis.

MALDI-MS analysis. Positive ion IR-MALDI-MS experiments were carried out with an in-house built linear/single stage reflectron time-of-flight (TOF) mass spectrometer of 3.5 m equivalent flight length (reflectron mode). In the split extraction source, ions were accelerated through total potential differences of 16–25 kV. A venetian blind secondary electron multiplier with a conversion dynode in front of the cathode (total ion impact energy 20–40 kV, depending on ion mass) was used for ion detection. Unless specifically mentioned, all experiments were carried out in reflectron mode with static ion extraction. An er-YAG-Laser emitting at 2.94 µm (Spectrum GmBH, Berlin, Germany; τ=80–90 ns, energy stability ca. ±2–4% from shot to shot) was used. The laser-pulse is focused to a spot diameter of ca. 140 µm on the sample under an angle of 45°. The instrument is described elsewhere herein (see, also Berkenkamp et al. *Rapid Commun. Mass Spectrom.* 1997, 11, 1399–1406). For IR-MALDI, typically 0.5–1 µL of the glycerol matrix was mixed on the stainless steel targets with ca. 0.5–1 µL of an aqueous analyte (typically 0.5 pmol/µl) to a molar analyte-to-glycerol ratio of $10^{-7-10^{-8}}$. To stabilize the ds-DNA, $NH_4$-acetate or Tris-HCl (pH 8.0) were added to a final concentration of about 40 mM. Before sample introduction into the mass spectrometer most of the water was evaporated off in the rough vacuum at a pressure $10_{-2}$–1 Pa. In order to have a more controlled and gradual evaporation of the remaining water under high vacuum conditions, the target with the samples was cooled by plunging it into liquid nitrogen before insertion into the mass spectrometer.

Positive ion UV-MALDI-MA spectra were recorded on a prototype Vision 2000 (ThermoBioanalysis, Hemel Hempstead, UK) mass spectrometer in the linear TOF mode using delayed ion extraction (DE). The ions were accelerated to 20 keV in the ion source and additionally post-accelerated through 10–19 KeV (depending on ion mass) by a conversion dynode in front of a secondary electron multiplier. This instrument is described in details elsewhere (Gruic-Sovolj et al. *J. of Biol. Chem.* 1997, 272, 32084–91). UV-MALDI matrices consisted of either ca. 10 $NH_4$-loaded cation exchange beads (Nordhoff et al. *Rapid Commun. Mass Spectrom.* 1992, 6, 771–6) added to 0.7 µl of 50 g/13-HPA in 20% acetonitrile or of 1 µl of 10 g/1 ATT plus 10 mM $(NH_4)_2$-citrate in 50% acetonitrile. In both cases, 0.5–1 µl of an aqueous analyte solution (10–20 pmol/µl) were then mixed with the matrix solution. Though not required, the high analyte concentration was also used for the 3-HPA preparations in order to allow direct comparison with the ATT preparations. The samples were dried in a stream of cold air.

Results
IR-MALDI-MS

As shown herein, IR-MALDI-MS with glycerol or other such composition as matrix is a remarkable combination for the analysis of large nucleic acids. Single stranded nucleic acids containing over 2000 nucleotides were successfully detected. Destabilization of the DNA double strand by the absence of salt in the pure glycerol matrix and by the IR laser exposure were probably responsible for the predominant observation of the single stranded form of the analytes.

In this Example, double stranded DNA is stabilized in solution by the addition of salts. In particular, the addition of $NH_4$-acetate or Tris-HCl, the latter present in the solution to about 50% as the protonated primary amine at the pH of 8.0 was used.

When pure glycerol was used as matrix, the barely resolved individual single stranded 70-mers form the base peak in the spectrum. After the addition of either $H_4N_4$-acetate or Tris-HCl at pH 8.0 to the sample preparation, the signal of the double stranded DNA forms the base peak in the spectra. A substantial fraction of the signal at the nominal mass of the single strands is probably comprised of the doubly charged ds-moiety. No signal corresponding to a non-specific trimer is present. Thus, it is this clear that the addition of salt to the IR-MALDI sample preparation allows the detection of specific double stranded DNA. There is no significant difference between the spectra obtained from the two samples containing either $NH_4$-acetate or Tris-HCl.

Salt-stabilized ds-DNA is still prone to acidic denaturation. In one experiment, a 750 bp fragment was first stabilized by TRIS-HCl resulting in a strong signal from the singly charged double stranded species. In contrast, only singly and doubly charged ions of the single strands are observed after the same sample was on-target acidified with succinic acid, a commonly used IR-MALDI matrix. A signal corresponding to the triply charged double strand was clearly evident. This result shows that the effect of succinic acid addition is a true denaturation, not a general increase in the charge state. Thus, ds-DNA can be stabilized and destabilized by physico-chemical means in the sample preparation. The sample used was actually an equimolar mixture of the observed 750 bp species and a fragment well above 3 kbp generated by restriction enzyme digest of a plasmid. The larger species could not be detected, because ions of this mass (>2.0 MDa) are beyond the current mass limit of ca. 700 kDa for IR-MALDI of large DNA. The spectra were recorded with delayed ion extraction in the linear TOF mode in order not to discriminate against ds-DNA surviving desorption and ion acceleration, but dissociating in the flight tube. These would not have been detected in a reflectron TOF configuration. The observed background signals, increasing strongly with decreasing mass is typical for the glycerol matrix, when measuring samples exceeding 100 kDa in the linear DE-TOF mode.

These observations of a stabilization of double strands via an increased ionic strength were extended using restriction enzyme digested plasmid DNA containing fragments of 280 bp, 360 bp, 920 bp, and 1.40 kbp. Peaks at masses of 175 kDa, 223 kDa, and 565 kDa, corresponding to the double stranded species of the three smaller fragments are observed in the spectrum. Peaks observed at 87.5 kDa, 112 kDa and 283 kDa nominally represent the single strands. Based on these results, it was shown that the doubly charged ds-ions contribute significantly if not dominantly to these signals. A very small signal of the monomer/doubly charged ds ion of the largest fragment of 1.40 kbp is seen at mass 432 kDa. The m/z-value of 864 kDa of the singly charged ion of this ds species is beyond the current limit of detection of ca. 700 kDa. The addition of stabilizers, in particular Tris-HCl, to a glycerol sample preparation lead to peak broadening compared to the spectra obtained from pure glycerol, noticeable as an extended peak tailing to the high mass side. The mass resolution decreases by a factor of two, to around 25 in reflectron TOF mode for the mid size species, whereas the mass resolution of the 920 bp fragment as well as the 70-mer ds-DNA in is about 50.

An observed, step rise of the peaks of ds-ion on the low-mass side testifies to a very limited metastable decay, as was already observed for the signals of ss-species as shown here. This very low degree or absence of metastable fragmentation is in sharp contrast to UV-MALDI-MS analysis of nucleic acids, where metastable (and in-source) fragmentation is a limiting factor, particularly for the analysis of larger DNA fragments.

Experiments demonstrating the specificity of the ds-detection were also performed. If a significant portion of the signals result from non-specific gas phase complex formation of single strands formed in solution or during the desorption process, non-specific complexes e.g. between single strands of the 280-mer and the 360-mer would have been observed. Such non-specific complexes, often observed for proteins, were not observed in the DNA spectrum. Hence, the ds-DNA present in the original analyte solution is predominantly retained as such throughout the MALDI process.

As shown herein, it is also possible to desorb intact ds-DNA from pure glycerol without a stabilizing salts. DNA fragments over a wide mass range were tested for intact detection without stabilization. The condition of the DNA sample was very crucial for these experiments. Only freshly prepared DNA samples were reproducibly detected as double stranded ions. In contrast to the salt-stabilized samples, the laser fluence had to be carefully controlled. Near the threshold fluence for the detection of analyte ions ($1.2 H_0$), a 190 bp fragment formed predominantly ds-ions. Increasing the fluence to 1.5 $H_0$ resulted in the exclusive detection of the ss-moiety with the two single strands partially resolved. Hence, it is possible to denature large DNA double strands by adjusting the laser irradiance alone. The largest ds-DNA desorbed from pure glycerol was a 750 bp fragment, the smallest had 100 bp. Generally, the smaller the-fragment, the closer to $H_0$ the laser fluence had to be when desorption of the double stranded analyte was desired. The 100 bp fragment required strictly threshold fluence and, in addition, a low field strength for the ion extraction ($\leq 150$ V/mm), For an intact desorption of a 500 bp and a 750 bp ds-fragment, fluences as high as 1.7 $H_0$ and 2 $H_0$, respectively, could be used.

UV-MALDI-MS

Attempts to analyze double stranded DNA with 60 base pairs by IR-MALDI were not reproducible with respect to detection of the ds-form, and smaller analytes did not show signals of specific ds-ions at all. Therefore, UV-MALDI-MS with 6-aza-2-thiothymine (ATT) matrix was used for detection of relatively small ds-DNA fragments. As was reported by Lecchi & Pannell (Lecchi et al. *J. Am. Soc. Mass Spectrom.* 1995, 6, 972–75), signals of the ds-species were obtained down to fully complementary synthetic 12 mers. In contrast, an equimolar mixture of a 12-mer and a fully complementary 8-mer did not generate any signal of the ds-ion, indicating that this is about the lower size limit for intact desorption of ds-DNA. It should be noted that no spectra could be obtained in reflectron TOF mode with the ATT matrix, probably because of excessive fragmentation, already noticeable in the linear TOF mode.

The upper limit for the detection of ds-ions by UV-MALDI with an ATT matrix was also determined for this system. The two completely complementary synthetic 70-mers, investigated by IR-MALDI produced a signal of the ds-ion in the ATT/UV-MALDI spectrum as well. Two barely resolved signals of the two individual 70-mers dominated the spectrum when 3-HPA is used as matrix. The resolution here was comparable to the one seen in the glycerol/IR-MALDI spectrum of the same sample. This experiment confirms that detection of larger analytes is feasible with ATT and that signals of ds-DNA cannot be obtained with 3-HPA, at least when prepared at room temperature. To prove rigorously that the signal at 43.5 kDa represented the intact ds-DNA rather than partially or fully unspecific homodimers, a synthetic 80-mer was annealed to either a complementary 70-mer (complementary over 62 consecutive nucleotides(or a non-complementary 70-mer, and analyzed by ATT/UV-MALDI. It was evident from the spectra that only the complementary 70/80-mer mixture produces a ds-signal, whereas the two non-complementary single strands form the base peaks in the spectrum. The results also showed that in spectra, for which the ds-moiety forms the base peak, minor signals appearing at half the mass represent the double charged ds-DNA, rather than the singly charged individual single strands. Therefore ATT is a highly selective matrix for the detection of ds-DNA by UV-MALDI even in the upper part of the mass range.

Discussion

The results in this Example show that MALDI-MS analysis of double stranded DNA is possible with analytes in the size range from about 12 bp to 920 bp. UV-MALDI-MS with ATT as matrix was used for fragments in the size range up to 70 bp; and IR-MALDI-MS with glycerol as matrix and salt addition was used for DNA molecules of 70 bp and upwards.

The rather large sample consumption (10–20 pmol) in UV-MALDI-MS with ATT at the 70-mer level limits the use of the method for larger analytes because this amount of sample is quite massive for samples of biological origin. The main reason for this reduced sensitivity is the extensive in-source fragmentation, apparent in all spectra employing the ATT matrix. Fragmentation of double stranded species was dominated by loss of single or multiple bases and/or backbone cleavages rather than dissociation into single strands. The fragmentation of the double stranded analyte was comparable in extent to that of the observed for single stranded analyte. This was observed even for the double stranded 70-mer, where every nucleotide should be base-paired. These results indicate that the non-covalent ds-structure is stable under conditions that induce cleavage of covalent bonds in UV-MALDI-MS, provided the DNA is maintained at a minimum ionic strength.

In contrast, very little fragmentation was observed for IR-MALDI-MS with glycerol. Even large DNA molecules when analyzed in reflectron TOF mode, having flight times longer than 1 ms, did not exhibit a substantial metastable fragmentation. This generally applies to analytes in single and double stranded form. In addition, for pure glycerol as matrix, excess laser energy in IR-MALDI-MS leads to denaturation of non-stabilized double strands rather than cleavage of covalent bonds.

Ds-DNA is stabilized in aqueous solution by salt addition, i.e. an increase of the ionic strength. The stabilization results from the condensation of positive ions near the phosphate backbone, thereby partially neutralizing the negative backbone charge and reducing the repulsive electrostatic interaction between the two strands. The results presented here and the fact that DNA is nearly insoluble in glycerol suggest that the DNA retains enough of a shell of solvent water in the glycerol to afford the cation condensation, even after some time in the vacuum of the analyzer.

A correlation between the length of the double stranded region in an analyte and the degree of ds-DNA in UV-MALDI-MS with ATT as matrix was observed. This corroborates the high specificity of UV-MALDI for the analysis of ds-DNA. The specificity is substantiated by the observation that a self-complementary RNA, forming more stable double strand than a corresponding DNA, gives a higher signal of the ds-form at the 12-mer level than a DNA of equal length.

The fact that UV- and IR-MALDI allow the specific analysis of ds-DNA indicates that these methods may also be used to study non-covalent complexes between DNA and proteins. The prerequisite for such investigations is the ability to keep the DNA in its double stranded form.

IR-MALDI-MS demonstrated a sensitivity in the subpicomole range making a method of choice for analyses, such as for use in diagnostic methods, that require high sensitivity. Furthermore, as shown herein, the sensitivity can be increased by at least a factor of 100 by a miniaturization of the sample volume using a piezo-electric pipette (see, published International PCT application No. WO 98/20166 and also copending, allowed, U.S. application Ser. No. 08/787, 639). The fact that the addition of Tris-HCl or $NH_4$-acetate is required for a reproducible acquisition of ds-DNA spectra is rather a benefit. Most nucleic acid/protein complexes need pH- and salt-adjusted environments for stability. Interactions between nucleic acids, DNA triple helices and the hybridization between modified oligonucleotides and native DNA are further fields of application.

EXAMPLE 4

Comparison of IR MALDI Using Lasers Emitting Electromagnetic Radiation at 10.6 $\mu$m Wavelength With Those Emitting 3 $\mu$m Small, sealed-off TEA-$CO_2$-lasers emitting in the 10 $\mu$m wavelength range are commercially available and are comparable in size, price and ease of operation to the nitrogen lasers commonly used for UV-MALDI-MS. The performance data of such lasers for IR-MALDI-MS has been investigated. This includes the use of delayed ion extraction for an enhancement in mass resolution and accuracy as well as spectra for the certain particular IR applications.

A sealed-off TEA-$CO_2$ laser of 10.59 $\mu$m wavelength ($\mu$-TEA, Laser Science, Inc. Franklin, Mass.) was coupled to an in-house-built TOF instrument with a linear (2.2 m) and a reflection port (3.5 m equivalent flight length). For comparison experiments an Er:YAG laser ($\lambda$=2.94 $\mu$m) or a frequency tripled Nd:YAG ($\lambda$=355 nm) are available on the same instrument.

RESULTS: Fumaric acid and glycerol were found to perform best as matrices for 10.6 $\mu$m wavelength. Whereas fumaric acid shows a better mass resolution in the mass range <40 kDa, especially with static ion extraction, glycerol performs best for high masses and gives an excellent reproducibility. The analytical sensitivity was tested for peptides and a fumaric acid matrix. A sample load of only a few fmoles and a molar analyte-to-matrix $\geq 10^{-7}$ were sufficient to generate spectra.

The low degree of metastable decay, particularly for proteins with a mass>100 kDa, described for IR-MALDI at 3 $\mu$m is observed for 10.6 $\mu$m as well. In combination with a reflection mass spectrometer, this leads to a larger accessible mass range. For example a mass resolution of 125 was obtained for a mouse monoclonal antibody (IgG) at 150 kDa using a glycerol matrix in the reflection mode. Homo-oligomers of the antibody up to a mass of 1.35 MDa were unambiguously identified in such spectra.

Delayed ion extraction substantially improves resolution for peptides, similar to UV- and IR-MALDI at 3 $\mu$m. In spectra of Substance P with glycerol and fumaric acid matrices, mass resolutions of 4500 and 5000–7000 are achieved. The isotopic distributions are somehow disturbed by intermediate and double peaks in the spectra, resulting in an overall inferior performance, compared to the UV or mid-infrared laser systems on the same instrument. This peak "fragmentation" is tentatively assigned to the heterogeneous beam profile of the $(\tau)_2$ laser. However, the mass resolution is still sufficient to get a mass accuracy in the low ppm range for peptides. The mass of Substance P, for example, was measured with an error of only 10 mDa, using internal calibration with Angiotensin and Renin.

A study was conducted of IR-$CO_2$-MALDI-MS of myoglobin (horse) electroblotted onto a polymer membrane (Immobilon P) after gel separation. A succinic acid matrix was used. A comparison of the spectra quality with that of spectra obtained from such membranes with the Er:YAG laser at 3 $\mu$m indicates that the latter may be preferable.

The analysis of double stranded DNA up to a mass of more than 300 kDa using a glycerol matrix was also conducted for a 515-bp PCR product. IR-MALDI-MS at 3 and 10.6 $\mu$m wavelength has very similar features; use of the 3 $\mu$m wavelength may be preferred in certain applications.

EXAMPLE 5

IR-MALDI of Large Nucleic Acids

MALDI-MS of proteins above ~20 kD with lasers emitting in the 3 $\mu$m wavelength region induces significantly less fragmentation of desorbed ions than UV-MALDI, particularly if glycerol as (liquid) matrix is used. Tests of lasers emitting at different wavelengths and various matrices for analysis of large nucleic acids have been conducted. It was found that the Er-YAG laser (2.94 $\mu$m) with a glycerol matrix is a gentle combination for the intact desorption/ionization of nucleic acids. The experiments were carried out with a single-stage reflectron, time of flight (refTOF) mass spectrometer with a split ion extraction source of 16 kV acceleration-potential operated with either prompt or delayed ion extraction [S. Berkenkamp, C. Menzel, M. Karns and F. Hillenkamp, *Rapid Commun. Mass Spectrom.*, 11, 1399, (1997)]. An Er:YAG laser ($\lambda$=2.94 $\mu$m, $\tau$=85 ns, Spektrum GmbH, Berlin, Germany) was used for desorption. Prior to sample preparation, the glycerol matrix was incubated with an equal volume of a $H^+$-cation exchange bead suspension.

As demonstrated for a plasmid DNA restriction enzyme digest (mixture of 1045 bp and 1913 bp fragments, 322 kDa and 592 kDa), IR-MALDI-MS with glycerol matrix can be used for oligomers of around 2000 nt. For all large DNA measured, the mass resolution of ion signal (FWHM) was about 50 and appeared to be relatively independent of the ion mass. IR-MALDI-MS of DNA could be used to measure masses of approximately 700 kDa. Large RNA can also be analyzed by IR-MALDI-MS as demonstrated for a 1206 nt transcript (ca 388 kDa), synthesized in vitro. Up to this mass RNA and DNA exhibit comparable stability. For all measured samples of high mass DNA and RNA the mass accuracy was between 0.5% and 1% of that calculated from the sequence. Even the mass of a 2180 nt fragment was determined with a 0.6% accuracy. Signals of IgG monoclonal antibodies of well defined mass and of their oligomers have been used for the mass calibration. The sensitivity of IR-MALDI-MS of large nucleic acids with glycerol as matrix, evaluated for a PCR-product of approximately 515 bp, was found to be in the low femtomol range. Spectra with reasonable quality could even be obtained from 300 amol total load of sample. All results reported above have been obtained with only limited efforts in a sample purification. For the restriction enzyme digest fragment a one step purification (precipitation) appeared to be sufficient. For the RNA, additionally a reverse phase column was prepared.

Since modifications will be apparent to those of skill in this art, it is intended that this invention be limited only by the scope of the appended claims.

What is claimed is:

1. A method for performing matrix assisted laser desorption/ionization (MALDI) of a nucleic acid molecule for analysis by mass spectrometry, comprising the steps of:
   (a) depositing a solution containing the nucleic acid and a liquid matrix on a substrate, thereby forming a homogeneous, thin layer of a nucleic acid/liquid matrix solution; and
   (b) illuminating the substrate with infrared radiation, whereby the nucleic acid in the solution is desorbed and ionized.

2. The method of claim 1, further comprising, determining the mass of the nucleic acid by MALDI.

3. The method of claim 1, further comprising, determining the mass of the nucleic acid by MALDI and thereby detecting the presence of the nucleic acid in a sample.

4. A method of claim 1, wherein the liquid matrix has at least one of the following properties: i) is miscible with a nucleic acid compatible solvent, ii) is vacuum stable, and iii) is of an appropriate viscosity for dispensing the thin layer of micro- to nano-liter volumes of matrix alone or mixed with a nucleic acid compatible solvent.

5. The method of claim 1, wherein the liquid matrix is sufficiently non-volatile to not evaporate during the illuminating, desorbing and ionizing step.

6. The method of claim 1, wherein the liquid matrix can form a glass when cooled and/or pressurized.

7. The method of claim 1, wherein the matrix comprises a sugar, a monosaccharide, or a polysaccharide.

8. The method of claim 1, wherein the matrix comprises a polyglycerol, sucrose, mannose, galactose, ethylene glycol, propylene glycol, trimethylolpropane, pentaerythritol, dextrose, methylglycoside or sorbitol, sucrose, mannose, triethanolamine, lactic acid, 3-nitrobenzylalcohol, diethanolamine, DMSO, nitrophenyloctylether (3-NPOE), 2,2'dithiodiethanol, tetraethyleneglycol, dithiothreitol/erythritol (DTT/DTE), 2,3-dihydroxy-propyl-benzyl ether, α-tocopherol, and thioglycerol.

9. A method of claim 1, wherein the liquid matrix contains at least one functional group that absorbs infrared radiation.

10. A method of claim 9, wherein the functional group is selected from the group consisting of nitro, sulfonyl, sulfonic acid, sulfonamide, nitrile, carbonyl, aldehyde, carboxylic acid, amide, ester, anhydride, ketone, amine, hydroxyl, an aromatic ring and a diene.

11. A method of claim 1, wherein the liquid matrix is selected from a group consisting of an alcohol, a carboxylic acid, a primary or secondary amide, a primary or secondary amine, a nitrile, hydrazine and hydrazide.

12. A method of claim 11, wherein the alcohol is selected from the group consisting of glycerol, 1,2- or 1,3-propane diol, 1,2-, 1,3- or 1,4-butane diol and triethanolamine.

13. A method of claim 11, wherein the carboxylic acid is selected from the group consisting of lactic acid, acetic acid, formic acid, propionic acid, butanoic acid, pentanoic acid, hexanoic acid and esters thereof.

14. A method of claim 11, wherein the amide is selected from the group consisting of acetamide, propanamide, butanamide, pentanamide and hexanamide, whether branched or unbranched.

15. A method of claim 11, wherein the amine is selected from the group consisting of propylamine, butylamine, pentylamine, hexylamine, heptylamine, diethylamine and dipropylamine.

16. A method of claim 4, wherein the liquid matrix is comprised of at least two liquids, each of which confers at least one of the properties.

17. A method of claim 1, wherein the liquid matrix comprises an additive.

18. A method of claim 17, wherein the additive is selected from the group consisting of a compound having a high extinction coefficient at the laser wavelength used for the analysis, an additive that acidifies the liquid matrix, and an additive that minimizes salt formation between the liquid matrix and the phosphate backbone of the nucleic acid.

19. A method of claim 17, wherein the additive increases the ionic strength of the matrix composition.

20. A method of claim 1, wherein prior to step (a), the liquid matrix is treated to minimize salt formation between the matrix and the phosphate backbone of the nucleic acid.

21. A method of claim 1, wherein the liquid matrix is treated by distillation or ion exchange.

22. A method of claim 1, wherein the liquid matrix is treated by further purification.

23. A method of claim 1, wherein the liquid matrix is selected from the group consisting of glycerol, lactic acid and triethanolamine.

24. A method of claim 23, wherein the liquid matrix is glycerol and the final analyte-to-glycerol molar ratio is about $10^{-4}$ to about $10^{-9}$.

25. A method of claim 1, wherein the liquid matrix is glycerol, the mass of the nucleic acid is in the range of from about $10^4$ to about $10^6$ Da and the glycerol is subjected to ion exchange prior to step (a).

26. A method of claim 1, wherein the nucleic acid is DNA.

27. A method of claim 26, wherein the DNA is less than or equal to about 2000 bases.

28. A method of claim 1, wherein the nucleic acid is RNA.

29. A method of claim 28, wherein the RNA is less than or equal to about 1200 bases.

30. A method of claim 1, wherein the nucleic acid comprises PNA.

31. A method of claim 1, wherein the nucleic acid comprises double-stranded nucleic acid.

32. A method of claim 1, wherein the nucleic acid comprises single-stranded nucleic acid.

33. A method of claim 1, wherein the infrared radiation is of a wavelength in the range of from about 2.5 $\mu$m to about 12 $\mu$m.

34. A method of claim 1, wherein the infrared radiation is generated in pulses having a duration in the range of about 500 ps to about 500 ns.

35. A method of claim 34, wherein the pulse duration is less than 200 ns.

36. A method of claim 35, wherein the pulse duration is less than 100 ns.

37. A method of claim 1, wherein the infrared radiation is generated from a source selected from the group consisting of a CO laser, a $CO_2$ laser, an Er laser and an optical parametric oscillator laser emitting in the range of about 2.5 to about 12 $\mu$m.

38. A method of claim 1, wherein the solution contains less than about 10 pmoles of nucleic acid.

39. A method of claim 1, wherein all or a portion of the method is automated.

40. A method of claim 1, wherein the solution is cooled to a temperature, which is below about 20° C.

41. A method of claim 1, wherein the solution is heated to a temperature which is greater than about 20° C. and less than about 80° C.

42. A method of claim 1, wherein the solution is cooled, whereby the matrix forms a glass.

43. A method of claim 42, wherein the glass is glassy water.

44. A method of claim 1, wherein the matrix comprises glycerol and the glycerol and nucleic acid solution is cooled, whereby the glycerol freezes.

45. A method of claim 1, wherein ions from the desorbed and ionized nucleic acid are extracted from an ion source by delayed extraction.

46. A method for analyzing a nucleic acid in a sample by mass spectrometry, comprising the steps of:
   (a) depositing a mixture containing the nucleic acid and a liquid matrix on a substrate, thereby forming a homogeneous, thin layer of a nucleic acid/liquid matrix mixture;
   (b) illuminating the substrate of (a) with infrared radiation from an infrared laser, so that the nucleic acid is desorbed and ionized; and
   (c) mass separating and detecting the ionized nucleic acid using a mass separation and analysis format.

47. The method of claim 46, wherein the liquid matrix is sufficiently non-volatile to not evaporate during the illuminating, desorbing and ionizing step.

48. The method of claim 46, wherein the liquid matrix can form a glass when cooled and/or pressurized.

49. The method of claim 46, wherein the matrix comprises a sugar, a monosaccharide, or a polysaccharide.

50. The method of claim 46, wherein the matrix comprises a polyglycerol, sucrose, mannose, galactose, ethylene glycol, propylene glycol, trimethylolpropane, pentaerythritol, dextrose, methylglycoside or sorbitol, sucrose, mannose, triethanolamine, lactic acid, 3-nitrobenzylalcohol, diethanolamine, DMSO, nitrophenyloctylether (3-NPOE), 2,2'dithiodiethanol, tetraethyleneglycol, dithiothreitol/erythritol(DTT/DTE), 2,3-dihydroxy-propyl-benzyl ether, α-tocopherol, and thioglycerol.

51. A method of claim 46, wherein the liquid matrix has at least one of the following properties: i) is miscible with a nucleic acid compatible solvent, ii) is vacuum stable, and iii) is of an appropriate viscosity to facilitate dispensing of micro- to nano- liter volumes of matrix alone or mixed with a nucleic acid compatible solvent.

52. A method of claim 46, wherein the liquid matrix contains at least one functional group that absorbs infrared radiation.

53. A method of claim 52, wherein the functional group is selected from the group consisting of nitro, sulfonyl, sulfonic acid, sulfonamide, nitrile, carbonyl, aldehyde, carboxylic acid, amide, ester, anhydride, ketone, amine, hydroxyl, an aromatic ring and a diene.

54. A method of claim 46, wherein the liquid matrix is selected from a group consisting of an alcohol, a carboxylic acid, a primary or secondary amide, a primary or secondary amine, a nitrile, hydrazine and hydrazide.

55. A method of claim 54, wherein the alcohol is selected from the group consisting of glycerol, 1,2- or 1,3-propane diol, 1,2-, 1,3- or 1,4-butane diol and triethanolamine.

56. A method of claim 54, wherein the carboxylic acid is selected from the group consisting of lactic acid, acetic acid, formic acid, propionic acid, butanoic acid, pentanoic acid, hexanoic acid and esters thereof.

57. A method of claim 54, wherein the amide is selected from the group consisting of acetamide, propanamide, butanamide, pentanamide and hexanamide, whether branched or unbranched.

58. A method of claim 54, wherein the amine is selected from the group consisting of propylamine, butylamine, pentylamine, hexylamine, heptylamine, diethylamine and dipropylamine.

59. A method of claim 51, wherein the liquid matrix is comprised of at least two liquids, each of which confers at least one of the properties.

60. A method of claim 46, wherein the liquid matrix comprises an additive.

61. A method of claim 60, wherein the additive is selected from the group consisting of a compound having a high extinction coefficient at the laser wavelength used for the analysis, an additive that acidifies the liquid matrix, and an additive that minimizes salt formation between the liquid matrix and the phosphate backbone of the nucleic acid.

62. A method of claim 60, wherein the additive increases the ionic strength of the matrix composition.

63. A method of claim 46, wherein prior to step (a), the liquid matrix is treated to minimize salt formation between the matrix and the phosphate backbone of the nucleic acid.

64. A method of claim 46, wherein the liquid matrix is treated by distillation or ion exchange.

65. A method of claim 46, wherein the liquid matrix is treated by further purification.

66. A method of claim 46, wherein the liquid matrix is selected from the group consisting of glycerol, lactic acid and triethanolamine.

67. A method of claim 46, wherein the liquid matrix is glycerol and the final analyte-to-glycerol molar ratio is about $10^{-4}$ to about $10^{-9}$.

68. A method of claim 46, wherein the liquid matrix is glycerol, the mass of the nucleic acid is in the range of from about $10^4$ to about $10^6$ Da and the glycerol is subjected to ion exchange prior to step (a).

69. A method of claim 46, wherein the nucleic acid is DNA.

70. A method of claim 69, wherein the DNA is less than or equal to about 2000 bases.

71. A method of claim 46, wherein the nucleic acid is RNA.

72. A method of claim 71, wherein the RNA is less than or equal to about 1200 bases.

73. A method of claim 46, wherein the nucleic acid comprises PNA.

74. A method of claim 46, wherein the nucleic acid comprises double-stranded nucleic acid.

75. A method of claim 46, wherein the nucleic acid comprises single-stranded nucleic acid.

76. A method of claim 46, wherein the infrared radiation is of a wavelength in the range of from about 2.5 $\mu$m to about 12 $\mu$m.

77. A method of claim 46, wherein the infrared radiation is generated in pulses having a width in the range of about 500 ps to about 500 ns.

78. A method of claim 46, wherein the infrared radiation is generated from a source selected from the group consisting of a CO laser, a $CO_2$ laser, an Er laser and an optical parametric oscillator laser emitting in the range of about 2.5 to about 12 $\mu$m.

79. A method of claim 46, wherein the sample contains less than about 10 pmoles of nucleic acid.

80. A method of claim 46, wherein all or a portion of the method is automated.

81. A method of claim 46, wherein the sample is cooled to a temperature that is below about 20° C.

82. A method of claim 46, wherein the sample is heated to a temperature which is greater than about 20° C. and less than about 80° C.

83. A method of claim 46, wherein the matrix and nucleic acid mixture are cooled, whereby the matrix forms a glass.

84. A method of claim 83, wherein the glass is glassy water.

85. A method of claim 46, wherein the matrix comprises glycerol and the glycerol and sample mixture are cooled, whereby the glycerol freezes.

86. A method of claim 46, wherein prior to step (c), ions from the ionized nucleic acid are extracted from an ion source by delayed extraction.

87. A method of claim 46, wherein the mass separation and analysis format is selected from the group consisting of: time-of-flight (TOF), quadrupole, magnetic sector, Fourier transform ion cyclotron resonance (FTICR), and ion trap or a combination thereof.

88. A method of claim 87, wherein the TOF is linear, or the TOF has a reflector.

89. A method of claim 88, wherein the TOF reflector has a linear field or a nonlinear field.

90. A method of claim 87, wherein the quadrupole is single or the quadrupole is multiple.

91. A method of claim 87, wherein the magnetic sector is single or the magnetic sector is multiple.

92. A method for determining the size of a primer extension product, comprising:

(a) hybridizing a primer with a target nucleic acid, where the primer (i) is complementary to the target nucleic acid; (ii) has a first region containing the 5' end of the primer and an immobilization attachment site, and (iii) has a second region containing the 3' end of the primer, where the 3' end is capable of serving as a priming site for enzymatic extension and where the second region contains a selected cleavable site;

(b) extending the primer enzymatically to generate a polynucleotide mixture containing an extension product composed of the primer and an extension segment;

(c) cleaving the extension product at the cleavable site to release the extension segment, where prior to the cleaving the primer is immobilized at the immobilization attachment site; and (d) sizing the extension segment by the method of claim 1, whereby the cleaving is effective to increase the read length of the extension segment relative to the read length of the product of (b).

93. A method for determining the size of a primer extension product, comprising:

(a) combining first and second primers with a target nucleic acid under conditions that promote the hybridization of the primers to the nucleic acid, thus generating primer/nucleic acid complexes, where the first primer (i) is complementary to the target nucleic acid; (ii) has a first region containing the 5' end of the primer and an immobilization attachment site, and (iii) has a second region containing the 3' end of the primer, where the 3' end is capable of serving as a priming site for enzymatic extension and where the second region contains a cleavable site, and where the second primer is homologous to the target nucleic acid;

(b) converting the primer/nucleic acid complexes to double-stranded fragments in the presence of a suitable polymerase and all four dNTPs;

(c) amplifying the primer-containing fragments by successively repeating the steps of (i) denaturing the double-stranded fragments to produce single-strand fragments, (ii) hybridizing the single strands with the primers to form strand/primer complexes, (iii) generating double-stranded fragments from the strand/primer complexes in the presence of DNA polymerase and all four dNTPs, and (iv) repeating steps (i) to (iii) until a desired degree of amplification has been achieved;

(d) denaturing the amplified fragments to generate a mixture including a product composed of the first primer and an extension segment;

(e) immobilizing amplified fragments containing the first primer, utilizing the immobilization attachment site, and removing non-immobilized amplified fragments;

(f) cleaving the immobilized fragments at the cleavable site to release the extension segment; and (g) sizing the extension segment by the method of claim 1, whereby the cleaving is effective to increase the read length of the extension segment relative to the read length of the product of (d).

94. A method for determining the DNA sequence of a target DNA sequence, comprising:

(a) hybridizing a primer with a target DNA, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a cleavable site;

(b) extending the primer with an enzyme in the presence of a first of four different dideoxy nucleotides to generate a mixture of primer extension products each product containing a primer and an extension segment;

(c) cleaving at the cleavable site to release the extension segments, where prior to the cleaving the primers are immobilized at the immobilization attachment sites;

(d) sizing the extension segments by the method of claim 1, whereby the cleaving is effective to increase the read length of the extension segment relative to the read length of the product of (b);

(e) repeating steps (a) through (d) with a second, third, and fourth of the four different dideoxynucleotides; and (f) determining the DNA sequence of the target DNA by comparison of the sizes of the extension segments obtained from each of the four extension reactions.

95. A method for determining the DNA sequence of a target DNA sequence, comprising:

(a) hybridizing a primer with a target DNA, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a cleavable site;

(b) extending the primer with an enzyme in the presence of a first of four different deoxynucleoside α-thiotriphosphate analogs (dNTPαS) to generate a mixture of primer extension products containing phosphorothioate linkages;

(c) treating the primer extension products with a reagent that cleaves specifically at the phosphorothioate linkages, where the treating is carried out under conditions producing limited cleavage, resulting in the production of a group of primer extension degradation products;

(d) washing the primer extension degradation products, where prior to the washing, the primer extension degradation products are immobilized at the immobilization attachment sites, each immobilized primer extension degradation product containing a primer and an extension segment, where the washing is effective to remove non-immobilized species;

(e) cleaving at the cleavable site to release the extension segments;

(f) sizing the extension segments by the method of claim 1, whereby the cleaving is effective to increase the read length of any given extension segment relative to the read length of its corresponding primer extension degradation product;

(g) repeating steps (a) through (f) with a second, third, and fourth of the four different dNTPαSs; and (h) determining the DNA sequence of the target DNA by comparison of the sizes of the extension segments obtained from each of the four extension reactions.

96. A method for determining the size of a primer extension product, comprising:

(a) hybridizing a primer with a target nucleic acid, where the primer (i) is complementary to the target nucleic acid; (ii) has a first region containing the 5' end of the primer, and (iii) has a second region containing the 3' end of the primer, where the 3' end is capable of serving as a priming site for enzymatic extension and where the second region contains a selected cleavable site;

(b) extending the primer enzymatically to generate a polynucleotide mixture containing an extension product composed of the primer and an extension segment;

(c) cleaving the extension product at the cleavable site to release the extension segment; and (d) sizing the extension segment by the method of claim 1, whereby the cleaving is effective to increase the read length of the extension segment relative to the read length of the product of (b).

97. A method for determining the size of a primer extension product, comprising:

(a) hybridizing a primer with a target nucleic acid, where the primer (i) is complementary to the target nucleic acid; (ii) has a first region containing the 5' end of the primer, and an immobilization attachment site, where the immobilization attachment site of the primer is composed of a series of bases complementary to an intermediary oligonucleotide, and (iii) has a second region containing the 3' end of the primer, where the 3' end is capable of serving as a priming site for enzymatic extension and where the second region contains a selected cleavable site;

(b) extending the primer enzymatically to generate a polynucleotide mixture containing an extension product composed of the primer and an extension segment;

(c) cleaving the extension product at the cleavable site to release the extension segment, where prior to the cleaving the primer is immobilized by specific hybridization of the immobilization attachment site to the intermediary oligonucleotide bound to a solid support; and (d) sizing the extension segment by the method of claim 1, whereby the cleaving is effective to increase the read length of the extension segment relative to the read length of the product of (b).

98. A method for determining the size of a primer extension product, comprising:

(a) combining first and second primers with a target nucleic acid, under conditions that promote hybridization of the primers to the nucleic acid, generating primer/nucleic acid complexes, where the first primer (i) has a 5' end and a 3' end, (ii) is complementary to the target nucleic acid, (iii) has a first region containing the 5' end of the first primer and (iv) has a second region containing the 3' end of the first primer, where the 3' end is capable of serving as a priming site for enzymatic extension and where the second region contains a cleavable site, and where the second primer (i) has a 5' end and a 3' end, (ii) is homologous to the target nucleic acid, (iii) has a first segment containing the 3' end of the second primer, and (iv) has a second segment containing the 5' end of the second primer and an immobilization attachment site;

(b) converting the primer/nucleic acid complexes to double-stranded fragments in the presence of a DNA polymerase and deoxynucleoside triphosphates;

(c) amplifying the primer-containing fragments by successively repeating the steps of (i) denaturing the double-stranded fragments to produce single-stranded fragments, (ii) hybridizing the single stranded fragments with the first and second primers to form strand/primer complexes, (iii) generating amplification products from the strand/primer complexes in the presence of DNA polymerase an deoxynucleoside triphosphates, and (iv) repeating steps (i) to (iii) until a desired degree of amplification has been achieved;

(d) immobilizing amplification products containing the second primer via the immobilization attachment site;

(e) removing non-immobilized amplified fragments;

(f) cleaving the immobilized amplification products at the cleavable site, to generate a mixture including a double-stranded product;

(g) denaturing the double-stranded product to release the extension segment; and (h) sizing the extension segment by the method of claim 1, whereby the cleaving is effective to increase the read length of the extension segment relative to the read length of the amplified strand-primer complexes of (c).

99. A method for determining a single base fingerprint of a target DNA sequence, comprising:

(a) hybridizing a primer with a target DNA, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a selected cleavable site;

(b) extending the primer with an enzyme in the presence of a dideoxynucleoside triphosphate corresponding to the single base, to generate a polynucleotide mixture of primer extension products, each product containing a primer and an extension segment;

(c) cleaving the extension products at the cleavable site to release the extension segments, where prior to the cleaving the primers are immobilized at the immobilization attachment sites;

(d) sizing the extension segments by the method of claim 1, whereby the cleaving is effective to increase the read length of any given extension segment relative to the read length of its corresponding primer extension product of (b); and (e) determining the positions of the single base in the target DNA by comparison of the sizes of the extension segments.

100. A method for an adenine fingerprint of a target DNA sequence, comprising:

(a) hybridizing a primer with a DNA target, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a selected cleavable site;

(b) extending the primer with an enzyme in the presence of deoxyadenosine triphosphate (dATP), deoxythymidine triphosphate (dTTP), deoxycytidine triphosphate (dCTP), deoxyguanosine triphosphate (dGTP), and deoxyuridine triphosphate (dUTP), to generate a polynucleotide mixture of primer extension products containing dUTP at positions corresponding to dATP in the target, each product containing a primer and an extension segment;

(c) treating the primer extension products with uracil DNA-glycosylase to fragment specifically at dUTP positions to produce a set of primer extension degradation products;

(d) washing the primer extension degradation products, where prior to the washing, the primer extension degradation products are immobilized at the immobilization attachment sites, each immobilized primer extension degradation product containing a primer and an extension segment, where the washing is effective to remove non-immobilized species;

(e) cleaving the immobilized primer extension degradation products at the cleavable site to release the extension segments;

(f) sizing the extension segments by the method of claim 1, whereby the cleaving is effective to increase the read length of any given extension segment relative to the read length of its corresponding primer extension degradation product; and (g) determining the positions of adenine in the target DNA by comparison of the sizes of the released extension segments.

101. A method of detecting mutations in a target nucleic acid, comprising:

a) obtaining from the target nucleic acid a set of nonrandom length fragments (NLFs) in single-stranded form, wherein the set comprises NLFs derived from one of either the positive or the negative strand of the target nucleic acid or the set is a subset of single-stranded NLFs derived from the positive and the negative strand of the target nucleic acid; and b) determining masses of the members of the set by the method of claim 1.

102. A method of detecting mutations in a target nucleic acid, comprising:
- a) nonrandomly fragmenting the target nucleic acid with one or more restriction endonucleases to form a set of double-stranded NLFs, wherein the nonrandomly fragmenting further comprises using volatile salts in a restriction buffer; and
- b) determining masses of the members of the set of double-stranded NLFs by the method of claim 1.

103. A method of detecting mutations in a double-stranded target nucleic acid comprising:
- a) nonrandomly fragmenting the target nucleic acid using one or more restriction endonucleases to form a first set of nonrandom length fragments (NLFs);
- b) hybridizing members of the first set of NLFs to a set of wild type probes;
- c) nonrandomly fragmenting one or more members of the set of NLFs with one or more mutation-specific cleaving reagents that specifically cleave at any regions of nucleotide mismatch that form between members of the first set of NLFs and complementary members of the set of wild type probes, wherein the nonrandomly fragmenting step forms a second set of NLFs; and
- d) determining masses of members of the second set of NLFs by the method of claim 1.

104. A method of detecting mutations in a target nucleic acid, comprising:
- a) nonrandomly fragmenting the target nucleic acid, using a mixture comprising one or more volatile salts to form a set of nonrandom length fragments (NLFs); and
- b) determining masses of members of the set of NLFs by the method of claim 1.

105. The method of claim 1, further comprising washing the nucleic acid sample with a mixture of volatile salts, and evaporating the mixture of volatile salts from the sample, thereby decreasing background noise.

106. A method for identifying DNA tandem nucleotide repeat alleles at a DNA tandem nucleotide repeat locus in a target nucleic acid by mass spectrometry, the method comprising:
- a) obtaining a target nucleic acid comprising a DNA tandem nucleotide repeat region;
- b) extending the target nucleic acid using one or more primers to obtain a limited size range of nucleic acid extension products, wherein one or more primers are complementary to a sequence flanking the DNA tandem nucleotide repeat of the locus; and
- c) determining the mass of the nucleic acid extension products by the method of claim 1.

107. A method for multiplexing the identification of more than one DNA tandem nucleotide repeat regions from more than one DNA tandem nucleotide repeat loci by mass spectrometry, which method comprises:
- a) obtaining more than one nucleic acid extension products by extending one or more primers complementary to sequences flanking the DNA tandem nucleotide repeat regions; and
- b) determining the mass of the more than one nucleic acid extension products simultaneously by the method of claim 1, wherein the nucleic acid extension products have overlapping allelic mass ranges.

108. A method for multiplexing the identification of more than one DNA tandem nucleotide repeat regions for more than one DNA tandem nucleotide repeat loci, which method comprises:
- a) obtaining more than one nucleic acid amplification products by amplifying two or more primers complementary to sequences flanking the DNA tandem nucleotide repeat regions; and
- b) determining the masses of more than one nucleic acid amplification products simultaneously by the method of claim 1, wherein the nucleic acid extension products have overlapping allelic mass ranges.

109. A method for identifying DNA tandem nucleotide repeat alleles at a DNA tandem nucleotide repeat locus in a target nucleic acid by mass spectrometry, the method comprising
- a) obtaining a target nucleic acid comprising a DNA tandem nucleotide repeat region;
- b) extending the target nucleic acid using one or more primers to obtain a limited size range of nucleic acid extension products, wherein one or more primers are complementary to a sequence flanking the DNA tandem nucleotide repeat of the locus; and
- c) determining the mass of the nucleic acid extension products by the method of claim 1.

110. The method of claim 109, wherein a 3' end of one or more primers immediately flanks a DNA tandem nucleotide repeat region.

111. The method of claim 109, wherein one or more primers comprise a sequence complementary to up to one tandem repeat of the DNA tandem nucleotide repeat locus.

112. The method of claim 111, wherein one or more primers comprise a sequence complementary to up to two tandem repeats of the DNA tandem nucleotide repeat locus.

113. The method of claim 112, wherein one or more primers comprise a sequence complementary to up to three tandem repeats of the DNA tandem nucleotide repeat locus.

114. The method of claim 109, wherein at least one primer comprises a cleavable site.

115. The method of claim 114, wherein the cleavable site comprises a recognition site for a restriction endonuclease, an exonuclease blocking site, or a chemically cleavable site.

116. The method of claim 114, wherein at least one primer is capable of attaching to a solid support.

117. The method of claim 116, wherein at least one primer comprises biotin or digoxigenin.

118. The method of claim 109, wherein the extension of at least one primer is terminated using a chain termination reagent.

119. The method of claim 118, wherein the chain termination reagent is a dideoxynucleotide triphospate.

120. A method for detecting a target molecule, comprising:
- (a) obtaining a target molecule;
- (b) amplifying the target molecule to produce an amplified target molecule;
- (c) obtaining a probe comprising a reactive group, a release group and a mass label;
- (d) hybridizing the amplified target molecule to the probe to produce a probe:amplified target molecule complex;
- (e) releasing the mass label from the probe:amplified target molecule complex to obtain a released mass label;
- (f) depositing a solution containing the released mass label and a liquid matrix on a substrate, thereby forming a homogeneous, thin layer of a mass label/liquid matrix solution;

(g) illuminating the substrate with infrared radiation, whereby the nucleic acid in the solution is desorbed and ionized; and (h) determining the mass of the released mass label by matrix assisted laser desorption/ionization (MALDI) mass spectrometry.

121. The method of claim 120, wherein prior to step (f), the mass label is mixed with the liquid matrix.

122. The method of claim 121, wherein the liquid matrix is glycerol.

123. A method for detecting a target molecule, comprising:

(a) obtaining a probe comprising a reactive group, a release group and a mass label;

(b) obtaining a target molecule;

(c) contacting the target molecule with the probe to produce a probe:target molecule complex;

(d) releasing the mass label from the probe:target molecule complex;

(e) depositing a solution containing the released mass label and a liquid matrix on a substrate, thereby forming a homogeneous, thin layer of a mass label/liquid matrix solution;

(f) illuminating the substrate with infrared radiation, whereby the nucleic acid in the solution is desorbed and ionized; and (g) determining the mass of the released mass label by matrix assisted laser desorption/ionization (MALDI) mass spectrometry.

124. The method of claim 123, wherein the mass label is nonvolatile and the mass label is selectively released from the probe:target molecule complex.

125. The method of claim 123, wherein prior to step (e), the mass label is mixed with a liquid matrix.

126. The method of claim 124, wherein the matrix is glycerol.

127. A method for multiplexing the detection of a target molecule, comprising:

(a) obtaining a plurality of probes, each comprising a reactive group, a release group and a mass label;

(b) contacting the target molecule with the plurality of probes to produce probe:target molecule complexes, wherein the target molecule is attached to the reactive group of the probe;

(c) releasing the mass labels from the probe:target molecule complexes to produce released mass labels;

(d) depositing a solution containing the released mass labels and a liquid matrix on a substrate, thereby forming a homogeneous, thin layer of a mass label/liquid matrix solution;

(e) illuminating the substrate with infrared radiation, whereby the nucleic acid in the solution is desorbed and ionized; and (f) determining the masses of the released mass labels by matrix assisted laser desorption/ionization (MALDI) mass spectrometry, wherein each reactive group in a probe:target molecule complex is associated with a unique set of mass labels.

128. The method of claim 127, wherein prior to step (d), the mass labels are mixed with a liquid matrix.

129. The method of claim 127, wherein the matrix is glycerol.

130. A method for multiplexing the detection of a plurality of target molecules, comprising:

(a) obtaining a plurality of probes, each comprising a reactive group, a release group and a mass label;

(b) contacting the plurality of target molecules with the plurality of probes to produce probe:target molecule complexes, wherein target molecules are attached to the reactive groups of the probes;

(c) releasing the mass labels from the probe:target molecule complexes to produce released mass labels;

(d) depositing a solution containing the released mass labels and a liquid matrix on a substrate, thereby forming a homogeneous, thin layer of a mass label/ liquid matrix solution;

(e) illuminating the substrate with infrared radiation, whereby the nucleic acid in the solution is desorbed and ionized; and (f) determining the masses of the released mass labels by matrix assisted laser desorption/ionization (MALDI) mass spectrometry, wherein each reactive group specific for a particular target molecule is associated with a unique mass label.

131. The method of claim 130, wherein prior to step (d), the mass labels are mixed with a liquid matrix.

132. The method of claim 131, wherein the matrix is glycerol.

133. A method for detecting a target biological macromolecule, comprising the steps of:

a) preparing a mixture, comprising a biological macromolecule and a liquid matrix, which absorbs infrared radiation; and b) performing IR-MALDI mass spectrometry on the mixture to identify the target biological macromolecule in the mixture, thereby detecting the target biological macromolecule.

134. The method of claim 133, wherein the target biological macromolecule is in a biological sample, whereby detection of the target biological macromolecule identifies the presence of the target biological macromolecule in the biological sample.

135. The method of claim 133, wherein the biological macromolecule is a nucleic acid.

136. The method of claim 133, wherein the biological macromolecule is a polypeptide.

137. The method of claim 133, wherein the biological macromolecule is selected from the group consisting of a carbohydrate, lipid, a nucleoprotein, a proteoglycan, and a macromolecular complex.

138. The method of claim 133, wherein the target biological macromolecule is immobilized on a solid support.

139. The method of claim 138, wherein the target biological macromolecule is immobilized to the solid support via a reversible linkage.

140. The method of claim 138, wherein the target biological macromolecule is immobilized to the solid support via a photocleavable bond.

141. The method of claim 139, wherein the reversible linkage is a thiol linkage or an ionic bond.

142. The method of claim 138, wherein the target biological macromolecule is cleaved from the support during the step of performing IR-MALDI mass spectrometry.

143. The method of claim 138, wherein the solid support is selected from the group consisting of a bead, a flat surface, a chip, a capillary, a pin, a comb, a wafer, a wafer with an arrow of nano-wells or pits, the terminus of a fiber optic cable, a support with a surface that comprises hydrophobic regions and a support with a surface that comprises hydrophilic regions, whereby the target molecule is constrained to a locus on the support.

144. The method of claim 138, wherein the solid support is a material selected from the group consisting of a metal, a ceramic, a plastic, a resin, a gel, and a membrane.

145. The method of claim 138, wherein the support is a silicon wafer, and wherein the target biological macromolecule is immobilized in an array.

146. The method of claim 135, wherein a target nucleic acid is immobilized by hybridization to a complementary capture nucleic acid molecule, which is immobilized to a solid support.

147. The method of claim 133, wherein the target biological macromolecule is conditioned prior to the step of performing IR-MALDI mass spectrometry.

148. The method of claim 147, wherein the target biological macromolecule is conditioned by ion exchange.

149. The method of claim 135, wherein the target nucleic acid is conditioned by a method selected from the group consisting of phosphodiester backbone modification effected by cation exchange; contact with an alkylating agent or trialkylsilyl chloride; incorporation of at least one nucleotide that reduces sensitivity for depurination in the target nucleic acid; incorporation of at least one mass modified nucleotide in the target nucleic acid; and hybridization of a tag probe to a portion of a nucleic acid molecule that contains the target nucleic acid but is distinct from a target nucleic acid sequence.

150. The method of claim 136, wherein the target polypeptide is obtained by in vitro translation, or by in vitro transcription followed by translation, of a nucleic acid encoding the target polypeptide.

151. The method of claim 150, wherein the nucleic acid encoding the target polypeptide further comprises a nucleotide sequence encoding a second polypeptide.

152. The method of claim 136, wherein the target polypeptide comprises a tag.

153. A method for detecting the presence of a target nucleic acid sequence in a biological sample containing nucleic acid molecules, comprising the steps of:
   a) contacting the nucleic acid molecules with a detector oligonucleotide, which can hybridize to a target nucleic acid sequence present in the biological sample;
   b) preparing a mixture for IR-MALDI, comprising the product of step a) and a liquid matrix, which absorbs infrared radiation;
   c) identifying duplex nucleic acid molecules in the mixture by IR-MALDI mass spectrometry, thereby detecting presence of the target nucleic acid sequence in the biological sample.

154. The method of claim 153, further comprising, prior to step a), a step of amplifying the nucleic acid molecules in the biological sample.

155. A method for detecting the presence of a target nucleic acid sequence in a biological sample containing nucleic acid molecules, comprising the steps of:
   a) specifically digesting the nucleic acid molecules using at least one appropriate nuclease, thereby producing digested fragments;
   b) hybridizing the digested fragments with complementary capture nucleic acid sequences, which are immobilized on a solid support and can hybridize to a digested fragment of a target nucleic acid to produce immobilized fragments;
   c) preparing a mixture for IR-MALDI, comprising the immobilized fragments and a liquid matrix, which absorbs infrared radiation; and
   d) identifying immobilized fragments by IR-MALDI mass spectrometry, thereby detecting the presence of the target nucleic acid sequence in the biological sample.

156. The method of claim 155, further comprising, prior to step a), a step of amplifying the nucleic acid molecules in the biological sample.

157. A method for detecting a target nucleic acid sequence, comprising the steps of:
   a) performing at least one hybridization on a nucleic acid molecule containing the target nucleic acid sequence with a set of ligation educts and a thermostable DNA ligase;
   b) preparing a mixture for IR-MALDI, comprising the product of step a) and a liquid matrix, which absorbs infrared radiation; and
   c) identifying a ligation product in the mixture by IR-MALDI mass spectrometry, thereby detecting the target nucleic acid sequence.

158. A method for detecting the presence of a target nucleic acid in a biological sample containing nucleic acid molecules, comprising the steps of:
   a) performing on the nucleic acid molecules, a first polymerase chain reaction using a first set of primers, which are capable of amplifying a portion of a nucleic acid molecule containing the target nucleic acid, thereby producing a first amplification product;
   b) preparing a mixture for IR-MALDI, comprising the first amplification product and a liquid matrix, which absorbs infrared radiation; and
   c) detecting the first amplification product in the mixture by IR-MALDI mass spectrometry, thereby detecting the presence of the target nucleic acid in the biological sample.

159. The method of claim 158, wherein prior to step b), a second polymerase chain reaction is performed on the first amplification product using a second set of primers, which are capable of amplifying at least a portion of the first amplification product, which contains the target nucleic acid.

160. A method for determining the identity of a target nucleotide, comprising the steps of:
   a) hybridizing a nucleic acid molecule containing the target nucleotide with a primer oligonucleotide that is complementary to the nucleic acid molecule at a site adjacent to the target nucleotide, thereby producing a hybridized nucleic acid molecule;
   b) contacting the hybridized nucleic acid molecule with a complete set of dideoxynucleosides or 3'-deoxynucleoside triphosphates and a DNA dependent DNA polymerase, so that only the dideoxynucleosides or 3'-deoxynucleoside triphosphate that is complementary to the target nucleotide is extended onto the primer, thereby producing an extended primer;
   c) preparing a mixture for IR-MALDI, comprising the extended primer and a liquid matrix, which absorbs infrared radiation; and
   d) detecting the extended primer in the mixture by IR-MALDI mass spectrometry, thereby determining the identity of the target nucleotide.

161. A method for detecting the presence or absence of a mutation in a target nucleic acid sequence, comprising the steps of:
   a) hybridizing a nucleic acid molecule containing the target nucleic acid sequence with at least one primer, the primer having 3' terminal base complementarity to the target nucleic acid sequence, thereby producing a hybridized product;

b) contacting the hybridized product with an appropriate polymerase enzyme and sequentially with one of the four nucleoside triphosphates;

c) preparing a mixture for IR-MALDI, comprising the product of step b) and a liquid matrix, which absorbs infrared radiation; and d) detecting the product of step b) in the mixture by IR-MALDI mass spectrometry, wherein the molecular weight of the product indicates the presence or absence of a mutation next to the 3' end of the primer in the target nucleic acid molecule.

162. The method of claim 161, wherein the nucleic acid molecule containing the target nucleic acid sequence is immobilized to a solid support.

163. The method of claim 161, wherein, prior to step a), the nucleic acid molecule containing the target nucleic acid sequence is amplified.

164. A method for detecting a mutation in a target nucleic acid, comprising the steps of:

a) hybridizing the target nucleic acid with an oligonucleotide probe, to produce a hybridized target nucleic acid, wherein a mismatch is formed at the site of a mutation;

b) contacting the hybridized target nucleic acid with a single strand specific endonuclease;

c) preparing a mixture for IR-MALDI, comprising the product of step b) and a liquid matrix, which absorbs infrared radiation; and d) analyzing the mixture by IR-MALDI mass spectrometry, wherein the presence of more than one fragment of the target nucleic acid in the mixture detects a mutation the target nucleic acid.

165. A method for identifying the absence or presence of a mutation in a target nucleic acid sequence, comprising the steps of:

a) performing at least one hybridization on a nucleic acid molecule containing the target nucleic acid sequence with a set of ligation educts and a DNA ligase;

b) preparing a mixture for IR-MALDI, comprising the product of step a) and a liquid matrix, which absorbs infrared radiation; and c) analyzing the mixture by IR-MALDI mass spectrometry, wherein detecting a ligation product in the mixture identifies the absence of a mutation in the target nucleic acid sequence, and wherein detecting only the set of ligation educts in the mixture identifies the presence of a mutation in the target nucleic sequence.

166. A method for determining the identity of each target biological macromolecule in a plurality of target biological macromolecules, comprising the steps of:

a) preparing a mixture for IR-MALDI, comprising a plurality of differentially mass modified target biological macromolecules and a liquid matrix, which absorbs infrared radiation;

b) determining the molecular mass of each differentially mass modified target biological macromolecule in the plurality by IR-MALDI mass spectrometry; and c) comparing the molecular mass of each differentially mass modified target biological macromolecule in the plurality with the molecular mass of a corresponding known biological macromolecule, thereby determining the identity of each target biological macromolecule in the plurality of target biological macromolecules or fragments thereof.

167. The method of claim 166, wherein each target biological macromolecule in the plurality is a fragment of a biological macromolecule, each fragment prepared by contacting the biological macromolecule with at least one agent that cleaves a bond involved in the formation of the biological macromolecule.

168. A method for determining the sequence of a target biological macromolecule, comprising the steps of:

a) generating at least two biological macromolecule fragments from the target biological macromolecule;

b) preparing a mixture for IR-MALDI, comprising the biological macromolecule fragments and a liquid matrix, which absorbs infrared radiation; and c) analyzing the biological macromolecule fragments in the mixture by IR-MALDI mass spectrometry, thereby determining the sequence of the target nucleic acid molecule.

169. A method of determining the subunit sequence of at least one species of target biological macromolecule, i, comprising the steps of:

a) contacting the species of target biological macromolecule with at least one agent that cleaves a bond involved in the formation of the target biological macromolecule such that each bond in involved in the formation of the target biological macromolecule is cleaved, thereby producing a nested set of deletion fragments of the species of biological macromolecule;

b) preparing a mixture for IR-MALDI, comprising the nested set of deletion fragments and a liquid matrix, which absorbs infrared radiation; and c) determining the molecular mass of each deletion fragment in mixture by IR-MALDI mass spectrometry, thereby determining the subunit sequence of the species of target biological macromolecule.

170. The method of claim 169, wherein the agent that cleaves is an agent that cleaves the target biological macromolecule unilaterally from a terminus.

171. The method of claim 170, wherein the target biological macromolecule is a nucleic acid and the agent that cleaves is an exonuclease.

172. The method of claim 170, wherein the target biological macromolecule is a polypeptide and the agent that cleaves is an exopeptidase.

173. The method of claim 170, wherein at least one species of target biological macromolecule comprises i+1 species of target biological macromolecules, and wherein each species of target biological macromolecule is differentially mass modified such that a deletion fragment of each species of target biological macromolecule can be distinguished from a deletion fragment of every other target biological macromolecule by IR-MALDI mass spectrometry.

174. A method of determining the nucleotide sequence of at least one species of nucleic acid, i, comprising the steps of:

a) synthesizing complementary nucleic acids, which are complementary to the species of nucleic acid to be sequenced, starting from an oligonucleotide primer and in the presence of chain terminating nucleoside triphosphates, thereby producing four sets of base-specifically terminated complementary polynucleotide fragments;

b) preparing a mixture for IR-MALDI, comprising the four sets of polynucleotide fragments and a liquid matrix, which absorbs infrared radiation; and c) determining the molecular weight value of each polynucleotide fragment by IR-MALDI mass spectrometry; and d) determining the nucleotide sequence of the species of nucleic acid by aligning the molecular weight values according to molecular weight.

175. The method of claim 174, wherein the species of nucleic acid is RNA, the chain terminating nucleoside triphosphates are ribonucleotide triphosphates or derivatives thereof, and the oligonucleotide primer is an initiator oligonucleotide.

176. The method of claim 173, wherein i+1 species of nucleic acids are concurrently sequenced by multiplex mass spectrometric nucleic acid sequencing employing i+1 primers, wherein one of the i+1 primers is an unmodified primer or a mass modified primer and the other i primers are mass modified primers, and each of the i+1 primers can be distinguished from the other by IR-MALDI mass spectroetry.

177. A method for determining a sequence of a target nucleic acid, comprising the steps of:

a) hybridizing at least one partially single stranded target nucleic acid to one or more nucleic acid probes, each probe comprising a double stranded portion, a single stranded portion, and a determinable variable sequence within the single stranded portion, thereby producing at least one hybridized target nucleic acid;

b) preparing a mixture for IR-MALDI, comprising the hybridized target nucleic acid and a liquid matrix, which absorbs infrared radiation;

c) determining a sequence of the hybridized target nucleic acid by IR-MALDI mass spectrometry based on the determinable variable sequence of the probe to which the target nucleic acid hybridized; and d) repeating steps a) to c) a sufficient number of times to determine a sequence of the target nucleic acid.

178. The method of claim 177, wherein the one or more nucleic acid probes are immobilized in an array.

179. The method of claim 177, wherein, prior to step b), the hybridized target nucleic acid is ligated to the determinable variable sequence.

180. A method for analyzing biological macromolecules in a sample comprising:

exposing the sample to infrared radiation, so that one or more of the biological macromolecules are desorbed and ionized; and analyzing the sample using matrix-assisted laser desorption/ionization mass spectrometry;

wherein the accuracy of mass determination by matrix-assisted laser desorption/ionization is in the range of about $10^2$ to about $5 \times 10^3$ ppm.

181. The method of claim 180, wherein the accuracy of mass determination by matrix-assisted laser desorption/ionization is in the range of about 100 to about 500 ppm.

182. The method of claim 180, wherein the accuracy of mass determination by matrix-assisted laser desorption/ionization is in the range of about $1 \times 10^3$ to about $5 \times 10^3$ ppm.

183. The method of claim 180, wherein the molecular weight of the biological macromolecule is 150 kDa or less; and the precision of mass determination by matrix-assisted laser desorption/ionization is in the range of about 400–500 ppm.

184. The method of claim 180, wherein the molecular weight of the biological macromolecule is 150 kDa or less; and the precision of mass determination by matrix-assisted laser desorption/ionization is in the range of about 200–400 ppm.

185. The method of claim 180, wherein the molecular weight of the biological macromolecule exceeds 1 MDa (megadalton).

186. The method of claim 180, further comprising extracting ions of the ionized biological macromolecules from an ion source by delayed extraction, whereby enhanced mass remixture is achieved.

187. The method of claim 180, wherein the matrix is glycerol.

188. The method of claim 180, wherein the matrix is succinic acid.

189. The method of claim 180, wherein the biological macromolecule is a polypeptide greater than 50 kDa and the matrix-assisted laser desorption/ionization mass spectrometry is performed using a reflectron time-of-flight format.

190. The method of claim 180 that is a method for detecting the presence or absence of a nucleic acid in a sample, wherein:

the sample is mixed with a matrix to form a homogeneous mixture with the nucleic acid; and the nucleic acid is detected if present in the sample.

191. The method of claim 190, wherein the sample is a biological sample.

192. The method of claim 190, wherein the nucleic acid comprises at least 2000 nucleotides.

193. The method of claim 190, wherein the nucleic acid comprises at least 280 nucleotides.

194. The method of claim 190, wherein the nucleic acid is DNA.

195. The method of claim 190, wherein the nucleic acid comprises at least 1200 nucleotides.

196. The method of claim 190, wherein the nucleic acid is RNA.

197. The method of claim 190, wherein the presence or absence of the nucleic acid is indicative of the presence or absence of a genetic disease.

198. The method of claim 190, wherein the presence or absence of the nucleic acid is indicative of the presence or absence of a birth defect.

199. The method of claim 190, wherein the presence or absence of the nucleic acid is indicative of the presence or absence of an infectious organism.

200. The method of claim 190, wherein the presence or absence of the nucleic acid is indicative of the identity of a subject.

201. The method of claim 190, wherein the matrix is a substituted or unsubstituted alcohol.

202. The method of claim 190, wherein the nucleic acid/matrix mixture is deposited onto fields of a chip array, arrays of pins or beads in pits of flat surfaces.

203. A method for determining the presence or absence of a target biological macromolecule in a sample, comprising:

analyzing the sample using infrared matrix-assisted laser desorption/ionization mass spectrometry and a liquid matrix;

wherein the target biological macromolecule is detected if present in the sample.

204. The method of claim 203, wherein the sample is a biological sample.

205. The method of claim 203, wherein the sample contains one or more biological macromolecules other than the target biological macromolecule.

206. The method of claim 203, wherein the target macromolecule is a biopolymer.

207. The method of claim 206, wherein the target biopolymer is a polypeptide.

208. The method of claim 206, wherein the target biological macromolecule is a nucleic acid.

209. The method of claim 206, wherein the target nucleic acid is a double-stranded nucleic acid or the target nucleic acid is a single-stranded nucleic acid or the target nucleic acid comprises double-stranded and single-stranded regions.

210. The method of claim 206, wherein the presence or absence of the target biological macromolecule is indicative of one or more of the following:

the presence or absence of a genetic disease or is indicative of the presence or absence of a birth defect;

the presence or absence of an infectious organism;

the identity of a subject.

211. The method of claim 203, wherein delayed ion extraction is used in the matrix-assisted laser desorption/ionization mass spectrometry.

212. The method of claim 203, wherein the biological macromolecule is selected from the group consisting of a carbohydrate, a nucleoprotein, a proteoglycan, lipids, nucleic acid analogs and a macromolecular complex.

213. The method of claim 203, wherein the target biological macromolecule is immobilized on a solid support.

214. The method of claim 213, wherein the target biological macromolecule is immobilized to the solid support via a cleavable linkage and/or a reversible linkage.

215. The method of claim 213, wherein the target biological macromolecule is cleaved from the support during the step of performing matrix-assisted laser desorption/ionization mass spectrometry.

216. The method of claim 213, wherein the support comprises one or more hydrophilic areas and each of the one or more areas is surrounded by a hydrophobic area or one or more hydrophobic areas and each of the one or more areas is surrounded by a hydrophilic area or is the terminus of a fiber optic cable.

217. The method of claim 209, wherein a target nucleic acid is immobilized by hybridization to a complementary capture nucleic acid molecule, which is immobilized to a solid support.

218. The method of claim 203, wherein the target biological macromolecule is conditioned prior to the step of performing matrix-assisted laser desorption/ionization mass spectrometry.

219. The method of claim 206, wherein the target biopolymer is conditioned by a method selected from the group consisting of ion exchange, phosphodiester backbone modification effected by cation exchange; contact with an alkylating agent or trialkylsilyl chloride; incorporation of at least one nucleotide that reduces sensitivity for depurination in the target nucleic acid; incorporation of at least one mass modified nucleotide in the target nucleic acid; and hybridization of a tag probe to a portion of a nucleic acid molecule that contains the target nucleic acid but is distinct from a target nucleic acid sequence.

220. The method of claim 207, wherein the target polypeptide is obtained by in vitro translation, or by in vitro transcription followed by translation, of a nucleic acid encoding the target polypeptide.

221. The method of claim 220, wherein the nucleic acid encoding the target polypeptide further comprises a nucleotide sequence encoding a second polypeptide.

222. The method of claim 207, wherein the target polypeptide comprises a tag.

223. The method of claim 203, wherein:

the liquid matrix is glycerol; and the biological macromolecule is a nucleic acid with a mass in the range from about $1 \times 10^4$ Daltons to about $1 \times 10^6$ Daltons.

224. The method of claim 203, further comprising, prior to analyzing the sample using matrix-assisted laser desorption/ionization mass spectrometry, depositing the sample on a substrate.

225. The method of claim 224, wherein said depositing is performed with an automated liquid dispensing device.

226. The method of claim 203, wherein infrared matrix-assisted laser desorption/ionization mass spectrometry is performed at a temperature in the range of about −80° C. to 20° C.

* * * * *

UNITED STATES PATENT AND TRADEMARK OFFICE
CERTIFICATE OF CORRECTION

PATENT NO.    : 6,558,902 B1
DATED         : May 6, 2003
INVENTOR(S)   : Hillenkamp, F.

It is certified that error appears in the above-identified patent and that said Letters Patent is hereby corrected as shown below:

<u>Column 16,</u>
Line 31, please replace "of" with -- in --
Line 32, please replace "in" with -- of --
Line 54, please replace "glycosydic" with -- glycosidic --

<u>Column 19,</u>
Line 24, please replace "dithiothreitol/erytritol" with -- dithiothreitol/erythritol --

<u>Column 22,</u>
Line 54, please replace "respectiyvely" with -- respectively --

<u>Column 23,</u>
Line 58, please delete the first "a"

<u>Column 31,</u>
Line 38, please replace "dithiotreitol/erythritol" with -- dithiothreitol/erythritol --

<u>Column 43,</u>
Line 61, please replace "H$_o$wever" with -- However --

<u>Column 65,</u>
Line 12, please replace "ionizing volatilizing" with -- ionizing/volatilizing --

<u>Column 71,</u>
Line 63, please replace "dideoxynucleotides" with -- dideoxynucleotide --

<u>Column 77,</u>
Lines 8-9, please delete the space between "dideoxy" and "nucleotides"

<u>Column 85,</u>
Line 21, please replace "Seal" with -- Sca I --

<u>Column 97,</u>
Line 40, please replace "$10^{-7-10-8}$" with -- $10^{-7}$-$10^{-8}$ --

UNITED STATES PATENT AND TRADEMARK OFFICE
CERTIFICATE OF CORRECTION

PATENT NO. : 6,558,902 B1
DATED : May 6, 2003
INVENTOR(S) : Hillenkamp, F.

It is certified that error appears in the above-identified patent and that said Letters Patent is hereby corrected as shown below:

Columns 104-124,

Claims 8, 50, 82, 94, 143, 153, 164, 169, and 226 should read as follows:

8. The method of claim 1, wherein the matrix comprises a polyglycerol, sucrose, mannose, galactose, ethylene glycol, propylene glycol, trimethylolpropane, pentaerythritol, dextrose, methylglycoside or sorbitol, triethanolamine, lactic acid, 3-nitrobenzylalcohol, diethanolamine, DMSO, nitrophenyloctylether (3-NPOE), 2,2'dithiodiethanol, tetraethyleneglycol, di-thiothreitol/erythritol (DTT/DTE), 2,3-dihydroxy-propyl-benzyl ether, $\alpha$-tocopherol, and thioglycerol.

50. The method of claim 46, wherein the matrix comprises a polyglycerol, sucrose, mannose, galactose, ethylene glycol, propylene glycol, trimethylolpropane, pentaerythritol, dextrose, methylglycoside or sorbitol, triethanolamine, lactic acid, 3-nitrobenzylalcohol, diethanolamine, DMSO, nitrophenyloctylether (3-NPOE), 2,2'dithiodiethanol, tetraethyleneglycol, di-thiothreitol/erythritol(DTT/DTE), 2,3-dihydroxy-propyl-benzyl ether, $\alpha$-tocopherol, and thioglycerol.

82. A method of claim 46, wherein the sample is heated to a temperature which is greater than about 20°C and less than about 80°C.

94. A method for determining the DNA sequence of a target DNA sequence, comprising:
(a) hybridizing a primer with a target DNA, where the primer (i) is complementary to the target DNA; (ii) has a first region containing the 5' end of the primer and an immobilization attachment site, and (iii) has a second region containing the 3' end of the primer, where the 3' end is capable of serving as a priming site for enzymatic extension and where the second region contains a cleavable site;
(b) extending the primer with an enzyme in the presence of a first of four different dideoxy nucleotides to generate a mixture of primer extension products, each product containing a primer and an extension segment;
(c) cleaving at the cleavable site to release the extension segments, where prior to the cleaving the primers are immobilized at the immobilization attachment sites;
(d) sizing the extension segments by the method of claim 1, whereby the cleaving is effective to increase the read length of the extension segment relative to the read length of the product of (b);
(e) repeating steps (a) through (d) with a second, third, and fourth of the four different dideoxynucleotides; and
(f) determining the DNA sequence of the target DNA by comparison of the sizes of the extension segments obtained from each of the four extension reactions.

143. The method of claim 138, wherein the solid support is selected from the group consisting of a bead, a flat surface, a chip, a capillary, a pin, a comb, a wafer, a wafer with an array of nano-wells or pits, the terminus of a fiber optic cable, a support with a surface that comprises hydrophobic regions and a support with a surface that comprises hydrophilic regions, whereby the target molecule is constrained to a locus on the support.

UNITED STATES PATENT AND TRADEMARK OFFICE
CERTIFICATE OF CORRECTION

PATENT NO. : 6,558,902 B1
DATED : May 6, 2003
INVENTOR(S) : Hillenkamp, F.

It is certified that error appears in the above-identified patent and that said Letters Patent is hereby corrected as shown below:

Columns 104-124 cont'd,

153. A method for detecting the presence of a target nucleic acid sequence in a biological sample containing nucleic acid molecules, comprising the steps of:
    a) contacting the nucleic acid molecules with a detector oligonucleotide, which can hybridize to a target nucleic acid sequence present in the biological sample;
    b) preparing a mixture for IR-MALDI, comprising the product of step a) and a liquid matrix, which absorbs infrared radiation;
    c) identifying duplex nucleic acid molecules in the mixture by IR-MALDI mass spectrometry, thereby detecting the presence of the target nucleic acid sequence in the biological sample.

164. A method for detecting a mutation in a target nucleic acid, comprising the steps of:
    a) hybridizing the target nucleic acid with an oligonucleotide probe, to produce a hybridized target nucleic acid, wherein a mismatch is formed at the site of a mutation;
    b) contacting the hybridized target nucleic acid with a single strand specific endonuclease;
    c) preparing a mixture for IR-MALDI, comprising the product of step b) and a liquid matrix, which absorbs infrared radiation; and
    d) analyzing the mixture by IR-MALDI mass spectrometry, wherein the presence of more than one fragment of the target nucleic acid in the mixture detects a mutation in the target nucleic acid.

UNITED STATES PATENT AND TRADEMARK OFFICE
CERTIFICATE OF CORRECTION

PATENT NO.    : 6,558,902 B1
DATED         : May 6, 2003
INVENTOR(S)   : Hillenkamp, F.

It is certified that error appears in the above-identified patent and that said Letters Patent is hereby corrected as shown below:

<u>Columns 104-124 cont'd,</u>

169. A method of determining the subunit sequence of at least one species of target biological macromolecule, i, comprising the steps of:
    a) contacting the species of target biological macromolecule with at least one agent that cleaves a bond involved in the formation of the target biological macromolecule such that each bond involved in the formation of the target biological macromolecule is cleaved, thereby producing a nested set of deletion fragments of the species of biological macromolecule;
    b) preparing a mixture for IR-MALDI, comprising the nested set of deletion fragments and a liquid matrix, which absorbs infrared radiation; and
    c) determining the molecular mass of each deletion fragment in mixture by IR-MALDI mass spectrometry, thereby determining the subunit sequence of the species of target biological macromolecule.

226. The method of claim 203, wherein infrared matrix-assisted laser desorption/ionization mass spectrometry is performed at a temperature in the range of about -80°C to 20°C.

Signed and Sealed this

Sixteenth Day of September, 2003

JAMES E. ROGAN
*Director of the United States Patent and Trademark Office*